US010273300B2

(12) United States Patent
Bedoya et al.

(10) Patent No.: US 10,273,300 B2
(45) Date of Patent: Apr. 30, 2019

(54) METHODS OF MAKING CHIMERIC ANTIGEN RECEPTOR-EXPRESSING CELLS

(71) Applicants: The Trustees of the University of Pennsylvania, Philadelphia, PA (US); Novartis AG, Basel (CH)

(72) Inventors: Felipe Bedoya, East Norristown, PA (US); Saba Ghassemi, Philadelphia, PA (US); Carl H. June, Merion Station, PA (US); Bruce L. Levine, Cherry Hill, NJ (US); Jan J. Melenhorst, Cherry Hill, MA (US); Michael C. Milone, Cherry Hill, NJ (US); Daniel J. Powell, Jr., Bala Cynwyd, PA (US); Zoe Zheng, Cherry Hill, NJ (US)

(73) Assignees: The Trustees of the University of Pennsylvania, Philadelphia, PA (US); Novartis AG, Basel (CH)

( * ) Notice: Subject to any disclaimer, the term of this patent is extended or adjusted under 35 U.S.C. 154(b) by 0 days.

(21) Appl. No.: 14/981,142

(22) Filed: Dec. 28, 2015

(65) Prior Publication Data

US 2016/0185861 A1 Jun. 30, 2016

Related U.S. Application Data

(60) Provisional application No. 62/133,137, filed on Mar. 13, 2015, provisional application No. 62/097,375, filed on Dec. 29, 2014.

(51) Int. Cl.

| | |
|---|---|
| ***C07K 16/28*** | (2006.01) |
| ***C07K 14/705*** | (2006.01) |
| ***C12N 9/12*** | (2006.01) |
| ***C07K 14/725*** | (2006.01) |
| ***C12N 5/0783*** | (2010.01) |
| ***A61K 35/17*** | (2015.01) |
| ***C12N 5/00*** | (2006.01) |
| *A61K 39/00* | (2006.01) |

(52) U.S. Cl.

CPC .......... *C07K 16/2803* (2013.01); *A61K 35/17* (2013.01); *C07K 14/7051* (2013.01); *C07K 14/70517* (2013.01); *C07K 14/70578* (2013.01); *C07K 16/28* (2013.01); *C12N 5/0087* (2013.01); *C12N 5/0636* (2013.01); *C12N 5/0638* (2013.01); *C12N 9/1276* (2013.01); *A61K 2039/5156* (2013.01); *A61K 2039/5158* (2013.01); *C07K 2317/14* (2013.01); *C07K 2317/622* (2013.01); *C07K 2319/03* (2013.01); *C07K 2319/74* (2013.01); *C12N 2501/2302* (2013.01); *C12N 2501/2307* (2013.01); *C12N 2501/2315* (2013.01); *C12N 2501/51* (2013.01); *C12N 2501/515* (2013.01); *C12N 2510/00* (2013.01); *C12Y 207/07049* (2013.01)

(58) Field of Classification Search

CPC ... C12N 5/00636–5/638; C12N 5/0093; C12N 5/0087; C12N 2740/16041; C12N 2740/43; C12N 2501/2307; C12N 2501/2315; C07K 14/705; A61K 35/17

See application file for complete search history.

(56) References Cited

U.S. PATENT DOCUMENTS

| | | | | |
|---|---|---|---|---|
| 5,359,046 | A | 10/1994 | Capon et al. | |
| 5,686,281 | A | 11/1997 | Roberts | |
| 5,712,149 | A | 1/1998 | Roberts | |
| 5,874,240 | A | 2/1999 | Ni et al. | |
| 5,906,936 | A | 5/1999 | Eshhar et al. | |
| 6,103,521 | A | 8/2000 | Capon et al. | |
| 6,319,494 | B1 | 11/2001 | Capon et al. | |
| 6,355,779 | B1 | 3/2002 | Goodwin et al. | |
| 6,410,319 | B1 | 6/2002 | Raubitschek et al. | |
| 6,475,481 | B2 * | 11/2002 | Talmadge ............ | C12N 5/0093 424/93.21 |
| 6,569,997 | B1 | 5/2003 | Kwon | |
| 7,049,136 | B2 | 5/2006 | Seed et al. | |
| 7,052,906 | B1 | 5/2006 | Lawson et al. | |
| 7,070,995 | B2 | 7/2006 | Jensen | |
| 7,265,209 | B2 | 9/2007 | Jensen | |
| 7,319,143 | B2 | 1/2008 | Gross et al. | |
| 7,320,787 | B2 | 1/2008 | Seed et al. | |
| 7,446,190 | B2 | 11/2008 | Sadelain et al. | |
| 7,446,191 | B2 | 11/2008 | Jensen | |
| 7,514,537 | B2 | 4/2009 | Jensen | |
| 7,638,326 | B2 | 12/2009 | June et al. | |
| 7,741,465 | B1 | 6/2010 | Eshhar et al. | |
| 7,745,140 | B2 | 6/2010 | June et al. | |
| 7,754,482 | B2 | 7/2010 | Riley et al. | |
| 7,994,298 | B2 | 8/2011 | Zhang et al. | |
| 8,211,422 | B2 | 7/2012 | Eshhar et al. | |

(Continued)

FOREIGN PATENT DOCUMENTS

| | | | |
|---|---|---|---|
| CN | 105158466 | A | 12/2015 |
| EP | 0574512 | A1 | 12/1993 |

(Continued)

OTHER PUBLICATIONS

Verbinnen et al., J. Immunol. 2008; 181:1034-42.*

(Continued)

*Primary Examiner* — Jessica H Roark

(74) *Attorney, Agent, or Firm* — Lando & Anastasi, LLP

(57) ABSTRACT

The invention provides methods of making immune effector cells (e.g., T cells, NK cells) that can be engineered to express a chimeric antigen receptor (CAR), and compositions and reaction mixtures comprising the same.

28 Claims, 57 Drawing Sheets

Specification includes a Sequence Listing.

(56) References Cited

U.S. PATENT DOCUMENTS 8,252,914 B2 8/2012 Zhang et al.
8,389,282 B2 3/2013 Sadelain et al.
8,399,645 B2 3/2013 Campana et al.
8,465,743 B2 6/2013 Rosenberg et al.
8,637,307 B2 1/2014 June et al.
8,722,400 B2 5/2014 Riley et al.
8,906,682 B2 12/2014 June et al.
8,911,993 B2 12/2014 June et al.
8,916,381 B1 12/2014 June et al.
8,975,071 B1 3/2015 June et al.
9,101,584 B2 8/2015 June et al.
9,102,760 B2 8/2015 June et al.
9,102,761 B2 8/2015 June et al.
9,272,002 B2 3/2016 Powell, Jr. et al.
9,328,156 B2 5/2016 June et al.
9,365,641 B2 6/2016 June et al.
9,394,368 B2 7/2016 Brogdon et al.
9,402,865 B2 8/2016 Powell et al.
9,422,351 B2 8/2016 Scholler et al.
9,446,105 B2 9/2016 Powell, Jr.
9,464,140 B2 10/2016 June et al.
9,481,728 B2 11/2016 June et al.
9,499,629 B2 11/2016 June et al.
9,518,123 B2 12/2016 June et al.
9,540,445 B2 1/2017 June et al.
9,572,836 B2 2/2017 June et al.
9,573,988 B2 2/2017 Brogdon et al.
9,598,489 B2 3/2017 Powell, Jr.
9,708,384 B2 7/2017 Scholler et al.
9,714,278 B2 7/2017 June et al.
9,745,368 B2 8/2017 Milone et al.
9,765,156 B2 9/2017 June et al.
9,777,061 B2 10/2017 Ebersbach et al.
9,815,901 B2 11/2017 Brogdon et al.
2003/0060444 A1 3/2003 Finney et al.
2003/0077249 A1 4/2003 Bebbington et al.
2003/0105000 A1 6/2003 Pero et al.
2003/0148982 A1 8/2003 Brenner et al.
2003/0224520 A1 12/2003 June et al.
2004/0038886 A1 2/2004 Finney et al.
2004/0043401 A1 3/2004 Sadelain et al.
2005/0113564 A1 5/2005 Campana et al.
2005/0129671 A1 6/2005 Cooper et al.
2007/0036773 A1 2/2007 Cooper et al.
2008/0131415 A1 6/2008 Riddell et al.
2008/0160090 A1* 7/2008 Oraevsky ........... A61K 41/0052 424/489
2009/0257994 A1 10/2009 Jensen
2011/0052554 A1 3/2011 Zakrzewski et al.
2012/0027802 A1* 2/2012 Bonini ............... A61K 48/0091 424/277.1
2012/0148552 A1 6/2012 Jensen
2012/0302466 A1 11/2012 Sentman
2012/0321667 A1 12/2012 Sentman
2013/0071409 A1 3/2013 Riley et al.
2013/0071414 A1 3/2013 Dotti et al.
2013/0149337 A1 6/2013 Cooper et al.
2013/0155909 A1 6/2013 Jackson et al.
2013/0287748 A1 10/2013 June et al.
2014/0050708 A1 2/2014 Powell et al.
2014/0099309 A1 4/2014 Powell, Jr. et al.
2014/0099340 A1 4/2014 June et al.
2014/0106449 A1 4/2014 June et al.
2014/0186947 A1 7/2014 June et al.
2014/0212446 A1 7/2014 Riley et al.
2014/0219975 A1 8/2014 June et al.
2014/0227237 A1 8/2014 June et al.
2014/0271635 A1 9/2014 Brogdon et al.
2014/0322169 A1 10/2014 Harper et al.
2014/0322183 A1 10/2014 Milone et al.
2014/0322212 A1 10/2014 Brogdon et al.
2014/0322275 A1 10/2014 Brogdon et al.
2014/0370045 A1 12/2014 June et al.
2015/0017141 A1 1/2015 June et al.
2015/0140019 A1 5/2015 June et al.
2015/0190428 A1 7/2015 June et al.
2015/0202286 A1 7/2015 June et al.
2015/0283178 A1 10/2015 June et al.
2015/0290244 A1 10/2015 June et al.
2015/0342994 A1 12/2015 Riley et al.
2016/0046724 A1 2/2016 Brogdon et al.
2016/0051651 A1 2/2016 Brogdon et al.
2016/0068601 A1 3/2016 Brogdon et al.
2016/0096892 A1 4/2016 Brogdon et al.
2016/0185861 A1 6/2016 Bedoya et al.
2016/0311907 A1 10/2016 Brogdon et al.
2016/0311917 A1 10/2016 Beatty et al.
2016/0340406 A1 11/2016 Zhao et al.
2016/0362472 A1 12/2016 Bitter et al.
2017/0008963 A1 1/2017 Brogdon et al.
2017/0081411 A1 3/2017 Engels et al.
2017/0137783 A1 5/2017 Bedoya et al.
2017/0183415 A1 6/2017 Brogdon et al.
2017/0209492 A1 7/2017 June et al.
2017/0211055 A1 7/2017 Brogdon et al.
2017/0226495 A1 8/2017 Guimaraes
2017/0239294 A1 8/2017 Thomas-Tikhonenko et al.
2017/0260268 A1 9/2017 Beatty et al.
2017/0274014 A1 9/2017 Brogdon et al.
2017/0306416 A1 10/2017 Bedoya et al.
2017/0335281 A1 11/2017 Loew et al.
2018/0022795 A1 1/2018 Milone et al.
2018/0044423 A1 2/2018 Ebersbach et al.
2018/0044424 A1 2/2018 June et al.
2018/0118834 A1 5/2018 Brogdon et al.
2018/0125892 A1 5/2018 Brannetti et al.
2018/0133296 A1 5/2018 Barrett et al.
2018/0140602 A1 5/2018 Angst et al.
2018/0230193 A1 8/2018 Loew et al.
2018/0252727 A1 9/2018 Garfall et al.
2018/0258149 A1 9/2018 Motz et al.
2018/0298068 A1 10/2018 Albelda
2018/0312595 A1 11/2018 Brogdon et al.

FOREIGN PATENT DOCUMENTS

EP 0871495 A1 10/1998
EP 1226244 A2 7/2002
WO 1992015322 A1 9/1992
WO 199530014 A1 11/1995
WO 9623814 A1 8/1996
WO 9624671 A1 8/1996
WO 1997015669 A1 5/1997
WO 9723613 A2 7/1997
WO 9818809 A1 5/1998
WO 9900494 A2 1/1999
WO 9957268 A1 11/1999
WO 0014257 A1 3/2000
WO 2002033101 A1 4/2002
WO 02077029 A2 10/2002
WO 02088334 A1 11/2002
WO 2003057171 A2 7/2003
WO 2005019429 A2 3/2005
WO 2005044996 A2 5/2005
WO 2005/118788 A2 12/2005
WO 2006060878 A1 6/2006
WO 2008045437 A2 4/2008
WO 2010085660 A2 7/2010
WO 2011059836 A2 5/2011
WO 2011097477 A1 8/2011
WO 2012058460 A2 5/2012
WO 2012079000 A1 6/2012
WO 2012082841 A2 6/2012
WO 2012/099973 A2 7/2012
WO 2012127464 A2 9/2012
WO 2012129514 A1 9/2012
WO 2012135854 A2 10/2012
WO 2012138858 A1 10/2012
WO 2013019615 A2 2/2013
WO 2013033626 A2 3/2013
WO 2013040371 A2 3/2013
WO 2013040557 A2 3/2013
WO 2013059593 A1 4/2013
WO 2013074916 A1 5/2013

(56) References Cited

FOREIGN PATENT DOCUMENTS

| | | | |
|---|---|---|---|
| WO | 2013/126712 | A1 | 8/2013 |
| WO | 2013126729 | A1 | 8/2013 |
| WO | 2013126733 | A1 | 8/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |
| WO | 2014039513 | A2 | 3/2014 |
| WO | 2014/055442 | A2 | 4/2014 |
| WO | 2014/055771 | A1 | 4/2014 |
| WO | 2014055657 | A1 | 4/2014 |
| WO | 2014130635 | A1 | 8/2014 |
| WO | 2014/145252 | A2 | 9/2014 |
| WO | 2014190273 | A1 | 11/2014 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2015157252 | A1 | 10/2015 |
| WO | 2015164745 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |
| WO | 2016/057705 | A1 | 4/2016 |
| WO | 2016/109410 | A2 | 7/2016 |
| WO | 2016/168595 | A1 | 10/2016 |
| WO | 2017015427 | A1 | 1/2017 |
| WO | 2017049166 | A1 | 3/2017 |
| WO | 2017117112 | A1 | 7/2017 |

OTHER PUBLICATIONS

Powell et al., J. Immunother. 2005; 28(4):403-11.*

Han et al., PLoS ONE, 2011; 6(12): e28649. doi: 10.1371/journal.pone.0028649.*

Terakura et al., Blood 2012; 119:72-82.*

Husebekk et al., Cytotherapy 2000; 2(3):187-93.*

E.V. Barsov, Immunotherapy 2011; 3(3):407-21.*

Baeksgaard & Sorensen, "Acute tumor lysis syndrome in solid tumors—a case report and review of the literature" Cancer Chemotherapy Pharmacology (2003) vol. 51 pp. 187-192.

Barrett et al. "Relation of clinical culture method to T-cell memory status and efficacy in xenograft models of adoptive immunotherapy", Cytotherapy (2014) vol. 16, No. 5, pp. 619-630.

Bondanza et al. "Suicide gene therapy of graft-versus-host disease induced by central memory human T lymphocytes" Blood (2006) vol. 107 No. 5 pp. 1828-1836.

Brentjens et al. "Genetically Targeted T Cells Eradicate Systemic Acute Lymphoblastic Leukemia Xenografts", Clinical Cancer Research(2007) vol. 13, No. 18, pp. 5426-5435.

Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.

Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.

Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).

Brentjens et al., "Eradication of systemic B-cell tumors by genetically targeted human T lymphocytes co-stimulated by CD80 and interleukin-15" Nature Medicine (2003) vol. 9 No. 3 pp. 279-286.

Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.

Brocker and Karjalainen, "Signals through T Cell Receptor-Chain alone Are Insufficient to Prime Resting T Lymphocytes" J. Exp. Met (1995) vol. 181 pp. 1653-1659.

Call & Wucherpfennig, "The T Cell Receptor: Critical Role of the Membrane Environment in Receptor Assembly and Function" Annu. Rev. Immunol. (2005) vol. 23 pp. 101-125.

Carpenito et al. "Control of large, established tumor xenografts with genetically retargeted human T cells containing CD28 and CD137 domains", Proc Natl Arad Sci USA (2009) vol. 106 pp. 3360-3365.

Cha et al. "IL-7+IL-15 are superior to IL-2 for the ex vivo expansion of 4T1 mammary carcinoma-specific T cells with greater efficacy against tumors in vivo", Breast Cancer Research and Treatment, Kluwer Academic Publishers (2009) vol. 122, No. 2, pp. 359-369.

Cheadle et al. "Cart cells: driving the road from the laboratory to the clinic", Immunological Reviews (2013), vol. 257, No. 1, pp. 91-106.

Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.

Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.

Dotti et al. "Design and development of therapies using chimeric antigen receptor-expressing T cells" Immunological Reviews (2013) vol. 257, No. 1, pp. 107-126.

Dropulic and June, "Gene-Based Immunotherapy for Human Immunodeficiency Virus Infection and Acquired Immunodeficiency Syndrome" Human Gene Therapy (2006) vol. 17 pp. 577-588.

Dull et al, "A Third-Generation Lentivirus Vector with a Conditional Packaging System" Journal of Virology (1998) vol. 72 No. 11 pp. 8463-8471.

Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).

Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).

Finney et al., "Chimeric receptors providing both primary and costimulatory signaling in T cells from a single gene product," J. Immunol. 161: 2791-2797 (1998).

Flynn et al. "Stem memory T cells (TSCM)—their role in cancer and HIV immunotherapies", Clinical & Translational Immunology (2014) vol. 3, No. 7, pp. 1-7.

Frey, N. "Genetically Engineered Lymphocyte Therapy in Treating Patients With B-Cell Leukemia or Lymphoma That is Resistant or Refractory to Chemotherapy" (2015) Clinical Trial NCT01029366.

Friedmann-Morvinski et al., "Redirected primary T cells harboring a chimeric receptor require costimulation for their antigen-specific activation," Blood 105: 3087-3093 (2005).

Geiger & Jyothi, "Development and Application of Receptor-Modified T Lymphocytes for Adoptive Immunotherapy" Transfusion Medicine Reviews (2001) vol. 15 No. 1 pp. 21-34.

Geiger et al., "Integrated src kinase and constimulatory activity enhances signal transduction through single-chain chimeric receptors in T lymphocytes," Blood 98(8): 2364-2371 (2001).

GenBank Accession No. NP_000725.1 accessed on Jan. 7, 2016 from //www.ncbi.nlm.nih.gov/protein/NP_000725.

GenBank Accession No. NP_932170.1 accessed Jan. 7, 2016 from //www.ncbi.nlm.nih.gov/protein/NP_932170.

Gilham et al., "Primary Polyclonal Human T Lymphocytes Targeted to Carcina-Embryonic Antigens and Neural Cell Adhesion Molecule Tumor Antigens by CD3-Based Chimeric Immune Receptors" Journal of Immunotherapy (2002) vol. 25 No. 2 pp. 139-151.

(56) References Cited

OTHER PUBLICATIONS

Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~ Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Hosing et al. "CARs in Chronic Lymphocytic Leukemia—Ready to Drive", Current Hematologic Malignancy Reports (2012) vol. 8, No. 1, pp. 60-70.
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing leukemic cells" Blood (2005) vol. 106 No. 1 pp. 376-383.
International Search Report and Written Opinion for International Application No. PCT/US2015/067635 dated Apr. 19, 2016.
International Search Report and Written Opinion for International Application No. PCT/US2016/043255 dated Dec. 16, 2016.
International Search Report and Written Opinion for International Application No. PCT/US2016/052260 dated Jan. 16, 2016.
International Search Report and Written Opinion for International Application No. PCT/US2016/068683 dated Mar. 29, 2017.
International Search Report and Written Opinion from International Application No. PCT/US2016/027751 dated Jan. 7, 2016.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-Of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Koehler et al. "Engineered T Cells for the Adoptive Therapy of B-Cell Chronic Lymphocytic Leukaemia", Advances in Hematology (2012) vol. 180, No. 9, pp. 6365-6413.
Kohn et al. "CARs on Track in the Clinic", Molecular Therapy (2011) vol. 19, No. 3, pp. 432-438.
Kraus et al., "Antigen-dependent CD28 Signaling Selectively Enhances Survival and Proliferation in Genetically Modified Activated Human Primary T Lymphocytes" J. Exp. Met (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34+-30 selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letoumeur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Lipowska-Bhalla et al. "Targeted immunotherapy of cancer with CAR T cells: achievements and challenges", (Cancer Immunology Immunotherapy 2012) vol. 61 pp. 953-962.
MacAllan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).

(56) References Cited

OTHER PUBLICATIONS

Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Moran-Crusio et al. "Tet2 Loss Leads to Increased Hematopoietic Stem Cell Self-Renewal and Myeloid Transformation" Cancer Cell (2011) vol. 20, pp. 11-24.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells"Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from //www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47, pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Partial International Search Report for International Application No. PCT/US2016/068683 dated Apr. 18, 2017.
Partial Search Report and Invitation to Pay Additional Fees for International Application No. PCT/US2016/052260 dated Nov. 16, 2016.
Patel et al., "Impact of chimeric immune receptor extracellular protein domains on T cell function" Gene Therapy (999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Priceman et al., "Smart CARs Engineered for Cancer Immunotherapy"Curr Opin Oncol (2015) vol. 27, No. 6, pp. 466-474.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Rufer et al. "Transfer of the human telomerase reverse transcriptase (TERT) gene into T lymphocytes results in extension of replicative potential", Blood (2001) pp. 597-603.
Sabbagh et al., "Tnf family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Scourzic et al. "TET proteins and the control of cytosine demethylation in cancer" Genome Medicine (2015) vol. 7, No. 9, pp. 10-16.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Singh et al. "Early memory phenotypes drive T cell proliferation in patients with pediatric malignancies", Science Translational Medicine (2016) vol. 8, No. 320, pp. 320ra3-320ra3.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Stroncek et al. "Highlights of the society for immunotherapy of cancer (SITC) 27th annual meeting" Journal for ImmunoTherapy of Cancer (2013) vol. 1, No. 4, pp. 1-11.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Wang et al. "CS-1 Re-Directed Central Memory T Cell Therapy for Multiple Myeloma" Blood (2014) vol. 124, No. 21, Meeting Abstract 1114.
Willemsen et al., "Genetic Engineering of T Cell Specificity for Immunotherapy of Cancer" Human Immunology (2003) vol. 64 pp. 56-68.
Wu et al. "Suppression of TET1-Dependent DNA Demethylation Is Essential for KRAS-Mediated Transformation" Cell Reports (2014) vol. 9, pp. 1827-1840.
Xu et al. "Oncometabolite 2-Hydroxyglutarate Is a Comparative Inhibitor of alpha-Ketoglutarate-Dependent Dioxygenases" Cancer Cell (2011) vol. 19, No. 1, pp. 17-30.
Zhang et al. "Down-regulation of TET2 in CD3+ and CD34+ cells of myelodysplastic syndromes and enhances CD34+ cells proliferation" Int J Clin Exp Pathol (2015) vol. 8, No. 9, pp. 10840-10846.
Zhang et al. "Efficiency of CD19 chimeric antigen receptor-modified T cells for treatment of B cell malignancies in phase I clinical trials: a meta analysis" Oncotarget (2015) vol. 6, No. 32, pp. 33961-33971.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Abaza et al. "Effects of Amino Acid Substituions Outside an Antigenic Site on Protein Binding to Monoclonal Antibodies of Predetermined Specificity Obtained by Peptide Immunization: Dem-

(56) References Cited

OTHER PUBLICATIONS onstration with Region 94-100 (Antigenic Site 3) of Myoglobin" Journal of Protein Chemistry (1992) vol. 11, No. 5, pp. 433-444.
Almagro et al. "Humanization of Antibodies" Frontiers in Bioscience (2008) vol. 13, pp. 1619-1633.
Colman et al. "Effects of amino acid sequence changes on antibody-antigen interactions" Research in Immunology (1994) vol. 145, No. 1, pp. 33-36.
Jena et al. "Chimeric Antigen Receptor (CAR)—Specific Monoclonal Antibody to Detect CD19-Specific T Cells in Clinical Trials" PLOS ONE (2013) vol. 8, No. 3, e57838, pp. 1-12.
Powell et al. "Partial Reduction of Human FOXP3+ CD4 T Cells In Vivo After CD25-directed Recombinant Immunotoxin Administration" J Immunother (2008) vol. 31, pp. 189-198.
Rudikoff et al. "Single amino acid substitution altering antigen-binding specificity" PNAS (1982) vol. 79, pp. 1979-1983.
Singapore Search Report and Written Opinion for Singapore Application No. 11201705293W dated Mar. 22, 2018.
Lee et al. "T cells expressing CD19 chimeric antigen receptors for acute lymphoblastic leukaemia in children and young adults: a phase 1 doseescalation trial" Lancet (2014) vol. 385, No. 9967, pp. 517-528.
Singapore Search Report and Written Opinion for Singapore Application No. 11201708516Y dated Sep. 25, 2018.
Wang et al. "Phenotypic and Functional Attributes of Lentivirus Modified CD19-specific Human CD8+ Central Memory T Cells Manufactured at Clinical Scale" J Immunother (2012) vol. 35, No. 9, pp. 689-701.

* cited by examiner

ND447 PBMCs activated, transduced, de-beaded, and harvested at Day 5 and D9 for comparative performance in vitro and in vivo

Initial expansion profile with 3x28 beads

Harvest time points indicated by arrows

Normal donor cells

Procedures replicated CVPF protocol

There is no difference in CART19 cell killing from cells isolated at day 5 and day 9 from expansion

Increased levels of multiple cytokines are produced in CART19 cells harvested at day 5 upon recognition of targets

- CART19 cells were stimulated with anti-CAR19-idiotype-Ab-coated or control beads for 24h.
- No cytokine or low levels (<200 pg/ml) of cytokine were detected with control beads.

CART19 cells harvested at day 5 possess a better cell-killing capacity

- CART19 cells were co-cultured with NALM6-Luc cells at increasing E:T ratios for 16h.
- Total cell lysates were examined by luciferase assay.

CART19 cells harvested at day 5 possess a better in vivo long-term cell-killing capacity

- $10^6$ NALM6 (CBG/GFP+)/mouse
- $10^6$ CART19 or UTD/mouse

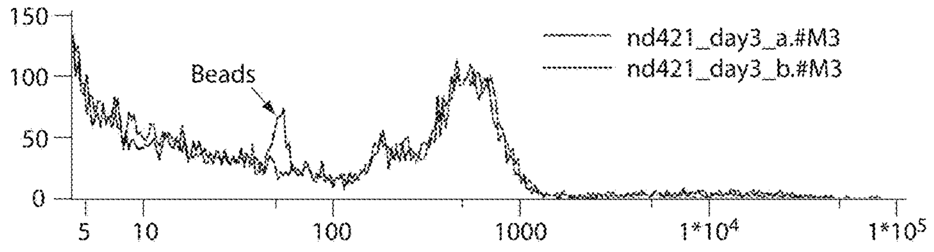
Fig. 27A
| bead removal | Day 2 e6 | Day 3 e6 | Day 4 e6 | Day 5 e6 | Day 6 e6 |
|---|---|---|---|---|---|
| Before | 1.5 | 3 | 1.1 | 1.78 | 0.72 |
| After | 1.45 | 3 | 1.2 | 1.8 | 0.84 |
Fig. 27B
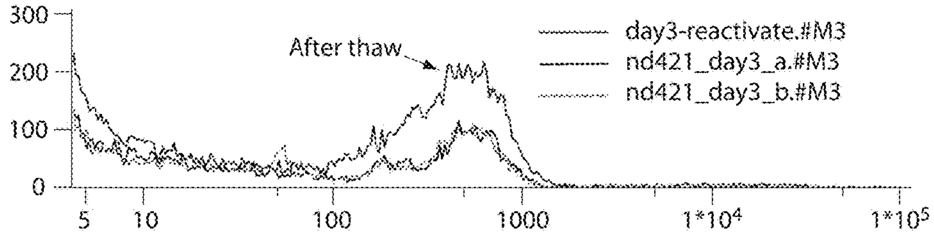
Fig. 27C

METHODS OF MAKING CHIMERIC ANTIGEN RECEPTOR-EXPRESSING CELLS

This application claims priority to U.S. Ser. No. 62/097,375 filed Dec. 29, 2014 and U.S. Ser. No. 62/133,137 filed Mar. 13, 2015, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 23, 2015, is named N2067-706710_SL.txt and is 243,586 bytes in size.

FIELD OF THE INVENTION

The present invention relates generally to methods of making immune effector cells (e.g., T cells, NK cells) engineered to express a Chimeric Antigen Receptor (CAR), and compositions comprising the same.

BACKGROUND OF THE INVENTION

Adoptive cell transfer (ACT) therapy with autologous T-cells, especially with T-cells transduced with Chimeric Antigen Receptors (CARs), has shown promise in several hematologic cancer trials.

SUMMARY OF THE INVENTION

The present disclosure pertains to methods of making immune effector cells (e.g., T cells, NK cells) that can be engineered to express a CAR, and compositions comprising the same.

Accordingly, in one aspect, the disclosure features a method of making a population of immune effector cells (e.g., T cells, NK cells) that can be engineered to express a CAR, the method comprising providing a population of immune effector cells (e.g., T cells), removing T regulatory cells, e.g., CD25+ T cells, from the population, to thereby provide a population of T regulatory-depleted cells, e.g., CD25+ depleted cells, that are suitable for expression of a CAR.

In one embodiment, the population of T regulatory-depleted cells contains less than 30%, 25%, 20%, 15%, 10%, 5%, 4%, 3%, 2%, 1% of CD25+ cells.

In one embodiment, the population of immune effector cells are cells of a subject having cancer, e.g., a subject having a CD25 expressing cancer such as, e.g., chronic lymphocytic leukemia (CLL). In one embodiment, the population of T regulatory-depleted cells contains less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of tumor cells.

In one embodiment, the population of immune effector cells are autologous to the subject who the cells will be administered to for treatment. In one embodiment, the population of immune effector cells are allogeneic to the subject who the cells will be administered to for treatment.

In one embodiment, the T regulatory cells, e.g., CD25+ T cells, are removed from the population using an anti-CD25 antibody, or fragment thereof, or a CD25-binding ligand, e.g. IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein. In one embodiment, the T regulatory cells, e.g., CD25+ T cells, are removed from the population using an anti-CD25 antibody molecule, or fragment thereof.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL.

In one embodiment, the population of T regulatory-depleted cells, e.g., CD25+ depleted cells, are suitable for expression of a CAR described herein, e.g., a CD19 CAR described herein. In one embodiment, the population of immune effector cells are obtained from a subject having a haematological cancer, e.g., a leukemia, e.g., chronic lymphocytic leukemia (CLL), acute lymphocytic leukemia (ALL), or a lymphoma, e.g., mantle cell lymphoma (MCL) or Hodgkin lymphoma (HL). In one embodiment, the population of T regulatory-depleted cells contains less than 30%, 25%, 20%, 15%, 10%, 5%, 4%, 3%, 2%, 1% of the leukemia cells, e.g., CLL cells, ALL cells, or lymphoma cells, e.g., MCL cells or HL cells. In one embodiment, the population of immune effector cells are obtained from a subject having CLL, and the population of T regulatory-depleted cells, e.g., CD25+ depleted cells, contains less than 30%, 25%, 20%, 15%, 10%, 5%, 4%, 3%, 2%, 1% of the leukemia cells, e.g., CLL cells and are suitable for expression of a CD19 CAR described herein. In one embodiment, the population of T regulatory-depleted cells contains less than 15%, 10%, 5%, 4%, 3%, 2%, 1% of CD25+ cells and less than 15%, 10%, 5%, 4%, 3%, 2%, 1% of tumor cells, e.g., CD25 expressing tumor cells, e.g., CLL cells. In one embodiment, the population of T regulatory-depleted cells contains less than 10%, 5%, 4%, 3%, 2%, 1% of CD25+ cells and less than 10%, 5%, 4%, 3%, 2%, 1% of tumor cells, e.g., CD25 expressing tumor cells, e.g., CLL cells.

In one embodiment, the population of immune effector cells are T cells isolated from peripheral blood lymphocytes. In an embodiment, the population of T cells are obtained by lysing the red blood cells and/or by depleting the monocytes. In an embodiment, the population of T cells is isolated from peripheral lymphocytes using, e.g., a method described herein.

In one embodiment, the population of immune effector cells can be obtained from a blood sample from a subject, e.g., obtained by apheresis. In one embodiment, the cells collected by apheresis are washed to remove the plasma fraction and, optionally, the cells are provided in an appropriate buffer or media for subsequent processing steps. In one embodiment, the cells are washed with a buffer such as, e.g., phosphate buffered saline (PBS). In an embodiment, the cells are washed in a wash solution that lacks one or more divalent cation such as calcium and magnesium, e.g., lacks both calcium and magnesium. In one embodiment, the cells are washed in a buffer that has substantially no divalent cations.

In one embodiment, the method further comprises removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

In one embodiment, the method further comprises removing cells from the population which express a check point inhibitor, e.g., a check point inhibitor described herein, e.g., one or more of (e.g., 2 or 3 of) PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. In embodiments, PD1+ cells and LAG3+ cells are removed; PD1+ cells and TIM3+ cells are removed; or LAG3+ and TIM3+ cells are removed. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

In one embodiment, the method further comprises removing cells from the population which express CD14, to thereby provide a population of T regulatory-depleted, e.g., CD25+ depleted cells, and CD14+ depleted cells. In one embodiment, CD14+ cells are removed simultaneously with the T regulatory, e.g., CD25+ cells. For example, an anti-CD25 antibody, or fragment thereof, and an anti-CD14 antibody, or fragment thereof, can be attached to the same bead which can be used to remove the cells; or an anti-CD25 antibody, or fragment thereof, and the anti-CD14 antibody, or fragment thereof, can be attached to separate beads, a mixture of which can be used to remove the cells. In other embodiments, the removal of T regulatory cells, e.g., CD25+ cells, and the removal of the CD14+ cells is sequential, and can occur, e.g., in either order. In one embodiment, the CD14+ cells are removed using a CD14 antibody molecule or fragment thereof.

In one embodiment, the population of immune effector cells provided have been selected based upon the expression of one or more markers (e.g., 2, 3, 4, 5, 6, 7, or more markers), e.g., CD3, CD28, CD4, CD8, CD27, CD127, CD45RA, and CD45RO, e.g., the provided population of immune effector cells (e.g., T cells) are CD3+ and/or CD28+.

In one embodiment, the method further comprises obtaining a population of immune effector cells, e.g., T cells, enriched for the expression of one or more markers (e.g., 2, 3, 4, 5, 6, 7, or more markers), e.g., CD3, CD28, CD4, CD8, CD27, CD127, CD45RA, and CD45RO. In an embodiment, population of immune effector cells are enriched for CD3+ and/or CD28+ cells. For example, T cells isolated by incubation with anti-CD3/anti-CD28 conjugated beads are obtained. In one embodiment, the method further comprises selecting cells from the population of T regulatory-depleted cells, e.g., CD25+ depleted cells, which express one or more markers (e.g., 2, 3, 4, 5, or more markers), e.g., CD3, CD28, CD4, CD8, CD45RA, and CD45RO.

In one embodiment, the method further comprises activating the population of T regulatory depleted cells, e.g., CD25+ depleted cells, e.g., by a method described herein.

In one embodiment, the method further comprises transducing a cell from the population of T regulatory-depleted cells, e.g., the population of CD25+ depleted cells, with a vector comprising a nucleic acid encoding a CAR, e.g., a CAR described herein, e.g., a CD19 CAR described herein. In one embodiment, the vector is selected from the group consisting of a DNA, a RNA, a plasmid, a lentivirus vector, adenoviral vector, or a retrovirus vector. In one embodiment, the cell from the population of T regulatory-depleted cells, e.g., the population of CD25+ depleted cells, is transduced with a vector once, e.g., within one day after population of immune effector cells are obtained from a blood sample from a subject, e.g., obtained by apheresis.

In one embodiment, the method further comprises generating a population of RNA-engineered cells transiently expressing exogenous RNA from the population of T regulatory-depleted cells, e.g., the population of CD25+ depleted cells. The method comprises introducing an in vitro transcribed RNA or synthetic RNA into a cell from the population, where the RNA comprises a nucleic acid encoding a CAR, e.g., a CAR described herein, e.g., a CD19 CAR described herein.

In one embodiment, cells transduced with a nucleic acid encoding a CAR, e.g., a CAR described herein, e.g., a CD19 CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 3 to 9 days. In one embodiment, the cells are expanded for a period of 4 to 9 days. In one embodiment, the cells are expanded for a period of 8 days or less, e.g., 7, 6, 5, 4, or 3 days. In one embodiment, the cells, e.g., a CD19 CAR cell described herein, are expanded in culture for 3 or 4 days, and the resulting cells are more potent than the same cells expanded in culture for 9 days under the same culture conditions. In one embodiment, the cells, e.g., a CD19 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 3 or 4 days show at least a one, two, three or four fold increase in cells doublings upon antigen stimulation as compared to the same cells expanded in culture for 9 days under the same culture conditions. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 3 or 4 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 3 or 4 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 3, 4, or 5 days show at least as high cytokine production in pg/ml, or at least a one, two, three, four, five, ten fold or more increase in pg/ml of cytokine production, e.g., IL2, IFN-gamma, GM-CSF, TNF-alpha, IL-1b, IL4, IL5, IL6, IL8, or IL10, levels, as compared to the same cells expanded in culture for 9 days under the same culture conditions.

In one embodiment, beads (e.g., CD3/28-stimulatory beads) are removed from the cells by mechanical disruption. In an embodiment, mechanical disruption comprises passage (e.g., repeat passage) cells through a pipette tip, e.g., a narrow bore pipette tip. In some embodiment, the cells are passed through one or more (e.g., 2, 3, 4, or 5 or more) tubes, e.g., narrow bore tubes. In one embodiment, the tubes are part of a closed cell culture system. In some embodiments, the interior diameter of the pipet tip or tubes is less than about 1 mm, 0.9 mm, 0.8 mm, 0.7 mm, 0.5 mm, 0.4 mm, 0.3 mm, or 0.2 mm, and optionally the diameter is greater than 0.1 mm, 0.2 mm, 0.3 mm, or 0.4 mm.

In one embodiment, the cells, e.g., CAR cells described herein, e.g., CD19 CAR cells described herein, expanded for 3, 4, or 5 days, have an increased proportion of Tem cells, Tcm cells, or both Tem and Tcm cells, compared to as compared to the same cells expanded in culture for 9 days under the same culture conditions. In one embodiment, the cells, e.g., CAR cells described herein, e.g., CD19 CAR cells described herein, expanded for 3, 4, or 5 days, have an increased proportion of Tem cells, Teff cells, or both Tem and Teff cells, compared to as compared to the same cells expanded in culture for 9 days under the same culture conditions. In one embodiment, a population of cells, e.g., CD19CAR cells described herein, expanded for 3, 4, or 5 days, has a percentage of Tnaive like cells (out of Tnaive like, Teff, and Tcm cells) of at least about 20%, 25%, 30%, 35%, 40%, 45%, or 50%, and optionally up to about 40% or 50%. In one embodiment, a population of cells, e.g., CD19CAR cells described herein, expanded for 3, 4, or 5 days, has a percentage of Tem cells (out of Tnaive like, Teff, and Tcm cells) of at least about 10%, 15%, or 20%, and optionally up to about 15% or 20%. In one embodiment, a population of cells, e.g., CD19CAR cells described herein, expanded for 3, 4, or 5 days, has a percentage of (Tnaive like+Tem) cells (out of Tnaive like, Teff, and Tcm cells) of at least about 20%, 25%, 30%, 35%, 40%, 45%, 50%, 55%, 60%, 65%, or 70%, and optionally up to about 50% or 70%.

In one embodiment, the cells, e.g., CD19 CAR cells described herein, expanded for 3, 4, or 5 days, when administered at a dose of $0.5\times10^6$ cells in the NALM6 assay of FIG. 31A have an activity greater than or equal to a dose of $1\times10^6$, $10.5\times10^6$, $2\times10^6$, $2.5\times10^6$, $3\times10^6$, $4\times10^6$, or $5\times10^6$ of the same cells expanded in culture for 9 days under the same culture conditions. In some embodiments activity is measured at 1, 2, 3, 4, 5, or 6 weeks.

In one embodiment, the cells are expanded by culturing the cells in the presence of an agent that stimulates a CD3/TCR complex associated signal and a ligand that stimulates a costimulatory molecule on the surface of the cells, e.g., as described herein. In one embodiment, the agent is a bead conjugated with anti-CD3 antibody, or a fragment thereof, and/or anti-CD28 antibody, or a fragment thereof.

In one embodiment, the cells are expanded in an appropriate media (e.g., media described herein) that may, optionally, contain one or more (e.g., 2, 3, 4, or 5 or more) factor for proliferation and/or viability, including serum (e.g., fetal bovine or human serum), interleukin-2 (IL-2), insulin, IFN-γ, IL-4, IL-7, GM-CSF, IL-10, IL-12, IL-15, IL-21, TGFβ, and TNF-α or any other additives for the growth of cells.

In one embodiment, the cells are expanded in an appropriate media (e.g., media described herein) that includes one or more (e.g., 2, 3, 4, or 5 or more) interleukins that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In one embodiment, the cells are cryopreserved after the appropriate expansion period. In one embodiment, the cells are cryopreserved according to a method described herein. In one embodiment, the expanded cells are cryopreserved in an appropriate media, e.g., an infusible media, e.g., as described herein.

In one embodiment, the method further comprises contacting the population of immune effector cells with a nucleic acid encoding a telomerase subunit, e.g., hTERT. In an embodiment, the nucleic acid is DNA or RNA.

In another aspect, the disclosure features a reaction mixture comprising a population of T regulatory-depleted cells containing less than 50%, 40%, 30%, 25%, 20%, 15%, 10%, 5%, 4%, 3%, 2%, 1% of CD25+ cells. In one embodiment, the reaction mixture comprises a population of T regulatory-depleted cells containing less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of CD25 expressing tumor cells, e.g., CLL cells. In one embodiment, the population of cells contains less than 15%, 10%, 5%, 4%, 3%, 2%, 1% of CD25+ cells and less than 15%, 10%, 5%, 4%, 3%, 2%, 1% of tumor cells, e.g., CD25 expressing tumor cells, e.g., CLL cells. In one embodiment, the population of cells contains less than 10%, 5%, 4%, 3%, 2%, 1% of CD25+ cells and less than 10%, 5%, 4%, 3%, 2%, 1% of tumor cells, e.g., CD25 expressing tumor cells, e.g., CLL cells.

In one embodiment, the reaction mixture comprises a population of T regulatory-depleted cells containing less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of a checkpoint inhibitor expressing cells, e.g., a PD1+ cells, LAG3+ cells, or TIM3+ cells. The reaction mixture may further comprise a buffer or other reagent, e.g., a PBS containing solution.

In one embodiment, the reaction mixture comprises a population of T regulatory-depleted cells containing less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of CD14+ cells. The reaction mixture may further comprise a buffer or other reagent, e.g., a PBS containing solution.

In one embodiment, the reaction mixture can further comprise an agent that activates and/or expands to cells of the population, e.g., an agent that stimulates a CD3/TCR complex associated signal and/or a ligand that stimulates a costimulatory molecule on the surface of the cells, e.g., as described herein. In one embodiment, the agent is a bead conjugated with anti-CD3 antibody, or a fragment thereof, and/or anti-CD28 antibody, or a fragment thereof.

In one embodiment, the reaction mixture further comprises one or more (e.g., 2, 3, 4, or 5) factor for proliferation and/or viability, including serum (e.g., fetal bovine or human serum), interleukin-2 (IL-2), insulin, IFN-γ, IL-4, IL-7, GM-CSF, IL-10, IL-12, IL-15, IL-21, TGFβ, and TNF-α or any other additives for the growth of cells. In one embodiment, the reaction mixture further comprises IL-15 and/or IL-7.

In one embodiment, a plurality of the cells of the population in the reaction mixture comprise a nucleic acid molecule, e.g., a nucleic acid molecule described herein, that comprises a CAR encoding sequence, e.g., a CD19 CAR encoding sequence, e.g., as described herein.

In one embodiment, a plurality of the cells of the population in the reaction mixture comprise a vector comprising a nucleic acid sequence encoding a CAR, e.g., a CAR described herein, e.g., a CD19 CAR described herein. In one embodiment, the vector is a vector described herein, e.g., a vector selected from the group consisting of a DNA, a RNA, a plasmid, a lentivirus vector, adenoviral vector, or a retrovirus vector.

In one embodiment, the reaction mixture further comprises a cryoprotectant or stabilizer such as, e.g., a saccharide, an oligosaccharide, a polysaccharide and a polyol (e.g., trehalose, mannitol, sorbitol, lactose, sucrose, glucose and dextran), salts and crown ethers. In one embodiment, the cryoprotectant is dextran.

In another aspect, the disclosure features a method of making a population of immune effector cells (e.g., T cells, NK cells) engineered to express a CAR, the method comprising providing a population of immune effector cells (e.g., T cells), wherein a plurality of the immune effector cells comprise a nucleic acid encoding a CAR, e.g., a CAR described herein, e.g., a CD19 CAR described herein, and expanding the cells of the population in the presence of one or more (e.g., 2, 3, 4, or 5) interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells of the population are expanded in the presence of IL-15 and/or IL-7, e.g., IL-15 and IL-7.

In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of less than 8 days, e.g., 7, 6 or 5 days. In one embodiment, the cells are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In one embodiment, the cells are expanded by culturing the cells in the presence of an agent that stimulates a CD3/TCR complex associated signal and a ligand that stimulates a costimulatory molecule on the surface of the cells, e.g., as described herein. In one embodiment, the agent is a bead conjugated with anti-CD3 antibody, or a fragment thereof, and/or anti-CD28 antibody, or a fragment thereof.

In one embodiment, the provided population of immune effector cells is a population of T regulatory-depleted cells containing less than 50%, 40%, 30%, 25%, 20%, 15%, 10%, 5%, 4%, 3%, 2%, 1% of CD25+ cells. In one embodiment, the provided population of immune effector cells is a population of T regulatory-depleted cells containing less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of CD25 expressing tumor cells, e.g., CLL cells. In one embodiment, the provided population of cells contains less than 15%, 10%, 5%, 4%, 3%, 2%, 1% of CD25+ cells and less than 15%, 10%, 5%, 4%, 3%, 2%, 1% of tumor cells, e.g., CD25 expressing tumor cells, e.g., CLL cells. In one embodiment, the provided population of cells contains less than 10%, 5%, 4%, 3%, 2%, 1% of CD25+ cells and less than 10%, 5%, 4%, 3%, 2%, 1% of tumor cells, e.g., CD25 expressing tumor cells, e.g., CLL cells.

In one embodiment, the provided population of immune effector cells is a population of T regulatory-depleted cells containing less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of a checkpoint inhibitor expressing cells, e.g., a PD1+ cells, LAG3+ cells, or TIM3+ cells.

In one embodiment, the provided population of immune effector cells is a population of T regulatory-depleted cells containing less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of CD14+ cells.

In one embodiment, the method further comprises, prior to expansion, removing T regulatory cells, e.g., CD25+ T cells, from the population, to thereby provide a population of T regulatory-depleted cells, e.g., CD25+ depleted cells to be expanded. In one embodiment, the T regulatory cells, e.g., CD25+ cells, are removed by a method described herein.

In one embodiment, the method further comprises, prior to expansion, removing T regulatory cells, e.g., CD14+ cells, from the population, to thereby provide a population of CD14+ depleted cells to be expanded. In one embodiment, the T regulatory cells, e.g., CD14+ cells, are removed by a method described herein.

In one embodiment, the method further comprises contacting the population of immune effector cells with a nucleic acid encoding a telomerase subunit, e.g., hTERT. In an embodiment, the nucleic acid is DNA or RNA.

In another aspect, the disclosure features a reaction mixture comprising a population of immune effector cells wherein a plurality of the cells of the population in the reaction mixture comprise a nucleic acid molecule, e.g., a nucleic acid molecule described herein, that comprises a CAR encoding sequence, e.g., a CD19 CAR encoding sequence, e.g., as described herein, and IL-7 and/or IL-15.

In one embodiment, a plurality of the cells of the population in the reaction mixture comprise a vector comprising a nucleic acid sequence encoding a CAR, e.g., a CAR described herein, e.g., a CD19 CAR described herein. In one embodiment, the vector is a vector described herein, e.g., a vector selected from the group consisting of a DNA, a RNA, a plasmid, a lentivirus vector, adenoviral vector, or a retrovirus vector.

In one embodiment, the reaction mixture can further comprise an agent that activates and/or expands to cells of the population, e.g., an agent that stimulates a CD3/TCR complex associated signal and/or a ligand that stimulates a costimulatory molecule on the surface of the cells, e.g., as described herein. In one embodiment, the agent is a bead conjugated with anti-CD3 antibody, or a fragment thereof, and/or anti-CD28 antibody, or a fragment thereof.

In another aspect, the disclosure features a method of making a population of immune effector cells (e.g., T cells, NK cells) engineered to express a CAR, the method comprising providing a population of immune effector cells (e.g., T cells), wherein a plurality of the immune effector cells comprise a nucleic acid encoding a CAR, e.g., a CAR described herein, e.g., a CD19 CAR described herein, and expanding the cells of the population in culture for 5 days, wherein the resulting cells are more potent, as measured by cell proliferation levels upon antigen stimulation, as compared to the same cells expanded in culture for 9 days under the same culture conditions.

In one embodiment, the cells expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In another aspect, the disclosure features methods comprising administering to a subject a population of immune effector cells made by a method described herein and engineered to express a CAR, e.g. a CAR described herein, e.g., a CD19 CAR described herein.

In one embodiment, method provides an anti-tumor immunity in a subject having cancer, e.g., a hematological cancer such as, e.g., CLL. In one embodiment, the method is a method of treating a subject having cancer, e.g., a hematological cancer described herein, such as, e.g., a leukemia (e.g., CLL, ALL) or a lymphoma (e.g., MCL, HL). In one embodiment, the population of cells are autologous to the subject administered the population. In one embodiment, the population of cells is allogeneic to the subject administered the population. In one embodiment, the subject is a human.

In one embodiment, the disease associated with a tumor antigen, e.g., a tumor antigen described herein, e.g., CD19, is selected from a proliferative disease such as a cancer or malignancy or a precancerous condition such as a myelodysplasia, a myelodysplastic syndrome or a preleukemia, or is a non-cancer related indication associated with expression of a tumor antigen described herein. In one embodiment, the disease is a cancer described herein, e.g., a cancer described herein as being associated with a target described herein. In one embodiment, the hematologic cancer is leukemia. In one embodiment, the cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with expression of a tumor antigen described herein include, but not limited to, atypical and/or non-classical cancers, malignancies, precancerous conditions or proliferative diseases expressing a tumor antigen as described herein; and any combination thereof. In another embodiment, the disease associated with a tumor antigen described herein is a solid tumor, e.g., a solid tumor described herein, e.g., prostatic, colorectal, pancreatic, cervical, gastric, ovarian, head, or lung cancer.

In one embodiment, the population of immune effector cells transduced with a nucleic acid encoding a CAR, e.g., a CAR described herein, e.g., a CD19 CAR described herein, are expanded, e.g., by a method described herein. In one embodiment, the cells are expanded for a period of 8 days or less, e.g., 7, 6, 5, 4, or 3 days. In one embodiment, the cells, e.g., a CD19 CAR cell described herein, are expanded in culture for 5 days, and the resulting cells are more potent than the same cells expanded in culture for 9 days under the same culture conditions, e.g., as described herein. In one embodiment, the subject is administered $10^4$ to $10^6$ immune effector cells per kg body weight of the subject. In one embodiment, the subject receives an initial administration of a population of immune effector cells (e.g., an initial administration of $10^4$ to $10^6$ immune effector cells per kg body weight of the subject, e.g., $10^4$ to $10^5$ immune effector cells per kg body weight of the subject), a plurality of which comprise the nucleic acid encoding a CAR, e.g., a CAR described herein, e.g., a CD19 CAR described herein, and one or more (e.g., 2, 3, 4, or 5) subsequent administrations of a population of immune effector cells (e.g., one or more subsequent administration of $10^4$ to $10^6$ immune effector cells per kg body weight of the subject, e.g., $10^4$ to $10^5$ immune effector cells per kg body weight of the subject), a plurality of which comprise a nucleic acid encoding a CAR, e.g., a CAR described herein, e.g., a CD19 CAR described herein. In one embodiment, the one or more subsequent administrations are administered less than 15 days, e.g., 14, 13, 12, 11, 10, 9, 8, 7, 6, 5, 4, 3, or 2 days after the previous administration, e.g., less than 4, 3, 2 days after the previous administration. In one embodiment, the subject receives a total of about $10^6$ immune effector cells per kg body weight of the subject over the course of at least three administrations of a population of immune effector cells, e.g., the subject receives an initial dose of $1\times10^5$ immune effector cells, a second administration of $3\times10^5$ immune effector cells, and a third administration of $6\times10^5$ immune effector cells, and, e.g., each administration is administered less than 4, 3, 2 days after the previous administration.

In one aspect, the disclosure features a population of autologous immune effector cells, a plurality of which are transfected or transduced with a vector comprising a nucleic acid molecule encoding a CAR, e.g., a CAR described herein, e.g., a CD19 CAR described herein, wherein the population of cells contains less than 50%, 40%, 30%, 25%, 20%, 15%, 10%, 5%, 4%, 3%, 2%, 1% of CD25+ cells and less than 50%, 40%, 30%, 25%, 20%, 15%, 10%, 5%, 4%, 3%, 2%, 1% of tumor cells, e.g., CLL cells. In one embodiment, the population of cells contains less than 15%, 10%, 5%, 4%, 3%, 2%, 1% of CD25+ cells and less than 15%, 10%, 5%, 4%, 3%, 2%, 1% of tumor cells, e.g., CD25 expressing tumor cells, e.g., CLL cells. In one embodiment, the population of cells contains less than 10%, 5%, 4%, 3%, 2%, 1% of CD25+ cells and less than 10%, 5%, 4%, 3%, 2%, 1% of tumor cells, e.g., CD25 expressing tumor cells, e.g., CLL cells.

In another aspect, the disclosure features a method of making a population of immune effector cells (e.g., T cells, NK cells). In an embodiment, the method comprises: providing a population of immune effector cells (e.g., T cells or NK cells), and contacting the population of immune effector cells with a nucleic acid encoding a CAR, and a nucleic acid encoding a telomerase subunit, e.g., hTERT, under conditions that allow for CAR and telomerase expression.

In an embodiment, the nucleic acid encoding the telomerase subunit is RNA. In another embodiment, the nucleic acid encoding the telomerase subunit is DNA. In an embodiment, the nucleic acid encoding the telomerase subunit comprises a promoter capable of driving expression of the telomerase subunit.

In a related aspect, the disclosure features a method of making a population of immune effector cells (e.g., T cells, NK cells) the method comprising: providing a population of immune effector cells (e.g., T cells), contacting the population of immune effector cells with a nucleic acid encoding a CAR and an RNA encoding a telomerase subunit, e.g., hTERT, under conditions that allow for CAR and telomerase expression.

In an embodiment, the nucleic acid encoding the CAR and the RNA encoding the telomerase subunit are part of the same nucleic acid molecule. In an embodiment the nucleic acid encoding the CAR and the RNA encoding the telomerase subunit are part of separate nucleic acid molecules.

In an embodiment, the method comprises contacting the population of immune effector cells with a nucleic acid encoding the CAR and the RNA encoding the telomerase subunit at substantially the same time. In an embodiment, the method comprises contacting the population of immune effector cells with a nucleic acid encoding the CAR before contacting the population of immune effector cells with the RNA encoding the telomerase subunit. In an embodiment, the method comprises contacting the population of immune effector cells with a nucleic acid encoding the CAR after contacting the population of immune effector cells with the RNA encoding the telomerase subunit.

In an embodiment, the RNA encoding the telomerase subunit is mRNA. In an embodiment, the RNA encoding the telomerase subunit comprises a poly(A) tail. In an embodiment, the RNA encoding the telomerase subunit comprises a 5' cap structure.

In an embodiment, the method comprises transfecting the immune effector cells with the RNA encoding the telomerase subunit. In an embodiment, the method comprises transducing the immune effector cells with the RNA encoding the telomerase subunit. In an embodiment, the method comprises electroporating the immune effector cells with the RNA encoding the telomerase subunit, under conditions that allow for CAR and telomerase expression.

In another aspect, the disclosure features a method of making a population of immune effector cells (e.g., T cells, NK cells) comprising: providing a population of immune effector cells (e.g., T cells or NK cells) that express a CAR and/or comprise a nucleic acid encoding a CAR; and contacting the population of immune effector cells with a nucleic acid encoding a telomerase subunit, e.g., hTERT, under conditions that allow for hTERT expression.

In another aspect, the disclosure features a method of making a population of immune effector cells (e.g., T cells, NK cells), comprising: providing a population of immune effector cells (e.g., T cells or NK cells) that express a nucleic acid encoding a telomerase subunit, e.g., hTERT, and contacting the population of immune effector cells with a nucleic acid encoding a CAR, under conditions that allow for CAR expression.

In one aspect, this disclosure provides an immune effector cell (e.g., T cell or NK cell) comprising: a nucleic acid encoding a CAR, e.g., a CAR as described herein; and a nucleic acid encoding an exogenous telomerase subunit, e.g., hTERT. In an embodiment, the nucleic acid encoding an exogenous telomerase subunit is RNA, e.g., mRNA.

In one aspect, this disclosure provides an immune effector cell (e.g., T cell or NK cell) comprising: a CAR, e.g., a CAR as described herein; and an exogenous telomerase subunit, e.g., hTERT. In an embodiment, the cell does not comprise DNA, e.g., exogenous DNA, e.g., a vector, encoding the exogenous telomerase subunit. For instance, the cell may have been contacted with mRNA encoding the exogenous telomerase subunit.

Although methods and materials similar or equivalent to those described herein can be used in the practice or testing of the present invention, suitable methods and materials are described below. All publications, patent applications, patents, and other references (e.g., sequence database reference numbers) mentioned herein are incorporated by reference in their entirety. For example, all GenBank, Unigene, and Entrez sequences referred to herein, e.g., in any Table herein, are incorporated by reference. Unless otherwise specified, the sequence accession numbers specified herein, including in any Table herein, refer to the database entries current as of Dec. 29, 2014. When one gene or protein references a plurality of sequence accession numbers, all of the sequence variants are encompassed.

In addition, the materials, methods, and examples are illustrative only and not intended to be limiting. Headings, sub-headings or numbered or lettered elements, e.g., (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE FIGURES

FIG. 1A is a schematic diagram of C4-27z CAR vector. FIG. 1B is two representative FACS histogram plots of CAR expression on CD4+ and CD8+ T cells 48 hours after lentiviral transduction. FIG. 1C is a graph showing the overall accumulation of CAR-T cells in response to various cytokines exposure. T cells were transduced and exposed to various exogenous cytokines with final concentrations of 10 ng/mL from the next day (day 0). The numbers of CAR-T cells were calculated based on the number of T cells and the percentages of CAR expression. The curves are representative of 6 donors. *P<0.05, *P<0.001. NC, no cytokine. FIG. 1**D is a graph showing CAR expression by T cells 15 days after lentiviral transduction. The bar graph depicts CAR expression levels (±SEM, n=6) on the surface of CD3+, CD4+ and CD8+ T cells, with the expression of CAR in NC group normalized as 1. *P<0.05 versus IL-2 group; N.S., no statistical difference. FIG. 1E is a histogram showing the proliferation of T cells in response to various cytokines. On day 7 after lentivirus transduction, T cells in NC group were labeled with CFSE (2.5 μM), and then exposed to various cytokines. Seven days later, T cells were analyzed for CFSE dilution by flow cytometry. FIG. 1F is a graph showing the viability of T cells 15 days after lentiviral transduction. T cells from various cytokine groups are stained with Annexin V and 7-AAD, and then analyzed for the proportions of viable cells (both Annexin V and 7-AAD negative). *P<0.05, P<0.01 versus IL-2 group (n=6). FIGS. 1G and 1H show Bcl-xL expression by CAR-T cells. On day 15 days after lentiviral transduction, CAR-T cells are assessed for expression of Bcl-2 protein by flow cytometry. FIG. 1G is a representative FACS histogram plot of Bcl-xL expression in various cytokine groups. FIG. 1**H is a graph depicting Bcl-xL expression (±SEM) in CD4+ and CD8+ CAR-T cells of 6 donors. *P<0.01 versus IL-2 group.

FIG. 2A are representative FACS plots showing the gating strategy of T cell subsets analysis. The T cells are split into four subsets based on CD45RA and CD62L expression, then the expression of CCR7, CD27, CD28 and CD95 are further evaluated for every subset. The CD95 expression is significantly upregulated upon lentiviral transduction. FIG. 2B shows CD95 expression in CD45RA+CD62L+ subpopulation of T cells before transduction and CAR-T cells 15 days after transduction. FIGS. 2C and 2D are graphs showing the increase of memory stem T cell (Tscm) proportions in CD4+(FIG. 2C) and CD8+ T cells (FIG. 2D) after lentiviral transduction. Tscm are defined as CD45RA+ CD62L+CD95+CCR7+ T cell subsets. FIG. 2E is a graph showing the correlation between the amount of naïve T (Tn, defined as CD45RA+CD62L+CD95− subpopulation) in T cells pre-transduction and the proportion of Tscm in CAR-T cells after transduction (n=6). Left bars represents the percentages of Tn in CD4+ and CD8+ T cells before transduction and right bars represents the percentages of Tscm in CD4+ and CD8+ CAR-T cells. *P<0.05, P<0.01. FIGS. 2F, 2G, and 2**H are graphs showing the distribution of subsets of CD4+ and CD8+ CAR-T cells. The T subsets in CD4+ and CD8+ CAR-T cells are defined based on the CD95, CD45RA and CD62L expression. The proportions of Tscm are compared among various cytokine groups, *P<0.05, P<0.01, versus IL-2 group (n=6). (F) Self-renew and differentiation of different subsets of CAR-T cells. FACS-sorted CAR+Tscm, Tcm, Tem and Temra cells are cultured exposed to IL-2 (10 ng/mL) for 3 days, then analyzed the phenotypes based on CD45RA and CD62L expression (n=3). FIG. 2**I is a histogram plot showing the proliferation of various subsets of CAR-T cells in response to IL-2. FACS-sorted CAR+Tscm, Tcm, Tem and Temra cells were labeled with CFSE (2.5 μM), and then cultured exposed to IL-2 (10 ng/mL) for 3 days. Three days later, T cells were analyzed for CFSE dilution.

FIG. 3A demonstrates that CD45 RAexpression is inversely correlated with CFSE intensity. FIG. 3B shows that for all cytokine groups (IL-2, IL-7, IL-15, IL-18 and IL-21), CD45RA+ T cells exhibited much lower CFSE levels than CD45RA dim and negative T cells indicating that CD45RA+ T cells had stronger proliferation activity than CD45RA− T cells.

FIG. 4A is representative FACS dot-plots showing the expression of CD45RA, CD62L, CCR7, CD27 and CD28 on CAR- and CAR+ T cells exposed to IL-2 for 14 days after lentiviral transduction. FIG. 4B is a series of graphs showing the quantitation of CD45RA, CD62L, CCR7, CD27, CD28 and IL7Ra expression on the surface of CAR-T cells in indicated cytokine groups. The histograms represent mean value±SEM of expression levels from 6 independent donors. *P<0.05, **P<0.01 versus IL-2 group.

FIG. 5A is representative FACS plots show the staining of intracellular IFN-γ, TNF-α and IL-2 in CAR-T cells. FIGS. 5B, 5C, and 5D are quantitative plots showing the percentages of cytokine-producing CAR-T cells in various cytokine groups (n=6) for production of IFNγ (FIG. 5B), TNF-α (FIG. 5C) and IL-2 (FIG. 5D). Lentiviral transduced T cells are exposed to indicated cytokines for 14 days, and then co-cultured with SKOV3 cells for 5 hours before harvested for flow cytometry analysis. FIG. 5E is a series of pie charts depicting the proportion of cells producing different numbers of cytokines (IFN-γ, TNF-α and IL-2) after SKOV3 stimulation. *P<0.05. FIG. 5F are representative FACS plots showing the expression of perforin and granzyme B (GranzB) in CAR-T cells. FIGS. 5G and 5H are quantitative plots showing the percentages of perforin (FIG. 5G) and Granzyme B expression (FIG. 5H) in CAR-T cells in various cytokine groups (n=6). Lentiviral transduced T cells are exposed to indicated cytokines for 14 days, and then co-cultured with SKOV3 cells for 5 hours before harvested for flow cytometry analysis. FIG. 5I is a graph showing the antigen specific cytotoxic activity of CAR-T cells. Fourteen days after indicated cytokine exposure, the CAR-T cells were assessed for cytolytic ability by using a luciferase-based assay after 18-hour coculture with SKOV3 at the indicated E/T ratios. Untransduced T cells (UNT) served as negative effector controls. Data shown are mean value±SEM of six independent cytolytic assays.

FIGS. 6A and 6B show that CD62L+CAR-T cells (Tscm and Tcm) exhibited less cytokine production activity (FIGS. 6A and 6B) and weaker cytolytic capacity (FIG. 6C) when compared with CD62L− CAR-T cells (Tem and Temra).

FIG. 7A is two graphs showing the overall accumulation and viability of CAR-T cells in the exposure to antigen and indicated cytokines. The T cells exposed to IL-2 are harvested on day 15, and then co-cultured with SKOV3 at E/T ratios of 5:1 and indicated cytokines (10 ng/mL) for 7 days, with the supplement of SKOV3 cells on the first and fourth day (The same protocol in FIGS. 7C, 7D, and 7E). The expansion folds are mean value±SEM. T cells are stained with Annexin V and 7-AAD, and then analyzed for the proportions of viable cells at the same day. *$P<0.05$ versus IL-2 group. FIG. 7B depicts two graphs showing the overall accumulation and viability of CAR-T previously exposed to indicated cytokines upon antigen challenge. The T cells exposed to indicated cytokines are harvested on day 15, and then co-cultured with SKOV3 at E/T ratios of 5:1 for 7 days. The expansions of CAR-T cells are calculated and the viability of T cells are evaluated on the seventh day. FIG. 7C is a graph showing CAR expression by T cells after 7-day's coculture with SKOV3 and indicated cytokines. *$P<0.05$ versus IL-2. FIG. 7D is two graphs showing the quantitation of CD27 and CD28 expression on CAR-T cells after 7-day's coculture with SKOV3 and indicated cytokines. *$P<0.05$ versus IL-2. FIG. 7E is two graphs showing the distribution of memory T subsets of CD4+ and CD8+ CAR-T cells in various cytokine groups. N.S., no statistical difference.

FIG. 8A is an in vivo experiment scheme. FIG. 8B Tumor growth curves of mice treated with various cytokine exposed C4-27z CAR-T cells, anti-CD19-27z CAR-T cells and untransduced T cells. The data are presented as mean value±SEM. The arrow indicates the time of T cell infusion. FIG. 8C is bioluminescence images show fLuc+SKOV3 tumors in NSG mice immediately before (day 38), two weeks (day53) and five weeks (day 74) after first intravenous injection of CAR-T cells. FIG. 8D is a graph showing the quantitation of circulating human CD4+ and CD8+ T cell counts in mice peripheral blood 15 days after the first dose of CAR-T cell infusion. FIG. 8E is a graph showing the quantitation of CAR expression on circulating human CD4+ and CD8+ T cells in mice blood. FIG. 8F is a graph showing the distribution of T-cell subsets of circulating human T cells in mice blood based on CD45RA and CD62L staining. FIG. 8G is a graph showing the quantitation of CD27 and CD28 expression on circulating human CD4+ and CD8+ T cells in mice blood.

FIG. 9A is a series of FACs plots showing the distribution of CD45, CD3, and CD25 expression in cells from apheresis of a CLL patient. FIG. 9B is a series of FACS plots (top) showing the CD3 and CD19 populations and histograms (bottom) showing CD14 expression of cells from apheresis, cells selected with anti-CD3/CD28, cells depleted for CD25, and the CD25 enriched cells.

FIG. 11A is a graph showing the total cell number at the indicated days in culture. FIG. 11B is a graph showing the quantified population doublings at each indicated day in culture. FIG. 11C shows the percentage of viable cells at the indicated days in culture.

FIG. 12A is a series of FACS plots showing the efficiency of CD25 depletion. FIG. 12B is a series of FACS plots showing the CAR19 expression of untransduced cells, CD3 selected cells, and the CD25 depleted cells.

FIGS. 27A-27D indicate that bead removal at early timepoints does not induce cell loss. FIG. 27A is a Coulter analysis illustrating mean T cell volume and concentration before and after removing αCD3/αCD28 coated magnetic beads via magnet on day 3. Cells were then frozen after bead removal. FIG. 27B shows that cell number was evaluated before and after removal of magnetic beads. The concentration was similar. FIG. 27C is an overlay showing the mean cell volume of same cells before and after thaw. Cells retain their volume during the freeze thaw process. Results are representative of at least 15 different experiments. FIG. 27D shows a representative Coulter analysis of T cell products before and after αCD3/αCD28 coated magnetic bead removal demonstrating the efficiency of process.

FIG. 28A, upper panel, four-hour killing assay using K562-WT cells. FIG. 28B, lower panel, four-hour killing assay using K562-19 cells. FIG. 28B upper panels, transduction efficiency using IL7/IL15 (left) or IL2 (right). FIG. 28B center panel, population doublings using IL7/IL15 compared to IL2. FIG. 28B lower panel, volume using IL7/IL15 compared to IL2.

FIG. 29C shows representative cytokine production in CART 19 T cells 24 h after thaw. The cytokine levels are minimal.

FIG. 31A shows the experimental setup for testing the potency of CART cells produced under different conditions. FIG. 31B shows the potency of IL2-treated CART cells in slowing Nalm6 tumor growth in mice. D3, D5, and D9 indicate CART cells that were harvested on day 3, day 5, or day 9. 3e6 and 0.5e6 indicate the number of CAR+ cells administered. Proportions of CAR+ cells are shown in FIG. 31C. FIG. 31D compares the potency of IL2-treated and IL7/IL15-treated CART cells in slowing Nalm6 tumor growth in mice.

DETAILED DESCRIPTION

Definitions

Figure 1A:
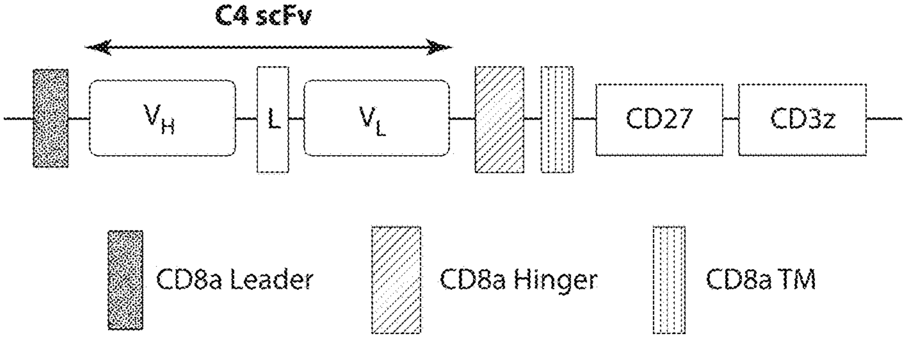
FIGS. 1A-1H show the differential effects of $\gamma_c$ cytokines and IL-18 on CAR-T cell accumulation.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some embodiments, the set of polypeptides are in the same polypeptide chain (e.g., comprise a chimeric fusion protein). In some embodiments, the set of polypeptides are not contiguous with each other, e.g., are in different polypeptide chains. In some embodiments, the set of polypeptides include a dimerization switch that, upon the presence of a dimerization molecule, can couple the polypeptides to one another, e.g., can couple an antigen binding domain to an intracellular signaling domain. In one embodiment, the stimulatory molecule of the CAR is the zeta chain associated with the T cell receptor complex. In one aspect, the cytoplasmic signaling domain comprises a primary signaling domain (e.g., a primary signaling domain of CD3-zeta). In one embodiment, the cytoplasmic signaling domain further comprises one or more functional signaling domains of at least one costimulatory molecule as defined below. In one embodiment, the costimulatory molecule is a costimulatory molecule described herein, e.g., 4-1BB (i.e., CD137), CD27, ICOS, and/or CD28. In one embodiment, the CAR comprises a chimeric fusion protein comprising an extracellular antigen binding domain, a transmembrane domain and an intracellular signaling domain comprising a functional signaling domain of a stimulatory molecule. In one embodiment, the CAR comprises a chimeric fusion protein comprising an extracellular antigen binding domain, a transmembrane domain and an intracellular signaling domain comprising a functional signaling domain of a co-stimulatory molecule and a functional signaling domain of a stimulatory molecule. In one embodiment, the CAR comprises a chimeric fusion protein comprising an extracellular antigen binding domain, a transmembrane domain and an intracellular signaling domain comprising two functional signaling domains of one or more co-stimulatory molecule(s) and a functional signaling domain of a stimulatory molecule. In one embodiment, the CAR comprises a chimeric fusion protein comprising an extracellular antigen binding domain, a transmembrane domain and an intracellular signaling domain comprising at least two functional signaling domains of one or more co-stimulatory molecule(s) and a functional signaling domain of a stimulatory molecule. In one embodiment, the CAR comprises an optional leader sequence at the amino-terminus (N-terminus) of the CAR fusion protein. In one embodiment, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

A CAR that comprises an antigen binding domain (e.g., a scFv, or TCR) that targets a specific tumor antigen X, such as those described herein, is also referred to as XCAR. For example, a CAR that comprises an antigen binding domain that targets CD19 is referred to as CD19CAR.

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', $F(ab')_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of a CAR comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one embodiment, the antigen binding domain of a CAR comprises an antibody fragment. In a further embodiment, the CAR comprises an antibody fragment that comprises a scFv.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to any material derived from an animal of a different species.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connote or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connote or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of a tumor antigen as described herein" includes, but is not limited to, a disease associated with expression of a tumor antigen as described herein or condition associated with cells which express a tumor antigen as described herein including, e.g., proliferative diseases such as a cancer or malignancy or a precancerous condition such as a myelodysplasia, a myelodysplastic syndrome or a preleukemia; or a noncancer related indication associated with cells which express a tumor antigen as described herein. In one embodiment, a cancer associated with expression of a tumor antigen as described herein is a hematological cancer. In one embodiment, a cancer associated with expression of a tumor antigen as described herein is a solid cancer. Further diseases associated with expression of a tumor antigen as described herein include, but not limited to, e.g., atypical and/or non-classical cancers, malignancies, precancerous conditions or proliferative diseases associated with expression of a tumor antigen as described herein. Non-cancer related indications associated with expression of a tumor antigen as described herein include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

The phrase "disease associated with expression of CD19" includes, but is not limited to, a disease associated with expression of CD19 or condition associated with cells which express CD19 including, e.g., proliferative diseases such as a cancer or malignancy or a precancerous condition such as a myelodysplasia, a myelodysplastic syndrome or a preleukemia; or a noncancer related indication associated with cells which express CD19. In one aspect, a cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., acute myeloid leukemia (AML), B-cell acute Lymphoid Leukemia (BALL), T-cell acute Lymphoid Leukemia (TALL), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma (MCL), Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, myeloproliferative neoplasm; a histiocytic disorder (e.g., a mast cell disorder or a blastic plasmacytoid dendritic cell neoplasm); a mast cell disorder, e.g., systemic mastocytosis or mast cell leukemia; B-cell prolymphocytic leukemia, plasma cell myeloma, and "preleukemia" which are a diverse collection of hematological conditions united by ineffective production (or dysplasia) of myeloid blood cells, and the like. Further diseases associated with expression of CD19 expression include, but not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus), inflammatory disorders (allergy and asthma) and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein. In other embodiments, the disease is a CD19-negative cancer, e.g., a CD19-negative relapsed cancer. In some embodiments, the tumor antigen (e.g., CD19)-expressing cell expresses, or at any time expressed, mRNA encoding the tumor antigen. In an embodiment, the tumor antigen (e.g., CD19)-expressing cell produces the tumor antigen protein (e.g., wild-type or mutant), and the tumor antigen protein may be present at normal levels or reduced levels. In an embodiment, the tumor antigen (e.g., CD19)-expressing cell produced detectable levels of a tumor antigen protein at one point, and subsequently produced substantially no detectable tumor antigen protein.

The phrase "disease associated with expression of a B-cell antigen" includes, but is not limited to, a disease associated with expression of one or more of CD19, CD20, CD22 or ROR1, or a condition associated with cells which express, or at any time expressed, one or more of CD19, CD20, CD22 or ROR1, including, e.g., proliferative diseases such as a cancer or malignancy or a precancerous condition such as a myelodysplasia, a myelodysplastic syndrome or a preleukemia; or a noncancer related indication associated with cells which express one or more of CD19, CD20, CD22 or ROR1. For the avoidance of doubt, a disease associated with expression of the B-cell antigen may include a condition associated with cells which do not presently express the B-cell antigen, e.g., because the antigen expression has been downregulated, e.g., due to treatment with a molecule targeting the B-cell antigen, e.g., a B-cell targeting CAR, but which at one time expressed the antigen. The phrase "disease associated with expression of a B-cell antigen" includes a disease associated with expression of CD19, as described herein. In embodiments, the CAR-expressing cells are used to treat a disease associated with a B-cell antigen. In embodiments, a CAR produced by a method herein comprises an antigen binding domain that targets a B-cell antigen.

The term "relapse" as used herein refers to reappearance of a disease (e.g., cancer) after an initial period of responsiveness, e.g., after prior treatment with a therapy, e.g., cancer therapy (e.g., complete response or partial response). The initial period of responsiveness may involve the level of cancer cells falling below a certain threshold, e.g., below 20%, 15%, 10%, 5%, 4%, 3%, 2%, or 1%. The reappearance may involve the level of cancer cells rising above a certain threshold, e.g., above 20%, 15%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR described herein can be replaced with other amino acid residues from the same side chain family and the altered CAR can be tested using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:9 (mutant CD3 zeta), or the equivalent residues from a non-human species, e.g., mouse, rodent, monkey, ape and the like. In a specific CAR of the invention, the primary signaling sequence of CD3-zeta is the sequence as provided in SEQ ID NO:10 (wild-type human CD3 zeta), or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain can generate a signal that promotes an immune effector function of the CAR containing cell, e.g., a CART cell. Examples of immune effector function, e.g., in a CART cell, include cytolytic activity and helper activity, including the secretion of cytokines. In embodiments, the intracellular signaling domain is the portion of a protein which transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 ("ICOS"), FcεRI, and CD66d, CD32, DAP10, and DAP12.

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:9. In one aspect, the "zeta stimulatory domain" or a "CD3-zeta stimulatory domain" is the sequence provided as SEQ ID NO:10.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to MHC class I molecule, TNF receptor proteins, Immunoglobulin-like proteins, cytokine receptors, integrins, signalling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain refers to an intracellular portion of a costimulatory molecule. The intracellular signaling domain can comprise the entire intracellular portion, or the entire native intracellular signaling domain, of the molecule from which it is derived, or a functional fragment thereof.

The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:7 or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron (s).

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acid (DNA) or ribonucleic acid (RNA), or a combination of a DNA or RNA thereof, and polymers thereof in either single- or double-stranded form. The term "nucleic acid" includes a gene, cDNA or an mRNA. In one embodiment, the nucleic acid molecule is synthetic (e.g., chemically synthesized) or recombinant. Unless specifically limited, the term encompasses nucleic acids containing analogues or derivatives of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically protein, carbohydrate or lipid) that is preferentially expressed on the surface of a cancer cell, either entirely or as a fragment (e.g., MHC/peptide), in comparison to a normal cell, and which is useful for the preferential targeting of a pharmacological agent to the cancer cell. In some embodiments, a tumor antigen is a marker expressed by both normal cells and cancer cells, e.g., a lineage marker, e.g., CD19 on B cells. In certain aspects, the tumor antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like. In some embodiments, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a cancer-associated antigen is a cell surface molecule that is inappropriately synthesized in the cancer cell, for instance, a molecule that contains deletions, additions or mutations in comparison to the molecule expressed on a normal cell. In some embodiments, a cancer-associated antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly-Gly-Gly-Ser)_n$ (SEQ ID NO: 15), where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, $(Gly_4\ Ser)_4$ (SEQ ID NO:27) or $(Gly_4\ Ser)_3$ (SEQ ID NO:28). In another embodiment, the linkers include multiple repeats of $(Gly_2Ser)$, (GlySer) or $(Gly_3Ser)$ (SEQ ID NO:29). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, e.g., mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In some embodiments of a construct for transient expression, the polyA is between 50 and 5000 (SEQ ID NO: 30), e.g., greater than 64, e.g., greater than 100, e.g., greater than 300 or 400 poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

Apheresis is the process in which whole blood is removed from an individual, separated into select components, and the remainder returned to circulation. Generally, there are two methods for the separation of blood components, centrifugal and non-centrifugal. Leukapheresis results in the active selection and removal of the patient's white blood cells.

As used herein, the terms "treat", "treatment" and "treating" refer to the reduction or amelioration of the progression, severity and/or duration of a proliferative disorder, or the amelioration of one or more symptoms (e.g., one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

In the context of the present invention, "tumor antigen" or "hyperproliferative disorder antigen" or "antigen associated with a hyperproliferative disorder" refers to antigens that are common to specific hyperproliferative disorders. In certain embodiments, the tumor antigen is derived from a cancer including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner protein present in a sample, but which antibody or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are methods of manufacturing immune effector cells (e.g., T cells, NK cells) that can be engineered with a CAR, e.g., a CAR described herein, and reaction mixtures and compositions comprising such cells.

In one aspect, the disclosure features an immune effector cell (e.g., T cell, NK cell) engineered to express a CAR, wherein the engineered immune effector cell exhibits an antitumor property. An exemplary antigen is a cancer associated antigen (i.e., tumor antigen) described herein. In one aspect, a cell is transformed with the CAR and the CAR is expressed on the cell surface. In some embodiments, the cell (e.g., T cell, NK cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell, NK cell) is transfected with a nucleic acid, e.g., mRNA, cDNA, DNA, encoding a CAR. In some such embodiments, the cell may transiently express the CAR.

Furthermore, the present invention provides CAR-expressing cell, e.g., CART compositions and their use in medicaments or methods for treating, among other diseases, cancer or any malignancy or autoimmune diseases involving cells or tissues which express a tumor antigen as described herein.

In one aspect, the CAR of the invention can be used to eradicate a normal cell that express a tumor antigen as described herein, thereby applicable for use as a cellular conditioning therapy prior to cell transplantation.

Sources of Immune Effector Cells

In embodiments, prior to expansion and genetic modification or other modification, a source of cells, e.g., T cells or natural killer (NK) cells, can be obtained from a subject. Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. In some embodiments, the population of T regulatory-depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, e.g. IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depleting reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory-depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product significantly reduces the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, mTOR inhibitor, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of a subject's relapse. In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. In an embodiment, methods of decreasing $T_{REG}$ cells include, but are not limited to, administration to the subject of one or more of cyclophosphamide, anti-GITR antibody, CD25-depletion, mTOR inhibitor, or a combination thereof. Administration of one or more of cyclophosphamide, anti-GITR antibody, CD25-depletion, or a combination thereof, can occur before, during or after an infusion of the CAR-expressing cell product. Administration of one or more of cyclophosphamide, anti-GITR antibody, CD25-depletion, mTOR inhibitor, or a combination thereof, can occur before, during or after an infusion of the CAR-expressing cell product.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with cyclophosphamide prior to collection of cells for CAR-expressing cell product manufacturing, thereby reducing the risk of subject relapse to CAR-expressing cell treatment (e.g., CTL019 treatment). In an embodiment, a subject is pre-treated with an anti-GITR antibody prior to collection of cells for CAR-expressing cell (e.g., T cell or NK cell) product manufacturing, thereby reducing the risk of subject relapse to CAR-expressing cell treatment.

In an embodiment, the CAR-expressing cell (e.g., T cell, NK cell) manufacturing process is modified to deplete $T_{REG}$ cells prior to manufacturing of the CAR-expressing cell (e.g., T cell, NK cell) product (e.g., a CTL019 product). In an embodiment, CD25-depletion is used to deplete $T_{REG}$ cells prior to manufacturing of the CAR-expressing cell (e.g., T cell, NK cell) product (e.g., a CTL019 product).

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory-depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory-depleted, e.g., CD25+ depleted cells, and check point inhibitor depleted cells, e.g., PD1+, LAG3+ and/or TIM3+ depleted cells. Exemplary check point inhibitors include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR (e.g., TGFRbeta), e.g., as described herein. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment thereof, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

In one embodiment, a plurality of the immune effector cells of the population do not express diaglycerol kinase (DGK), e.g., is DGK-deficient. In one embodiment, a plurality of the immune effector cells of the population do not express Ikaros, e.g., is Ikaros-deficient. In one embodiment, a plurality of the immune effector cells of the population do not express DGK and Ikaros, e.g., is both DGK and Ikaros-deficient.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" Clinical & Translational Immunology (2015) 4, e31; doi:10.1038/cti.2014.31.

In one embodiment, the methods of the application can utilize culture media conditions comprising serum-free medium. In one embodiment, the serum free medium is OpTmizer CTS (LifeTech), Immunocult XF (Stemcell technologies), CellGro (CellGenix), TexMacs (Miltenyi), Stemline (Sigma), Xvivo15 (Lonza), PrimeXV (Irvine Scientific), or StemXVivo (RandD systems). The serum-free medium can be supplemented with a serum substitute such as ICSR (immune cell serum replacement) from LifeTech. The level of serum substitute (e.g., ICSR) can be, e.g., up to 5%, e.g., about 1%, 2%, 3%, 4%, or 5%.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some embodiments, downregulation of HLA may be accomplished by reducing or eliminating expression of beta-2 microglobulin (B2M).

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR (e.g., TGFRbeta). Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

Expression systems for siRNA and shRNAs, and exemplary shRNAs, are described, e.g., in paragraphs 649 and 650 of International Application WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

The CRISPR/Cas system, and uses thereof, are described, e.g., in paragraphs 651-658 of International Application WO2015/142675, filed Mar. 13, 2015, which is incorporated by reference in its entirety.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

TALENs, and uses thereof, are described, e.g., in paragraphs 659-665 of International Application WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

ZFNs, and uses thereof, are described, e.g., in paragraphs 666-671 of International Application WO2015/142675, filed Mar. 13, 2015, which is incorporated by reference in its entirety.

Telomerase Expression

Telomeres play a crucial role in somatic cell persistence, and their length is maintained by telomerase (TERT). Telomere length in CLL cells may be very short (Roth et al., "Significantly shorter telomeres in T-cells of patients with ZAP-70+/CD38 chronic lymphocytic leukaemia" British Journal of Haematology, 143, 383-386, Aug. 28, 2008), and may be even shorter in manufactured CAR-expressing cells, e.g., CART19 cells, limiting their potential to expand after adoptive transfer to a patient. Telomerase expression can rescue CAR-expressing cells from replicative exhaustion.

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

Telomerase expression may be stable (e.g., the nucleic acid may integrate into the cell's genome) or transient (e.g., the nucleic acid does not integrate, and expression declines after a period of time, e.g., several days). Stable expression may be accomplished by transfecting or transducing the cell with DNA encoding the telomerase subunit and a selectable marker, and selecting for stable integrants. Alternatively or in combination, stable expression may be accomplished by site-specific recombination, e.g., using the Cre/Lox or FLP/FRT system.

Transient expression may involve transfection or transduction with a nucleic acid, e.g., DNA or RNA such as mRNA. In some embodiments, transient mRNA transfection avoids the genetic instability sometimes associated with stable transfection with TERT. Transient expression of exogenous telomerase activity is described, e.g., in International Application WO2014/130909, which is incorporated by reference herein in its entirety. In embodiments, mRNA-based transfection of a telomerase subunit is performed according to the messenger RNA Therapeutics™ platform commercialized by Moderna Therapeutics. For instance, the method may be a method described in U.S. Pat. Nos. 8,710,200, 8,822,663, 8,680,069, 8,754,062, 8,664,194, or 8680069.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

(SEQ ID NO: 108)

```
MPRAPRCRAVRSLLRSHYREVLPLATFVRRLGPQGWRLVQRGDP
AAFRALVAQCLVCVPWDARPPPAAPSFRQVSCLKELVARVLQRLCERGA
KNVLAFGFALLDGARGGPPEAFTTSVRSYLPNTVTDALRGSGAWGLLLR
RVGDDVLVHLLARCALFVLVAPSCAYQVCGPPLYQLGAATQARPPPHAS
GPRRRLGCERAWNHSVREAGVPLGLPAPGARRRGGSASRSLPLPKRPRR
GAAPEPERTPVGQGSWAHPGRTRGPSDRGFCVVSPARPAEEATSLEGAL
SGTRHSHPSVGRQHHAGPPSTSRPPRPWDTPCPPVYAETKHFLYSSGDK
EQLRPSFLLSSLRPSLTGARRLVETIFLGSRPWMPGTPRRLPRLPQRYW
QMRPLFLELLGNHAQCPYGVLLKTHCPLRAAVTPAAGVCAREKPQGSVA
APEEEDTDPRRLVQLLRQHSSPWQVYGFVRACLRRLVPPGLWGSRHNER
RFLRNTKKFISLGKHAKLSLQELTWKMSVRGCAWLRRSPGVGCVPAAEH
RLREEILAKFLHWLMSVYVVELLRSFFYVTETTFQKNRLFFYRKSVWSK
LQSIGIRQHLKRVQLRELSEAEVRQHREARPALLTSRLRFIPKPDGLRP
IVNMDYVVGARTERREKRAERLTSRVKALFSVLNYERARRPGLLGASVL
GLDDIHRAWRTFVLRVRAQDPPPELYFVKVDVTGAYDTIPQDRLTEVIA
SIIKPQNTYCVRRYAVVQKAAHGHVRKAFKSHVSTLTDLQPYMRQFVAH
LQETSPLRDAVVIEQSSSLNEASSGLFDVFLRFMCHHAVRIRGKSYVQC
QGIPQGSILSTLLCSLCYGDMENKLFAGIRRDGLLLRLVDDFLLVTPHL
```

-continued

THAKTFLRTLVRGVPEYGCVVNLRKTVVNFPVEDEALGGTAFVQMPAHG

LFPWCGLLLDTRTLEVQSDYSSYARTSIRASLTFNRGFKAGRNMRRKLE

GVLRLKCHSLELDLQVNSLQTVCTNIYKILLLQAYRFHACVLQLPFHQQ

VWKNPTFFLRVISDTASLCYSILKAKNAGMSLGAKGAAGPLPSEAVQWL

CHQAFLLKLTRHRVTYVPLLGSLRTAQTQLSRKLPGTTLTALEAAANPA

LPSDFKTILD

In an embodiment, the hTERT has a sequence at least 80%, 85%, 90%, 95%, 96%, 97%, 98%, or 99% identical to the sequence of SEQ ID NO: 108. In an embodiment, the hTERT has a sequence of SEQ ID NO: 108. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

(SEQ ID NO: 23)

```
   1 caggcagcgt ggtcctgctg cgcacgtggg aagccctggc cccggccacc cccgcgatgc
  61 cgcgcgctcc ccgctgccga gccgtgcgct ccctgctgcg cagccactac cgcgaggtgc
 121 tgccgctggc cacgttcgtg cggcgcctgg ggccccaggg ctggcggctg gtgcagcgcg
 181 gggacccggc ggctttccgc gcgctggtgg cccagtgcct ggtgtgcgtg ccctgggacg
 241 cacggccgcc ccccgccgcc ccctccttcc gccaggtgtc ctgcctgaag gagctggtgg
 301 cccgagtgct gcagaggctg tgcgagcgcg gcgcgaagaa cgtgctggcc ttcggcttcg
 361 cgctgctgga cggggcccgc gggggccccc ccgaggcctt caccaccagc gtgcgcagct
 421 acctgcccaa cacggtgacc gacgcactgc gggggagcgg ggcgtggggg ctgctgttgc
 481 gccgcgtggg cgacgacgtg ctggttcacc tgctggcacg ctgcgcgctc tttgtgctgg
 541 tggctcccag ctgcgcctac caggtgtgcg ggccgccgct gtaccagctc ggcgctgcca
 601 ctcaggcccg gcccccgcca cacgctagtg gaccccgaag gcgtctggga tgcgaacggg
 661 cctggaacca tagcgtcagg gaggccgggg tcccccctggg cctgccagcc ccgggtgcga
 721 ggaggcgcgg gggcagtgcc agccgaagtc tgccgttgcc caagaggccc aggcgtggcg
 781 ctgcccctga gccggagcgg acgcccgttg ggcaggggtc ctgggcccac ccgggcagga
 841 cgcgtggacc gagtgaccgt ggtttctgtg tggtgtcacc tgccagaccc gccgaagaag
 901 ccacctcttt ggagggtgcg ctctctggca cgcgccactc ccacccatcc gtgggccgcc
 961 agcaccacgc gggcccccca tccacatcgc ggccaccacg tccctgggac acgccttgtc
1021 ccccggtgta cgccgagacc aagcacttcc tctactcctc aggcgacaag gagcagctgc
1081 ggccctcctt cctactcagc tctctgaggc ccagcctgac tggcgctcgg aggctcgtgg
1141 agaccatctt tctgggttcc aggccctgga tgccagggac tccccgcagg ttgccccgcc
1201 tgccccagcg ctactggcaa atgcggcccc tgtttctgga gctgcttggg aaccacgcgc
1261 agtgccccta cggggtgctc ctcaagacgc actgcccgct gcgagctgcg gtcaccccag
1321 cagccggtgt ctgtgcccgg gagaagcccc agggctctgt ggcggccccc gaggaggagg
1381 acacagaccc ccgtcgcctg gtgcagctgc tccgccagca cagcagcccc tggcaggtgt
1441 acggcttcgt gcgggcctgc ctgcgccggc tggtgccccc aggcctctgg ggctccaggc
1501 acaacgaacg ccgcttcctc aggaacacca agaagttcat ctccctgggg aagcatgcca
1561 agctctcgct gcaggagctg acgtggaaga tgagcgtgcg gggctgcgct tggctgcgca
1621 ggagcccagg ggttggctgt gttccggccg cagagcaccg tctgcgtgag gagatcctgg
1681 ccaagttcct gcactggctg atgagtgtgt acgtcgtcga gctgctcagg tctttctttt
1741 atgtcacgga gaccacgttt caaaagaaca ggctcttttt ctaccggaag agtgtctgga
1801 gcaagttgca aagcattgga atcagacagc acttgaagag ggtgcagctg cgggagctgt
```

-continued

```
1861   cggaagcaga ggtcaggcag catcgggaag ccaggcccgc cctgctgacg tccagactcc
1921   gcttcatccc caagcctgac gggctgcggc cgattgtgaa catggactac gtcgtgggag
1981   ccagaacgtt ccgcagagaa aagagggccg agcgtctcac ctcgagggtg aaggcactgt
2041   tcagcgtgct caactacgag cgggcgcggc gccccggcct cctgggcgcc tctgtgctgg
2101   gcctggacga tatccacagg gcctggcgca ccttcgtgct gcgtgtgcgg gcccaggacc
2161   cgccgcctga gctgtacttt gtcaaggtgg atgtgacggg cgcgtacgac accatccccc
2221   aggacaggct cacggaggtc atcgccagca tcatcaaacc ccagaacacg tactgcgtgc
2281   gtcggtatgc cgtggtccag aaggccgccc atgggcacgt ccgcaaggcc ttcaagagcc
2341   acgtctctac cttgacagac ctccagccgt acatgcgaca gttcgtggct cacctgcagg
2401   agaccagccc gctgagggat gccgtcgtca tcgagcagag ctcctccctg aatgaggcca
2461   gcagtggcct cttcgacgtc ttcctacgct tcatgtgcca ccacgccgtg cgcatcaggg
2521   gcaagtccta cgtccagtgc caggggatcc cgcagggctc catcctctcc acgctgctct
2581   gcagcctgtg ctacggcgac atggagaaca agctgtttgc ggggattcgg cgggacgggc
2641   tgctcctgcg tttggtggat gatttcttgt tggtgacacc tcacctcacc cacgcgaaaa
2701   ccttcctcag gaccctggtc cgaggtgtcc ctgagtatgg ctgcgtggtg aacttgcgga
2761   agacagtggt gaacttccct gtagaagacg aggccctggg tggcacggct tttgttcaga
2821   tgccggccca cggcctattc cctggtgcg gcctgctgct ggatacccgg accctggagg
2881   tgcagagcga ctactccagc tatgcccgga cctccatcag agccagtctc accttcaacc
2941   gcggcttcaa ggctgggagg aacatgcgtc gcaaactctt tggggtcttg cggctgaagt
3001   gtcacagcct gtttctggat ttgcaggtga acagcctcca gacggtgtgc accaacatct
3061   acaagatcct cctgctgcag gcgtacaggt ttcacgcatg tgtgctgcag ctcccatttc
3121   atcagcaagt ttggaagaac cccacatttt tcctgcgcgt catctctgac acggcctccc
3181   tctgctactc catcctgaaa gccaagaacg cagggatgtc gctgggggcc aagggcgccg
3241   ccggccctct gccctccgag gccgtgcagt ggctgtgcca ccaagcattc ctgctcaagc
3301   tgactcgaca ccgtgtcacc tacgtgccac tcctggggtc actcaggaca gcccagacgc
3361   agctgagtcg gaagctcccg gggacgacgc tgactgccct ggaggccgca gccaacccgg
3421   cactgccctc agacttcaag accatcctgg actgatggcc acccgcccac agccaggccg
3481   agagcagaca ccagcagccc tgtcacgccg ggctctacgt cccagggagg gaggggcggc
3541   ccacacccag gcccgcaccg ctgggagtct gaggcctgag tgagtgtttg gccgaggcct
3601   gcatgtccgg ctgaaggctg agtgtccggc tgaggcctga gcgagtgtcc agccaagggc
3661   tgagtgtcca gcacacctgc cgtcttcact tccccacagg ctggcgctcg gctccacccc
3721   agggccagct tttcctcacc aggagcccgg cttccactcc ccacatagga atagtccatc
3781   cccagattcg ccattgttca cccctcgccc tgccctcctt tgccttccac cccccaccatc
3841   caggtggaga ccctgagaag gaccctggga gctctgggaa tttggagtga ccaaaggtgt
3901   gccctgtaca caggcgagga ccctgcacct ggatgggggt ccctgtgggt caaattgggg
3961   ggaggtgctg tgggagtaaa atactgaata tatgagtttt tcagttttga aaaaaaaaaa
4021   aaaaaaa
```

In an embodiment, the hTERT is encoded by a nucleic acid having a sequence at least 80%, 85%, 90%, 95%, 96%, 97%, 98%, or 99% identical to the sequence of SEQ ID NO: 23. In an embodiment, the hTERT is encoded by a nucleic acid of SEQ ID NO: 23.

Chimeric Antigen Receptor (CAR)

The present invention provides immune effector cells (e.g., T cells, NK cells) that are engineered to contain one or more CARs that direct the immune effector cells to cancer. This is achieved through an antigen binding domain on the CAR that is specific for a cancer associated antigen. There are two classes of cancer associated antigens (tumor antigens) that can be targeted by the CARs described herein: (1) cancer associated antigens that are expressed on the surface of cancer cells; and (2) cancer associated antigens that itself is intracellar, however, a fragment of such antigen (peptide) is presented on the surface of the cancer cells by MHC (major histocompatibility complex).

Accordingly, an immune effector cell, e.g., obtained by a method described herein, can be engineered to contain a CAR that target one of the following cancer associated antigens (tumor antigens): CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, and mut hsp70-2.

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multi-specific (e.g., a bispecific or a trispecific) antibody molecule. Protocols for generating bispecific or heterodimeric antibody molecules, and various configurations for bispecific antibody molecules, are described in, e.g., paragraphs 455-458 of WO2015/142675, filed Mar. 13, 2015, which is incorporated by reference in its entirety.

In one aspect, the bispecific antibody molecule is characterized by a first immunoglobulin variable domain sequence, e.g., a scFv, which has binding specificity for CD19, e.g., comprises a scFv as described herein, or comprises the light chain CDRs and/or heavy chain CDRs from a scFv described herein, and a second immunoglobulin variable domain sequence that has binding specificity for a second epitope on a different antigen.

Chimeric TCR

In one aspect, the antibodies and antibody fragments of the present invention (e.g., CD19 antibodies and fragments) can be grafted to one or more constant domain of a T cell receptor ("TCR") chain, for example, a TCR alpha or TCR beta chain, to create a chimeric TCR. Without being bound by theory, it is believed that chimeric TCRs will signal through the TCR complex upon antigen binding. For example, an scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, an antibody fragment, for example a VL domain as described herein, can be grafted to the constant domain of a TCR alpha chain, and an antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of an antibody or antibody fragment may be grafted into a TCR alpha and/or beta chain to create a chimeric TCR. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced, e.g., by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Non-Antibody Scaffolds

In embodiments, the antigen binding domain comprises a non-antibody scaffold, e.g., a fibronectin, ankyrin, domain antibody, lipocalin, small modular immuno-pharmaceutical, maxybody, Protein A, or affilin. The non-antibody scaffold has the ability to bind to target antigen on a cell. In embodiments, the antigen binding domain is a polypeptide or fragment thereof of a naturally occurring protein expressed on a cell. In some embodiments, the antigen binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

In an embodiment the antigen binding domain comprises the extracellular domain, or a counter-ligand binding fragment thereof, of molecule that binds a counterligand on the surface of a target cell.

The immune effector cells can comprise a recombinant DNA construct comprising sequences encoding a CAR, wherein the CAR comprises an antigen binding domain (e.g., antibody or antibody fragment, TCR or TCR fragment) that binds specifically to a tumor antigen, e.g., an tumor antigen described herein, and an intracellular signaling domain. The intracellular signaling domain can comprise a costimulatory signaling domain and/or a primary signaling domain, e.g., a zeta chain. As described elsewhere, the methods described herein can include transducing a cell, e.g., from the population of T regulatory-depleted cells, with a nucleic acid encoding a CAR, e.g., a CAR described herein.

In specific aspects, a CAR comprises a scFv domain, wherein the scFv may be preceded by an optional leader sequence such as provided in SEQ ID NO: 1, and followed by an optional hinge sequence such as provided in SEQ ID NO:2 or SEQ ID NO:36 or SEQ ID NO:38, a transmembrane region such as provided in SEQ ID NO:6, an intracellular signalling domain that includes SEQ ID NO:7 or SEQ ID NO:16 and a CD3 zeta sequence that includes SEQ ID NO:9 or SEQ ID NO:10, e.g., wherein the domains are contiguous with and in the same reading frame to form a single fusion protein.

In one aspect, an exemplary CAR constructs comprise an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), and an intracellular stimulatory domain (e.g., an intracellular stimulatory domain described herein). In one aspect, an exemplary CAR construct comprises an optional leader sequence (e.g., a leader sequence described herein), an extracellular antigen binding domain (e.g., an antigen binding domain described herein), a hinge (e.g., a hinge region described herein), a transmembrane domain (e.g., a transmembrane domain described herein), an intracellular costimulatory signaling domain (e.g., a costimulatory signaling domain described herein) and/or an intracellular primary signaling domain (e.g., a primary signaling domain described herein).

An exemplary leader sequence is provided as SEQ ID NO: 1. An exemplary hinge/spacer sequence is provided as SEQ ID NO: 2 or SEQ ID NO:36 or SEQ ID NO:38. An exemplary transmembrane domain sequence is provided as SEQ ID NO:6. An exemplary sequence of the intracellular signaling domain of the 4-1BB protein is provided as SEQ ID NO: 7. An exemplary sequence of the intracellular signaling domain of CD27 is provided as SEQ ID NO:16. An exemplary CD3zeta domain sequence is provided as SEQ ID NO: 9 or SEQ ID NO:10.

In one aspect, the immune effector cell comprises a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, CD27, 4-1BB, and the like. In some instances, the CAR can comprise any combination of CD3-zeta, CD28, 4-1BB, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

Nucleic acids encoding a CAR can be introduced into the immune effector cells using, e.g., a retroviral or lentiviral vector construct.

Nucleic acids encoding a CAR can also be introduced into the immune effector cell using, e.g., an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR") (e.g., a 3' and/or 5' UTR described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length (e.g., described in the Examples, e.g., SEQ ID NO:35). RNA so produced can efficiently transfect different kinds of cells. In one embodiment, the template includes sequences for the CAR. In an embodiment, an RNA CAR vector is transduced into a cell, e.g., a T cell by electroporation.

Antigen Binding Domain

In one aspect, a plurality of the immune effector cells, e.g., the population of T regulatory-depleted cells, include a nucleic acid encoding a CAR that comprises a target-specific binding element otherwise referred to as an antigen binding domain. The choice of binding element depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR described herein include those associated with viral, bacterial and parasitic infections, autoimmune disease and cancer cells.

In one aspect, the portion of the CAR comprising the antigen binding domain comprises an antigen binding domain that targets a tumor antigen, e.g., a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In an embodiment, the antigen binding domain comprises an anti-CD19 antibody, or fragment thereof, e.g., an scFv. For example, the antigen binding domain comprises a variable heavy chain and a variable light chain listed in Table 1. The linker sequence joining the variable heavy and variable light chains can be, e.g., any of the linker sequences described herein, or alternatively, can be GSTSGSGKPGS-GEGSTKG (SEQ ID NO:104).

TABLE 1

| Anti-CD19 antibody binding domains | | |
|---|---|---|
| CD19 | huscFv1 (SEQ ID NO: 39) | EIVMTQSPATLSLSPGERATLSCRASQDISKYLNWYQQKPGQAPRLLIYHTSRLHSGIPARFSGSGSGTDYTLTISSLQPEDFAVYFCQQGNTLPYTFGQGTKLEIKGGGGSGGGGSGGGGSQVQLQESGPGLVKPSETLSLTCTVSGVSLPDYGVSWIRQPPGKGLEWIGVIWGSETTYYSSSLKSRVTISKDNSKNQVSLKLSSVTAADTAVYYCAKHYYYGGSYAMDYWGQGTLVTVSS |
| CD19 | huscFv2 (SEQ ID NO: 40) | Eivmtqspatlslspgeratlscrasqdiskylnwyqqkpgqaprlliyhtsrlhsgiparfsgsgsgtdytltisslqpedfavyfcqqgntlpytfgqgtkleikggggsggggsggggsqvqlqesgpglvkpsetlsltctvsgvslpdygvswirqppgkglewigviwgsettyyqsslksrvtiskdnsknqvslklssvtaadtavyycakhyyyggsyamdywgqgtlvtvss |
| CD19 | huscFv3 (SEQ ID NO: 41) | Qvqlqesgpglvkpsetlsltctvsgvslpdygvswirqppgkglewigviwgsettyyssslksrvtiskdnsknqvslklssvtaadtavyycakhyyyggsyamdywgqgtlvtvssggggsggggsggggseivmtqspatlslspgeratlscrasqdiskylnwyqqkpgqaprlliyhtsrlhsgiparfsgsgsgtdytltisslqpedfavyfcqqgntlpytfgqgtkleik |
| CD19 | huscFv4 (SEQ ID NO: 42) | Qvqlqesgpglvkpsetlsltctvsgvslpdygvswirqppgkglewigviwgsettyyqsslksrvtiskdnsknqvslklssvtaadtavyycakhyyyggsyamdywgqgtlvtvssggggsggggsggggseivmtqspatlslspgeratlscrasqdiskylnwyqqkpgqaprlliyhtsrlhsgiparfsgsgsgtdytltisslqpedfavyfcqqgntlpytfgqgtkleik |
| CD19 | huscFv5 (SEQ ID NO: 43) | Eivmtqspatlslspgeratlscrasqdiskylnwyqqkpgqaprlliyhtsrlhsgiparfsgsgsgtdytltisslqpedfavyfcqqgntlpytfgqgtkleikggggsggggsggggsggggsqvqlqesgpglvkpsetlsltctvsgvslpdygvswirqppgkglewigviwgsettyyssslksrvtiskdnsknqvslklssvtaadtavyycakhyyyggsyamdywgqgtlvtvss |
| CD19 | huscFv6 (SEQ ID NO: 44) | Eivmtqspatlslspgeratlscrasqdiskylnwyqqkpgqaprlliyhtsrlhsgiparfsgsgsgtdytltisslqpedfavyfcqqgntlpytfgqgtkleikggggsggggsggggsggggsqvqlqesgpglvkpsetlsltctvsgvslpdygvswirqppgkglewigviwgsettyyqsslksrvtiskdnsknqvslklssvtaadtavyycakhyyyggsyamdywgqgtlvtvss |
| CD19 | huscFv7 (SEQ ID NO: 45) | Qvqlqesgpglvkpsetlsltctvsgvslpdygvswirqppgkglewigviwgsettyyssslksrvtiskdnsknqvslklssvtaadtavyycakhyyyggsyamdywgqgtlvtvssggggsggggsggggsggggseivmtqspatlslspgeratlscrasqdiskylnwyqqkpgqaprlliyhtsrlhsgiparfsgsgsgtdytltisslqpedfavyfcqqgntlpytfgqgtkleik |
| CD19 | huscFv8 (SEQ ID NO: 46) | Qvqlqesgpglvkpsetlsltctvsgvslpdygvswirqppgkglewigviwgsettyyqsslksrvtiskdnsknqvslklssvtaadtavyycakhyyyggsyamdywgqgtlvtvssggggsggggsggggsggggseivmtqspatlslspgeratlscrasqdiskylnwyqqkpgqaprlliyhtsrlhsgiparfsgsgsgtdytltisslqpedfavyfcqqgntlpytfgqgtkleik |
| CD19 | huscFv9 (SEQ ID NO: 47) | Eivmtqspatlslspgeratlscrasqdiskylnwyqqkpgqaprlliyhtsrlhsgiparfsgsgsgtdytltisslqpedfavyfcqqgntlpytfgqgtkleikggggsggggsggggsggggsqvqlqesgpglvkpsetlsltctvsgvslpdygvswirqppgkglewigviwgsettyynsslksrvtiskdnsknqvslklssvtaadtavyycakhyyyggsyamdywgqgtivtvss |
| CD19 | Hu scFv10 (SEQ ID NO: 48) | Qvqlqesgpglvkpsetlsltctvsgvslpdygvswirqppgkglewigviwgsettyynsslksrvtiskdnsknqvslklssvtaadtavyycakhyyyggsyamdywgqgtlvtvssggggsggggsggggsggggseivmtqspatlslspgeratlscrasqdiskylnwyqqkpgqaprlliyhtsrlhsgiparfsgsgsgtdytltisslqpedfavyfcqqgntlpytfgqgtkleik |
| CD19 | Hu scFv11 (SEQ ID | Eivmtqspatlslspgeratlscrasqdiskylnwyqqkpgqaprlliyhtsrlhsgiparfsgsgsgtdytltisslqpedfavyfcqqgntlpytfgqgtkleikggggsggggsggggsqvqlqesgpglvkpsetlsltctvsgvslpdygvswirqppgkglewigviwgse |

TABLE 1-continued

| Anti-CD19 antibody binding domains | | |
|---|---|---|
| | NO: 49) | ttyynsslksrvtiskdnsknqvslklssvtaadtavyycakhyyyggsyamdywgqgt lvtvss |
| CD19 | Hu scFv12 (SEQ ID NO: 50) | Qvqlqesgpglvkpsetlsltctvsgvslpdygvswirqppgkglewigviwgsettyy nsslksrvtiskdnsknqvslklssvtaadtavyycakhyyyggsyamdywgqgtlvtv ssggggsggggsggggseivmtqspatlslspgeratlscrasqdiskylnwyqqkpgq aprlliyhtsrlhsgiparfsgsgsgtdytltisslqpedfavyfcqqgntlpytfgqg tkleik |
| CD19 | muCTL019 (SEQ ID NO: 51) | Diqmtqttsslsaslgdrvtiscrasqdiskylnwyqqkpdgtvklliyhtsrlhsgvp srfsgsgsgtdysltisnleqediatyfcqqgntlpytfgggtkleitggggsggggsg gggsevklqesgpglvapsqslsvtctvsgvslpdygvswirqpprkglewlgviwgse ttyynsalksrltiikdnsksqvflkmnslqtddtaiyycakhyyyggsyamdywgqgt svtvss |

TABLE 2

| anti-CD19 antibody binding domains | | |
|---|---|---|
| Antibody | VH Sequence | VL Sequence |
| SSJ25-C1 | QVQLLESGAELVRPGSSVKISCKASGYAFSS YWMNWVKQRPGQGLEWIGQIYPGDGDTNYNG KFKGQATLTADKSSSTAYMQLSGLTSEDSAV YSCARKTISSVVDFYFDYWGQGTTVT (SEQ ID NO: 3) | ELVLTQSPKFMSTSVGDRVSVTCKASQNVGTNVA WYQQKPGQSPKPLIYSATYRNSGVPDRFTGSGSG TDFTLTITNVQSKDLADYFYFCQYNRYPYTSGGG TKLEIKRRS (SEQ ID NO: 4) |

Any CD19 CAR, e.g., the CD19 antigen binding domain of any known CD19 CAR, can be used in accordance with the present disclosure. For example, LG-740; CD19 CAR described in the U.S. Pat. No. 8,399,645; U.S. Pat. No. 7,446,190; Xu et al., Leuk Lymphoma. 2013 54(2):255-260 (2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10.

Exemplary target antigens that can be targeted using the CAR-expressing cells, include, but are not limited to, CD19, CD123, EGFRvIII, mesothelin, among others, as described in, for example, WO 2014/130635, WO 2014/130657, and WO 2015/090230, each of which is herein incorporated by reference in its entirety.

In one embodiment, the CAR T cell that specifically binds to CD19 has the USAN designation TISAGENLECLEUCEL-T. CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CAR-expressing cells can specifically bind to human CD19, e.g., can include a CAR molecule, or an antigen binding domain (e.g., a humanized antigen binding domain) according to Table 3 of WO2014/153270, incorporated herein by reference.

In other embodiments, the CAR-expressing cells can specifically bind to CD123, e.g., can include a CAR molecule (e.g., any of the CAR1-CARE), or an antigen binding domain according to Tables 1-2 of WO 2014/130635, incorporated herein by reference.

In other embodiments, the CAR-expressing cells can specifically bind to EGFRvIII, e.g., can include a CAR molecule, or an antigen binding domain according to Table 2 or SEQ ID NO:11 of WO 2014/130657, incorporated herein by reference.

In other embodiments, the CAR-expressing cells can specifically bind to mesothelin, e.g., can include a CAR molecule, or an antigen binding domain according to Tables 2-3 of WO 2015/090230, incorporated herein by reference.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed or described above.

In some embodiments, the tumor antigen is a tumor antigen described in International Application WO2015/142675, filed Mar. 13, 2015, which is herein incorporated by reference in its entirety. In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGicp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed or described above.

In one aspect, the anti-tumor antigen binding domain is a fragment, e.g., a single chain variable fragment (scFv). In one aspect, the anti-a cancer associate antigen as described herein binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a cancer associate antigen as described herein protein with wild-type or enhanced affinity.

In some instances, scFvs can be prepared according to a method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, which are incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO:25). In one embodiment, the linker can be $(Gly_4Ser)_4$ (SEQ ID NO:27) or $(Gly_4Ser)_3$ (SEQ ID NO:28). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellar, however, a fragment of such antigen (peptide) is presented on the surface of the cancer cells by MHC.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CART.

The transmembrane domain may be derived either from a natural or from a recombinant source. Where the source is natural, the domain may be derived from any membrane-bound or transmembrane protein. In one aspect the transmembrane domain is capable of signalling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIR2DS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, or CD19.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence ESKYGPP-CPPCPAPEFLGGPSVFLFPPKPKDTLMISRTPEVTCV-VVDVSQEDPEVQFNW YVDGVEVHNAKTKPREEQF-NSTYRVVSVLTVLHQDWLNGKEYKCKVSNKGLPSSI EK TISKAKGQPREPQVYTLPPSQEEMTKNQVSLT-CLVKGFYPSDIAVEWESNGQPENNYK TTPPVLDS-DGSFFLYSRLTVDKSRWQEGNVFSCSVMHEALHN-HYTQKSLSLSLGKM (SEQ ID NO:36). In some embodiments, the hinge or spacer comprises a hinge encoded by a nucleotide sequence of GAGAGCAAG-TACGGCCCTCCCTGCCCCCCTTGCCCTGC-CCCCGAGTTCCTGGGCGG ACCCAGCGTGTTCCT-GTTCCCCCCCAAGCCCAAGGACACCCTGATGATCA GCCGGA CCCCCGAGGTGACCTGTGTGGTGGTG-GACGTGTCCCAGGAGGACCCCGAGGTCCA GTTCAACTGGTACGTGGACGGCGTGGAGGTGCA-CAACGCCAAGACCAAGCCCCGG GAGGAGCAGT-TCAATAGCACCTACCGGGTGGTGTCCGTGCTGAC-CGTGCTGCACCA GGACTGGCTGAACGGCAAGGAATACAAGTG-TAAGGTGTCCAACAAGGGCCTGCCC AGCAGCATC-GAGAAAACCATCAGCAAGGCCAAGGGCCAGC-CTCGGGAGCCCCAGG TGTACACCCTGCCCCCTAGCCAAGAGGAGATGAC-CAAGAACCAGGTGTCCCTGAC CTGCCTGGT-GAAGGGCTTCTACCCCAGCGACATCGCCGTG-GAGTGGGAGAGCAAC GGCCAGCCCGAGAACAACTACAAGACCAC-CCCCCCTGTGCTGGACAGCGACGGCA GCTTCTTC-CTGTACAGCCGGCTGACCGTGGACAAGAGCCG-GTGGCAGGAGGGCAA CGTCTTTAGCTGCTCCGTGATGCACGAGGCCCTG-CACAACCACTACACCCAGAAGA GCCTGAGCCT-GTCCCTGGGCAAGATG (SEQ ID NO:37).

In one aspect, the hinge or spacer comprises an IgD hinge. For example, in one embodiment, the hinge or spacer comprises a hinge of the amino acid sequence RWPESP-KAQASSVPTAQPQAEGSLAKATTAPATTRNTGRG-GEEKKKEKEKEEQEERET KTPECPSHTQPLGVYLLT-PAVQDLWLRDKATFTCFVVGSDLKDAHLTWEVAG KVPTG GVEEGLLERHSNGSQSQHSRLTL-PRSLWNAGTSVTCTLNHPSLPPQRLMALREPAAQA PVKLSLNLLASSDPPEAASWLLCEVSGFSPPNILLM-WLEDQREVNTSGFAPARPPPQPG STTFWAWSVLRV-PAPPSPQPATYTCVVSHEDSRTLL-NASRSLEVSYVTDH (SEQ ID NO:38). In some embodiments, the hinge or spacer comprises a hinge encoded by a nucleotide sequence of AGGTGGC-CCGAAAGTCCCAAGGCCCAGGCATCTAGTGTTC-CTACTGCACAGCCCCA GGCAGAAGGCAGCCTAGC-CAAAGCTACTACTGCACCTGCCACTACGCGCAATA CT GGCCGTGGCGGGGAGGAGAAGAAAAAGGA-GAAAGAGAAAGAAGAACAGGAAGA GAGGGA-GACCAAGACCCCTGAATGTCCATCCCATACCCAGC-CGCTGGGCGTCTATC TCTTGACTCCCGCAGTACAGGACTTGTGGCTTAGA-GATAAGGCCACCTTTACATGT TTCGTCGTGGGCTCTGACCTGAAGGATGCCCATTT- GACTTGGGAGGTTGCCGGAAA GGTACCCACA-GGGGGGGTTGAGGAAGGGTTGCTGGAGCGCCAT-TCCAATGGCTCT CAGAGCCAGCACTCAAGACTCACCCTTCCGA-GATCCCTGTGGAACGCCGGGACCTC TGTCACATG-TACTCTAAATCATCCTAGCCTGCCCCCACAGCGTCT-GATGGCCCTTAG AGAGCCAGCCGCCCAGGCACCAGTTAAGCTTAGC-CTGAATCTGCTCGCCAGTAGTG ATCCCCCAGAG-GCCGCCAGCTGGCTCTTATGCGAAGTGTCCGGCTT-TAGCCCGCCC AACATCTTGCTCATGTGGCTGGAGGACCAGCGA-GAAGTGAACACCAGCGGCTTCG CTCCAGCCCGGC-CCCCACCCCAGCCGGGTTCTACCACATTCTGGGC-CTGGAGTGTC TTAAGGGTCCCAGCACCACCTAGCCCCCAGCCA-GCCACATACACCTGTGTTGTGTC CCATGAAGA-TAGCAGGACCCTGCTAAATGCTTCTAGGAGTCTG-GAGGTTTCCTACG TGACTGACCATT (SEQ ID NO:103).

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO: 5). In some embodiments, the linker is encoded by a nucleotide sequence of GGTG-GCGGAGGTTCTGGAGGTGGAGGTTCC (SEQ ID NO: 8).

In one aspect, the hinge or spacer comprises a KIR2DS2 hinge.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced.

Examples of intracellular signaling domains for use in a CAR described herein include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In one embodiment, a CAR of the invention comprises an intracellular signaling domain, e.g., a primary signaling domain of CD3-zeta, e.g., a CD3-zeta sequence described herein.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Costimulatory Signaling Domain

The intracellular signalling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. In one embodiment, the intracellular domain is designed to comprise the signaling domain of CD3-zeta and the signaling domain of CD28. In one aspect, the intracellular domain is designed to comprise the signaling domain of CD3-zeta and the signaling domain of ICOS.

A costimulatory molecule can be a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1), NKp30, NKp44, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, NKG2D, NKG2C and PAG/Cbp.

The intracellular signaling sequences within the cytoplasmic portion of the CAR may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO:16). In one aspect, the signalling domain of CD27 is encoded by a nucleic acid sequence of AGGAGTAAGAGGAGCAGGCTCCTG-CACAGTGACTACATGAACATGACTCCCCGCC GCCCCGGGCCCACCCGCAAGCATTACCAGCCCTAT-GCCCCACCACGCGACTTCGCA GCCTATCGCTCC (SEQ ID NO:14).

In one aspect, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein, e.g., CD19, CD33, CLL-1, CD34, FLT3, or folate receptor beta). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, ICOS, CD27 or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In another aspect, the disclosure features a population of CAR-expressing cells, e.g., CART cells. In some embodiments, the population of CAR-expressing cells comprises a mixture of cells expressing different CARs.

For example, in one embodiment, the population of CART cells can include a first cell expressing a CAR having an antigen binding domain to a cancer associated antigen described herein, and a second cell expressing a CAR having a different antigen binding domain, e.g., an antigen binding domain to a different a cancer associated antigen described herein, e.g., an antigen binding domain to a cancer associated antigen described herein that differs from the cancer associate antigen bound by the antigen binding domain of the CAR expressed by the first cell.

As another example, the population of CAR-expressing cells can include a first cell expressing a CAR that includes an antigen binding domain to a cancer associated antigen described herein, and a second cell expressing a CAR that includes an antigen binding domain to a target other than a cancer associate antigen as described herein. In one embodiment, the population of CAR-expressing cells includes, e.g., a first cell expressing a CAR that includes a primary intracellular signaling domain, and a second cell expressing a CAR that includes a secondary signaling domain.

In another aspect, the disclosure features a population of cells wherein at least one cell in the population expresses a CAR having an antigen binding domain to a cancer associated antigen described herein, and a second cell expressing another agent, e.g., an agent which enhances the activity of a CAR-expressing cell. For example, in one embodiment, the agent can be an agent which inhibits an inhibitory molecule. Inhibitory molecules, e.g., PD-1, can, in some embodiments, decrease the ability of a CAR-expressing cell to mount an immune effector response. Examples of inhibitory molecules include PD-1, PD-L1, PD-L2, CTLA4, TIM3, CEACAM (CEACAM-1, CEACAM-3, and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR (e.g., TGFRbeta). In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA4, TIM3, CEACAM (CEACAM-1, CEACAM-3, and/or CEACAM-5), LAG3, VISTA, BTLA, TIGIT, LAIR1, CD160, 2B4 and TGFR beta, or a fragment of any of these, and a second polypeptide which is an intracellular signaling domain described herein (e.g., comprising a costimulatory domain (e.g., 41BB, CD27, OX40 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28 signaling domain described herein and/or a CD3 zeta signaling domain described herein).

The sequences of anti-CD19 binding domains are provided herein in Table 1. Full CAR constructs can be generated using any of the antigen binding domains described in Table 1 with one or more additional CAR component provided below.

leader (amino acid sequence)
(SEQ ID NO: 1)
MALPVTALLLPLALLLHAARP leader (nucleic acid sequence)
(SEQ ID NO: 12)
ATGGCCCTGCCTGTGACAGCCCTGCTGCTGCCTCTGGCTCTGCTGCTGCA
TGCCGCTAGACCC CD8 hinge (amino acid sequence)
(SEQ ID NO: 2)
QPLSLRPEACRPAAGGAVHTRGLDFACD CD8 hinge (nucleic acid sequence)
(SEQ ID NO: 13)
ACCACGACGCCAGCGCCGCGACCACCAACACCGGCGCCCACCATCGCGTC
GCAGCCCCTGTCCCTGCGCCCAGAGGCGTGCCGGCCAGCGGCGGGGGGCG
CAGTGCACACGAGGGGGCTGGACTTCGCCTGTGAT CD8 transmembrane (amino acid sequence)
(SEQ ID NO: 6)
IYIWAPLAGTCGVLLLSLVITLYC transmembrane (nucleic acid sequence)
(SEQ ID NO: 17)
ATCTACATCTGGGCGCCCTTGGCCGGGACTTGTGGGGTCCTTCTCCTGTC
ACTGGTTATCACCCTTTACTGC 4-1BB Intracellular domain (amino acid sequence)
(SEQ ID NO: 7)
KRGRKKLLYIFKQPFMRPVQTTQEEDGCSCRFPEEEEGGCEL 4-1BB Intracellular domain (nucleic acid sequence)
(SEQ ID NO: 18)
AAACGGGGCAGAAAGAAACTCCTGTATATATTCAAACAACCATTTATGAG
ACCAGTACAAACTACTCAAGAGGAAGATGGCTGTAGCTGCCGATTTCCAG
AAGAAGAAGAAGGAGGATGTGAACTG CD3 zeta domain (amino acid sequence)
(SEQ ID NO: 9)
RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR CD3 zeta (nucleic acid sequence)
(SEQ ID NO: 20)
AGAGTGAAGTTCAGCAGGAGCGCAGACGCCCCCGCGTACAAGCAGGGCCA
GAACCAGCTCTATAACGAGCTCAATCTAGGACGAAGAGAGGAGTACGATG
TTTTGGACAAGAGACGTGGCCGGGACCCTGAGATGGGGGGAAAGCCGAGA
AGGAAGAACCCTCAGGAAGGCCTGTACAATGAACTGCAGAAAGATAAGAT
GGCGGAGGCCTACAGTGAGATTGGGATGAAAGGCGAGCGCCGGAGGGGCA
AGGGGCACGATGGCCTTTACCAGGGTCTCAGTACAGCCACCAAGGACACC
TACGACGCCCTTCACATGCAGGCCCTGCCCCCTCGC CD3 zeta domain (amino acid sequence; NCBI Reference Sequence NM_000734.3)
(SEQ ID NO: 10)
RVKFSRSADAPAYQQGQNQLYNELNLGRREEYDVLDKRRGRDPEMGGKPR -continued

RKNPQEGLYNELQKDKMAEAYSEIGMKGERRRGKGHDGLYQGLSTATKDT
YDALHMQALPPR

CD3 zeta (nucleic acid sequence; NCBI Reference Sequence NM_000734.3);
(SEQ ID NO: 21)
agagtgaagttcagcaggagcgcagacgcccccgcgtaccagcagggcca
gaaccagctctataacgagctcaatctaggacgaagagaggagtacgatg
ttttggacaagagacgtggccgggaccctgagatggggggaaagccgaga
aggaagaaccctcaggaaggcctgtacaatgaactgcagaaagataagat
ggcggaggcctacagtgagattgggatgaaaggcgagcgccggaggggca
aggggcacgatggcctttaccagggtctcagtacagccaccaaggacacc
tacgacgcccttcacatgcaggccctgccccctcgc IgG4 Hinge (amino acid sequence)
(SEQ ID NO: 36)
ESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGKM IgG4 Hinge (nucleotide sequence)
(SEQ ID NO: 37)
GAGAGCAAGTACGGCCCTCCCTGCCCCCCTTGCCCTGCCCCCGAGTTCCT
GGGCGGACCCAGCGTGTTCCTGTTCCCCCCCAAGCCCAAGGACACCCTGA
TGATCAGCCGGACCCCCGAGGTGACCTGTGTGGTGGTGGACGTGTCCCAG
GAGGACCCCGAGGTCCAGTTCAACTGGTACGTGGACGGCGTGGAGGTGCA
CAACGCCAAGACCAAGCCCCGGGAGGAGCAGTTCAATAGCACCTACCGGG
TGGTGTCCGTGCTGACCGTGCTGCACCAGGACTGGCTGAACGGCAAGGAA
TACAAGTGTAAGGTGTCCAACAAGGGCCTGCCCAGCAGCATCGAGAAAAC
CATCAGCAAGGCCAAGGGCCAGCCTCGGGAGCCCCAGGTGTACACCCTGC
CCCCTAGCCAAGAGGAGATGACCAAGAACCAGGTGTCCCTGACCTGCCTG
GTGAAGGGCTTCTACCCCAGCGACATCGCCGTGGAGTGGGAGAGCAACGG
CCAGCCCGAGAACAACTACAAGACCACCCCCCCTGTGCTGGACAGCGACG
GCAGCTTCTTCCTGTACAGCCGGCTGACCGTGGACAAGAGCCGGTGGCAG
GAGGGCAACGTCTTTAGCTGCTCCGTGATGCACGAGGCCCTGCACAACCA
CTACACCCAGAAGAGCCTGAGCCTGTCCCTGGGCAAGATG EF1 alpha promoter
(SEQ ID NO: 11)
CGTGAGGCTCCGGTGCCCGTCAGTGGGCAGAGCGCACATCGCCCACAGTC
CCCGAGAAGTTGGGGGGAGGGGTCGGCAATTGAACCGGTGCCTAGAGAAG
GTGGCGCGGGGTAAACTGGGAAAGTGATGTCGTGTACTGGCTCCGCCTTT
TTCCCGAGGGTGGGGGAGAACCGTATATAAGTGCAGTAGTCGCCGTGAAC
GTTCTTTTTCGCAACGGGTTTGCCGCCAGAACACAGGTAAGTGCCGTGTG
TGGTTCCCGCGGGCCTGGCCTCTTTACGGGTTATGGCCCTTGCGTGCCTT
GAATTACTTCCACCTGGCTGCAGTACGTGATTCTTGATCCCGAGCTTCGG
GTTGGAAGTGGGTGGGAGAGTTCGAGGCCTTGCGCTTAAGGAGCCCCTTC -continued

GCCTCGTGCTTGAGTTGAGGCCTGGCCTGGGCGCTGGGGCCGCCGCGTGC

GAATCTGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

TTGGGGGGAGGGGTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTTCTTCCATTTCAGGTGTCGTGA.

Gly/Ser (SEQ ID NO: 25)

GGGGS

Gly/Ser (SEQ ID NO: 26): This sequence may encompass 1-6 "Gly Gly Gly Gly Ser" repeating units

GGGGSGGGGS GGGGSGGGGS GGGGSGGGGS

Gly/Ser (SEQ ID NO: 27)

GGGGSGGGGS GGGGSGGGGS

Gly/Ser (SEQ ID NO: 28)

GGGGSGGGGS GGGGS

Gly/Ser (SEQ ID NO: 29)

GGGS

PolyA (SEQ ID NO: 30):
A5000

PolyA (SEQ ID NO: 31):
A100

PolyT (SEQ ID NO: 32):
T5000

PolyA (SEQ ID NO: 33):
A5000

PolyA (SEQ ID NO: 34):
A400

PolyA (SEQ ID NO: 35):
A2000

Gly/Ser (SEQ ID NO: 15): This sequence may encompass 1-10 "Gly Gly Gly Ser" repeating units
GGGSGGGSGG GSGGGSGGGS GGGSGGGSGG GSGGGSGGGS Exemplary CD19 CAR constructs that can be used in the methods described herein are shown in Table 3:

TABLE 3

CD19 CAR Constructs

| Name | SEQ ID | Sequence |
|---|---|---|
| CAR1 | | |
| CAR1 scFv domain | 39 | EIVMTQSPATLSLSPGERATLSCRASQDISKYLNWYQQKPGQAPRLLIYHT SRLHSGIPARFSGSGSGTDYTLTISSLQPEDFAVYFCQQGNTLPYTFGQGT KLEIKGGGGSGGGGSGGGGSQVQLQESGPGLVKPSETLSLTCTVSGVSLPD YGVSWIRQPPGKGLEWIGVIWGSETTYYSSSLKSRVTISKDNSKNQVSLKL SSVTAADTAVYYCAKHYYYGGSYAMDYWGQGTLVTVSS |
| 103101 CAR1 Soluble scFv-nt | 52 | atggccctccctgtcaccgccctgctgcttccgctggctcttctgctccacgccgc tcggcccgaaattgtgatgacccagtcacccgccactcttagcctttcacccggtg agcgcgcaaccctgtcttgcagagcctcccaagacatctcaaaataccttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagccaggtccaactccaagaaa gcggaccgggtcttgtgaagccatcagaaactctttcactgacttgtactgtgagc ggagtgtctctccccgattacggggtgtcttggatcagacagccaccggggaaggg tctggaatggattggagtgatttggggctctgagactacttactactcttcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtactctggtcaccgtgt ccagccaccaccatcatcaccatcaccat |
| 103101 CAR1 Soluble scFv-aa | 64 | **MALPVTALLLPLALLLHAARP**eivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsqvqlqesgpglvkpsetlsltctvs gvslpdygvswirqppgkglewigviwgsettyyssslksrvtiskdnsknqvslk lssvtaadtavyycakhyyyggsyamdywgqgtlvtvss**hhhhhhhh** |

TABLE 3-continued

CD19 CAR Constructs

| Name | SEQ ID | Sequence |
|---|---|---|
| 104875<br>CAR 1-<br>Full-nt | 90 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttggggctctgagactacttactactcttcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagcaccactaccccagcaccgaggccacccaccccggctcctaccatcgcctcc<br>cagcctctgtccctgcgtccggaggcatgtagacccgcagctggtggggccgtgca<br>tacccggggtcttgacttcgcctgcgatatctacatttgggcccctctggctggta<br>cttgcggggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaaggggaacgcagaagaggcaaaggccacgacggactgtaccagggact<br>cagcaccgccaccaaggacacctatgacgctcttcacatgcaggccctgccgcctc<br>gg |
| 104875<br>CAR 1-<br>Full-aa | 77 | MALPVTALLLPLALLLHAARPeivmtqspatlslspgeratlsc**rasqdiskyln**w<br>yqqkpgqaprlliy**htsrlhs**giparfsgsgsgtdytltisslqpedfavyfc**qqg**<br>**ntlpyt**fgqgtkleikggggsggggsggggsqvqlqesgpglvkpsetlsltctvs<br>gvslp**dygvs**wirqppgkglewig**viwgsettyyssslks**rvtiskdnsknqvslk<br>lssvtaadtavyycak**hyyyggsyamdy**wgqgtivtvsstttpaprpptpaptias<br>qplslrpeacrpaaggavhtrgldfacdiyiwaplagtcgvlllslvitlyckrgr<br>kkllyifkqpfmrpvqttgeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |
| CAR2 | | |
| CAR2 scFv<br>domain | 40 | eivmtqspatlslspgeratlscrasqdiskylnwyqqkpgqaprlliyhtsrlhs<br>giparfsgsgsgtdytltisslqpedfavyfcqqgntlpytfgqgtkleikggggs<br>ggggsggggsqvqlqesgpglvkpsetlsltctvsgvslpdygvswirqppgkgle<br>wigviwgsettyyqsslksrvtiskdnsknqvslklssvtaadtavyycakhyyyg<br>gsyamdywgqgtlvtvss |
| 103102<br>CAR2-<br>Soluble<br>scFv-nt | 53 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttggggctctgagactacttactaccaatcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagccaccaccatcatcaccatcaccat |
| 103102<br>CAR2-<br>Soluble<br>scFv-aa | 65 | **MALPVTALLLPLALLLHAARP**eivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsqvqlqesgpglvkpsetlsltctvs<br>gvslpdygvswirqppgkglewigviwgsettyyqsslksrvtiskdnsknqvslk<br>lssvtaadtavyycakhyyyggsyamdywgqgtivtvss**hhhhhhhh** |
| 104876<br>CAR 2-<br>Full-nt | 91 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg |

TABLE 3-continued

CD19 CAR Constructs

| Name | SEQ ID | Sequence |
|---|---|---|
| | | tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttggggctctgagactacttactaccaatcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagcaccactaccccagcaccgaggccacccaccccggctcctaccatcgcctcc<br>cagcctctgtccctgcgtccggaggcatgtagacccgcagctggtggggccgtgca<br>tacccggggtcttgacttcgcctgcgatatctacatttgggcccctctggctggta<br>cttgcggggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaaggggaacgcagaagaggcaaaggccacgacggactgtaccagggact<br>cagcaccgccaccaaggacacctatgacgctcttcacatgcaggccctgccgcctc<br>gg |
| 104876<br>CAR 2-<br>Full-aa | 78 | MALPVTALLLPLALLLHAARPeivmtqspatlslspgeratlsc**rasgdiskyln**w<br>yqqkpgqaprlliy**htsrlhs**giparfsgsgsgtdytltisslqpedfavyfc**qqg<br>ntlpyt**fgqgtkleikggggsggggsggggsqvqlqesgpglvkpsetlsltctvs<br>gyslp**dygvs**wirqppgkglewig**viwgsettyyqsslks**rvtiskdnsknqvslk<br>lssvtaadtavyycak**hyyyggsyamdy**wgqgtivtvsstttpaprpptpaptias<br>qplslrpeacrpaaggavhtrgldfacdiyiwaplagtcgvlllslvitlyckrgr<br>kkllyifkqpfmrpvqttgeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |
| CAR 3 | | |
| CAR3 scFv<br>domain | 41 | qvqlqesgpglvkpsetlsltctvsgvslpdygvswirqppgkglewigviwgset<br>tyysssLksrvtiskdnsknqvslklssvtaadtavyycakhyyyggsyamdywgq<br>gtlvtvssggggsggggsggggseivmtqspatlslspgeratlscrasqdiskyl<br>nwyqqkpgqaprlliyhtsrlhsgiparfsgsgsgtdytltisslqpedfavyfcq<br>qgntlpytfgqgtkleik |
| 103104<br>CAR 3-<br>Soluble<br>scFv-nt | 54 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactattcatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctaccctttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacaccctgccgtacaccttcggccagggcaccaagcttgaga<br>tcaaacatcaccaccatcatcaccatcac |
| 103104<br>CAR 3-<br>Soluble<br>scFv-aa | 66 | **MALPVTALLLPLALLLHAARP**qvqlqesgpglvkpsetlsltctvsgvslpdygys<br>wirqppgkglewigviwgsettyysssLksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleik**hhhhhhhh** |
| 104877<br>CAR 3-<br>Full-nt | 92 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactattcatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctaccctttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacaccctgccgtacaccttcggccagggcaccaagcttgaga<br>tcaaaaccactactcccgctccaaggccacccacccctgccccgaccatcgcctct<br>cagccgctttccctgcgtccggaggcatgtagacccgcagctggtggggccgtgca |

TABLE 3-continued

| CD19 CAR Constructs | | |
|---|---|---|
| Name | SEQ ID | Sequence |
| | | tacccggggtcttgacttcgcctgcgatatctacatttgggcccctctggctggta<br>cttgcggggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaaggggaacgcagaagaggcaaaggccacgacggactgtaccagggact<br>cagcaccgccaccaaggacacctatgacgctcttcacatgcaggccctgccgcctc<br>gg |
| 104877<br>CAR 3-<br>Full-aa | 79 | MALPVTALLLPLALLLHAARPqvqlqesgpglvkpsetlsltctvsgvslpd**ygvs**<br>wirqppgkglewig**viwgsettyyssslks**rvtiskdnsknqvslklssvtaadta<br>vyycak**hyyyggsyamdy**wgqgtivtvssggggsggggsggggseivmtqspatls<br>lspgeratlsc**rasqdiskyln**wyqqkpgqaprlliy**htsrlhs**giparfsgsgsg<br>tdytltisslqpedfavyfc**qqgntlpyt**fgqgtkleikttttpaprpptpaptias<br>qplslrpeacrpaaggavhtrgldfacdiyiwaplagtcgylllslvitlyckrgr<br>kkllyifkufmrpvqttcleedgcscrfpeeeeggcelrykfsrsadapaykqgqn<br>qlynelnlgrreeydvldkrrgrdpemggkprrknpqeglynelqkdkmaeaysei<br>gmkgerrrgkghdglyccl statkdtydalhmcialppr |
| CAR 4 | | |
| CAR4 scFv<br>domain | 42 | qvqlqesgpglvkpsetlsltctvsgvslpdygvswirqppgkglewigviwgset<br>tyyqsslksrvtiskdnsknqvslklssvtaadtavyycakhyyyggsyamdywgq<br>gtlvtvssggggsggggsggggseivmtqspatlslspgeratlscrasqdiskyl<br>nwyqqkpgqaprlliyhtsrlhsgiparfsgsgsgtdytltisslqpedfavyfcq<br>qgntlpytfgqgtkleik |
| 103106<br>CAR4-<br>Soluble<br>scFv-nt | 55 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactatcaatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctaccctttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacaccctgccgtacaccttcggccagggcaccaagcttgaga<br>tcaaacatcaccaccatcatcaccatcac |
| 103106<br>CAR4-<br>Soluble<br>scFv-aa | 67 | **MALPVTALLLPLALLLHAARP**qvqlqesgpglvkpsetlsltctvsgvslpdygvs<br>wirqppgkglewigviwgsettyyqsslksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleik**hhhhhhhh** |
| 104878<br>CAR 4-<br>Full nt | 93 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactatcaatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctaccctttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacaccctgccgtacaccttcggccagggcaccaagcttgaga<br>tcaaaaccactactcccgctccaaggccacccaccccctgccccgaccatcgcctct<br>cagccgctttccctgcgtccggaggcatgtagacccgcagctggtggggccgtgca<br>tacccggggtcttgacttcgcctgcgatatctacatttgggcccctctggctggta<br>cttgcggggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaaggggaacgcagaagaggcaaaggccacgacggactgtaccagggact |

TABLE 3-continued

CD19 CAR Constructs

| Name | SEQ ID | Sequence |
|---|---|---|
| | | cagcaccgccaccaaggacacctatgacgctcttcacatgcaggccctgccgcctc<br>gg |
| 104878<br>CAR 4-<br>Full-aa | 80 | MALPVTALLLPLALLLHAARPqvqlqesgpglvkpsetlsltctvsgvslp**dygvs**<br>wirqppgkglewig**viwgsettyygsslks**rvtiskdnsknqvslklssvtaadta<br>vyycak**hyyyggsyamdy**wgqgtlvtvssggggsggggsggggseivmtqspatls<br>lspgeratlsc**rasqdiskyln**wyqqkpgqaprlliy**htsrlhs**giparfsgsgsg<br>tdytltisslqpedfavyfc**qqgntlpyt**fgqgtkleikttptpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |
| CAR 5 | | |
| CAR5 scFv<br>domain | 43 | eivmtqspatlslspgeratlscrasqdiskylnwyqqkpgqaprlliyhtsrlhs<br>giparfsgsgsgtdytltisslqpedfavyfcqqgntlpytfgqgtkleikggggs<br>ggggsggggsggggsqvqlqesgpglvkpsetlsltctvsgvslpdygvswirqpp<br>gkglewigviwgsettyyssslksrvtiskdnsknqvslklssvtaadtavyycak<br>hyyyggsyamdywgqgtlvtvss |
| 99789<br>CAR5-<br>Soluble<br>scFv-nt | 56 | atggccctcccagtgaccgctctgctgctgcctctcgcacttcttctccatgccgc<br>tcggcctgagatcgtcatgacccaaagccccgctaccctgtccctgtcacccggcg<br>agagggcaaccctttcatgcagggccagccaggacatttctaagtacctcaactgg<br>tatcagcagaagccagggcaggctcctcgcctgctgatctaccacaccagccgcct<br>ccacagcggtatccccgccagattttccgggagcgggtctggaaccgactacaccc<br>tcaccatctcttctctgcagcccgaggatttcgccgtctatttctgccagcagggg<br>aatactctgccgtacaccttcggtcaaggtaccaagctggaaatcaagggaggcgg<br>aggatcaggcggtggcggaagcggaggaggtggctccggaggaggaggttcccaag<br>tgcagcttcaagaatcaggacccggacttgtgaagccatcagaaaccctctccctg<br>acttgtaccgtgtccggtgtgagcctccccgactacggagtctcttggattcgcca<br>gcctccggggaagggtcttgaatggattggggtgatttggggatcagagactactt<br>actactcttcatcacttaagtcacgggtcaccatcagcaaagataatagcaagaac<br>caagtgtcacttaagctgtcatctgtgaccgccgctgacaccgccgtgtactattg<br>tgccaaacattactattacggagggtcttatgctatggactactggggacagggga<br>ccctggtgactgtctctagccatcaccatcaccaccatcatcac |
| 99789<br>CAR5-<br>Soluble<br>scFv-aa | 68 | **MALPVTALLLPLALLLHAARP**eivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsggggsqvqlqesgpglvkpsetlsl<br>tctvsgvslpdygvswirqppgkglewigviwgsettyyssslksrvtiskdnskn<br>qvslklssvtaadtavyycakhyyyggsyamdywgqgtlvtvss**hhhhhhhh** |
| 104879<br>CAR 5-<br>Full-nt | 94 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagcggcggaggcgggagccagg<br>tccaactccaagaaagcggaccgggtcttgtgaagccatcagaaactctttcactg<br>acttgtactgtgagcggagtgtctctccccgattacggggtgtcttggatcagaca<br>gccaccggggaagggtctggaatggattggagtgatttggggctctgagactactt<br>actactcttcatccctcaagtcacgcgtcaccatctcaaaggacaactctaagaat<br>caggtgtcactgaaactgtcatctgtgaccgcagccgacaccgccgtgtactattg<br>cgctaagcattactattatggcgggagctacgcaatggattactggggacagggta<br>ctctggtcaccgtgtccagcaccactaccccagcaccgaggccacccaccccggct<br>cctaccatcgcctcccagcctctgtccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 104879<br>CAR 5-<br>Full-aa | 81 | MALPVTALLLPLALLLHAARPeivmtqspatlslspgeratlsc**rasqdiskyln**w<br>yqqkpgqaprlliy**htsrlhs**giparfsgsgsgtdytltisslqpedfavyfc**qqg**<br>**ntlpyt**fgqgtkleikggggsggggsggggsggggsqvqlqesgpglvkpsetlsl<br>tctvsgvslp**dygvs**wirqppgkglewig**viwgsettyyssslks**rvtiskdnskn<br>qvslklssvtaadtavyycak**hyyyggsyamdy**wgqgtlvtvsstttpaprpptpa<br>ptiasqplslrpeacrpaaggavhtrgldfacdiyiwaplagtcgvlllslvitly |

TABLE 3-continued

CD19 CAR Constructs

| Name | SEQ ID | Sequence |
|---|---|---|
| | | ckrgrkkllyifkqpfmrpvqttgeedgcscrfpeeeeggcelrvkfsrsadapay<br>kqgqnqlynelnlgrreeydvldkrrgrdpemggkprrknpqeglynelqkdkmae<br>ayseigmkgerrrgkghdglyqglstatkdtydalhmqalppr |
| CAR6 | | |
| CAR6 scFv domain | 44 | eivmtqspatlslspgeratlscrasqdiskylnwyqqkpgqaprlliyhtsrlhs<br>giparfsgsgsgtdytltisslqpedfavyfcqqgntlpytfgqgtkleikggggs<br>ggggsggggsggggsqvqlqesgpglvkpsetlsltctvsgvslpdygvswirqpp<br>gkglewigviwgsettyyqsslksrvtiskdnsknqvslklssvtaadtavyycak<br>hyyyggsyamdywgqgtlvtvss |
| 99790 CAR6-Soluble scFv-nt | 57 | atggccctcccagtgaccgctctgctgctgcctctcgcacttcttctccatgccgc<br>tcggcctgagatcgtcatgacccaaagccccgctaccctgtccctgtcacccggcg<br>agagggcaaccctttcatgcagggccagccaggacatttctaagtacctcaactgg<br>tatcagcagaagccagggcaggctcctcgcctgctgatctaccacaccagccgcct<br>ccacagcggtatccccgccagattttccgggagcgggtctggaaccgactacaccc<br>tcaccatctcttctctgcagcccgaggatttcgccgtctatttctgccagcagggg<br>aatactctgccgtacaccttcggtcaaggtaccaagctggaaatcaagggaggcgg<br>aggatcaggcggtggcggaagcggaggaggtggctccggaggaggaggttcccaag<br>tgcagcttcaagaatcaggacccggacttgtgaagccatcagaaaccctctccctg<br>acttgtaccgtgtccggtgtgagcctccccgactacggagtctcttggattcgcca<br>gcctccggggaagggtcttgaatggattggggtgatttggggatcagagactactt<br>actaccagtcatcacttaagtcacgggtcaccatcagcaaagataatagcaagaac<br>caagtgtcacttaagctgtcatctgtgaccgccgctgacaccgccgtgtactattg<br>tgccaaacattactattacggagggtcttatgctatggactactggggacaggga<br>ccctggtgactgtctctagccatcaccatcaccaccatcatcac |
| 99790 CAR6-Soluble scFv-aa | 69 | **MALPVTALLLPLALLLHAARP**eivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsggggsqvqlqesgpglvkpsetlsl<br>tctvsgvslpdygvswirqppgkglewigviwgsettyyqsslksrvtiskdnskn<br>qvslklssvtaadtavyycakhyyyggsyamdywgqgtilvtvss**hhhhhhhh** |
| 104880 CAR6-Full-nt | 95 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagcggaggcggagggagccagg<br>tccaactccaagaaagcggaccgggtcttgtgaagccatcagaaactctttcactg<br>acttgtactgtgagcggagtgtctctccccgattacggggtgtcttggatcagaca<br>gccaccggggaagggtctggaatggattggagtgatttggggctctgagactactt<br>actaccaatcatccctcaagtcacgcgtcaccatctcaaaggacaactctaagaat<br>caggtgtcactgaaactgtcatctgtgaccgcagccgacaccgccgtgtactattg<br>cgctaagcattactattatggcgggagctacgcaatggattactggggacagggta<br>ctctggtcaccgtgtccagcaccactaccccagcaccgaggccacccaccccggct<br>cctaccatcgcctcccagcctctgtccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 104880 CARE6-Full-aa | 82 | MALPVTALLLPLALLLHAARPeivmtqspatlslspgeratlsc**rasgdiskyln**w<br>yqqkpgqaprlliy**htsrlhs**giparfsgsgsgtdytltisslqpedfavyfc**qqg**<br>**ntlpyt**fgqgtkleikggggsggggsggggsggggsqvqlqesgpglvkpsetlsl<br>tctvsgvslp**dygvs**wirqppgkglewig**viwgsettyygsslks**rvtiskdnskn<br>qvslklssvtaadtavyycak**hyyyggsyamdy**wgqgtivtvsstttpaprpptpa<br>ptiasqplslrpeacrpaaggavhtrgldfacdiyiwaplagtcgvlllslvitly<br>ckrgrkkllyifkqpfmrpvqttgeedgcscrfpeeeeggcelrvkfsrsadapay<br>kqgqnqlynelnlgrreeydvldkrrgrdpemggkprrknpqeglynelqkdkmae<br>ayseigmkgerrrgkghdglyqglstatkdtydalhmqalppr |
| CAR7 | | |
| CAR7 scFv domain | 45 | qvqlqesgpglvkpsetlsltctvsgvslpdygvswirqppgkglewigviwgset<br>tyyssslksrvtiskdnsknqvslklssvtaadtavyycakhyyyggsyamdywgq<br>gtivtvssggggsggggsggggsggggseivmtqspatlslspgeratlscrasqd |

TABLE 3-continued

CD19 CAR Constructs

| Name | SEQ ID | Sequence |
|---|---|---|
| | | iskylnwyqqkpgqaprlliyhtsrlhsgiparfsgsgsgtdytltisslqpedfa<br>vyfcqqgntlpytfgqgtkleik |
| 100796<br>CAR7-<br>Soluble<br>scFv-nt | 58 | atggcactgcctgtcactgccctcctgctgcctctggccctccttctgcatgccgc<br>caggccccaagtccagctgcaagagtcaggacccggactggtgaagccgtctgaga<br>ctctctcactgacttgtaccgtcagcggcgtgtccctccccgactacggagtgtca<br>tggatccgccaacctcccgggaaagggcttgaatggattggtgtcatctggggttc<br>tgaaaccacctactactcatcttccctgaagtccagggtgaccatcagcaaggata<br>attccaagaaccaggtcagccttaagctgtcatctgtgaccgctgctgacaccgcc<br>gtgtattactgcgccaagcactactattacggaggaagctacgctatggactattg<br>gggacagggcactctcgtgactgtgagcagcggcggtggagggtctggaggtggag<br>gatccggtggtggtgggtcaggcggaggagggagcgagattgtgatgactcagtca<br>ccagccaccctttctctttcacccggcgagagagcaaccctgagctgtagagccag<br>ccaggacatttctaagtacctcaactggtatcagcaaaaaccggggcaggcccctc<br>gcctcctgatctaccatacctcacgccttcactctggtatccccgctcggtttagc<br>ggatcaggatctggtaccgactacactctgaccatttccagcctgcagccagaaga<br>tttcgcagtgtatttctgccagcagggcaatacccttccttacaccttcggtcagg<br>gaaccaagctcgaaatcaagcaccatcaccatcatcaccaccat |
| 100796<br>CAR7-<br>Soluble<br>scFv-aa | 70 | **MALPVTALLLPLALLLHAARP**qvqlqesgpglvkpsetlsltctvsgvslpdygvs<br>wirqppgkglewigviwgsettyyssslksrvtiskdnsknqvslklssvtaadta<br>vyycakhyyyggsyamdywgqgtivtvssggggsggggsggggsggggseivmtqs<br>patlslspgeratlscrasqdiskylnwyqqkpgqaprlliyhtsrlhsgiparfs<br>gsgsgtdytltisslqpedfavyfcqqgntlpytfgqgtkleik**hhhhhhhh** |
| 104881<br>CAR7<br>Full-nt | 96 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactattcatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccggaggtggcggaagcgaaatcgtgatgacccagagc<br>cctgcaaccctgtccctttctcccggggaacgggctaccctttcttgtcgggcatc<br>acaagatatctcaaaatacctcaattggtatcaacagaagccgggacaggccccta<br>ggcttcttatctaccacacctctcgcctgcatagcgggattcccgcacgctttagc<br>gggtctggaagcgggaccgactacactctgaccatctcatctctccagcccgagga<br>cttcgccgtctacttctgccagcagggtaacaccctgccgtacaccttcggccagg<br>gcaccaagcttgagatcaaaaccactactcccgctccaaggccacccacccctgcc<br>ccgaccatcgcctctcagccgctttccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 104881<br>CAR 7<br>Full-aa | 83 | MALPVTALLLPLALLLHAARPqvqlqesgpglvkpsetlsltctvsgvslp**dygvs**<br>wirqppgkglewig**viwgsettyyssslks**rvtiskdnsknqvslklssvtaadta<br>vyycak**hyyyggsyamdy**wgqgtlvtvssggggsggggsggggsggggseivmtqs<br>patlslspgeratlsc**rasqdiskyln**wyqqkpgqaprlliy**htsrlhs**giparfs<br>gsgsgtdytltisslqpedfavyfc**qqgntlpyt**fgqgtkleiktttpaprpptpa<br>ptiasqplslrpeacrpaaggavhtrgldfacdiyiwaplagtcgvlllslvitly<br>ckrgrkkllyifkqpfmrpvqttqeedgcscrfpeeeeggcelrvkfsrsadapay<br>kqgqnqlynelnlgrreeydvldkrrgrdpemggkprrknpqeglynelqkdkmae<br>ayseigmkgerrrgkghdglyqglstatkdtydalhmqalppr |
| CAR 8 | | |
| CAR8 scFv<br>domain | 46 | qvqlqesgpglvkpsetlsltctvsgvslpdygvswirqppgkglewigviwgset<br>tyyqsslksrvtiskdnsknqvslklssvtaadtavyycakhyyyggsyamdywgq<br>gtivtvssggggsggggsggggsggggseivmtqspatlslspgeratlscrasqd<br>iskylnwyqqkpgqaprlliyhtsrlhsgiparfsgsgsgtdytltisslqpedfa<br>vyfcqqgntlpytfgqgtkleik |
| 100798<br>CARS8-<br>Soluble<br>scFv-nt | 59 | atggcactgcctgtcactgccctcctgctgcctctggccctccttctgcatgccgc<br>caggccccaagtccagctgcaagagtcaggacccggactggtgaagccgtctgaga<br>ctctctcactgacttgtaccgtcagcggcgtgtccctccccgactacggagtgtca<br>tggatccgccaacctcccgggaaagggcttgaatggattggtgtcatctggggttc<br>tgaaaccacctactaccagtcttccctgaagtccagggtgaccatcagcaaggata |

TABLE 3-continued

CD19 CAR Constructs

| Name | SEQ ID | Sequence |
|---|---|---|
| | | attccaagaaccaggtcagccttaagctgtcatctgtgaccgctgctgacaccgcc<br>gtgtattactgcgccaagcactactattacggaggaagctacgctatggactattg<br>gggacagggcactctcgtgactgtgagcagcggcggtggagggtctggaggtggag<br>gatccggtggtggtgggtcaggcggaggagggagcgagattgtgatgactcagtca<br>ccagccaccctttctctttcacccggcgagagagcaaccctgagctgtagagccag<br>ccaggacatttctaagtacctcaactggtatcagcaaaaaccggggcaggcccctc<br>gcctcctgatctaccatacctcacgccttcactctggtatccccgctcggtttagc<br>ggatcaggatctggtaccgactacactctgaccatttccagcctgcagccagaaga<br>tttcgcagtgtatttctgccagcagggcaataccctcccttacaccttcggtcagg<br>gaaccaagctcgaaatcaagcaccatcaccatcatcatcaccac |
| 100798<br>CAR8-<br>Soluble<br>scFv-aa | 71 | **MALPVTALLLPLALLLHAARP**qvqlqesgpglvkpsetlsltctvsgvslpdygvs<br>wirqppgkglewigviwgsettyyqsslksrvtiskdnsknqvslklssvtaadta<br>vyycakhyyyggsyamdywgqgtlvtvssggggsggggsggggsggggseivmtqs<br>patlslspgeratlscrasqdiskylnwyqqkpgqaprlliyhtsrlhsgiparfs<br>gsgsgtdytltisslqpedfavyfcqqgntlpytfgqgtkleik**hhhhhhhh** |
| 104882<br>CAR 8-<br>Full-nt | 97 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactatcaatcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccggaggcggtgggtcagaaatcgtgatgacccagagc<br>cctgcaaccctgtccctttctcccggggaacgggctaccctttcttgtcgggcatc<br>acaagatatctcaaaatacctcaattggtatcaacagaagccgggacaggccccta<br>ggcttcttatctaccacacctctcgcctgcatagcgggattcccgcacgctttagc<br>gggtctggaagcgggaccgactacactctgaccatctcatctctccagcccgagga<br>cttcgccgtctacttctgccagcagggtaacaccctgccgtacaccttcggccagg<br>gcaccaagcttgagatcaaaaccactactcccgctccaaggccacccacccctgcc<br>ccgaccatcgcctctcagccgctttccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 104882<br>CAR 8-<br>Full-aa | 84 | MALPVTALLLPLALLLHAARPqvqlqesgpglvkpsetlsltctvsgvslp**dygvs**<br>wirqppgkglewig**viwgsettyygsslks**rvtiskdnsknqvslklssvtaadta<br>vyycak**hyyyggsyamdy**wgqgtivtvssggggsggggsggggsggggseivmtqs<br>patlslspgeratlsc**rasqdiskyln**wyqqkpgqaprlliy**htsrlhs**giparfs<br>gsgsgtdytltisslqpedfavyfc**qqgntlpyt**fgqgtkleiktttpaprpptpa<br>ptiasqplslrpeacrpaaggavhtrgldfacdiyiwaplagtcgvlllslvitly<br>ckrgrkkllyifkqpfmrpvqttgeedgcscrfpeeeeggcelrvkfsrsadapay<br>kqgqnqlynelnlgrreeydvldkrrgrdpemggkprrknpqeglynelqkdkmae<br>ayseigmkgerrrgkghdglyqglstatkdtydalhmqalppr |
| CAR 9 | | |
| CAR9 scFv<br>domain | 47 | eivmtqspatlslspgeratlscrasqdiskylnwyqqkpgqaprlliyhtsrlhs<br>giparfsgsgsgtdytltisslqpedfavyfcqqgntlpytfgqgtkleikggggs<br>ggggsggggsggggsqvqlqesgpglvkpsetlsltctvsgvslpdygvswirqpp<br>gkglewigviwgsettyynsslksrvtiskdnsknqvslklssvtaadtavyycak<br>hyyyggsyamdywgqgtlvtvss |
| 99789<br>CAR9-<br>Soluble<br>scFv-nt | 60 | atggccctcccagtgaccgctctgctgctgcctctcgcacttcttctccatgccgc<br>tcggcctgagatcgtcatgacccaaagccccgctaccctgtccctgtcacccggcg<br>agagggcaaccctttcatgcagggccagccaggacatttctaagtacctcaactgg<br>tatcagcagaagccagggcaggctcctcgcctgctgatctaccacaccagccgcct<br>ccacagcggtatccccgccagattttccgggagcgggtctggaaccgactacaccc<br>tcaccatctcttctctgcagcccgaggatttcgccgtctatttctgccagcagggg<br>aatactctgccgtacaccttcggtcaaggtaccaagctggaaatcaagggaggcgg<br>aggatcaggcggtggcggaagcggaggaggtggctccggaggaggaggttcccaag<br>tgcagcttcaagaatcaggacccggacttgtgaagccatcagaaaccctctccctg<br>acttgtaccgtgtccggtgtgagcctccccgactacggagtctcttggattcgcca<br>gcctccggggaagggtcttgaatggattggggtgatttggggatcagagactactt<br>actacaattcatcacttaagtcacgggtcaccatcagcaaagataatagcaagaac |

TABLE 3-continued

| CD19 CAR Constructs | | |
|---|---|---|
| Name | SEQ ID | Sequence |
| | | caagtgtcacttaagctgtcatctgtgaccgccgctgacaccgccgtgtactattg<br>tgccaaacattactattacggagggtcttatgctatggactactggggacagggga<br>ccctggtgactgtctctagccatcaccatcaccaccatcatcac |
| 99789<br>CAR9-<br>Soluble<br>scFv-aa | 72 | **MALPVTALLLPLALLLHAARP**eivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsggggsqvqlqesgpglvkpsetlsl<br>tctvsgvslpdygvswirqppgkglewigviwgsettyynsslksrvtiskdnskn<br>qvslklssvtaadtavyycakhyyyggsyamdywgqgtlvtvss**hhhhhhhh** |
| 105974<br>CAR 9-<br>Full-nt | 98 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagcggaggcggtgggagccagg<br>tccaactccaagaaagcggaccgggtcttgtgaagccatcagaaactctttcactg<br>acttgtactgtgagcggagtgtctctccccgattacggggtgtcttggatcagaca<br>gccaccggggaagggtctggaatggattggagtgatttggggctctgagactactt<br>actacaactcatccctcaagtcacgcgtcaccatctcaaaggacaactctaagaat<br>caggtgtcactgaaactgtcatctgtgaccgcagccgacaccgccgtgtactattg<br>cgctaagcattactattatggcgggagctacgcaatggattactggggacagggta<br>ctctggtcaccgtgtccagcaccactaccccagcaccgaggccacccaccccggct<br>cctaccatcgcctcccagcctctgtccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 105974<br>CAR 9-<br>Full-aa | 85 | MALPVTALLLPLALLLHAARPeivmtqspatlslspgeratlsc**rasgdiskyln**w<br>yqqkpgqaprlliy**htsrlhs**giparfsgsgsgtdytltisslqpedfavyfc**qqg**<br>**ntlpyt**fgqgtkleikggggsggggsggggsggggsqvqlqesgpglvkpsetlsl<br>tctvsgvslp**dygvs**wirqppgkglewig**viwgsettyynsslks**rvtiskdnskn<br>qvslklssvtaadtavyycak**hyyyggsyamdy**wgqgtivtvssttpaprpptpa<br>ptiasqplslrpeacrpaaggavhtrgldfacdiyiwaplagtcgvlllslvitly<br>ckrgrkkllyifkqpfmrpvqttgeedgcscrfpeeeeggcelrvkfsrsadapay<br>kqgqnqlynelnlgrreeydvldkrrgrdpemggkprrknpqeglynelqkdkmae<br>ayseigmkgerrrgkghdglyqglstatkdtydalhmqalppr |
| CAR10 | | |
| CAR10<br>scFv<br>domain | 48 | qvqlqesgpglvkpsetlsltctvsgvslpdygvswirqppgkglewigviwgset<br>tyynsslksrvtiskdnsknqvslklssvtaadtavyycakhyyyggsyamdywgq<br>gtivtvssggggsggggsggggsggggseivmtqspatlslspgeratlscrasqd<br>iskylnwyqqkpgqaprlliyhtsrlhsgiparfsgsgsgtdytltisslqpedfa<br>vyfcqqgntlpytfgqgtkleik |
| 100796<br>CAR10-<br>Soluble<br>scFv-nt | 61 | atggcactgcctgtcactgccctcctgctgcctctggccctccttctgcatgccgc<br>caggccccaagtccagctgcaagagtcaggacccggactggtgaagccgtctgaga<br>ctctctcactgacttgtaccgtcagcggcgtgtccctccccgactacggagtgtca<br>tggatccgccaacctcccgggaaagggcttgaatggattggtgtcatctggggttc<br>tgaaaccacctactacaactcttccctgaagtccagggtgaccatcagcaaggata<br>attccaagaaccaggtcagccttaagctgtcatctgtgaccgctgctgacaccgcc<br>gtgtattactgcgccaagcactactattacggaggaagctacgctatggactattg<br>gggacagggcactctcgtgactgtgagcagcggcggtggagggtctggaggtggag<br>gatccggtggtggtgggtcaggcggaggagggagcgagattgtgatgactcagtca<br>ccagccaccctttctctttcacccggcgagagagcaaccctgagctgtagagccag<br>ccaggacatttctaagtacctcaactggtatcagcaaaaaccggggcaggcccctc<br>gcctcctgatctaccatacctcacgccttcactctggtatccccgctcggtttagc<br>ggatcaggatctggtaccgactacactctgaccatttccagcctgcagccagaaga<br>tttcgcagtgtatttctgccagcagggcaatacccttccttacaccttcggtcagg<br>gaaccaagctcgaaatcaagcaccatcaccatcatcaccaccat |
| 100796<br>CVOR10 -<br>Soluble<br>scFv-aa | 73 | **MALPVTALLLPLALLLHAARP**qvqlqesgpglvkpsetlsltctvsgvslpdygvs<br>wirqppgkglewigviwgsettyynsslksrvtiskdnsknqvslklssvtaadta<br>vyycakhyyyggsyamdywgqgtivtvssggggsggggsggggsggggseivmtqs<br>patlslspgeratlscrasqdiskylnwyqqkpgqaprlliyhtsrlhsgiparfs<br>gsgsgtdytltisslqpedfavyfcqqgntlpytfgqgtkleik**hhhhhhhh** |

TABLE 3-continued

CD19 CAR Constructs

| Name | SEQ ID | Sequence |
|---|---|---|
| 105975<br>CAR 10<br>Full-nt | 99 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagcggaggcggtgggagccagg<br>tccaactccaagaaagcggaccgggtcttgtgaagccatcagaaactctttcactg<br>acttgtactgtgagcggagtgtctctccccgattacggggtgtcttggatcagaca<br>gccaccggggaagggtctggaatggattggagtgatttggggctctgagactactt<br>actacaactcatccctcaagtcacgcgtcaccatctcaaaggacaactctaagaat<br>caggtgtcactgaaactgtcatctgtgaccgcagccgacaccgccgtgtactattg<br>cgctaagcattactattatggcgggagctacgcaatggattactggggacagggta<br>ctctggtcaccgtgtccagcaccactaccccagcaccgaggccacccaccccggct<br>cctaccatcgcctcccagcctctgtccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 105975<br>CAR 10<br>Full-aa | 86 | MALPVTALLLPLALLLHAARPEIVMTQSPATLSLSPGERATLSC**RASQDISKYLN**W<br>YQQKPGQAPRLLIY**HTSRLHS**GIPARFSGSGSGTDYTLTISSLQPEDFAVYFC**QQG**<br>**NTLPYT**FGQGTKLEIKGGGGSGGGGSGGGGSGGGGSQVQLQESGPGLVKPSETLSL<br>TCTVSGVSLP**DYGVS**WIRQPPGKGLEWIG**VIWGSETTYYNSSLKS**RVTISKDNSKN<br>QVSLKLSSVTAADTAVYYCAK**HYYYGGSYAMDY**WGQGTLVTVSSTTTPAPRPPTPA<br>PTIASQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSADAPAY<br>KQGQNQLYNELNLGRREEYDVLDKRRGRDPEMGGKPRRKNPQEGLYNELQKDKMAE<br>AYSEIGMKGERRRGKGHDGLYQGLSTATKDTYDALHMQALPPR |
| CAR11 | | |
| CAR11<br>scFv<br>domain | 49 | eivmtqspatlslspgeratlscrasqdiskylnwyqqkpgqaprlliyhtsrlhs<br>giparfsgsgsgtdytltisslqpedfavyfcqqgntlpytfgqgtkleikggggs<br>ggggsggggsqvqlqesgpglvkpsetlsltctvsgvslpdygvswirqppgkgle<br>wigviwgsettyynsslksrvtiskdnsknqvslklssvtaadtavyycakhyyyg<br>gsyamdywgqgtlvtvss |
| 103101<br>CAR11-<br>Soluble<br>scFv-nt | 62 | Atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttggggctctgagactacttactacaattcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagccaccaccatcatcaccatcaccat |
| 103101<br>CAR11-<br>Soluble<br>scFv-aa | 74 | **MALPVTALLLPLALLLHAARP**eivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsqvqlqesgpglvkpsetlsltctvs<br>gvslpdygvswirqppgkglewigviwgsettyynsslksrvtiskdnsknqvslk<br>lssvtaadtavyycakhyyyggsyamdywgqgtlvtvss**hhhhhhhh** |
| 105976<br>CAR 11<br>Full-nt | 100 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactataactcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg |

TABLE 3-continued

CD19 CAR Constructs

| Name | SEQ ID | Sequence |
|---|---|---|
| | | gggccagggaactctggtcactgtgtcatctggtggaggaggtagcggaggaggcg<br>ggagcggtggaggtggctccggaggtggcggaagcgaaatcgtgatgacccagagc<br>cctgcaaccctgtccctttctcccggggaacgggctaccctttcttgtcgggcatc<br>acaagatatctcaaaatacctcaattggtatcaacagaagccgggacaggcccta<br>ggcttcttatctaccacacctctcgcctgcatagcgggattcccgcacgctttagc<br>gggtctggaagcgggaccgactacactctgaccatctcatctctccagcccgagga<br>cttcgccgtctacttctgccagcagggtaacaccctgccgtacaccttcggccagg<br>gcaccaagcttgagatcaaaaccactactcccgctccaaggccacccacccctgcc<br>ccgaccatcgcctctcagccgctttccctgcgtccggaggcatgtagacccgcagc<br>tggtggggccgtgcatacccggggtcttgacttcgcctgcgatatctacatttggg<br>cccctctggctggtacttgcggggtcctgctgctttcactcgtgatcactctttac<br>tgtaagcgcggtcggaagaagctgctgtacatctttaagcaacccttcatgaggcc<br>tgtgcagactactcaagaggaggacggctgttcatgccggttcccagaggaggagg<br>aaggcggctgcgaactgcgcgtgaaattcagccgcagcgcagatgctccagcctac<br>aagcaggggcagaaccagctctacaacgaactcaatcttggtcggagagaggagta<br>cgacgtgctggacaagcggagaggacgggacccagaaatgggcgggaagccgcgca<br>gaaagaatccccaagagggcctgtacaacgagctccaaaaggataagatggcagaa<br>gcctatagcgagattggtatgaaaggggaacgcagaagaggcaaaggccacgacgg<br>actgtaccagggactcagcaccgccaccaaggacacctatgacgctcttcacatgc<br>aggccctgccgcctcgg |
| 105976<br>CAR 11<br>Full-aa | 87 | MALPVTALLLPLALLLRAARPQVQLQESGPGLVKPSETLSLTCTVSGVSLP**DYGVS**<br>WIRQPPGKGLEWIG**VIWGSETTYYNSSLKS**RVTISKDNSKNQVSLKLSSVTAADTA<br>VYYCAK**HYYYGGSYAMDY**WGQGTLVTVSSGGGGSGGGGSGGGGSGGGGSEIVMTQS<br>PATLSLSPGERATLSCR**ASQDISKYLN**WYQQKPGQAPRLLIY**HTSRLHS**GIPARFS<br>GSGSGTDYTLTISSLQPEDFAVYFC**QQGNTLPYT**FGQGTKLEIKTTTPAPRPPTPA<br>PTIASQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSADAPAY<br>KQGQNQLYNELNLGRREEYDVLDKRRGRDPEMGGKPRRKNPQEGLYNELQKDKMAE<br>AYSEIGMKGERRRGKGHDGLYQGLSTATKDTYDALHMQALPPR |
| CAR12 | | |
| CAR12<br>scFv<br>domain | 50 | qvqlqesgpglvkpsetlsltctvsgvslpdygvswirqppgkglewigviwgset<br>tyynsslksrvtiskdnsknqvslklssvtaadtavyycakhyyyggsyamdywgq<br>gtivtvssggggsggggsggggseivmtqspatlslspgeratlscrasqdiskyl<br>nwyqqkpgqaprlliyhtsrlhsgiparfsgsgsgtdytltisslqpedfavyfcq<br>qgntlpytfgqgtkleik |
| 103104<br>CAR12 -<br>Soluble<br>scFv-nt | 63 | atggctctgcccgtgaccgcactcctcctgccactggctctgctgcttcacgccgc<br>tcgcccacaagtccagcttcaagaatcagggcctggtctggtgaagccatctgaga<br>ctctgtccctcacttgcaccgtgagcggagtgtccctcccagactacggagtgagc<br>tggattagacagcctcccggaaagggactggagtggatcggagtgatttggggtag<br>cgaaaccacttactataactcttccctgaagtcacgggtcaccatttcaaaggata<br>actcaaagaatcaagtgagcctcaagctctcatcagtcaccgccgctgacaccgcc<br>gtgtattactgtgccaagcattactactatggagggtcctacgccatggactactg<br>gggccagggaactctggtcactgtgtcatctggtggaggaggtagcggaggaggcg<br>ggagcggtggaggtggctccgaaatcgtgatgacccagagccctgcaaccctgtcc<br>ctttctcccggggaacgggctaccctttcttgtcgggcatcacaagatatctcaaa<br>atacctcaattggtatcaacagaagccgggacaggcccctaggcttcttatctacc<br>acacctctcgcctgcatagcgggattcccgcacgctttagcgggtctggaagcggg<br>accgactacactctgaccatctcatctctccagcccgaggacttcgccgtctactt<br>ctgccagcagggtaacaccctgccgtacaccttcggccagggcaccaagcttgaga<br>tcaaacatcaccaccatcatcaccatcac |
| 103104<br>CAR12 -<br>Soluble<br>scFv -aa | 75 | **MALPVTALLLPLALLLHAARP**qvqlqesgpglvkpsetlsltctvsgvslpdygys<br>wirqppgkglewigviwgsettyynsslksrvtiskdnsknqvslklssvtaadta<br>vyycakhyyyggsyamdywgqgtlvtvssggggsggggsggggseivmtqspatls<br>lspgeratlscrasqdiskylnwyqqkpgqaprlliyhtsrlhsgiparfsgsgsg<br>tdytltisslqpedfavyfcqqgntlpytfgqgtkleik**hhhhhhhh** |
| 105977<br>CAR 12-<br>Full-nt | 101 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaaataccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacaccctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttggggctctgagactacttactacaactcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagcaccactaccccagcaccgaggccacccaccccggctcctaccatcgcctcc |

TABLE 3-continued

CD19 CAR Constructs

| Name | SEQ ID | Sequence |
|---|---|---|
| | | cagcctctgtccctgcgtccggaggcatgtagacccgcagctggtggggccgtgca<br>tacccggggtcttgacttcgcctgcgatatctacatttgggcccctctggctggta<br>cttgcggggtcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaaggggaacgcagaagaggcaaaggccacgacggactgtaccagggact<br>cagcaccgccaccaaggacacctatgacgctcttcacatgcaggccctgccgcctc<br>gg |
| 105977 CAR 12-Full-aa | 88 | MALPVTALLLPLALLLHAARPEIVMTQSPATLSLSPGERATLSC**RASQDISKYLN**W<br>YQQKPGQAPRLLIY**HTSRLHS**GIPARFSGSGSGTDYTLTISSLQPEDFAVYFC**QQG**<br>**NTLPYT**FGQGTKLEIKGGGGSGGGGSGGGGSQVQLQESGPGLVKPSETLSLTCTVS<br>GVSLP**DYGVS**WIRQPPGKGLEWIG**VIWGSETTYYNSSLKS**RVTISKDNSKNQVSLK<br>LSSVTAADTAVYYCAK**HYYYGGSYAMDY**WGQGTLVTVSSTTTPAPRPPTPAPTIAS<br>QPLSLRPEACRPAAGGAVHTRGLDFACDIYIWAPLAGTCGVLLLSLVITLYCKRGR<br>KKLLYIFKQPFMRPVQTTQEEDGCSCRFPEEEEGGCELRVKFSRSADAPAYKQGQN<br>QLYNELNLGRREEYDVLDKRRGRDPEMGGKPRRKNPQEGLYNELQKDKMAEAYSEI<br>GMKGERRRGKGHDGLYQGLSTATKDTYDALHMQALPPR |
| CTL019 | | |
| CTL019-Soluble scFv-Histag-nt | 22 | atggccctgcccgtcaccgctctgctgctgccccttgctctgcttcttcatgcagc<br>aaggccggacatccagatgacccaaaccacctcatccctctctgcctctcttggag<br>acagggtgaccatttcttgtcgcgccagccaggacatcagcaagtatctgaactgg<br>tatcagcagaagccggacggaaccgtgaagctcctgatctaccatacctctcgcct<br>gcatagcggcgtgccctcacgcttctctggaagcggatcaggaaccgattattctc<br>tcactatttcaaatcttgagcaggaagatattgccacctatttctgccagcagggt<br>aataccctgccctacaccttcggaggagggaccaagctcgaaatcaccggtggagg<br>aggcagcggcggtggagggtctggtggaggtggttctgaggtgaagctgcaagaat<br>caggccctggacttgtggccccttcacagtccctgagcgtgacttgcaccgtgtcc<br>ggagtctccctgcccgactacggagtgtcatggatcagacaacctccacggaaagg<br>actggaatggctcggtgtcatctggggtagcgaaactacttactacaattcagccc<br>tcaaaagcaggctgactattatcaaggacaacagcaagtcccaagtctttcttaag<br>atgaactcactccagactgacgacaccgcaatctactattgtgctaagcactacta<br>ctacggaggatcctacgctatggattactggggacaaggtacttccgtcactgtct<br>cttcacaccatcatcaccatcaccatcac |
| CTL019-Soluble scFv-Histag- | 76 | **MALPVTALLLPLALLLHAARP**diqmtqttsslsaslgdrvtiscrasqdiskylnw<br>yqqkpdgtvklliyhtsrlhsgvpsrfsgsgsgtdysltisnleqediatyfcqqg<br>ntlpytfgggtkleitggggsggggsggggsevklqesgpglvapsqslsvtctvs<br>gvslpdygvswirqpprkglewlgviwgsettyynsalksrltiikdnsksqvflk<br>mnslqtddtaiyycakhyyyggsyamdywgqgtsvtvss**hhhhhhhh** |
| CTL019 Full-nt | 102 | atggccttaccagtgaccgccttgctcctgccgctggccttgctgctccacgccgc<br>caggccggacatccagatgacacagactacatcctccctgtctgcctctctgggag<br>acagagtcaccatcagttgcagggcaagtcaggacattagtaaatatttaaattgg<br>tatcagcagaaaccagatggaactgttaaactcctgatctaccatacatcaagatt<br>acactcaggagtcccatcaaggttcagtggcagtgggtctggaacagattattctc<br>tcaccattagcaacctggagcaagaagatattgccacttacttttgccaacagggt<br>aatacgcttccgtacacgttcggaggggggaccaagctggagatcacaggtggcgg<br>tggctcgggcggtggtgggtcgggtggcggcggatctgaggtgaaactgcaggagt<br>caggacctggcctggtggcgccctcacagagcctgtccgtcacatgcactgtctca<br>ggggtctcattacccgactatggtgtaagctggattcgccagcctccacgaaaggg<br>tctggagtggctgggagtaatatggggtagtgaaaccacatactataattcagctc<br>tcaaatccagactgaccatcatcaaggacaactccaagagccaagttttcttaaaa<br>atgaacagtctgcaaactgatgacacagccatttactactgtgccaaacattatta<br>ctacggtggtagctatgctatggactactggggccaaggaacctcagtcaccgtct<br>cctcaaccacgacgccagcgccgcgaccaccaacaccggcgcccaccatcgcgtcg<br>cagcccctgtccctgcgcccagaggcgtgccggccagcggcgggggggcgcagtgca<br>cacgagggggctggacttcgcctgtgatatctacatctgggcgcccttggccggga<br>cttgtggggtccttctcctgtcactggttatcaccctttactgcaaacggggcaga<br>aagaaactcctgtatatattcaaacaaccatttatgagaccagtacaaactactca<br>agaggaagatggctgtagctgccgatttccagaagaagaagaaggaggatgtgaac<br>tgagagtgaagttcagcaggagcgcagacgcccccgcgtacaagcagggccagaac<br>cagctctataacgagctcaatctaggacgaagagaggagtacgatgttttggacaa<br>gagacgtggccgggaccctgagatggggggaaagccgagaaggaagaaccctcagg<br>aaggcctgtacaatgaactgcagaaagataagatggcggaggcctacagtgagatt<br>gggatgaaaggcgagcgccggaggggcaaggggcacgatggcctttaccagggtct<br>cagtacagccaccaaggacacctacgacgcccttcacatgcaggccctgccccctc<br>gc |

TABLE 3-continued

| CD19 CAR Constructs | | |
|---|---|---|
| Name | SEQ ID | Sequence |
| CTL019 Full-aa | 89 | MALPVTALLLPLALLLHAARPdiqmtqttsslsaslgdrvtiscrasqdiskylnw yqqkpdgtvklliyhtsrlhsgvpsrfsgsgsgtdysltisnleqediatyfcqqg ntlpytfgggtkleitggggsggggsggggsevklqesgpglvapsqslsvtctvs gvslpdygvswirqpprkglewlgviwgsettyynsalksrltiikdnsksqvflk mnslqtddtaiyycakhyyyggsyamdywgqgtsvtvsstttpaprpptpaptias qplslrpeacrpaaggavhtrgldfacdiyiwaplagtcgvlllslvitlyckrgr kkllyifkqpfmrpvqttgeedgcscrfpeeeeggcelrvkfsrsadapaykqgqn qlynelnlgrreeydvldkrrgrdpemggkprrknpqeglynelqkdkmaeaysei gmkgerrrgkghdglyqglstatkdtydalhmqalppr |
| CTL019 scFv domain | 51 | diqmtqttsslsaslgdrvtiscrasqdiskylnwyqqkpdgtvklliyhtsrlhs gvpsrfsgsgsgtdysltisnleqediatyfcqqgntlpytfgggtkleitggggs ggggsggggsevklqesgpglvapsqslsvtctvsgvslpdygvswirqpprkgle wlgviwgsettyynsalksrltiikdnsksqvflkmnslqtddtaiyycakhyyyg gsyamdywgqgtsvtvss |

Co-Expression of CAR with Other Molecules or Agents

Co-Expression of a Second CAR

In one aspect, the CAR-expressing cell described herein can further comprise a second CAR, e.g., a second CAR that includes a different antigen binding domain, e.g., to the same target (e.g., CD19) or a different target (e.g., a target other than CD19, e.g., a target described herein). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, e.g., 4-1BB, CD28, CD27, OX-40 or ICOS, onto the first CAR, and the primary signaling domain, e.g., CD3 zeta, on the second CAR can limit the CAR activity to cells where both targets are expressed. In one embodiment, the CAR expressing cell comprises a first CAR that includes an antigen binding domain, a transmembrane domain and a costimulatory domain and a second CAR that targets another antigen and includes an antigen binding domain, a transmembrane domain and a primary signaling domain. In another embodiment, the CAR expressing cell comprises a first CAR that includes an antigen binding domain, a transmembrane domain and a primary signaling domain and a second CAR that targets another antigen and includes an antigen binding domain to the antigen, a transmembrane domain and a costimulatory signaling domain.

In one embodiment, the CAR-expressing cell comprises an XCAR described herein and an inhibitory CAR. In one embodiment, the inhibitory CAR comprises an antigen binding domain that binds an antigen found on normal cells but not cancer cells, e.g., normal cells that also express X. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (CEACAM-1, CEACAM-3, and/or CEACAM-5), LAGS, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR (e.g., TGFRbeta).

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids. In an embodiment the antigen binding domain of one of the first and the second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, a composition herein comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, e.g., a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and the second CAR comprises an scFv, and the other comprises a single VH domain, e.g., a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is at least 85%, 90%, 95%, 96%, 97%, 98% or 99%, e.g., 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another at least 85%, 90%, 95%, 96%, 97%, 98% or 99% less than, e.g., 85%, 90%, 95%, 96%, 97%, 98% or 99% less than if both were scFv antigen binding domains.

Co-Expression of an Agent that Enhances CAR Activity

In another aspect, the CAR-expressing cell described herein can further express another agent, e.g., an agent that enhances the activity or fitness of a CAR-expressing cell.

For example, in one embodiment, the agent can be an agent which inhibits a molecule that modulates or regulates, e.g., inhibits, T cell function. In some embodiments, the molecule that modulates or regulates T cell function is an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta.

In embodiments, an agent, e.g., an inhibitory nucleic acid, e.g., a dsRNA, e.g., an siRNA or shRNA; or e.g., an inhibitory protein or system, e.g., a clustered regularly interspaced short palindromic repeats (CRISPR), a transcription-activator like effector nuclease (TALEN), or a zinc finger endonuclease (ZFN), e.g., as described herein, can be used to inhibit expression of a molecule that modulates or regulates, e.g., inhibits, T-cell function in the CAR-expressing cell. In an embodiment the agent is an shRNA, e.g., an shRNA described herein. In an embodiment, the agent that modulates or regulates, e.g., inhibits, T-cell function is inhibited within a CAR-expressing cell. For example, a dsRNA molecule that inhibits expression of a molecule that modulates or regulates, e.g., inhibits, T-cell function is linked to the nucleic acid that encodes a component, e.g., all of the components, of the CAR.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with an XCAR described herein, improves the persistence of the T cell. In one embodiment, the CAR is a PD1 CAR comprising the extracellular domain of PD1 indicated as underlined in SEQ ID NO: 105. In one embodiment, the PD1 CAR comprises the amino acid sequence of SEQ ID NO:105.

(SEQ ID NO: 105)

Malpvtalllplalllhaarppgwfldspdrpwnpptfspallvvtegd
natftcsfsntsesfvlnwyrmspsnqtdklaafpedrsqpgqdcrfrv
tqlpngrdfhmsvvrarrndsgtylcgaislapkaqikeslraelrvte
rraevptahpspsprpsgqfqtlvtttpaprpptpaptiasqplslrpe
acrpaaggavhtrgldfacdiyiwaplagtcgvlllslvitlyckrgrk
kllyifkqpfmrpvqttqeedgcscrfpeeeeggcelrvkfsrsadapa
ykqgqnqlynelnlgreeydvldkrrgrdpemggkpffknpqeglyne
lqkdkmaeayseigmkgerrrgkghdglyqglstatkdtydalhmqalp
pr.

In one embodiment, the PD1 CAR comprises the amino acid sequence provided below (SEQ ID NO:106).

(SEQ ID NO: 106)

pgwfldspdrpwnpptfspallvvtegdnatftcsfsntsesfylnwyrm
spsnqtdklaafpedrsqpgqdcrfrvtqlpngrdfhmsvvrarrndsgt
ylcgaislapkaqikeslraelryterraevptahpspsprpagqfqtlv
tttpaprpptpaptiasqplslrpeacrpaaggavhtrgldfacdiyiwa
plagtcgvillslvidycicrgrkkllyiflcqpfmrpvqttqeedgcsc
rfpeeeeggcelrvkfsrsadapaykqgqnqlynelnlgrreeydvldkr
rgrdpemggkprrknpqeglynelqkdkmaeayseigmkgerrrgkghdg
lyqglstatkdtydalhmqalppr.

In one embodiment, the agent comprises a nucleic acid sequence encoding the PD1 CAR, e.g., the PD1 CAR described herein. In one embodiment, the nucleic acid sequence for the PD1 CAR is shown below, with the PD1 ECD underlined below in SEQ ID NO: 107

(SEQ ID NO: 107)

atggccctccctgtcactgccctgcttctccccctcgcactcctgctcca
cgccgctagaccacccggatggtttctggactctccggatcgcccgtgga
atcccccaaccttctcaccggcactcttggttgtgactgagggcgataat
gcgaccttcacgtgctcgttctccaacacctccgaatcattcgtgctgaa
ctggtaccgcatgagcccgtcaaaccagaccgacaagctcgccgcgtttc
cggaagatcggtcgcaaccgggacaggattgtcggttccgcgtgactcaa
ctgccgaatggcagagacttccacatgagcgtggtccgcgctaggcgaaa
cgactccgggacctacctgtgcggagccatctcgctggcgcctaaggccc
aaatcaaagagagcttgagggccgaactgagagtgaccgagcgcagagct
gaggtgccaactgcacatccatccccatcgcctcggcctgcggggcagtt -continued tcagaccctggtcacgaccactccggcgccgcgcccaccgactccggccc
caactatcgcgagccagcccctgtcgctgaggccggaagcatgccgccct
gccgccggaggtgctgtgcatacccggggattggacttcgcatgcgacat
ctacatttgggctcctctcgccggaacttgtggcgtgctccttctgtccc
tggtcatcaccctgtactgcaagcggggtcggaaaaagcttctgtacatt
ttcaagcagcccttcatgaggcccgtgcaaaccacccaggaggaggacgg
ttgctcctgccggttccccgaagaggaagaaggaggttgcgagctgcgcg
tgaagttctcccggagcgccgacgcccccgcctataagcagggccagaac
cagctgtacaacgaactgaacctgggacggcgggaagagtacgatgtgct
ggacaagcggcgcggccgggaccccgaaatgggcgggaagcctagaagaa
agaaccctcaggaaggcctgtataacgagctgcagaaggacaagatggcc
gaggcctactccgaaattgggatgaagggagagcggcggaggggaaaggg
gcacgacggcctgtaccaaggactgtccaccgccaccaaggacacatacg
atgccctgcacatgcaggcccttccccctcgc.

In another example, in one embodiment, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, e.g., as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In an embodiment, the costimulatory molecule ligand is 4-1BBL. In an embodiment, the costimulatory ligand is CD80 or CD86. In an embodiment, the costimulatory molecule ligand is CD70. In embodiments, a CAR-expressing immune effector cell described herein can be further engineered to express one or more additional costimulatory molecules or costimulatory molecule ligands.

Co-Expression of CAR with a Chemokine Receptor

In embodiments, the CAR-expressing cell described herein, e.g., CD19 CAR-expressing cell, further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., *J Immunother.* 2010 October; 33(8):780-8 and Kershaw et al., *Hum Gene Ther.* 2002 Nov. 1; 13(16):1971-80). Thus, without wishing to be bound by theory, it is believed that chemokine receptors expressed in CAR-expressing cells that recognize chemokines secreted by tumors, e.g., solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell (e.g., CAR-Tx) described herein include a CXC chemokine receptor (e.g., CXCR1, CXCR2, CXCR3, CXCR4, CXCR5, CXCR6, or CXCR7), a CC chemokine receptor (e.g., CCR1, CCR2, CCR3, CCR4, CCR5, CCR6, CCR7, CCR8, CCR9, CCR10, or CCR11), a CX3C chemokine receptor (e.g., CX3CR1), a XC chemokine receptor (e.g., XCR1), or a chemokine-binding fragment thereof. In one embodiment, the chemokine receptor molecule to be expressed with a CAR described herein is selected based on the chemokine(s) secreted by the tumor. In one embodiment, the CAR-expressing cell described herein further comprises, e.g., expresses, a CCR2b receptor or a CXCR2 receptor. In an embodiment, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Nucleic Acid Constructs Encoding a CAR

The present invention also provides an immune effector cell, e.g., made by a method described herein, that includes a nucleic acid molecules encoding one or more CAR constructs described herein. In one aspect, the nucleic acid molecule is provided as a messenger RNA transcript. In one aspect, the nucleic acid molecule is provided as a DNA construct.

The nucleic acid molecules described herein can be a DNA molecule, an RNA molecule, or a combination thereof. In one embodiment, the nucleic acid molecule is an mRNA encoding a CAR polypeptide as described herein. In other embodiments, the nucleic acid molecule is a vector that includes any of the aforesaid nucleic acid molecules.

In one aspect, the antigen binding domain of a CAR of the invention (e.g., a scFv) is encoded by a nucleic acid molecule whose sequence has been codon optimized for expression in a mammalian cell. In one aspect, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

Accordingly, in one aspect, an immune effector cell, e.g., made by a method described herein, includes a nucleic acid molecule encoding a chimeric antigen receptor (CAR), wherein the CAR comprises an antigen binding domain that binds to a tumor antigen described herein, a transmembrane domain (e.g., a transmembrane domain described herein), and an intracellular signaling domain (e.g., an intracellular signaling domain described herein) comprising a stimulatory domain, e.g., a costimulatory signaling domain (e.g., a costimulatory signaling domain described herein) and/or a primary signaling domain (e.g., a primary signaling domain described herein, e.g., a zeta chain described herein).

The present invention also provides vectors in which a nucleic acid molecule encoding a CAR, e.g., a nucleic acid molecule described herein, is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR encoding nucleic acid molecule in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from nucleic acid molecules cloned into a lentiviral vector. See, e.g., Milone et al., Mol. Ther. 17(8): 1453-1464 (2009). In one aspect, the EF1a promoter comprises the sequence provided in the Examples.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired.

The nucleotide sequences of exemplary PGK promoters are provided below.

```
WT PGK Promoter:
                                              (SEQ ID NO: 109)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT

Exemplary truncated PGK Promoters:
PGK100:
                                              (SEQ ID NO: 110)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK200:
                                              (SEQ ID NO: 111)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:
                                              (SEQ ID NO: 112)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG

PGK400:
                                              (SEQ ID NO: 113)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC
```

-continued

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In embodiments, the vector may comprise two or more nucleic acid sequences encoding a CAR, e.g., a CAR described herein, e.g., a CD19 CAR, and a second CAR, e.g., an inhibitory CAR or a CAR that specifically binds to an antigen other than CD19. In such embodiments, the two or more nucleic acid sequences encoding the CAR are encoded by a single nucleic molecule in the same frame and as a single polypeptide chain. In this aspect, the two or more CARs, can, e.g., be separated by one or more peptide cleavage sites. (e.g., an auto-cleavage site or a substrate for an intracellular protease). Examples of peptide cleavage sites include T2A, P2A, E2A, or F2A sites.

Methods of introducing and expressing genes into a cell are known in the art. In the context of an expression vector, the vector can be readily introduced into a host cell, e.g., mammalian, bacterial, yeast, or insect cell by any method, e.g., one known in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A suitable method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant nucleic acid sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

Strategies for Regulating Chimeric Antigen Receptors

In some embodiments, a regulatable CAR (RCAR) where the CAR activity can be controlled is desirable to optimize the safety and efficacy of a CAR therapy. There are many ways CAR activities can be regulated. For example, inducible apoptosis using, e.g., a caspase fused to a dimerization domain (see, e.g., Di Stasa et al., N Engl. J. Med. 2011 Nov. 3; 365(18):1673-1683), can be used as a safety switch in the CAR therapy of the instant invention. In one embodiment, the cells (e.g., T cells or NK cells) expressing a CAR of the present invention further comprise an inducible apoptosis switch, wherein a human caspase (e.g., caspase 9) or a modified version is fused to a modification of the human FKB protein that allows conditional dimerization. In the presence of a small molecule, such as a rapalog (e.g., AP 1903, AP20187), the inducible caspase (e.g., caspase 9) is activated and leads to the rapid apoptosis and death of the cells (e.g., T cells or NK cells) expressing a CAR of the present invention. Examples of a caspase-based inducible apoptosis switch (or one or more aspects of such a switch) have been described in, e.g., US2004040047; US20110286980; US20140255360; WO1997031899; WO2014151960; WO2014164348; WO2014197638; WO2014197638; all of which are incorporated by reference herein.

In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or complement-induced cell death. For example, CAR expressing cells described herein may also express a receptor capable of being targeted by an antibody or antibody fragment. Examples of such receptors include EpCAM, VEGFR, integrins (e.g., integrins $\alpha v\beta 3$, $\alpha 4$, $\alpha I3/4\beta 3$, $\alpha 4\beta 7$, $\alpha 5\beta 1$, $\alpha v\beta 3$, $\alpha v$), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11 a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain).

For example, a CAR-expressing cell described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8) 853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g., ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In other embodiments, a CAR-expressing cell described herein may also express a target protein recognized by the T cell depleting agent. In one embodiment, the target protein is CD20 and the T cell depleting agent is an anti-CD20 antibody, e.g., rituximab. In such embodiment, the T cell depleting agent is administered once it is desirable to reduce or eliminate the CAR-expressing cell, e.g., to mitigate the CAR induced toxicity. In other embodiments, the T cell depleting agent is an anti-CD52 antibody, e.g., alemtuzumab, as described in the Examples herein.

In other embodiments, an RCAR comprises a set of polypeptides, typically two in the simplest embodiments, in which the components of a standard CAR described herein, e.g., an antigen binding domain and an intracellular signalling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signalling domain. In one embodiment, a CAR of the present invention utilizes a dimerization switch as those described in, e.g., WO2014127261, which is incorporated by reference herein. Additional description and exemplary configurations of such regulatable CARs are provided herein and in, e.g., paragraphs 527-551 of International Publication No. WO 2015/090229 filed Mar. 13, 2015, which is incorporated by reference in its entirety. In some embodiments, an RCAR involves a switch domain, e.g., a FKBP switch domain, as set out SEQ ID NO: 114, or comprise a fragment of FKBP having the ability to bind with FRB, e.g., as set out in SEQ ID NO: 115. In some embodiments, the RCAR involves a switch domain comprising a FRB sequence, e.g., as set out in SEQ ID NO: 116, or a mutant FRB sequence, e.g., as set out in any of SEQ ID Nos. 117-122.

(SEQ ID NO: 114)
DVPDYASLGGPSSPKKKRKVSRGVQVETISPGDGRTFPKRGQTCVVHYTG

MLEDGKKFDSSRDRNKPFKFMLGKQEVIRGWEEGVAQMSVGQRAKLTISP

DYAYGATGHPGIIPPHATLVFDVELLKLETSY (SEQ ID NO: 115)
VQVETISPGDGRTFPKRGQTCVVHYTGMLEDGKKFDSSRDRNKPFKFMLG

KQEVIRGWEEGVAQMSVGQRAKLTISPDYAYGATGHPGIIPPHATLVFDV

ELLKLETS (SEQ ID NO: 116)
ILWHEMWHEGLEEASRLYFGERNVKGMFEVLEPLHAMMERGPQTLKETSF

NQAYGRDLMEAQEWCRKYMKSGNVKDLTQAWDLYYHVFRRISK

TABLE 4

Exemplary mutant FRB having increased affinity for a dimerization molecule.

| FRB mutant | Amino Acid Sequence | SEQ ID NO: |
|---|---|---|
| E20321 mutant | ILWHEMWHEGLIEASRLYFGERNVKGMFEVLEPLHAMMERGPQTLKETSFNQAYG RDLMEAQEWCRKYMKSGNVKDLTQAWDLYYHVFRRISKTS | 117 |
| E2032L mutant | ILWHEMWHEGLLEASRLYFGERNVKGMFEVLEPLHAMMERGPQTLKETSFNQAYG RDLMEAQEWCRKYMKSGNVKDLTQAWDLYYHVFRRISKTS | 118 |
| T2098L mutant | ILWHEMWHEGLEEASRLYFGERNVKGMFEVLEPLHAMMERGPQTLKETSFNQAYG RDLMEAQEWCRKYMKSGNVKDLLQAWDLYYHVFRRISKTS | 119 |
| E2032, T2098 mutant | ILWHEMWHEGL**X**EASRLYFGERNVKGMFEVLEPLHAMMERGPQTLKETSFNQAYG RDLMEAQEWCRKYMKSGNVKDL**X**QAWDLYYHVFRRISKTS | 120 |
| E2032I, T2098L mutant | ILWHEMWHEGLIEASRLYFGERNVKGMFEVLEPLHAMMERGPQTLKETSFNQAYG RDLMEAQEWCRKYMKSGNVKDLLQAWDLYYHVFRRISKTS | 121 |
| E2032L, T2098L mutant | ILWHEMWHEGLLEASRLYFGERNVKGMFEVLEPLHAMMERGPQTLKETSFNQAYG RDLMEAQEWCRKYMKSGNVKDLLQAWDLYYHVFRRISKTS | 122 |

RNA Transfection

Disclosed herein are methods for producing an in vitro transcribed RNA CAR. RNA CAR and methods of using the same are described, e.g., in paragraphs 553-570 of in International Application WO2015/142675, filed Mar. 13, 2015, which is herein incorporated by reference in its entirety.

An immune effector cell can include a CAR encoded by a messenger RNA (mRNA). In one aspect, the mRNA encoding a CAR described herein is introduced into an immune effector cell, e.g., made by a method described herein, for production of a CAR-expressing cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR described herein. For example, the template for the RNA CAR comprises an extracellular region comprising a single chain variable domain of an antibody to a tumor associated antigen described herein; a hinge region (e.g., a hinge region described herein), a transmembrane domain (e.g., a transmembrane domain described herein such as a transmembrane domain of CD8a); and a cytoplasmic region that includes an intracellular signaling domain, e.g., an intracellular signaling domain described herein, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA in embodiments has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In an embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (e.g., SEQ ID NO: 33).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In an embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1 (2011):R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013): 166; Williams. Molecular Therapy 16.9(2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3(2013): 1829-47; and Singh et al. Cancer Res. 68.8(2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Methods of Manufacture/Production

In some embodiments, the methods disclosed herein further include administering a T cell depleting agent after treatment with the cell (e.g., an immune effector cell as described herein), thereby reducing (e.g., depleting) the CAR-expressing cells (e.g., the CD19CAR-expressing cells). Such T cell depleting agents can be used to effectively deplete CAR-expressing cells (e.g., CD19CAR-expressing cells) to mitigate toxicity. In some embodiments, the CAR-expressing cells were manufactured according to a method herein, e.g., assayed (e.g., before or after transfection or transduction) according to a method herein.

In some embodiments, the T cell depleting agent is administered one, two, three, four, or five weeks after administration of the cell, e.g., the population of immune effector cells, described herein.

In one embodiment, the T cell depleting agent is an agent that depletes CAR-expressing cells, e.g., by inducing antibody dependent cell-mediated cytotoxicity (ADCC) and/or complement-induced cell death. For example, CAR-expressing cells described herein may also express an antigen (e.g., a target antigen) that is recognized by molecules capable of inducing cell death, e.g., ADCC or complement-induced cell death. For example, CAR expressing cells described herein may also express a target protein (e.g., a receptor) capable of being targeted by an antibody or antibody fragment. Examples of such target proteins include, but are not limited to, EpCAM, VEGFR, integrins (e.g., integrins αvβ3, α4, αI3/4β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain).

In some embodiments, the CAR expressing cell co-expresses the CAR and the target protein, e.g., naturally expresses the target protein or is engineered to express the target protein. For example, the cell, e.g., the population of immune effector cells, can include a nucleic acid (e.g., vector) comprising the CAR nucleic acid (e.g., a CAR nucleic acid as described herein) and a nucleic acid encoding the target protein.

In one embodiment, the T cell depleting agent is a CD52 inhibitor, e.g., an anti-CD52 antibody molecule, e.g., alemtuzumab.

In other embodiments, the cell, e.g., the population of immune effector cells, expresses a CAR molecule as described herein (e.g., CD19CAR) and the target protein recognized by the T cell depleting agent. In one embodiment, the target protein is CD20. In embodiments where the target protein is CD20, the T cell depleting agent is an anti-CD20 antibody, e.g., rituximab.

In further embodiments of any of the aforesaid methods, the methods further include transplanting a cell, e.g., a hematopoietic stem cell, or a bone marrow, into the mammal.

In another aspect, the invention features a method of conditioning a mammal prior to cell transplantation. The method includes administering to the mammal an effective amount of the cell comprising a CAR nucleic acid or polypeptide, e.g., a CD19 CAR nucleic acid or polypeptide. In some embodiments, the cell transplantation is a stem cell transplantation, e.g., a hematopoietic stem cell transplantation, or a bone marrow transplantation. In other embodiments, conditioning a subject prior to cell transplantation includes reducing the number of target-expressing cells in a subject, e.g., CD19-expressing normal cells or CD19-expressing cancer cells.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells, e.g., T regulatory cell depleted cells, may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain suitable values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one suitable ratio being at least 1:1 particles per T cell. In one aspect, a ratio of particles to cells of 1:1 or less is used. In one particular aspect, a suitable particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, e.g., a CD19 CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a CD19 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a CD19 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CAR of the present invention are described in further detail below Western blot analysis of CAR expression in primary T cells can be used to detect the presence of monomers and dimers, e.g., as described in paragraph 695 of International Application WO2015/142675, filed Mar. 13, 2015, which is herein incorporated by reference in its entirety.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described $herein^+$ K562 cells (K562-expressing a cancer associated antigen as described herein), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. $GFP^+$ T cells are enumerated by flow cytometry using bead-based counting. See, e.g., Milone et al., Molecular Therapy 17(8): 1453-1464 (2009).

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CAR-expressing cell activity, e.g., as described in paragraph 698 of International Application WO2015/142675, filed Mar. 13, 2015, which is herein incorporated by reference in its entirety.

Dose dependent CAR treatment response can be evaluated, e.g., as described in paragraph 699 of International Application WO2015/142675, filed Mar. 13, 2015, which is herein incorporated by reference in its entirety.

Assessment of cell proliferation and cytokine production has been previously described, as described in paragraph 700 of International Application WO2015/142675, filed Mar. 13, 2015, which is herein incorporated by reference in its entirety.

Cytotoxicity can be assessed by a standard 51Cr-release assay, e.g., as described in paragraph 701 of International Application WO2015/142675, filed Mar. 13, 2015, which is herein incorporated by reference in its entirety.

Cytotoxicity can also be assessed by measuring changes in adherent cell's electrical impedance, e.g., using an xCELLigence real time cell analyzer (RTCA). In some embodiments, cytotoxicity is measured at multiple time points.

Imaging technologies can be used to evaluate specific trafficking and proliferation of CARs in tumor-bearing animal models, e.g., as described in paragraph 702 of International Application WO2015/142675, filed Mar. 13, 2015, which is herein incorporated by reference in its entirety.

Other assays, including those described in the Example section herein as well as those that are known in the art can also be used to evaluate the CARs described herein.

Alternatively, or in combination to the methods disclosed herein, methods and compositions for one or more of: detection and/or quantification of CAR-expressing cells (e.g., in vitro or in vivo (e.g., clinical monitoring)); immune cell expansion and/or activation; and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CAR-expressing cells is disclosed. For example, the CAR ligand can be used to detect and/or quantify CAR-expressing cells in vitro or in vivo (e.g., clinical monitoring of CAR-expressing cells in a patient, or dosing a patient). The method includes:

providing the CAR ligand (optionally, a labelled CAR ligand, e.g., a CAR ligand that includes a tag, a bead, a radioactive or fluorescent label);

acquiring the CAR-expressing cell (e.g., acquiring a sample containing CAR-expressing cells, such as a manufacturing sample or a clinical sample);

contacting the CAR-expressing cell with the CAR ligand under conditions where binding occurs, thereby detecting the level (e.g., amount) of the CAR-expressing cells present. Binding of the CAR-expressing cell with the CAR ligand can be detected using standard techniques such as FACS, ELISA and the like.

In another aspect, a method of expanding and/or activating cells (e.g., immune effector cells) is disclosed. The method includes:

providing a CAR-expressing cell (e.g., a first CAR-expressing cell or a transiently expressing CAR cell);

contacting said CAR-expressing cell with a CAR ligand, e.g., a CAR ligand as described herein), under conditions where immune cell expansion and/or proliferation occurs, thereby producing the activated and/or expanded cell population.

In certain embodiments, the CAR ligand is present on a substrate (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In one embodiment, the CAR ligand is attached (e.g., covalently attached) to a bead. In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In yet another aspect, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In one embodiment, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference.

In some aspects and embodiments, the compositions and methods herein are optimized for a specific subset of T cells, e.g., as described in US Serial No. PCT/US2015/043219 filed Jul. 31, 2015, the contents of which are incorporated herein by reference in their entirety. In some embodiments, the optimized subsets of T cells display an enhanced persistence compared to a control T cell, e.g., a T cell of a different type (e.g., CD8+ or CD4+) expressing the same construct.

In some embodiments, a CD4+ T cell comprises a CAR described herein, which CAR comprises an intracellular signaling domain suitable for (e.g., optimized for, e.g., leading to enhanced persistence in) a CD4+ T cell, e.g., an ICOS domain. In some embodiments, a CD8+ T cell comprises a CAR described herein, which CAR comprises an intracellular signaling domain suitable for (e.g., optimized for, e.g., leading to enhanced persistence of) a CD8+ T cell, e.g., a 4-1BB domain, a CD28 domain, or another costimulatory domain other than an ICOS domain. In some embodiments, the CAR described herein comprises an antigen binding domain described herein, e.g., a CAR comprising an antigen binding domain.

In an aspect, described herein is a method of treating a subject, e.g., a subject having cancer. The method includes administering to said subject, an effective amount of:

1) a CD4+ T cell comprising a CAR (the CARCD4+) comprising:

an antigen binding domain, e.g., an antigen binding domain described herein;

a transmembrane domain; and an intracellular signaling domain, e.g., a first costimulatory domain, e.g., an ICOS domain; and 2) a CD8+ T cell comprising a CAR (the CARCD8+) comprising:

an antigen binding domain, e.g., an antigen binding domain described herein;

a transmembrane domain; and an intracellular signaling domain, e.g., a second co stimulatory domain, e.g., a 4-1BB domain, a CD28 domain, or another costimulatory domain other than an ICOS domain;

wherein the CARCD4+ and the CARCD8+ differ from one another.

Optionally, the method further includes administering:

3) a second CD8+ T cell comprising a CAR (the second CARCD8+) comprising:

an antigen binding domain, e.g., an antigen binding domain described herein;

a transmembrane domain; and an intracellular signaling domain, wherein the second CARCD8+ comprises an intracellular signaling domain, e.g., a costimulatory signaling domain, not present on the CARCD8+, and, optionally, does not comprise an ICOS signaling domain.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic. Exemplary biopolymers are described, e.g., in paragraphs 1004-1006 of International Application WO2015/142675, filed Mar. 13, 2015, which is herein incorporated by reference in its entirety.

Pharmaceutical Compositions and Treatments

In some aspects, the disclosure provides a method of treating a patient, comprising administering CAR-expressing cells produced as described herein, optionally in combination with one or more other therapies. In some aspects, the disclosure provides a method of treating a patient, comprising administering a reaction mixture comprising CAR-expressing cells as described herein, optionally in combination with one or more other therapies. In some aspects, the disclosure provides a method of shipping or receiving a reaction mixture comprising CAR-expressing cells as described herein. In some aspects, the disclosure provides a method of treating a patient, comprising receiving a CAR-expressing cell that was produced as described herein, and further comprising administering the CAR-expressing cell to the patient, optionally in combination with one or more other therapies. In some aspects, the disclosure provides a method of treating a patient, comprising producing a CAR-expressing cell as described herein, and further comprising administering the CAR-expressing cell to the patient, optionally in combination with one or more other therapies. The other therapy may be, e.g., a cancer therapy such as chemotherapy.

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, a therapy described herein, e.g., a CAR-expressing cell, is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide.

In one embodiment, the GITR binding molecules and/or molecules modulating GITR functions (e.g., GITR agonist and/or Treg depleting GITR antibodies) are administered prior to the CAR-expressing cell. For example, in one embodiment, a GITR agonist can be administered prior to apheresis of the cells. In embodiments, cyclophosphamide is administered to the subject prior to administration (e.g., infusion or re-infusion) of the CAR-expressing cell or prior to apheresis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as ALL or CLL). In one embodiment, the subject has CLL. In embodiments, the subject has ALL. In embodiments, the subject has a solid cancer, e.g., a solid cancer described herein. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

The methods described herein can further include formulating a CAR-expressing cell in a pharmaceutical composition. Pharmaceutical compositions may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions can be formulated, e.g., for intravenous administration.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-cancer effective amount," "a cancer-inhibiting effective amount," or "therapeutic amount" is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In some embodiments, a dose of CAR cells (e.g., CD19 CAR cells) comprises about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (e.g., CD19 CAR cells) comprises at least about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (e.g., CD19 CAR cells) comprises up to about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (e.g., CD19 CAR cells) comprises about $1.1\times10^6$-$1.8\times10^7$ cells/kg. In some embodiments, a dose of CAR cells (e.g., CD19 CAR cells) comprises about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (e.g., CD19 CAR cells) comprises at least about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (e.g., CD19 CAR cells) comprises up to about $1\times10^7$, $2\times10^7$, $5\times10^7$, $1\times10^8$, $2\times10^8$, $5\times10^8$, $1\times10^9$, $2\times10^9$, or $5\times10^9$ cells.

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner. The compositions described herein may be administered to a patient trans arterially, subcutaneously, intradermally, intratumorally, intranodally, intramedullary, intramuscularly, by intravenous (i.v.) injection, or intraperitoneally, e.g., by intradermal or subcutaneous injection. The compositions of immune effector cells (e.g., T cells, NK cells) may be injected directly into a tumor, lymph node, or site of infection.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Optimizing CART Production with Exogenous Cytokines

Cytokines have important functions related to T cell expansion, differentiation, survival and homeostasis. One of the most important cytokine families for clinical use is the common γ-chain ($\gamma_c$) family cytokines, which includes interleukin (IL)-2, IL-4, IL-7, IL-9, IL-15 and IL-21 (Liao et al., 2013, *Immunity,* 38:13-25. IL-2 has been widely studied as an immunotherapeutic agent for cancer. The supplement of IL-2 enhanced the antitumor ability of anti-CD19 CAR-T cells in the clinical trials (Xu et al., 2013, *Lymphoma,* 54:255-60). However, the administration of IL-2 is limited by side effects and a propensity for expansion of regulatory T cells and the effect of activated induced cell death (AICD) (Malek et al., 2010, *Immunity,* 33:153-65; and Lenardo et al., 1999, *Annu Rev Immunol,* 17:221-53). IL-7, IL-15, and IL-21 each can enhance the effectiveness of adoptive immunotherapies and seems to be less toxicity compared with IL-2 (Alves et al., 2007, *Immunol Lett,* 108:113-20). Despite extensive preclinical and clinical studies on the role of the above cytokines, multi-parameter comparative studies on the roles of various exogenous $\gamma_c$ cytokines on CAR-T cell adoptive therapy are lacking.

Besides γ-chain cytokines, IL-18 is another immunostimulatory cytokine regulating immune responses, which enhances the production of IFN-γ by T cells and augments the cytolytic activity of CTLs (Srivastava et al., 2010, *Curr Med Chem,* 17:3353-7). Administration of IL-18 is safe and well tolerated, even when the dose reaching as high as 1000 μg/kg (Robertson et al., 2006, *Clin Cancer Res,* 12:4265-73). Therefore, IL-18 could be another candidate used to boost the antitumor of CAR-T cells.

In this example, the effect of administration of different exogenous cytokines was examined for expansion, phenotype, in vitro effector functions, and in vivo anti-tumor efficacy of T cells and folate receptor alpha (FRα) CART cells.

The following materials and methods were used in the experiments described in this example.

CAR Construction and Lentivirus Preparation

The pELNS-C4-27z CAR vector was constructed as described previously (manuscript under review), Briefly, the pHEN2 plasmid containing the anti-FRα C4/AFRA4 scFv was used as a template for PCR amplification of C4 fragment using the primers of 5'-ata ggatcccagctggtggagtctgggggaggc-3' (SEQ ID NO: 19) and 5'-atagctagcacctaggacggtcagcttggtccc-3' (SEQ ID NO: 24) (BamHI and NheI were underlined). The PCR product and the third generation self-inactivating lentiviral expression vectors pELNS were digested with BamHI and NheI. The digested PCR products were then inserted into the pELNS vector containing CD27-CD3z T-cell signaling domain in which transgene expression is driven by the elongation factor-1α (EF-1α) promoter.

High-titer replication-defective lentivirus was generated by transfection of human embryonic kidney cell line 293T (293T) cells with four plasmids (pVSV-G, pRSV.REV, pMDLg/p.RRE and pELNS-C4-27z CAR) by using Express In (Open Biosystems) as described previously. Supernatants were collected at 24 h and 48 h after transfection and concentrated by ultracentrifugation. The virus titers were determined based on the transduction efficiency of lentivirus to SupT1 cells by using limiting dilution method.

T Cells and Cell Lines

Peripheral blood lymphocytes were obtained from healthy donors after informed consent under a protocol approved by University Institutional Review Board at the University of Pennsylvania. The primary T cells were purchased from the Human Immunology Core after purified by negative selection. T cells were cultured in complete media (RPMI 1640 supplemented with 10% FBS, 100 U/mL penicillin, 100 m/mL streptomycin sulfate) and stimulated with anti-CD3 and anti-CD28 mAbs-coated beads (Invitrogen) at a ratio of 1:1 following the instruction. Twenty-four hours after activation, cells were transduced with lentivirus at MOI of 5. Indicated cytokines were added to the transduced T cells from the next day with a final concentration of 10 ng/mL. The cytokines were replaced every 3 days.

The 293T cell used for lentivirus packaging and the SupT1 cell used for lentiviral titration were obtained from ATCC. The established ovarian cancer cell lines SKOV3 (FRα+) and C30 (FRα−) was used as target cell for cytokine-secreting and cytotoxicity assay. For bioluminescence assays, SKOV3 was transduced with lentivirus to express firefly luciferase (fLuc).

Flow Cytometric Analysis and Cell Sorting

Flow cytometry was performed on a BD FACSCanto. Anti-human CD45 (HI30), CD3 (HIT3a), CD8 (HIT8a), CD45RA (HI100), CD62L (DREG-56), CCR7 (G043H7), IL-7Rα (A019D5), CD27 (M-T271), CD28 (CD28.2), CD95 (DX2), TNF-α (MAb11), IFN-γ (4S.B3), IL-2 (MQ1-17H12), perforin (B-D48), granzym-B (GB11) were obtained from Biolegend. Biotin-SP-conjugated rabbit anti-human IgG (H+L) was purchased from Jackson Immunoresearch and APC conjugated streptavidin was purchased from Biolegand. Anti-human Bcl-xl (7B2.5) was purchased from SouhernBiotech. Apoptosis kit and TruCount tubes were obtained from BD Bioscience. For peripheral blood T cell count, blood was obtained via retro-orbital bleeding and stained for the presence of human CD45, CD3, CD4 and CD8 T cells. Human CD45+-gated, CD3+, CD4+ and CD8+ subsets were quantified with the TruCount tubes following the manufacturer's instructions.

In Vivo Study of Adoptive Cell Therapy

Female non-obese diabetic/severe combined immunodeficiency/γ-chain$^{-/-}$ (NSG) mice 8 to 12 weeks of age were obtained from the Stem Cell and Xenograft Core of the Abramson Cancer Center, University of Pennsylvania. The mice were inoculated subcutaneously with $3\times10^6$ fLuc$^+$ SKOV3 cells on the flank on day 0. Four or Five mice were randomized per group before treatment. After tumors became palpable, human primary T cells were activated and transduced as described previously. T cells were expanded in the presence of IL-2 (5 ng/mL) for about 2 weeks. When the tumor burden was ~250-300 mm$^3$, the mice were injected with $5\times10^6$ CAR-T cells or 100 μl saline intravenously and then received daily intraperitoneal injection of 5 μg of IL-2, IL-7, IL-15, IL-18, IL-21 or phosphate buffer solution (PBS) for 7 days. Tumor dimensions were measured with calipers and tumor volumes were calculated with the following formula: tumor volume=(length×width$^2$)/2. The number and phenotype of transferred T cells in recipient mouse blood was determined by flow cytometry after retro-orbital bleeding. The mice were euthanized when the tumor volumes were more than 2000 mm$^3$ and tumors were resected immediately for further analysis.

Statistical Analysis

Statistical analysis was performed with Prism 5 (GraphPad software) and IBM SPSS Statistics 20.0 software. The data were shown as mean±SEM unless clarified. Paired sample t-tests or nonparametric Wilcoxon rank tests were used for comparison of two groups and repeated measures ANOVA or Friedman test were used to test statistical significance of differences among three or more groups. Findings were considered as statistically significant when P-values were less than 0.05.

Results

1. Construction and Expression of Anti-FRα C4 CAR

Figure 1B:
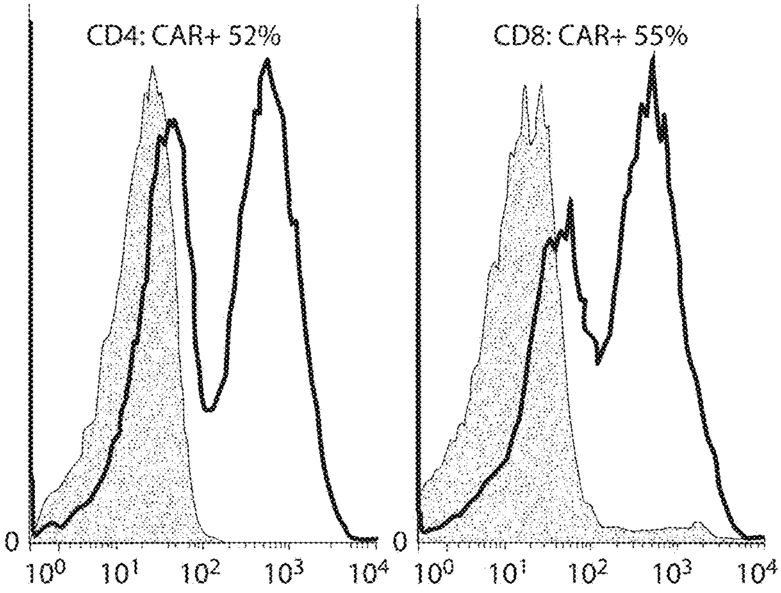

The pELNS-C4-27z CAR comprised of the anti-FRα C4 scFv linked to a CD8α hinge and transmembrane region, followed by a CD3ζ signaling moiety in tandem with the CD27 intracellular signaling motif (FIG. 1A). Primary human T cells were efficiently transduced with C4 CAR lentiviral vectors with transduction efficiencies of 43%~65% when detected at 48 h after transduction (FIG. 1B). CAR expression levels were comparable between CD4+ and CD8+ T cells (52.6±10.2% vs. 49.5±17.1%, P=0.713).

2. Influence of Cytokines on Expansion of CAR Transduced T (CAR-T) Cell

Figure 1C:
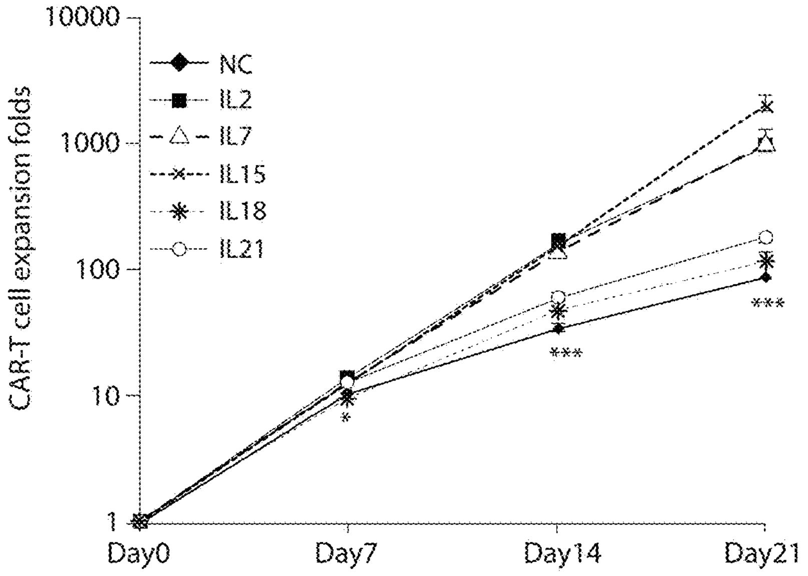

The expansion and accumulation of CAR-T cells in the presence of various γc cytokines and IL-18 was investigated. Three weeks after exposure to the different cytokines in culture, CAR-T cells that had been cultured in the presence of IL2, IL-7 or IL-5 had expanded 1000-2000 fold. CAR-T cells that had been cultured in the presence of IL-18, IL-21 or NC (control, no cytokine) demonstrated a less than 200 fold expansion (FIG. 1C).

Figure 1D:
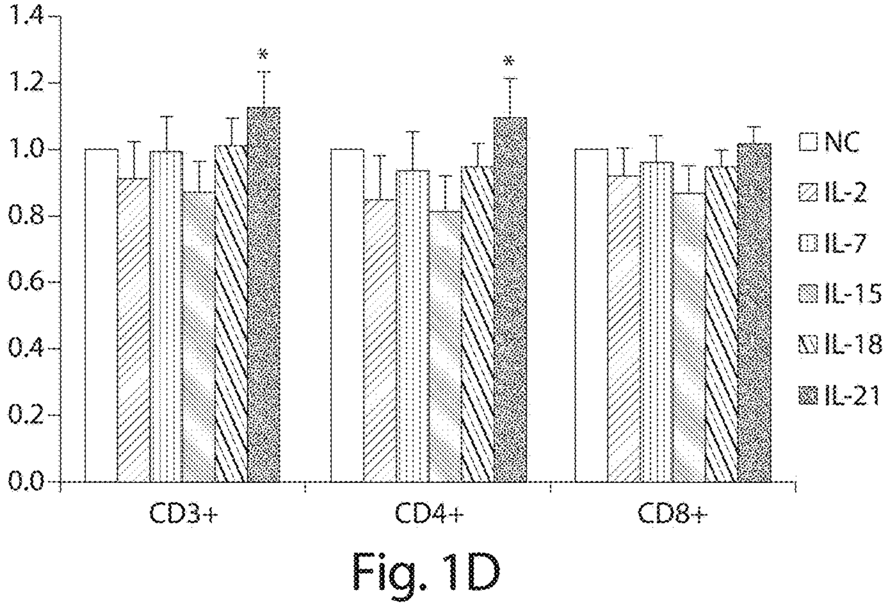

CAR expression levels were compared 15 days after transduction in different T cell populations: CD3+, CD4+, and CD8+ T cells. CAR expression levels of each group of CAR-T cells grown in the presence of the different cytokines were similar in CD3+, CD4+, and CD8+ T cell populations. CAR-T cells that had been cultured in the presence of IL-21 showed higher levels of CAR expression than the CAR-T cells exposed to other cytokines (including IL-2 and the control cells that were not grown in the presence of cytokines (NC) in the CD3+ and CD4+ T cell populations (FIG. 1D).

Figure 1E:
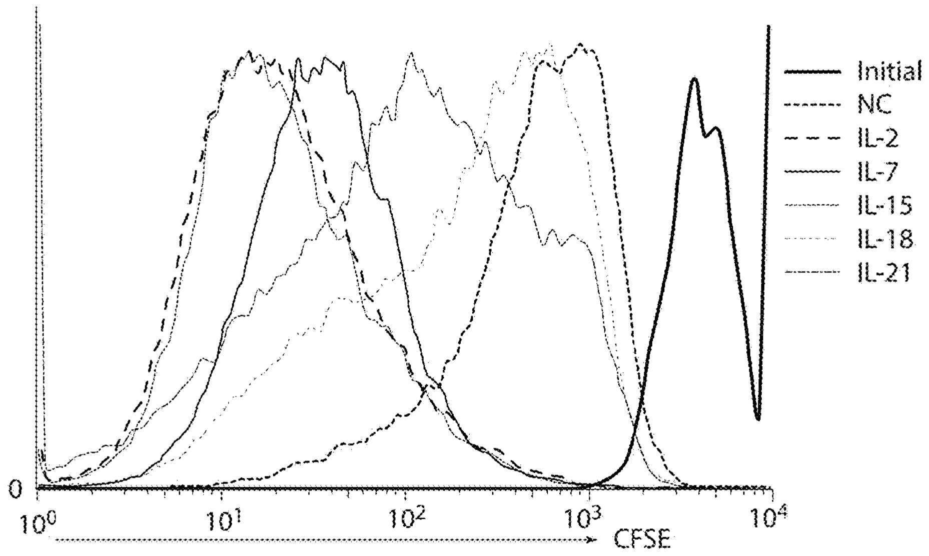
Figure 1F:
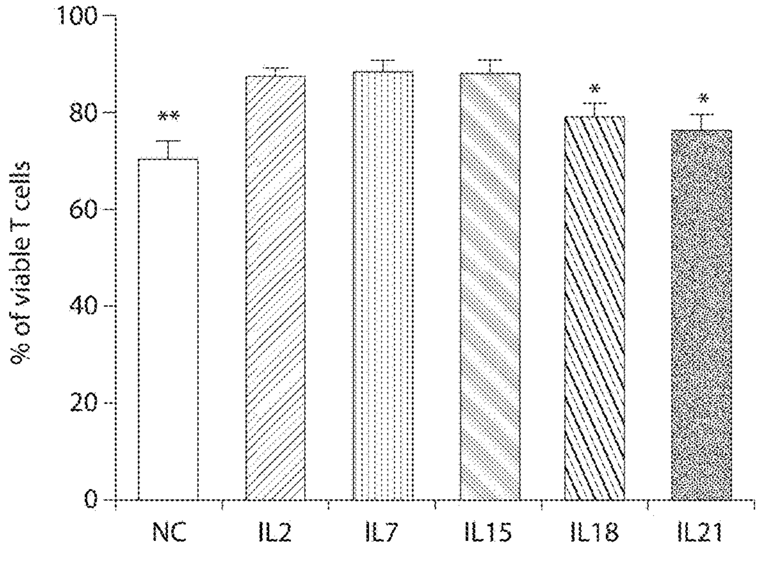
Figure 1G:
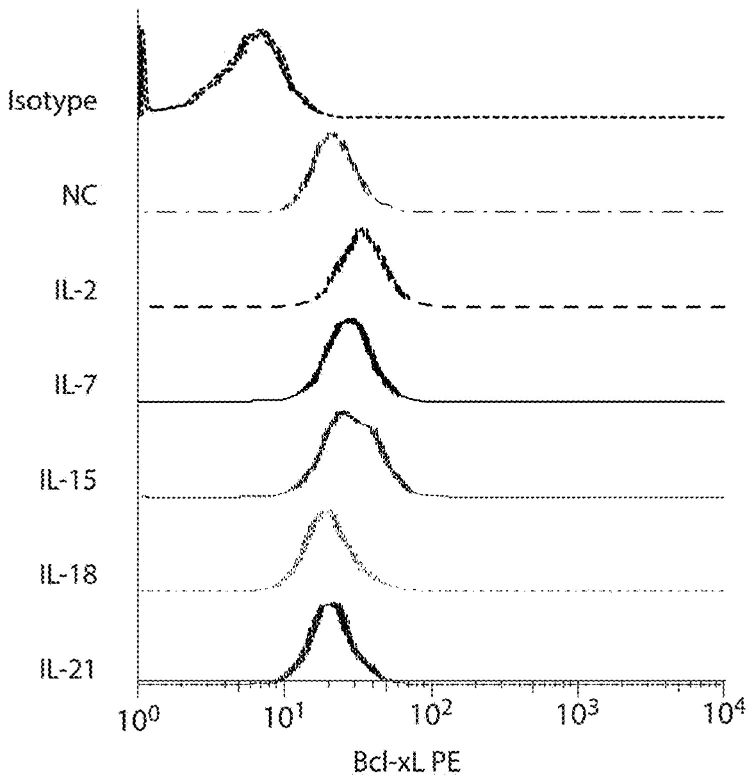
Figure 1H:
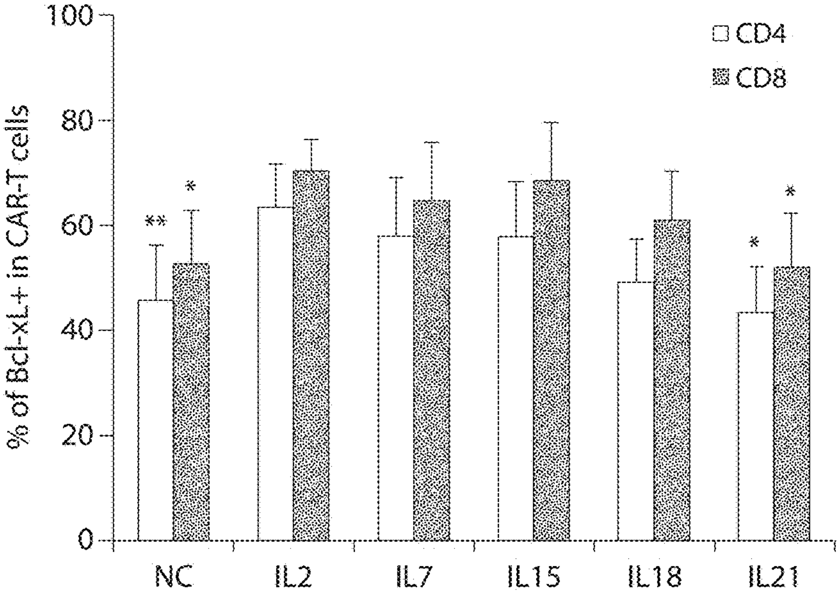

The reasons contributing to the higher accumulation of CAR-T cells were analyzed, specifically, proliferation and apoptosis of the T cells was assessed. The proliferative response was measured by monitoring cell division of CFSE labeled T cells cultured for 7 days. As shown in FIG. 1E, T cells cultured with IL-2 and IL-15 showed the highest proliferative ability, followed by IL-7; while IL-21 and IL-18 were less potent mitogenic stimulants. Apoptosis of the T cells cultured in the different cytokines was tested using Annexin-V staining. The results indicated that T cells cultured in IL-2, IL-7 and IL-15 underwent less apoptosis when compared with NC, IL-18 and IL-21 groups (FIG. 1F). Next, the expression of Bcl-xL, a key negative regulator of lymphocyte apoptosis, was examined by FACs analysis. Consistent with the apoptosis results in FIG. 1F, there is a trend that IL-2, IL-7 and IL-15 exposure results in the up-regulation of Bcl-xL expression both in CD4+ and CD8+ T cells, while IL-21 did not increase Bcl-xL expression (FIGS. 1G and 1H). These results indicate that increased accumulation of T cells expanded in the presence of cytokines, e.g., IL-2, IL-7, or IL-15, may be caused by both an increase in proliferation and a decrease in apoptosis by activation of the Bcl-xl anti-apoptotic pathway.

3. Influence of Cytokines on the Phenotypes of CAR-T Cells

Figure 2A:
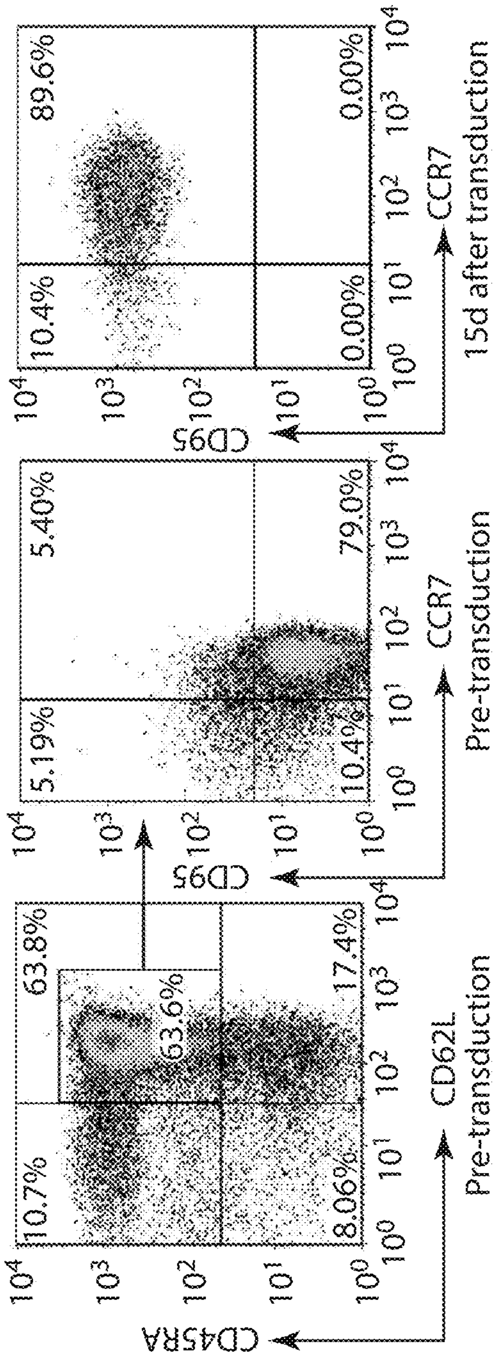
FIGS. 2A-2I shows the memory T cell subsets of CAR-T cells.
Figure 2B:
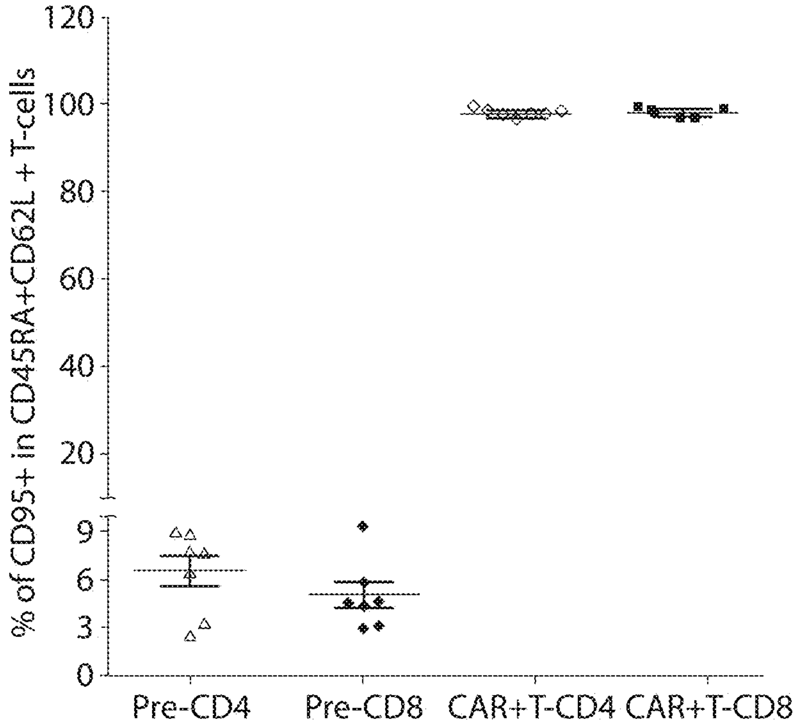
Figure 2C:
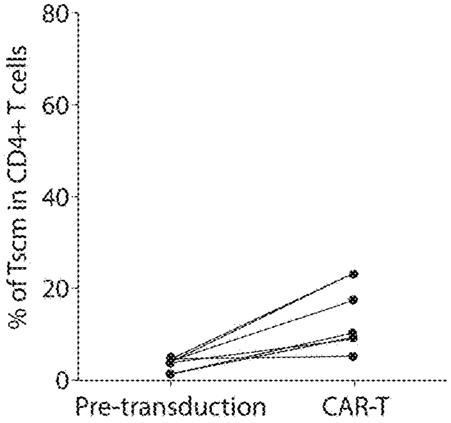
Figure 2D:
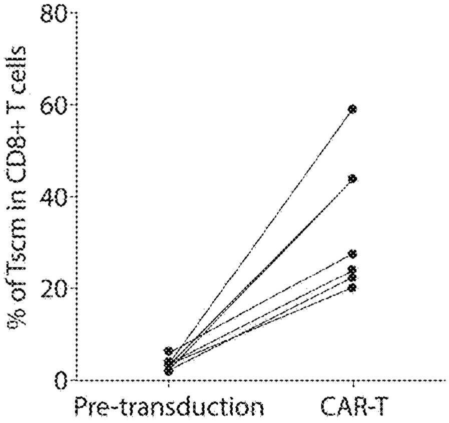
Figure 2E:
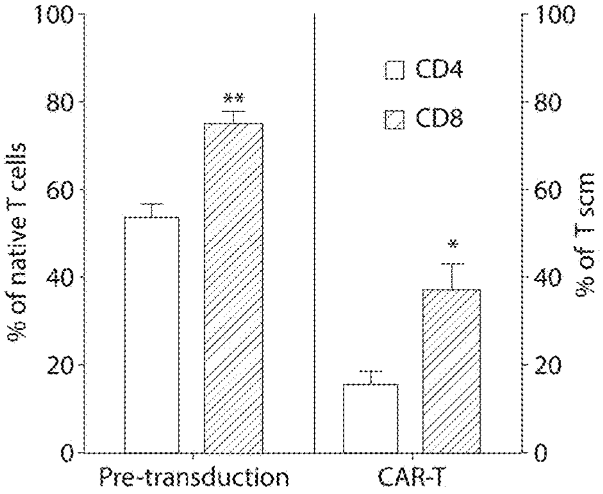
Figure 2F:
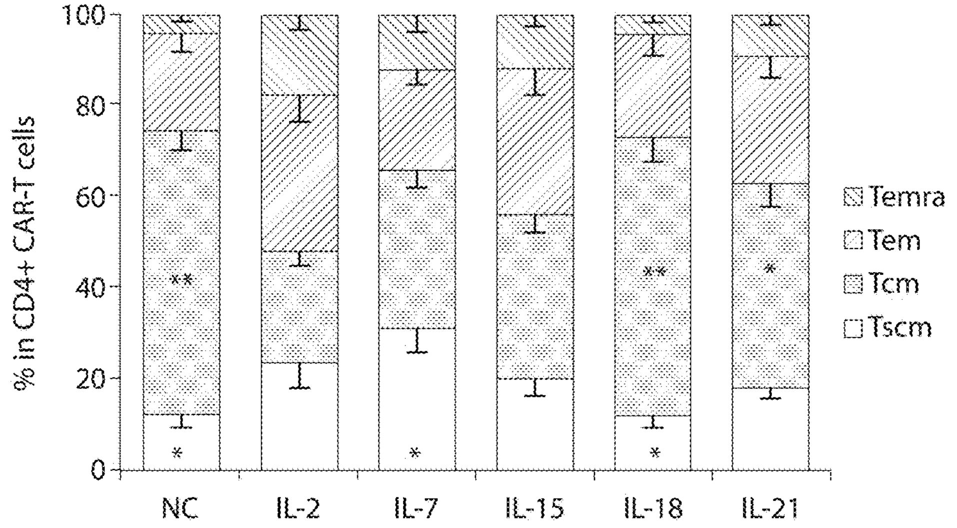
Figure 2G:
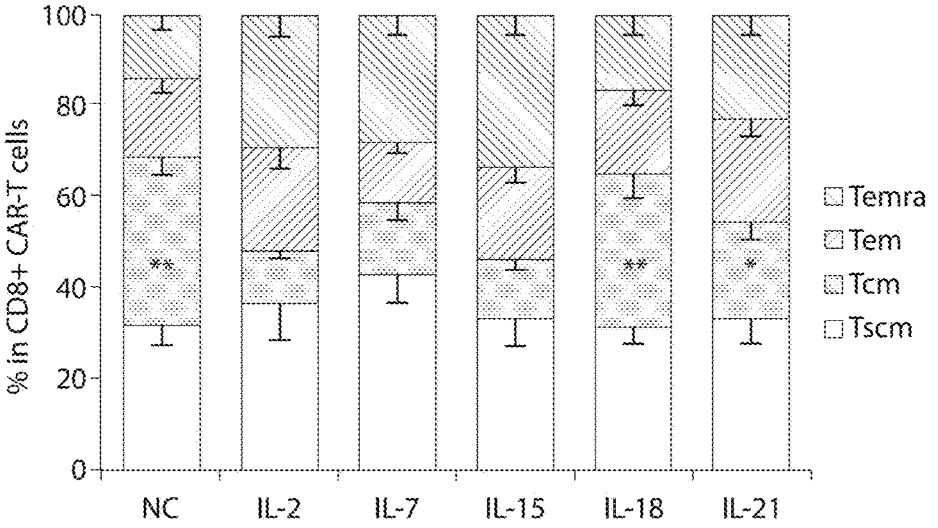

Next, the phenotype of the CAR-T cells expanded in the presence of exogenous cytokines was examined. The fresh T cells from healthy donors were generally divided into four subsets based on CD45RA and CD62L expression: 1) naïve T cell (CD45RA+CD62L+, referred to as Tn), 2) central memory T cell (CD45RA−CD62L+, referred to as Tcm), 3) effector memory T cell (CD45RA−CD62L−, referred to as Tem) and 4) CD45RA positive effector T cell (CD45RA+CD62L−, referred to as Temra). Then the expression of CCR7, CD27, CD28, and CD95 are further evaluated for each subset (FIG. 2A). The latter three T cell subsets were positive for CD95 while only small part of Tn expressed CD95 (3.6±1.4% in CD4+ and 3.7±1.3% in CD8+ T cells). This small population also co-expressed CD27, CD28 and CCR7, and was considered as memory stem T cells (Tscm). However, after stimulation with anti-CD3/CD28 beads before and after lentiviral transduction with CAR, CD95 was greatly up-regulated to nearly 100% in this population (FIG. 2B). The percentages of CD45RA+CD62L+CD95+ T cells were greatly expanded after anti-CD3/CD28 bead stimulation in both CD4+ and CD8+ T and CAR-T cells when compared with the fresh T cells (FIGS. 2C and 2D). This population highly expressed CD27, CD28 and CCR7 simultaneously (FIG. 2A), indicating it could be defined as Tscm. Furthermore, CD8+ CAR-T cells had a higher percentage of Tscm cells, which may be related to the higher proportion of Tn in initial CD8+ T cells (FIGS. 2F and 2G).

Fourteen days after co-culture with various cytokines, the proportion of T cell subsets of CAR-T cells were investigated by measuring the expression of CD45RA, CD62L and CD95. As shown in FIG. 2E, of the CD4+ CAR-T cells, a significantly higher percentage of Tscm cells existed in the IL-7 group compared with the IL-2 group, while the NC and IL-18 groups presented lower percentages of Tscm but higher percentages of Tcm. The distribution of T cell subsets in the IL-15 group was similar with the IL-2 group, while the IL-21 group presented a higher percentage of Tcm, while percentage of Tscm was comparable with the IL-2 group. The CD8+ CAR-T cells demonstrated a similar trend as that of the CD4+ CAR-T cells on the differentiation and distribution of the four T cell subsets for each cytokine-administered group, with higher proportions of Tscm compared with CD4+ CAR-T cells in the corresponding group of CD8+ CAR-T cells.

Figure 2H:
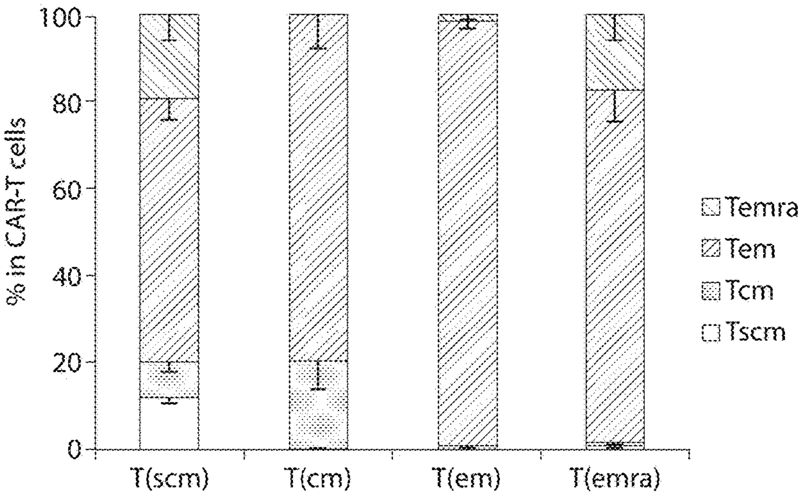
Figure 2I:
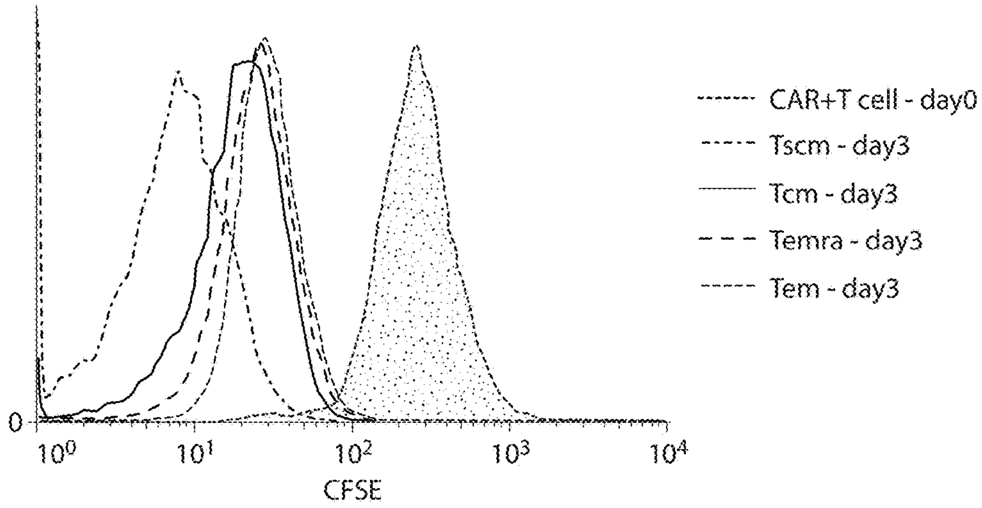
Figure 3A:
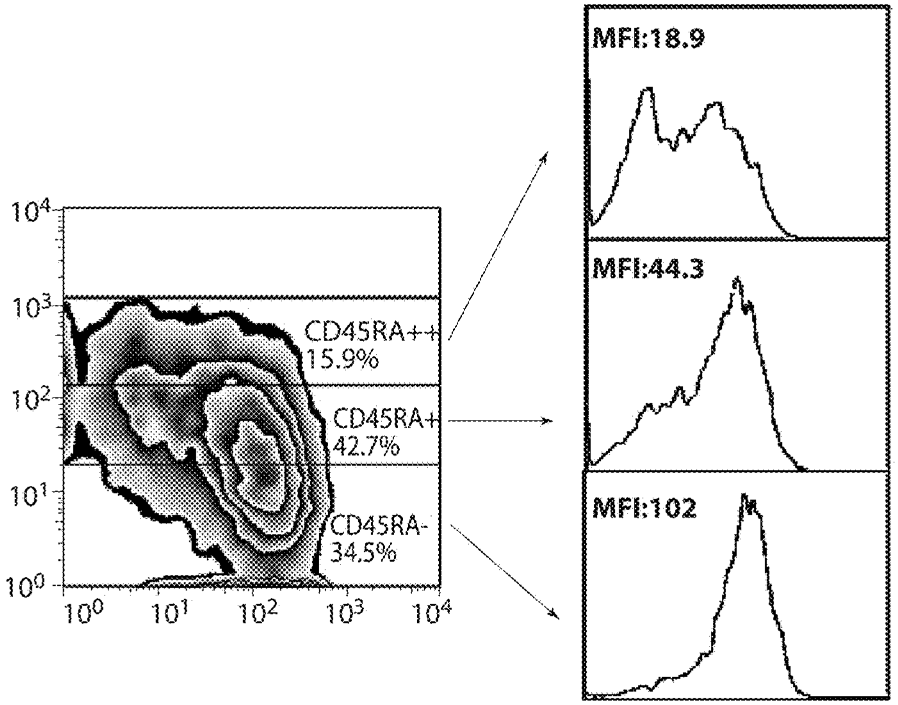
FIGS. 3A-3B: shows the correlation between CD45 RA expression and CFSE intensity.
Figure 3B:
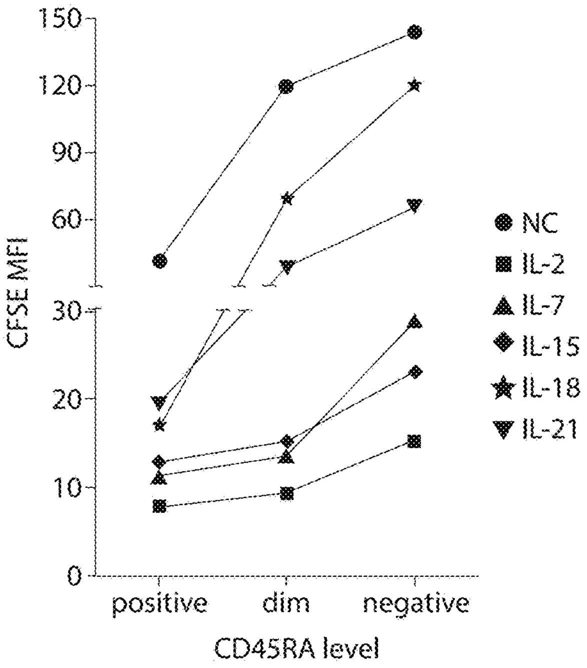

The abilities of various CAR-T cell subpopulations to self-renew and to differentiate into other cell types were further studied. The four subsets of CAR-T cells were sorted based on CAR, CD45RA and CD62L expression and cultured separately in medium containing IL-2 for 3 days. As shown in FIG. 2H, the Tscm subset was able to differentiate into all the other three subsets, and Tcm and Temra subsets were able to differentiate into Tem. These results indicate that CD62L+ and CD45RA+ T cells were able to differentiate into CD62L- and CD45RA− T cells, respectively. The proliferation capacity of the four subsets was assessed by CFSE dilution and then compared. The results showed the Tscm presented stronger proliferation ability than other subsets (FIG. 2I). Furthermore, CD45RA expression inversely correlated with CFSE intensity while CD62L and CCR7 expression directly correlated with proliferation. In all cytokine groups, CD45RA+ T cells exhibited much lower CFSE levels than CD45RA dim and negative T cells (FIG. 3), indicating that CD45RA+ T cells had stronger proliferation activity than CD45RA− T cells. Thus, the increased accumulation of T cells grown in the presence of IL-2, IL-7 and IL-15 may be related to the increased proportion of CD45RA+ T cells (which have increased proliferation capacity) (FIG. 4B).

Figure 4A:
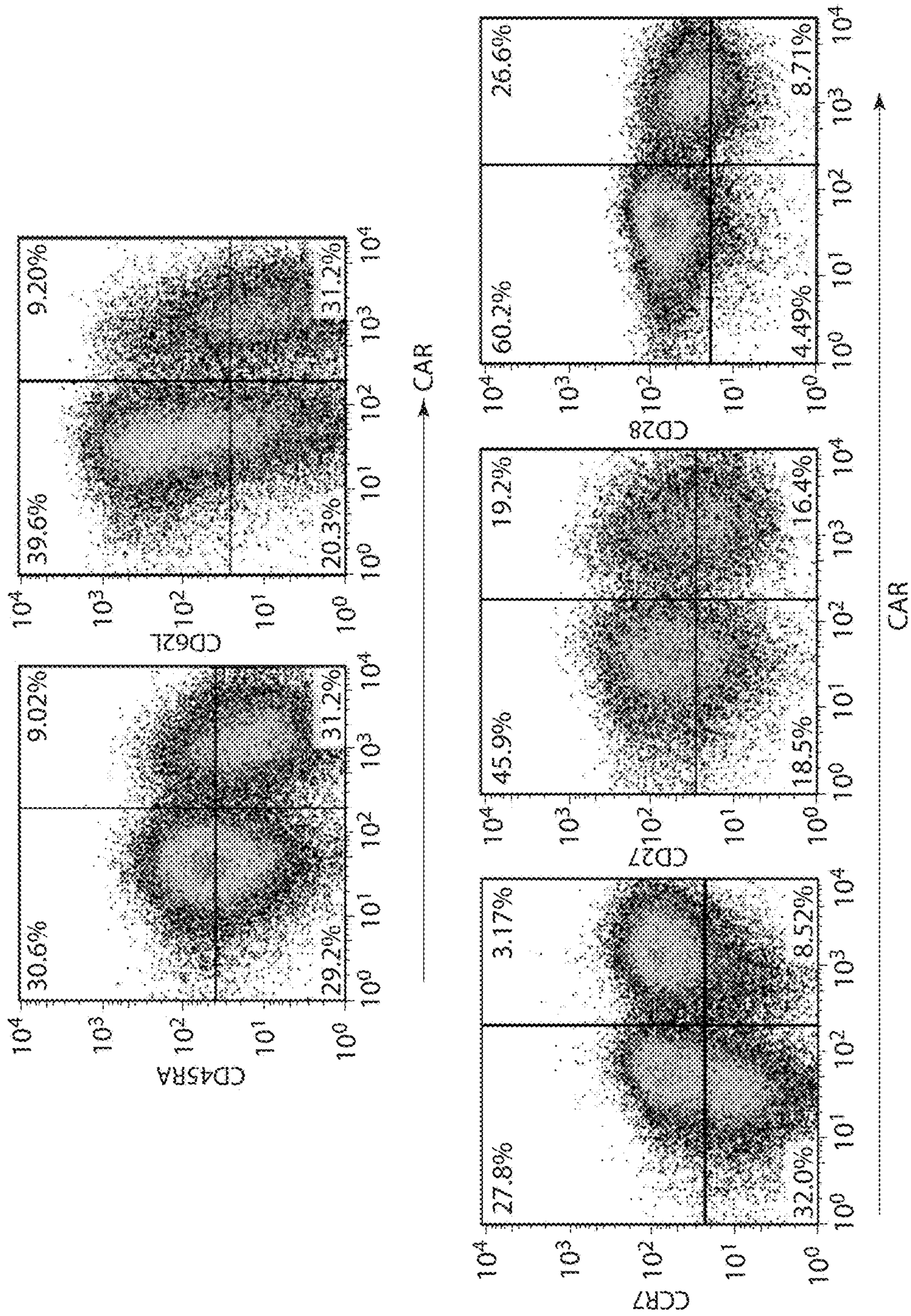
FIGS. 4A-4B show the phenotypes of CAR-T cells resulting from exposure to different cytokines.
Figure 4B:
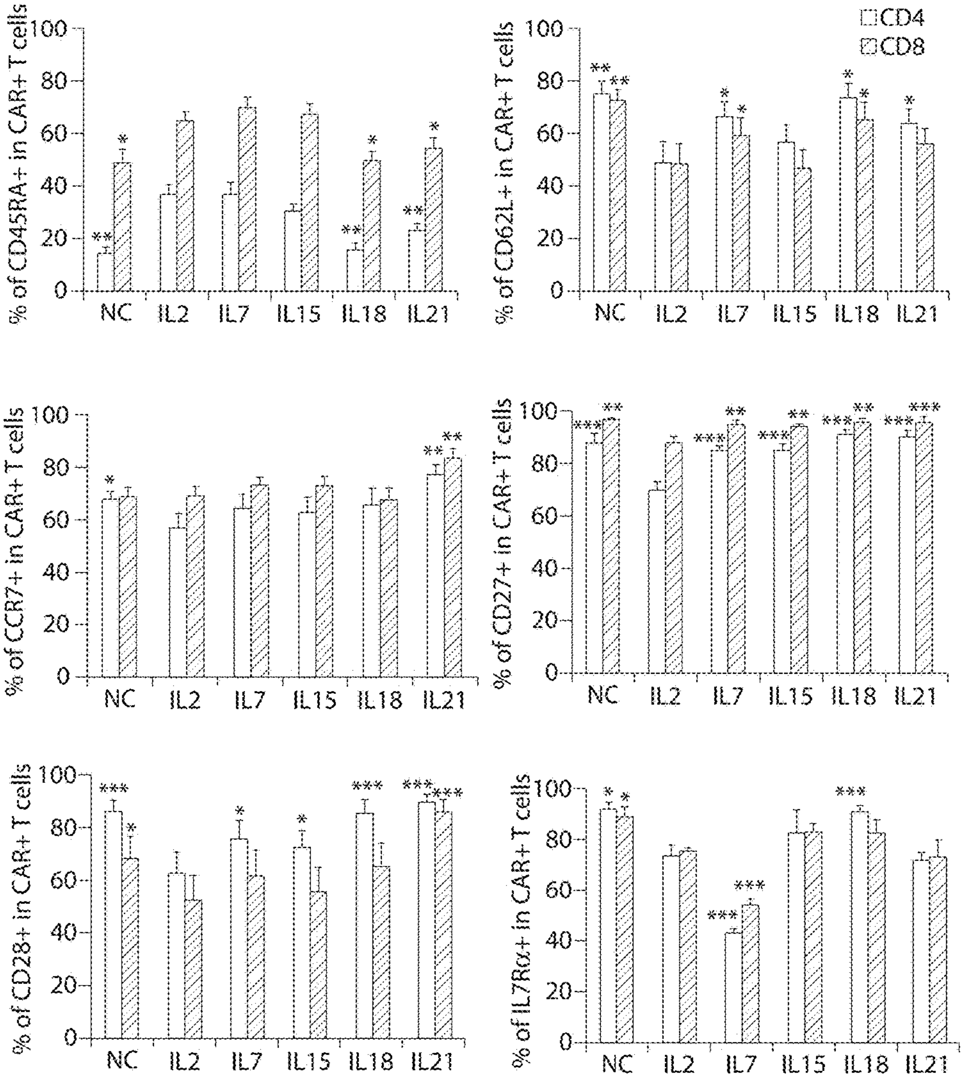

With regard to the phenotype of the CAR-T cells, CAR-T cells presented lower expression of CD45RA, CD62L, CD27 and CD28, but higher expression of CCR7 on the surface of T cells (FIG. 4A). The influence of cytokines on the phenotype of CAR-T cells were further assessed based on the expression of the following surface markers: CD27, CD28, CD62L, CCR7 and IL7Ra. CAR-T cells grow in the presence of IL-18 showed quite similar expression pattern with those grown without cytokine supplement. IL-2 dramatically downregulated the expressions of CD27, CD28 CD62L, CCR7 and ILR7α when compared with NC control. Of the other γc cytokines, compared with IL-2 exposed CAR-T cells, IL-7 exposed CAR-T cells presented higher CD62L, CD27 and CD28 expression but significantly decreased CCR7 expression; IL-15 group CAR-T cells presented higher CD27 and CD28 expression; and IL-21 exposed CAR-T cells presented higher CD62L, CCR7, CD27 and CD28 expression, indicating that IL-2 exposure induced the expansion of a subset of T cells with a much more mature T cell phenotype than all other groups (FIG. 4B).

4. Influence of Cytokines on the Effector Function of CAR-T Cells

Figure 5A:
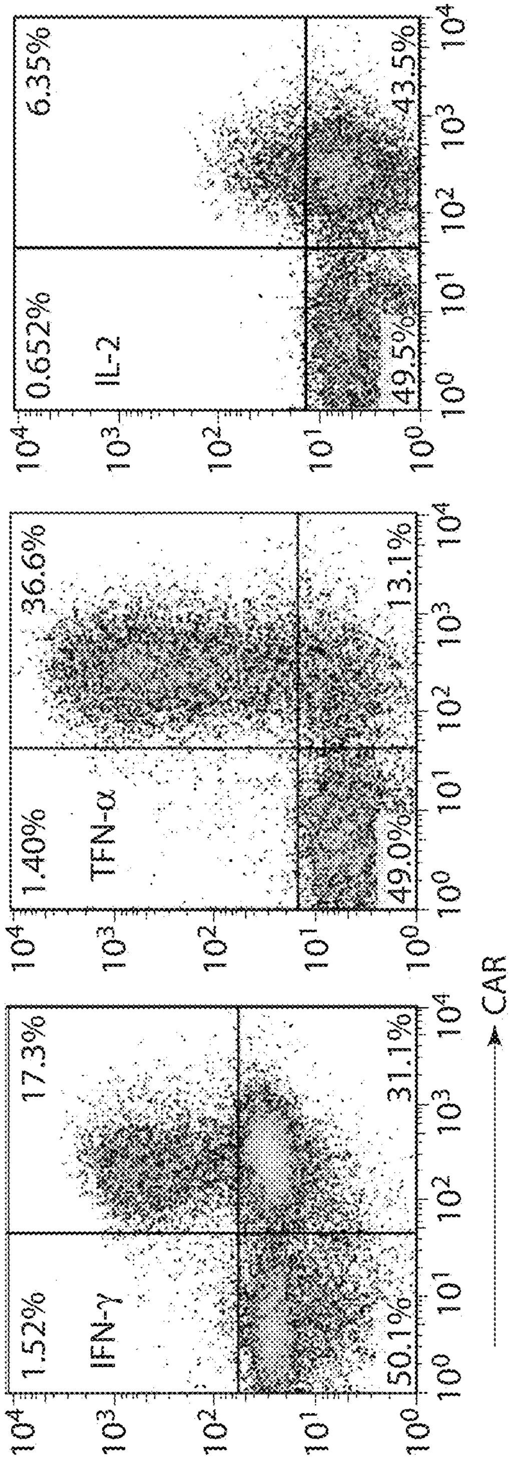
FIGS. 5A-5I show the Functional analysis of CAR-T cells exposed to different cytokines.
Figure 5B:
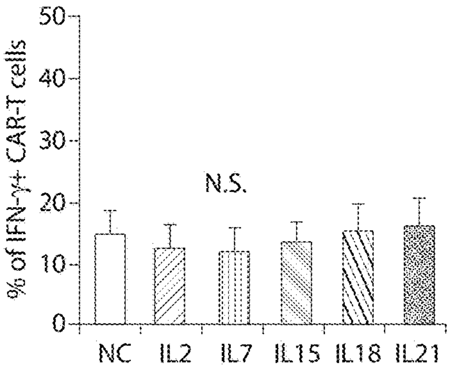
Figure 5C:
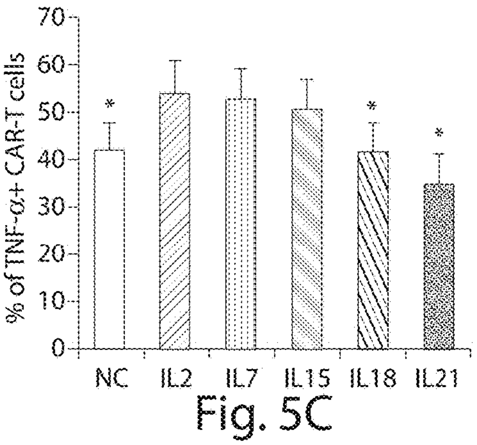
Figure 5D:
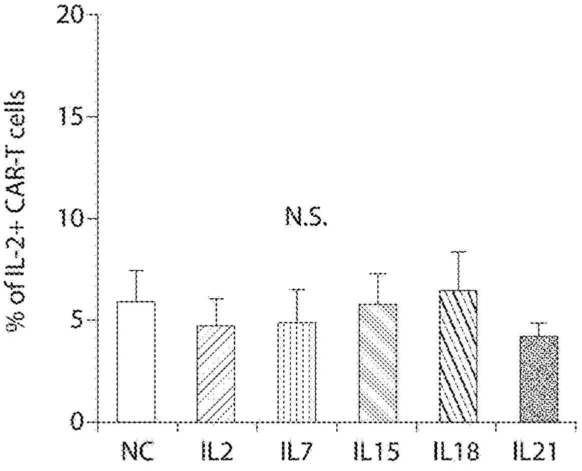
Figure 5E:
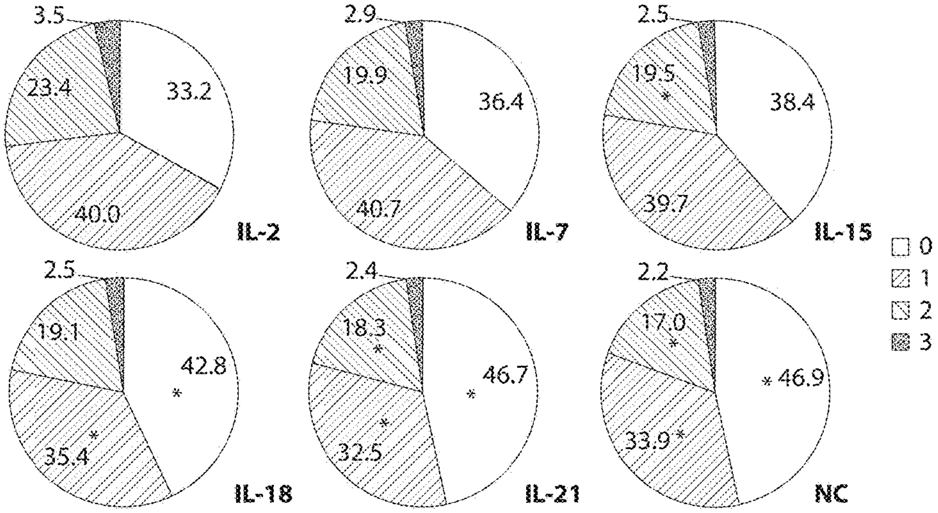

To investigate the influence of cytokines on CAR-T cell effector function, the cytokine production capability of CAR-T cells after stimulation with FRα-expressing SKOV3 cells was assessed. Following 5 hours stimulation, TNF-α, IFN-γ and IL-2 were detectable in the cytoplasm of CAR-T cells, with 41.5-54.0% of the CAR-T cells produced TNF-α, 12.4-15.3% of the CAR-T cells produced IFNγ, and 4.3-6.5% of CAR-T cells produced and IL-2 (FIGS. 5A&B). IL-2, IL-7 and IL-15 exposure during expansion promoted CAR-T cells to produce TNF-α, while the numbers of IFN-γ and IL-2 producing CAR-T cells were comparable among all the cytokine groups (FIGS. 5B, 5C, and 5D). Next, the fractions of responding CAR-T cells and their polyfunctionality were compared (FIG. 5E). In comparison to exposure to IL-2 during expansion, exposure to IL-18, IL-21 or no cytokine exposure during expansion induced less cytokine-producing CAR-T cells, and less CAR-T cells possessed the ability to produce multiple cytokines when stimulated by target cells. These results are consistent with the phenotype that the CAR-T cells in IL-18, IL-21 and NC groups were less differentiated than those in the IL-2 exposed group.

Figure 5F:
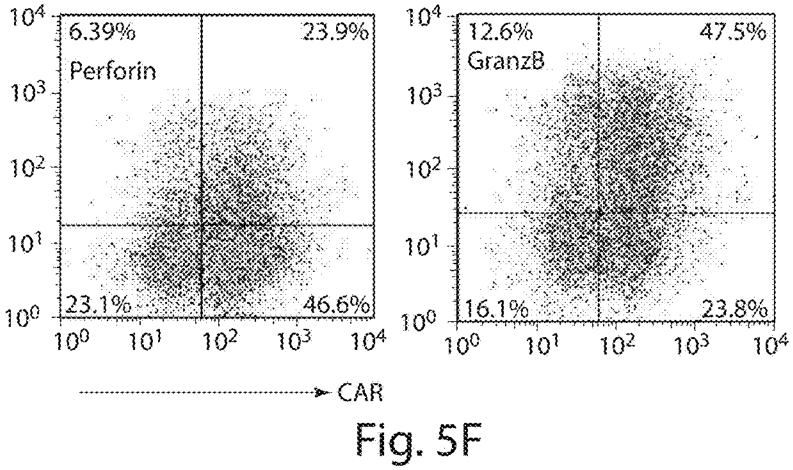
Figure 5G:
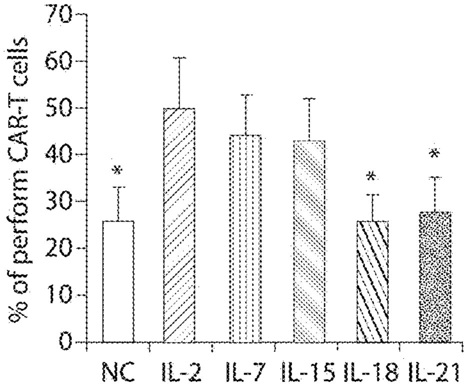
Figure 5H:
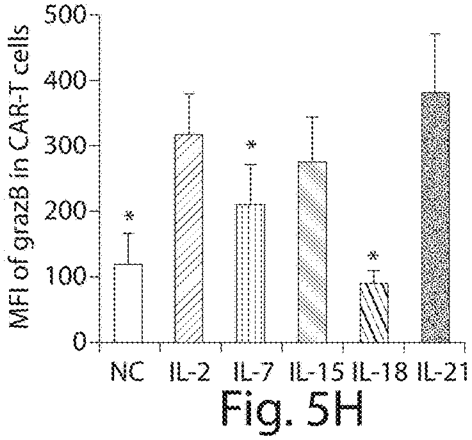
Figure 5I:
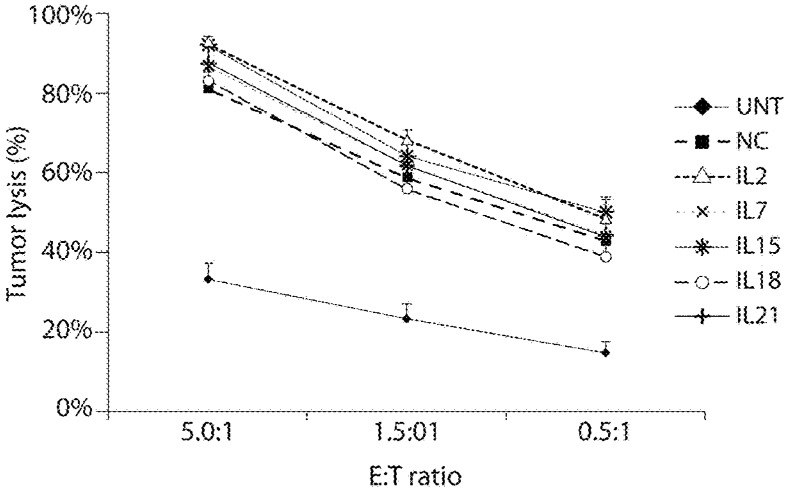

Then, the effect of cytokine exposure during expansion on the expression of the cytolytic molecules perforin and granzyme-B after antigen stimulation was determined (FIG. 5I). Similar with TNF-α production, the CAR-T cells exposed to IL-2, IL-7, and IL-15 demonstrated increased perforin expression compared with CAR-T cells exposed to NC, IL-18 and IL-21. However, although CAR-T cells exposed to IL-21 produce less TNF-α and perforin, they produced the highest level of granzyme-B. The next highest levels of granzyme-B production were observed in CAR-T cells exposed to IL-2 and IL-15 during expansion. CAR-T cells in IL-18 group presented the least amount of both perforin and granzyme-B expression after antigen stimulation (FIGS. 5G and 5H).

Finally, the tumor lysis activity by CAR-T cells exposed to various cytokines during exposure was quantified by luciferase assay. As shown in FIG. 5F, CAR-T cells co-cultured with IL-2 and IL-15 lysed the SKOV3 more efficiently than those with NC and IL-18 (both $P<0.05$).

Figure 6A:
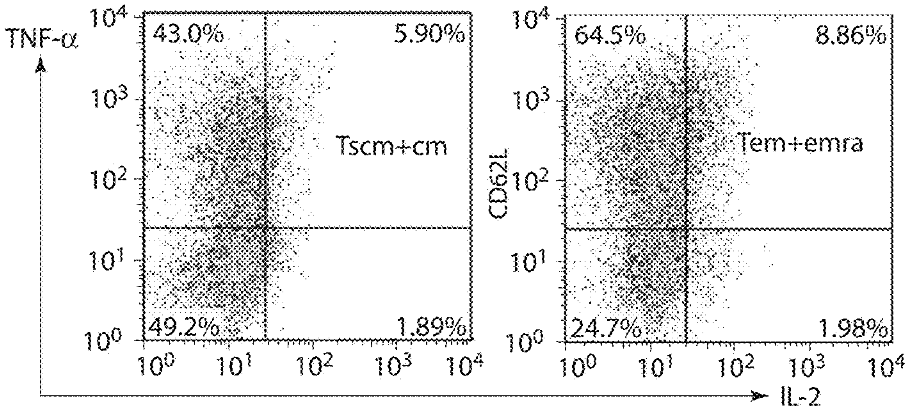
FIG. 6A-6C: shows the phenotype and function of the CAR-T cells described above in FIGS. 5A-5I.
Figure 6B:
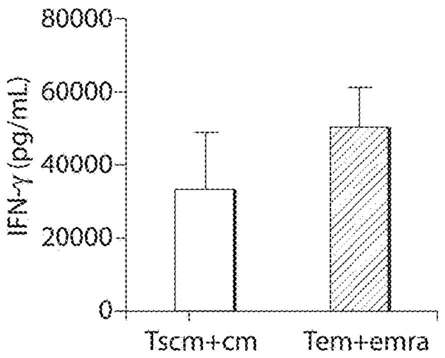
Figure 6C:
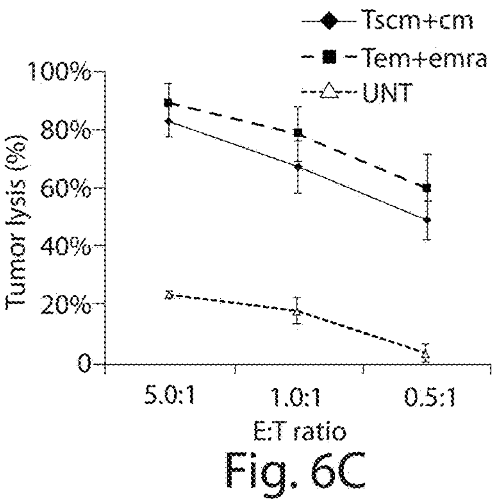

The association between phenotype of the CAR-T cells and their function was further confirmed. The T cells 14 days were sorted after lentiviral transduction based on CAR and CD62L expression. The CD62L+CAR-T cells (Tscm and Tcm) exhibited less cytokine production activity and weaker cytolytic capacity when compared with CD62L− CAR-T cells (Tem and Temra) (FIG. 6). In this perspective, CAR-T cells exposed to IL-2 and IL-15 produced more cytokines and presented stronger tumor lysis activity, which might be partially attributed to the higher proportions of Tem and Temra in these groups.

5. Expansion and Phenotype of CAR-T Cells after Antigen Challenge

Figure 7A:
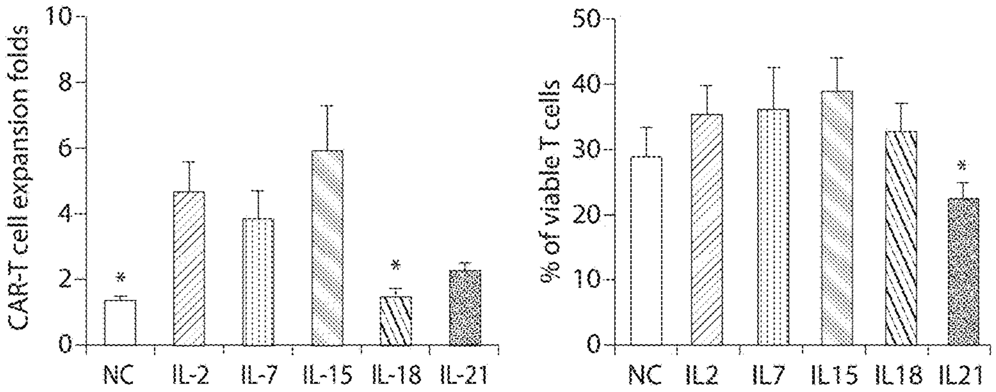
FIGS. 7A-7E show the expansion and phenotype of CAR-T cells exposed to antigen challenge.
Figure 7B:
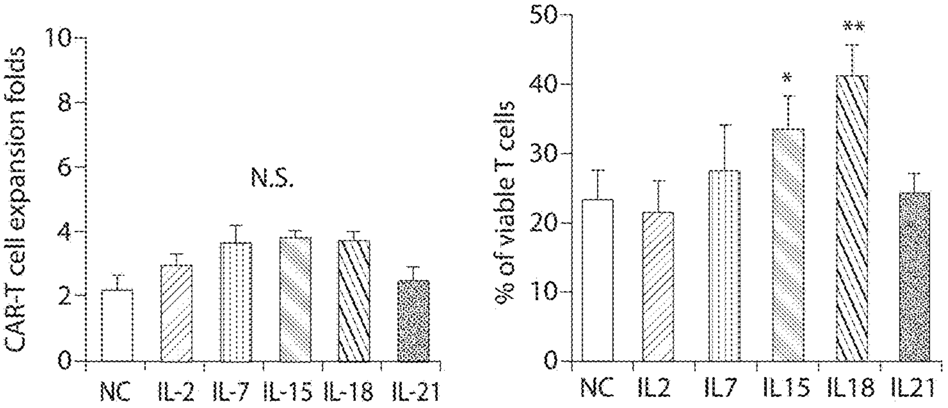
Figure 7C:
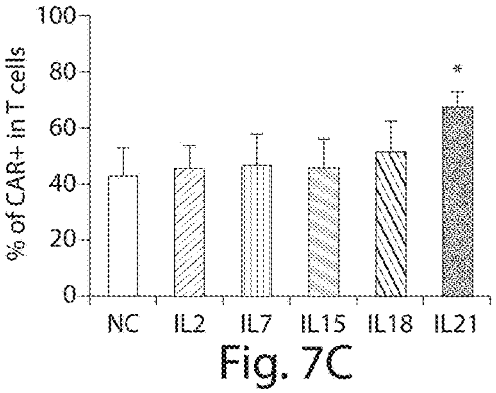
Figure 7D:
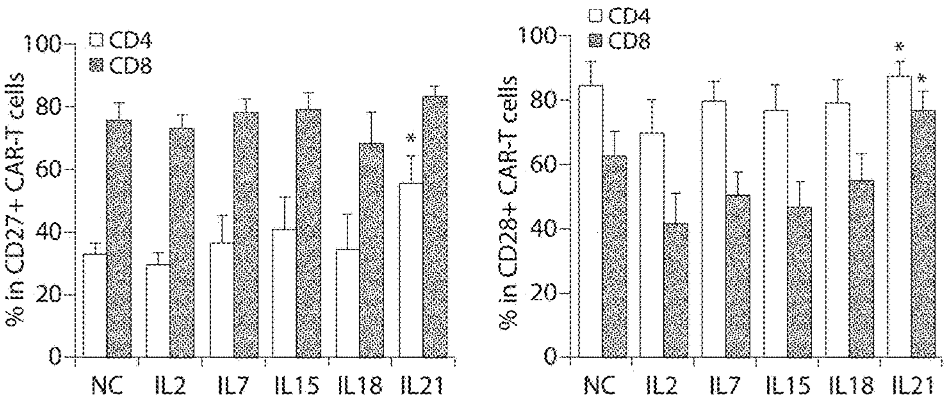
Figure 7E:
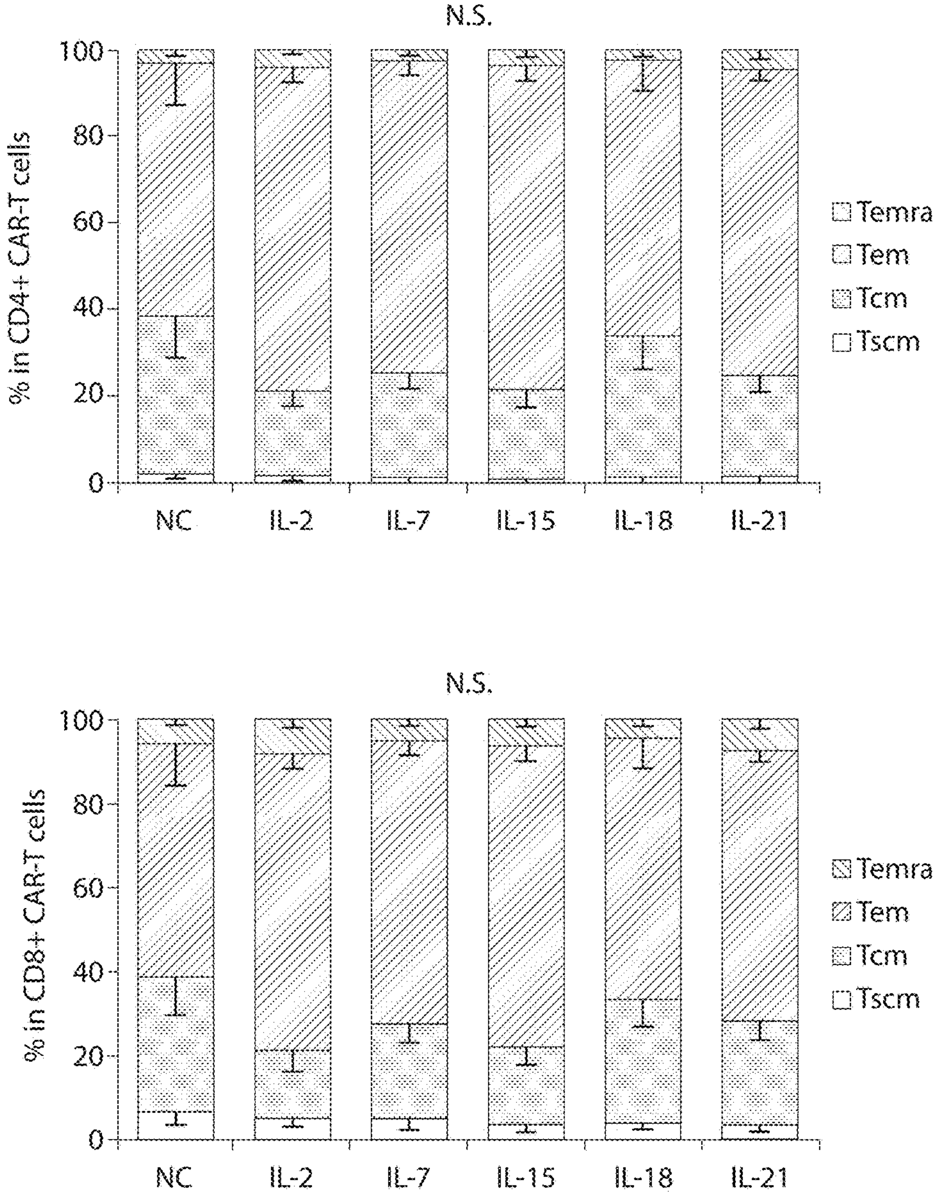

To investigate the influence of cytokines on CAR-T cell expansion under the challenge of specific antigen, the CAR-T cells exposed to IL-2 for two weeks were co-cultured with SKOV3 (FRα+) or C30 (FRα−) cells in the presence of indicated cytokines for 7 days. Similar to the antigen-free circumstance, CAR-T cells exposed to IL-2, IL-7 and IL-15 presented higher fold expansion than CAR-T cells exposed to other cytokines. The CAR-T cells exposed to IL-21 during expansion were more likely to undergo apoptosis (FIG. 7A). However, when the CAR-T cells exposed to the indicated cytokines for two weeks were co-cultured with SKOV3 or C30 cells without further cytokine supplement for 7 days, the accumulation of CAR-T cells were comparable among all groups, with those having been exposed to IL-15 and IL-18 undergoing the least amount of apoptosis (FIG. 7B). The T cells with the highest CAR expression was the group exposed to IL-21 during expansion (FIG. 7C). The phenotypes of CAR-T cells were also analyzed. CD27 and CD28 were highly expressed in CD8+ and CD4+CAR-T cells in all cytokine groups, respectively. Similar to antigen-free expansion, IL-21 exposure increased the expression of CD27 and CD28 in CAR-T cells (FIG. 7D). As to the four subsets of memory T cells, the results were different from antigen-free study: Tscm was rare and Tem accounted for more than 50% in no cytokine, IL-18 and IL-21 all groups. Cytokines had no significant impact on the composition of memory T subsets and IL-7 exposure did not favor the increase of Tscm (FIG. 7E).

6. Anti-Tumor Efficacy of Various Cytokines in Animal Models

Figure 8A:
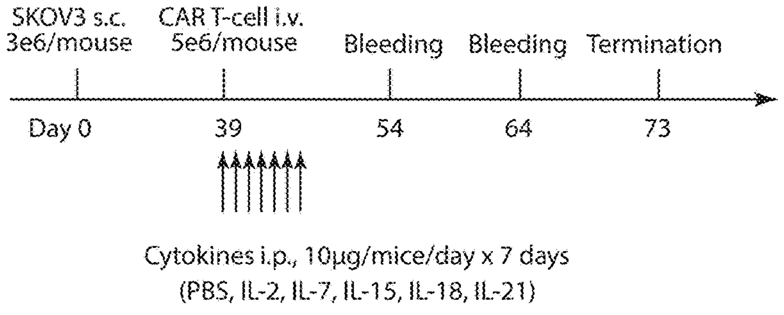
FIGS. 8A-8G show the antitumor activity of various CAR-T cells with previous cytokine exposure.
Figure 8B:
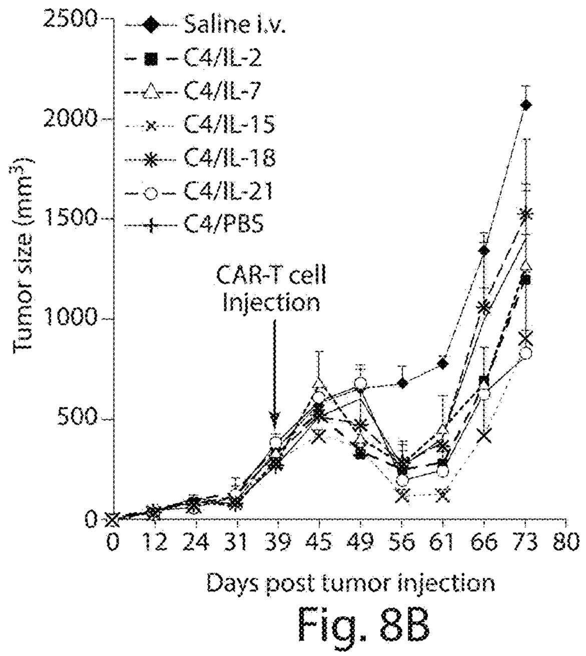
Figure 8C:
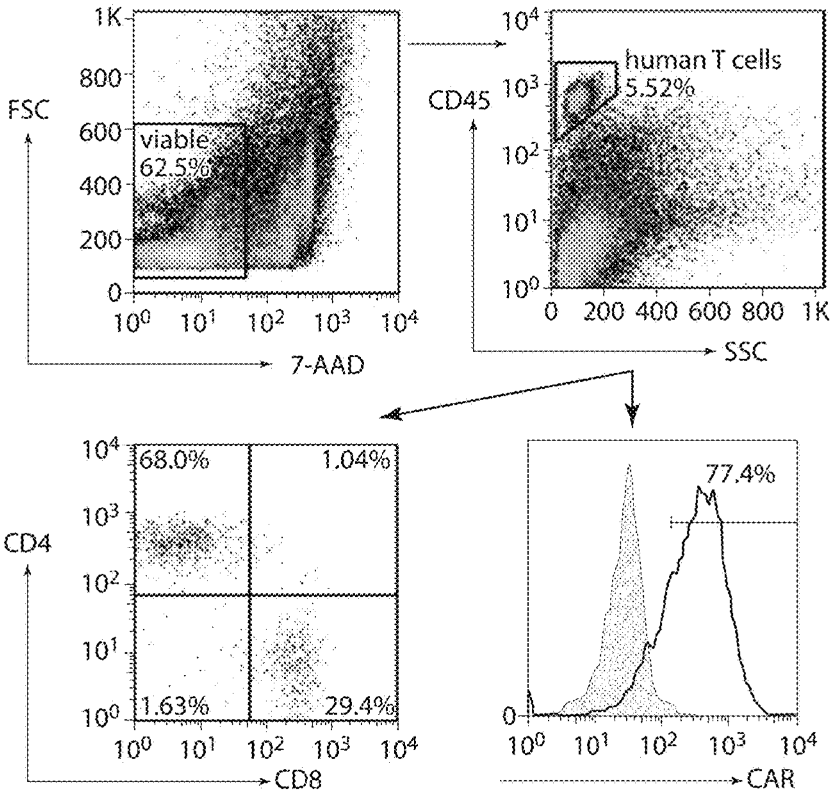
Figure 8D:
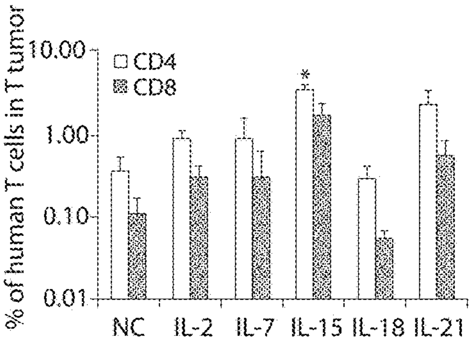
Figure 8E:
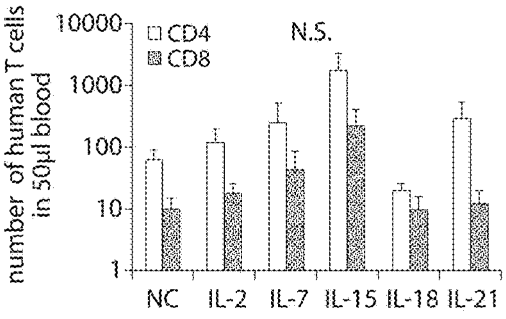
Figure 8F:
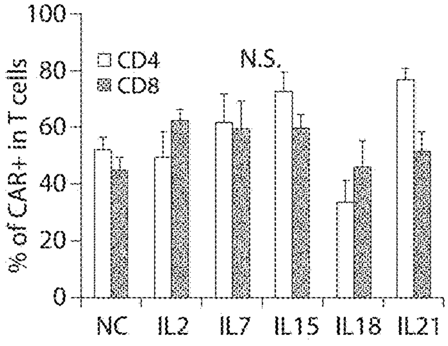
Figure 8G:
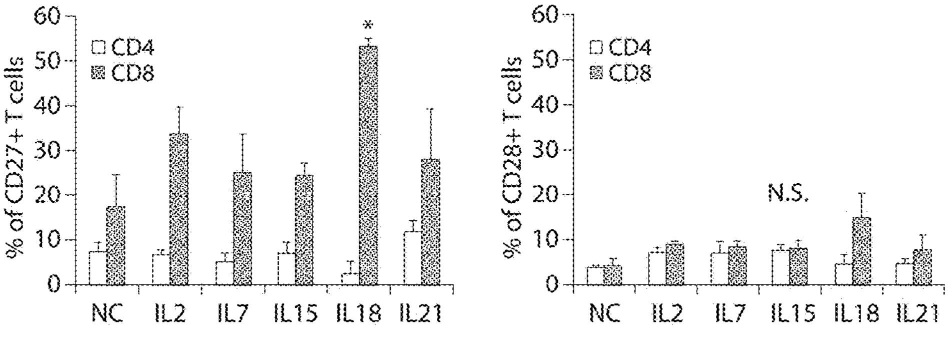

To evaluate the effects of various cytokines during ex vivo expansion of CAR-T cells on the efficacy of CAR-T cells in vivo, the persistence of CAR-T cells and outcome was investigated by using a NSG mouse xenograft model of ovarian cancer. Mice bearing subcutaneous SKOV3 tumors were intravenously injected with two doses of 5×106 C4-27z CAR-T cells which had been exposed to the indicated cytokines ex vivo for 2 weeks previously (FIG. 8A). All mice receiving C4-27z CAR-T cell infusion presented less tumor burden when compared with those injected with untransduced T cells and anti-CD19 CAR-T cells (FIGS. 8B&8C). Of the various cytokine groups, mice receiving CAR-T cells with previous IL-2 exposure showed the highest tumor burden, consistent with the least amount of circulating human T cell in these mice. The tumors in NC, IL-7, IL-15, IL-18 and IL-21 groups were all significantly suppressed or even disappeared, without any statistical difference on tumor size. The persistence of transferred T cells in the peripheral blood was determined 15 and 32 days after adoptive transfer. Mice receiving IL-7 and IL-21 treated CAR-T cells seemed to have higher amount of human T cells than other groups in the peripheral blood on day +15, while mice receiving IL-2 treated CAR-T cells had the lowest number of human T cells (FIG. 8D). As to the percentages of different CAR-T cell populations, NC, IL-15, IL-18 and IL-21 exposed groups all presented higher CD4+ CAR-T cells when compared with IL-2 group, while the percentages of CD8+ CAR-T cells were comparable among all the groups (FIG. 8E). Of the T cell phenotypes, CD62L, CD27 and CD28 were expressed only on about 5-10% of T cells and were comparable among all groups, except that CD8+ T cells in IL-21 group expressed higher CD28 than those in IL-2 and NC group (both P<0.05) (FIGS. 8F&8G). Interestingly, NC and IL-18 had a much higher amount of CD45RA+CD62L+ T cells in the blood, which was opposite to the result obtained from the in vitro experiment (FIGS. 8F, 2E&2F). On day +32, the circulating human T cells in all CAR-T cell groups expanded significantly except the IL-2 group, with an average T cell account of 14907/μl to 19651/μl (and only 242/μl in the IL-2 group). Two mice died although the tumors were regressed.

Discussion

IL-2 is the most frequently used cytokine for generating lymphocytes for adoptive immunotherapy. It promotes T cell survival and expansion, enhances tumor-killing ability of T cells. However, the action of IL-2 is limited as it results in activation induced cell death (AICD) of T-cell and the development of regulatory T-cell (Malek et al., *Immunity,* 2010, 33:153-65; and Lenardo et al., *Annu Rev Immunol,* 1999, 17:221-53). In this example, IL-2 significantly increased the accumulation of CAR-T cells and their cytotoxicity ability, but IL-2 exposed CAR-T cells presented inferior antitumor immunity in vivo following adoptive transfer. This finding demonstrates an inverse relationship between in vitro tumor-lysis and in vivo tumor eradication. IL-2 exposed CAR-T cells displayed a relative mature phenotype with low expression of CD62L, CCR7, CD27 and CD28, which are less persistent in vivo (Yang et al., *Cancer Immunol Immunother,* 2013, 62:727-36). Recent studies have indicated that adoptive transfer of less differentiated T cells correlates with superior tumor regression, which supports the finding that IL-2 exposed CAR-T cells are less effective than other group (Gattinoni et al., *Nat Med,* 2011, 17:1290-7; and Markley et al., *Blood,* 2010, 115:3508-19).

IL-15 presented similar performance of stimulating CAR-T cell expansion and tumor-lysis function as IL-2, but induced a less differentiated phenotype (higher expression of CD27 and CD28). Therefore, IL-15 supports the persistence of CAR-T cells in vivo and shows better antitumor immunity in animal models.

Compared with IL-2 and IL-15, IL-7 showed similar capability to promote CAR-T cell expansion, but induced higher level of CD62L expression and exhibited the highest proportion of CAR-Tscm cells in an antigen-free circumstance. Therefore, compared to CAR-T cells exposed to IL-2, ex vivo exposure of IL-7 without antigen challenge enhanced the antitumor efficacy of the CAR-T cells. IL-7 exposed CAR-T cells did not result in better in vivo antitumor efficacy than IL-2, and efficacy was inferior to IL-15 due to the less expansion of CAR-T cells under antigen challenge.

IL-21 exerted few effects on CAR-T cell accumulation as it could not enhance anti-apoptosis ability, e.g., by promoting Bcl-xL expression. However, IL-21 induced the expansion of less differentiated CAR-T cells, with a phenotype of high expression of CD62L, CCR7, CD27 and CD28, even under the circumstance of antigen challenge. Therefore, IL-21 exposed CAR-T cells showed best persistence in animal models and IL-21 injection in vivo, and also presented a better efficacy in promoting tumor eradication than other cytokine groups except IL-15. These results are consistent with previous finding that less differentiated CAR-T cells correlates with superior tumor regression.

IL-18 is proinflammatory cytokine belonging to the IL-1 family, which regulates both innate and adaptive immune responses by activating monocytes, NK cells, and T cells and production of IFN-γ as well as other cytokines in vivo (Srivastava et al., *Curr Med Chem,* 2010, 17:3353-7). The results presented herein indicates that IL-18 has little impact on CAR-T cell's expansion, phenotype and function in ex vivo experiments, as most of the results in IL-18 groups are similar and comparable with NC group. IL-18 promoted little proliferation of T cells and maintained more T cell survival under antigen challenge compared to the control (NC) group. In vivo studies show that IL-18 has no significant impact on CAR-T cell efficacy when compared with mice without cytokine supplement.

In summary, the findings of these experiments indicate that IL-2 supplement ex vivo for CAR-T cell expansion is not an optimal strategy although it is widely used. As to IL-18, IL-21 or no cytokine supplement, although they may induced relative effective CAR-T cells, they do not promote CAR-T cell expansion effectively enough, such that enough CAR-T cells could be prepared for clinical use in a limited expansion time. Therefore, IL-15 and IL-7 may be better agents for CAR-T cell expansion. Furthermore, the combination of IL-7 and IL-15 supplement instructs the generation of Tscm, which is beneficial to produce more "young" CAR-T cells. As to in vivo cytokine injection, all γc cytokines supplement enhance antitumor efficacy, as many of them favor the expansion of CAR-T cells, with IL-15 presenting best effect. Mice receiving IL-15 exposed CAR-T cells by injection had increased efficacy, due in part to the increased expansion ability and increased persistence of the CAR-T cells during tumor treatment. Thus, the results of these experiments indicate that IL-7 and IL-15 show promise to promote CAR-T cell expansion and induce T cell phenotypes that are most efficacious for therapeutic treatment.

Example 2: Effect of CD25 Depletion on Cell Growth and Transduction Efficiency The interleukin-2 a-chain, also known as CD25, is expressed by regulatory T cells (Tregs) but has also been observed on chronic B cell leukemia (CLL) cells (in greater than 85% of CLL patients). Tregs have immune suppressing functions and can impede the efficacy of immunotherapy, e.g., by inhibiting T cell proliferation. Current isolation or enrichment of T cells from CLL patients by apheresis usually contains a significantly increased proportion of Tregs as well as CLL cells. The depletion of Tregs and CLL cells in the starting material by CD25 depletion methods may significantly improve the purity of effector T cells, and thereby increase the potency of CAR19 expressing T cells, e.g., CART19 cells.

Figure 9A:
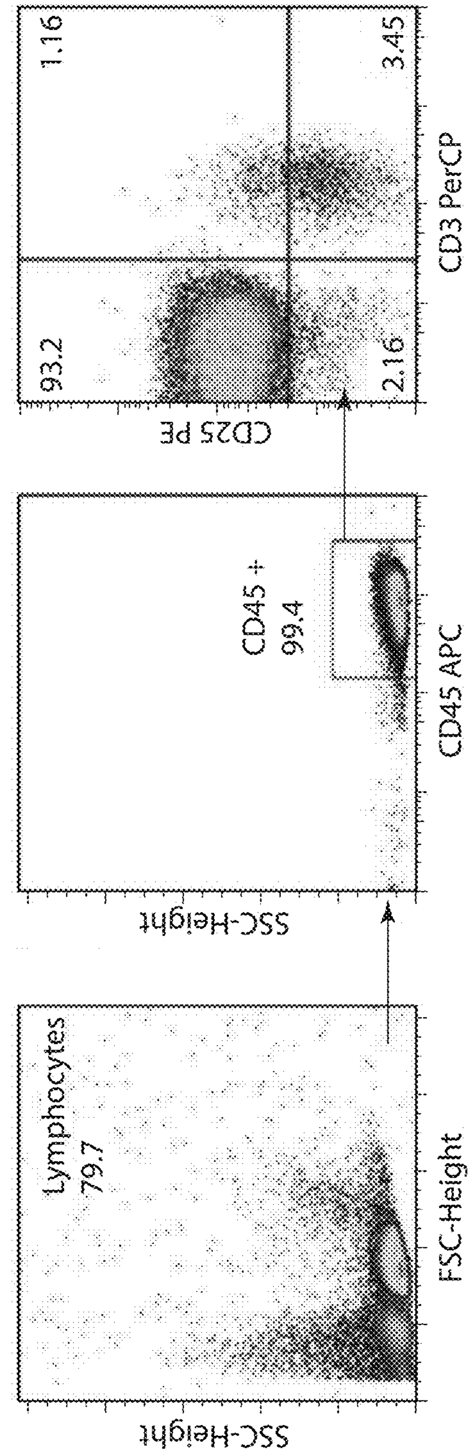
FIGS. 9A and 9B show FAC plots.

FIG. 9A shows flow cytometry analysis plots of the cells from an apheresis of a CLL patient. Cells were first sorted for CD45 expression, and the CD45-expressing (CD45+) subset was then further analyzed for CD25 and CD3 expression. As shown in the panel on the right of FIG. 9A, CLL patients exhibit a high percentage of CD25 expressing cells.

Optimizing CD25 Depletion

A validation experiment was performed to identify the optimal conditions for CD25 depletion from the aphereses from two patients using CD25 Reagent from Miltenyi in a CliniMACS System. CD25 depletion reagent was used at 100%, 70%, and 30% of the manufacturer's recommended amount to identify whether the same depletion efficiency could be obtained by using less reagent. Two different tubing sets from Miltenyi were also tested. The depletion was performed in accordance with the manufacturer's directions. The results from the experiments are shown in the table below. For control, selection using anti-CD3/CD28 immunomagnetic beads was performed.

TABLE 5

Experimental results from CD25 depletion.

| CD25 depletion arms | | 100% | 70% | 30% |
|---|---|---|---|---|
| Miltenyl tubing set | 161-01 | | | |
| CliniMACS program | ENRICHMENT1.1 | | | |
| Patient cells | UPCC04409-15 | | | |
| % CD45+CD25+ cells | 83.56% | | | |
| % CD45+CD3+ cells | 8.66% | | | |
| % CD45+CD3+CD25− cells | 5.70% | | | |
| #CD25+ cells to target | | 2.E+09 | 2.E+09 | 2.E+09 |
| #apheresed cells for CD25 depletion | | 2.39E+09 | 3.41E+09 | 7.97.E+09 |
| CD25 bead volume used (mL) | | 2.5 | 2.5 | 2.5 |
| Cell# in CD25-depleted fraction | | 1.05E+09 | 1.86E+09 | 3.36E+09 |
| Cell# in CD25-enriched fraction | | 2.05E+08 | 2.58E+08 | 5.19E+08 |
| Expected CD25− T-cell yield | | 1.36E+08 | 1.95E+08 | 4.54E+08 |
| % T cells in depleted fraction | | 6.26% | 4.08% | 2.50% |
| Observed yield CD25− T cells | | 6.57E+07 | 7.55E+07 | 8.40E+07 |
| Yield of CD3+CD25− as % of expected | | 48% | 39% | 18% |
| % B cells in depleted fraction | | 90.50% | 91.6% | 95.30% |
| Viability CD25+ fraction | | 94.4% | 96.2% | 91.1% |
| Viability CD25− fraction | | 95.8% | 95.0% | 99.0% |

The expected CD25− (CD25-negative) T cell yield represents the calculated CD25− T cell yield calculated by assuming 100% efficiency in the respective manipulations. The observed yield of CD25− T cells represents the number of CD25− T cells after the respective manipulations. As shown in Table 5, using less reagent than recommended by the manufacturer did not result in the same efficiency in CD25 depletion. Using different tubing resulted in an increase in T cell enrichment by one log.

Figure 9B:
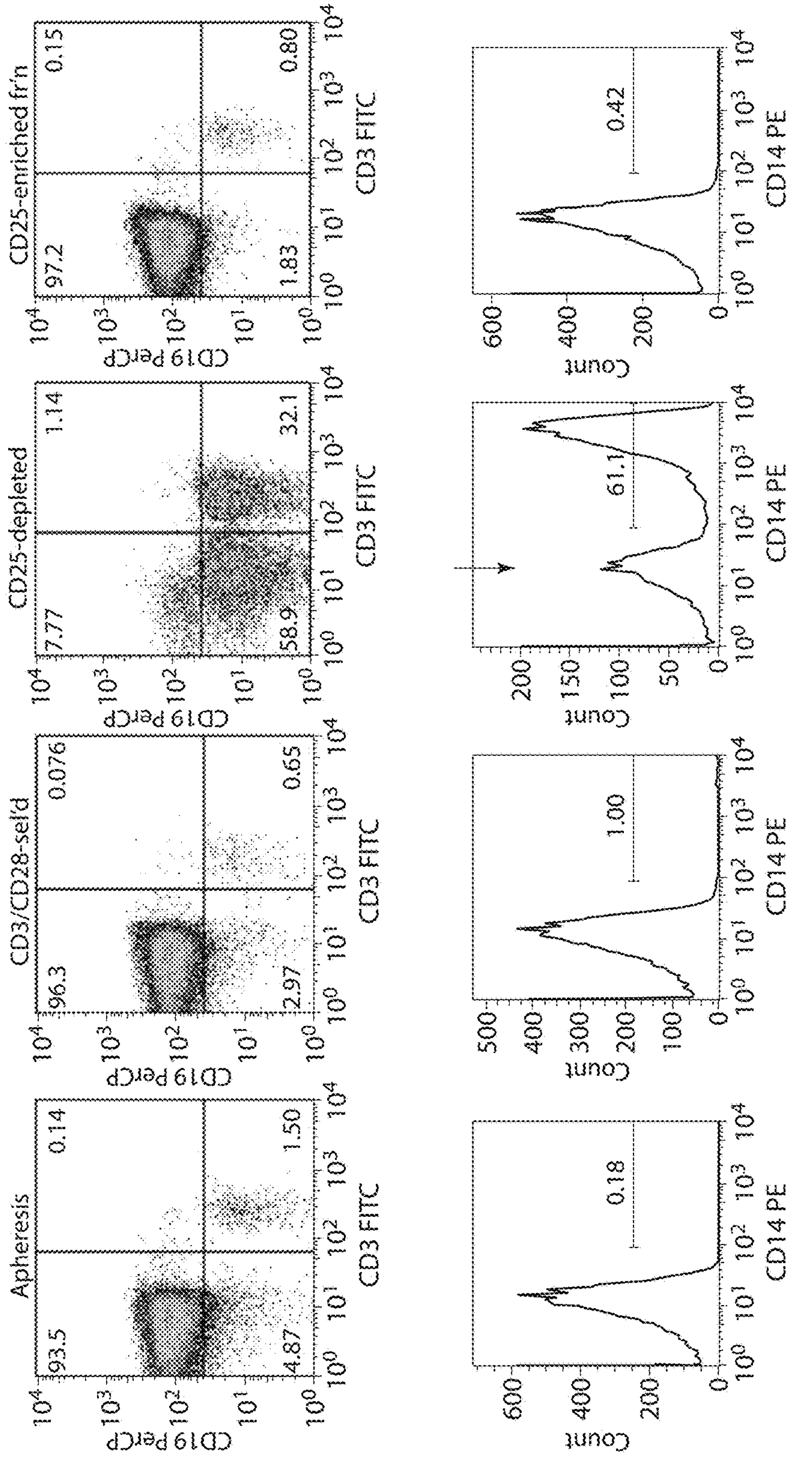

FIG. 9B shows representative flow cytometry analysis plots (top panels) demonstrating the efficiency of CD25 depletion compared to the total cells from the apheresis (top left panel of FIG. 9B), control CD3/CD28 selected cells (top middle left panel of FIG. 9B), CD25 depleted cells (top middle right panel of FIG. 9B), and CD25 enriched cells (top right panel of FIG. 9B). The histograms (bottom panels) show the monocyte content of the cell population, as determined by CD14 expression of the CD3-CD19− subset. These results indicate efficient CD25 depletion and that CD25 depletion also resulted in significant monocyte content (61.1% CD14-expressing cells compared to less than 2% in the total cells from apheresis, control, and the CD25 enriched cells.

Effect of CD25 Depletion on T Cell Population and Proliferation

Next, the quality of the T cell product after CD25 depletion was assessed by determining the proportion of CD4+ and CD8+ T cells and proliferation capacity.

Figure 10:
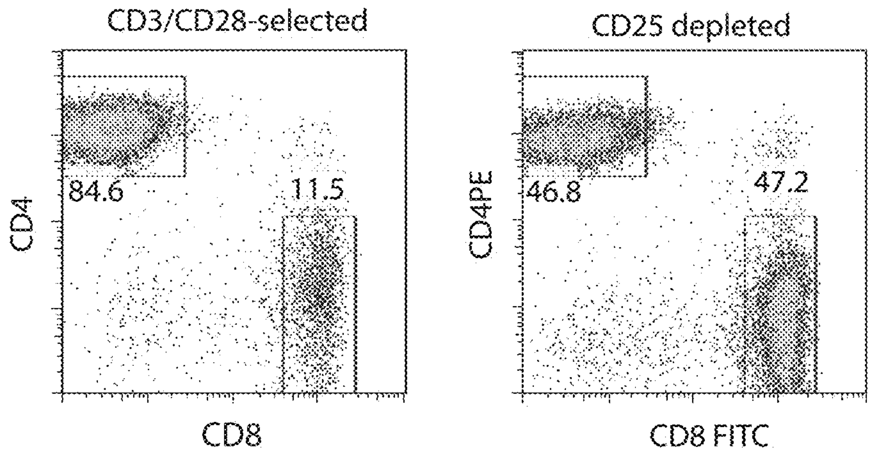
FIG. 10 is two FACs plots comparing the distribution of CD4+ and CD8+ T cell populations after CD3/CD28 selection or CD25 depletion.

To determine the proportion of specific T cells populations, cells were analyzed by flow cytometry nine days after selection by anti-CD3/CD28 or CD25 depletion as described above. The results show that CD3/CD28-selected T cells had a greater proportion of CD4+ T cells compared to CD25 depleted cells (84.6% compared to 46.8% CD4+ T cells, boxes at the top left of the panels in FIG. 10). Conversely, CD25 depleted cells had a greater proportion of CD8+ T cells compared to the CD3/CD28-selected cells (47.2% compared to 11.5% CD8+ T cells; boxes at the bottom right of the panels in FIG. 10). Therefore, CD25 depletion results in T cells with a greater proportion of CD8+ T effector cells.

Figure 11A:
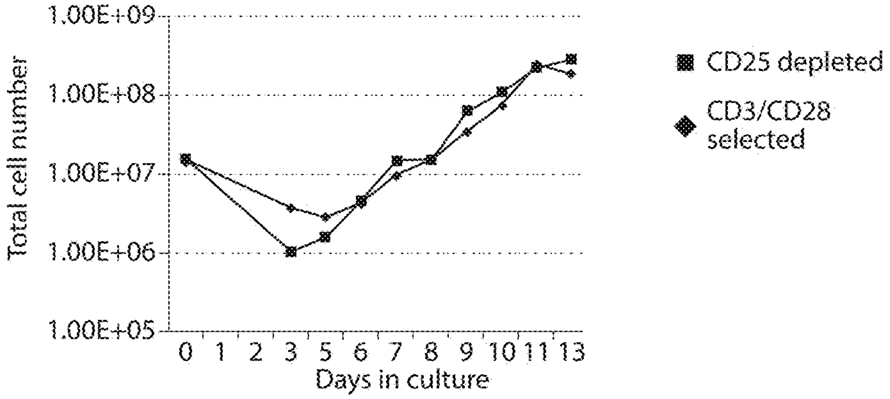
FIGS. 11A-11C show the comparison of proliferation capacity between CD3/CD28 selected cells and CD25 depleted cells.
Figure 11B:
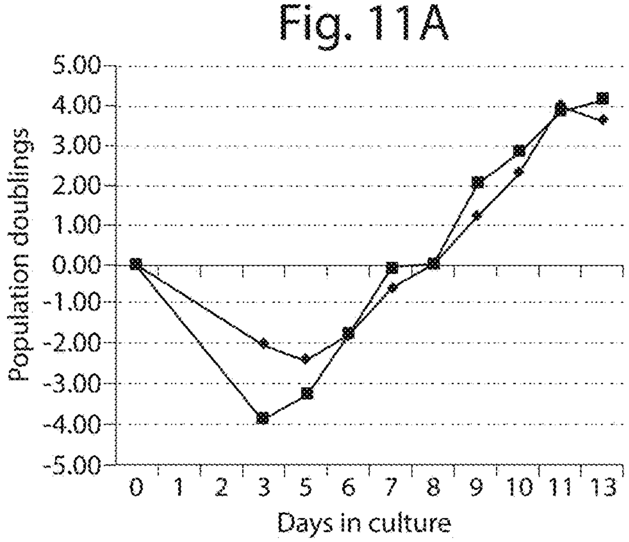
Figure 11C:
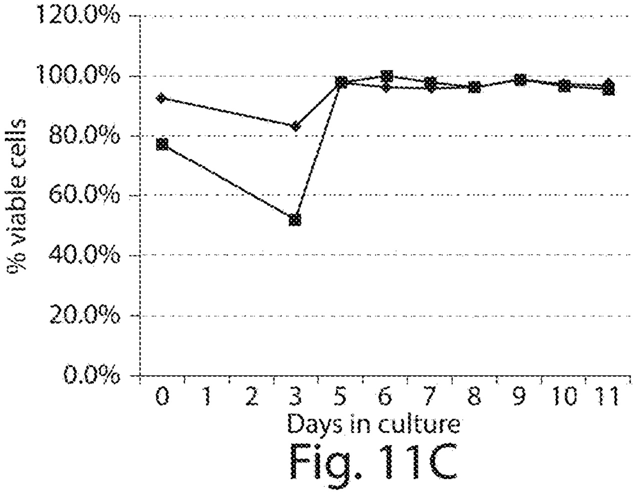

Proliferation capacity and cell viability was also assessed in control (CD3/CD28 selected cells) and CD25 depleted cells. $1.6\times10^7$ cells from control and CD25 depleted cells were plated and the cell number and viability was determined over 10-13 days. FIG. 11A shows the total cell number over time and FIG. 11B shows the calculated population doublings (calculated from the total number of cells). The results indicate that the CD25 depleted cells demonstrated similar growth characteristics to the control cells. FIG. 11C shows the percentage of viable cells, and the results show that viability was also similar between control and CD25 depleted cells.

Effect of CD25 Depletion on Lentiviral Transduction Efficiency

Figure 12A:
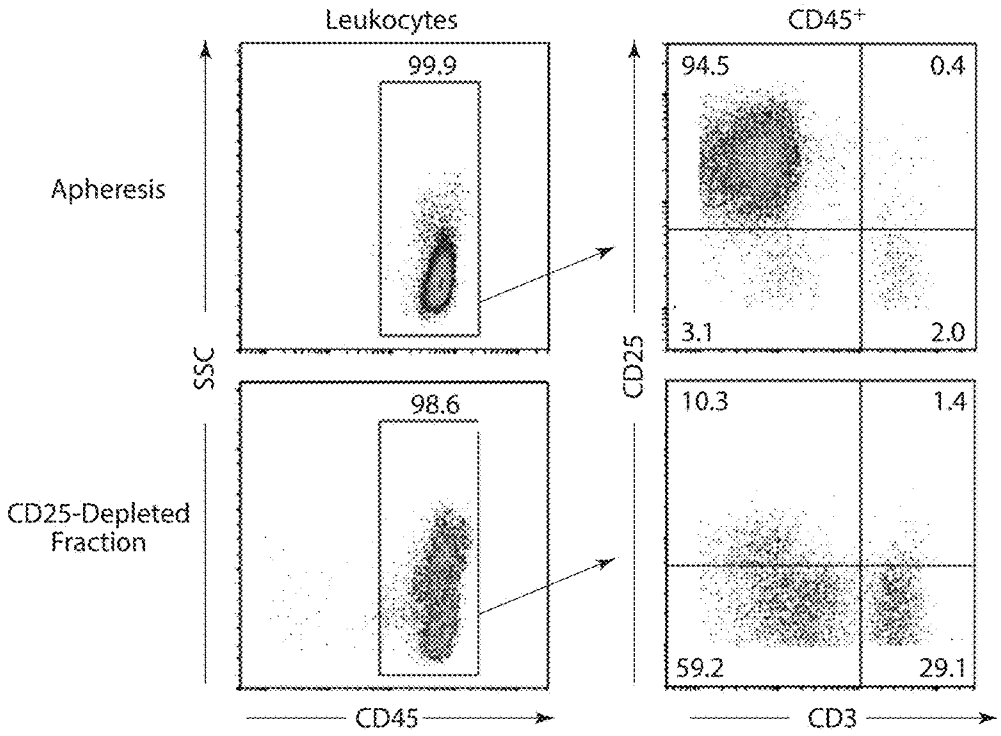
FIGS. 12A and 12B show the effect of CD25 depletion on lentiviral transduction of CAR19.

The effect of CD25 depletion on lentiviral transduction efficiency was assessed by determining the expression of CAR after transduction. A patient apheresis was depleted with CD25 cells as described above. The efficiency of the CD25 depletion is demonstrated in the flow cytometry analysis plots comparing the CD25-expressing population before (apheresis sample) and after CD25 depletion (CD25-depleted fraction) (FIG. 12A). After CD25 depletion, the CD25 depleted fraction contained about 59.2% of CD25 negative cells and only 10.3% CD25 positive cells.

Figure 12B:
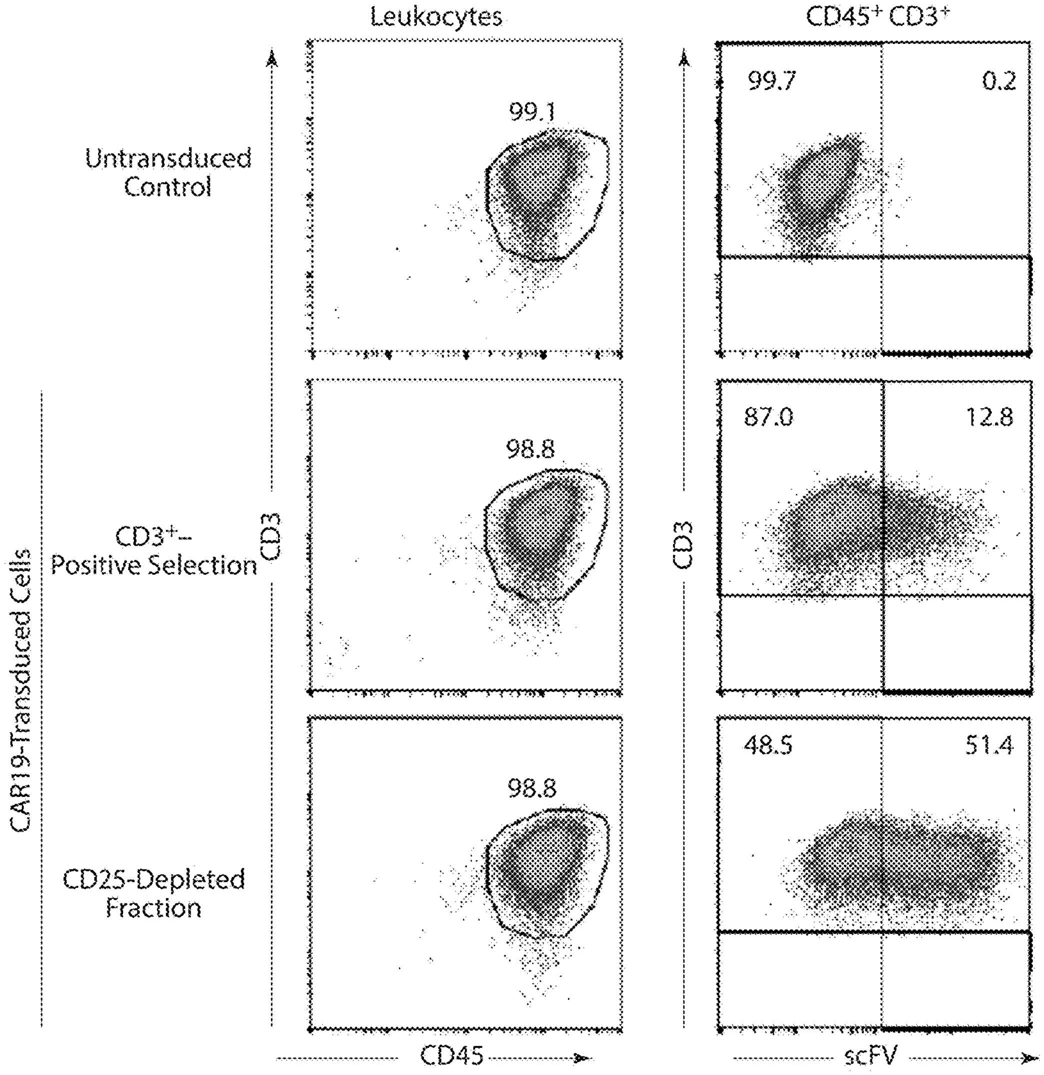

The CD25 depleted fraction was transduced with a lentiviral construct encoding CAR19. After 11 days of culture, CAR expression was assessed by flow cytometry. Cells that were untransduced and transduced CD3 selected cells were used as controls. As shown in FIG. 12B, CAR19 expression was significantly higher in CD25 depleted cells compared to CD3 selected cells (51.4% compared to 12.8%). This result demonstrates that CD25 depleted cells have improved lentiviral transduction efficiency, which may be important for improved therapeutic effect in CART therapy.

Example 3: Using Cytokines with CD25-Depleted Cells

In this example, the effect of CD25 depletion with cytokine supplement during expansion in culture was examined Peripheral blood mononuclear cells (PBMCs) were isolated from a patient and were either left unmanipulated or were depleted of CD25-expressing cells as described in Example 2. T cell enrichment was achieved by stimulation with anti-CD3 and CD28 coated beads. The T cells were immediately cultured in media supplemented with 10 ng/ml IL-7, 10 ng/ml IL-15, or the combination of 10 ng/ml IL-7 and 10 ng/ml IL-15. At day 3, medium was changed with the same cytokines added. At day 5, the medium containing 100 IU IL-2/ml was added, and the cells were grown for a total of 10 days.

Figure 13:
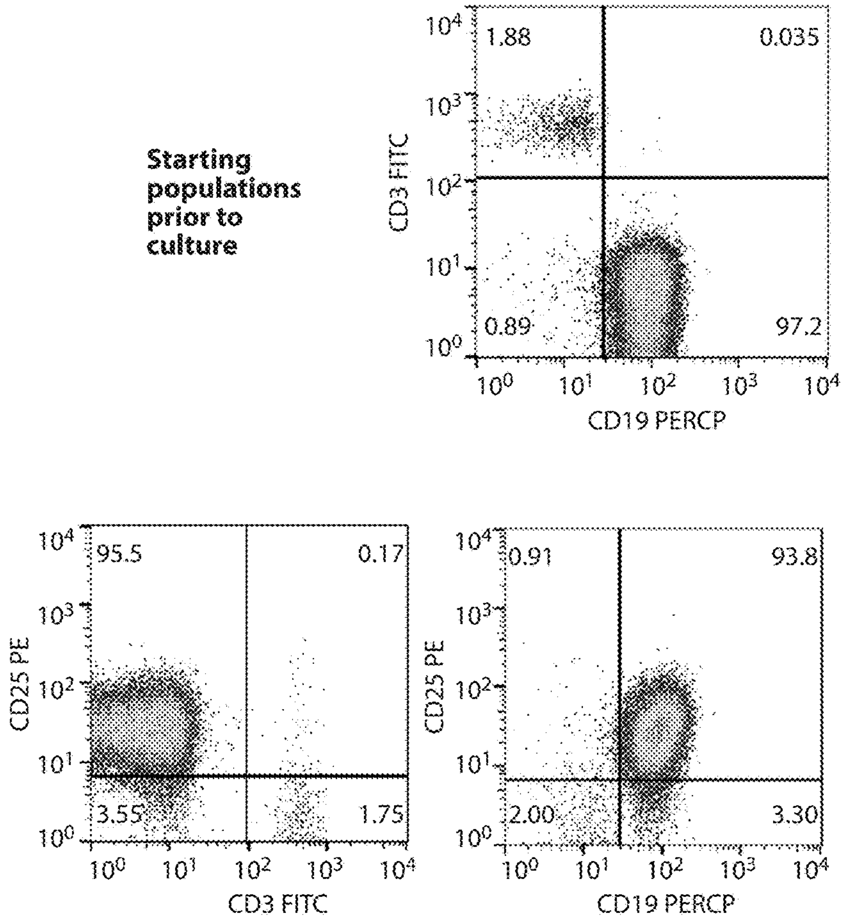
FIG. 13 is a series of FACS plots showing the distribution of CD3, CD19, and CD25 expression in cells from PBMCs from a patient before CD25 depletion or culture with cytokine supplement.
Figure 14:
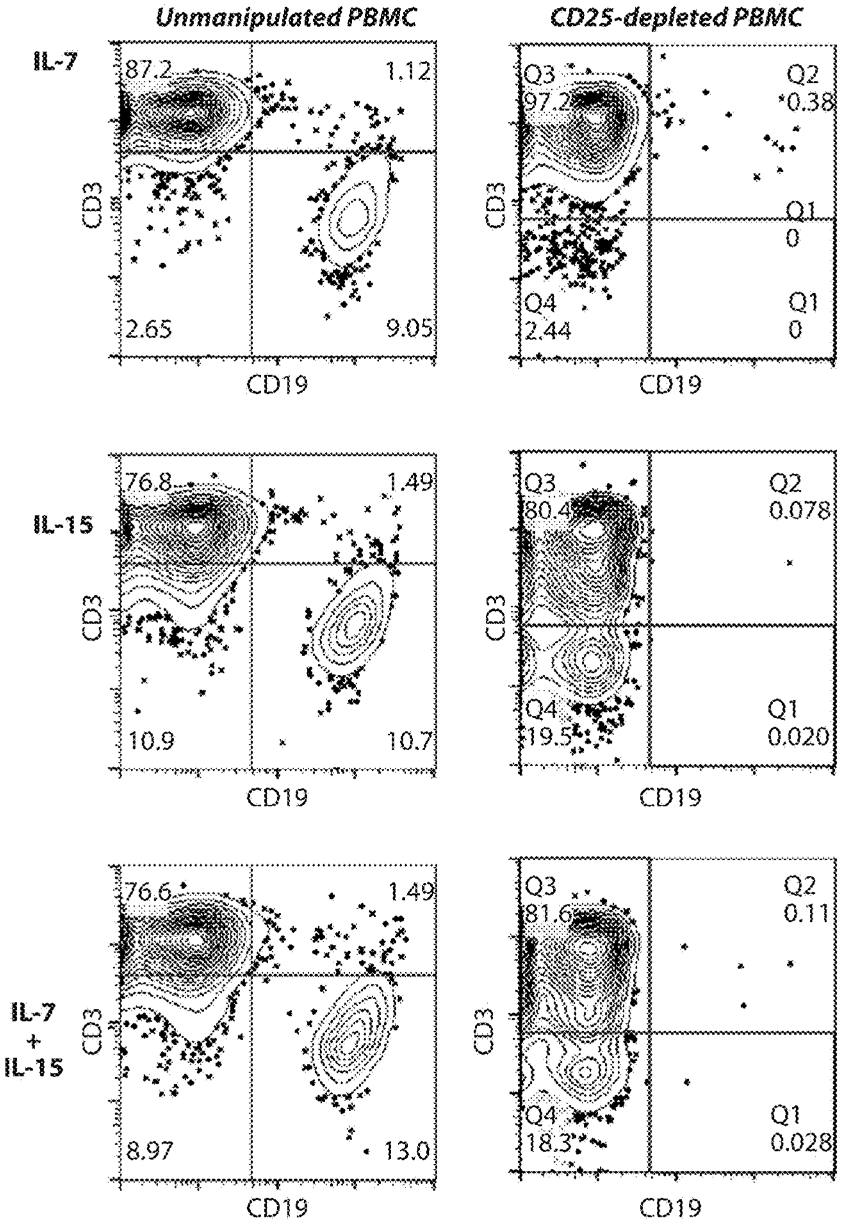
FIG. 14 is a series of FACs plots showing the distribution of CD3 and CD19 in unmanipulated PBMCs and CD25-depleted PBMCs after culture with the indicated cytokine supplements, IL-7, IL-15, or IL-7 and IL-15.

Flow cytometric analysis shows the change in distribution of CD3 and CD19 cells in CD25 depleted cells compared to unmanipulated PBMC (standard CD3/CD28 selection) after culture in the presence of IL7, IL-15, or IL7 and IL15. The distribution of CD3, CD19, and CD25 expressing cells in the starting population (e.g., before CD25 depletion and before culture with cytokine supplementation) is shown in FIG. 13. The starting population had a high proportion of CD3-CD19+ cells (top panel, FIG. 11) and a high proportion of CD25-expressing cells (bottom panels, FIG. 13). After manipulation (CD25 depletion) and culture with cytokines, the distribution changed as shown in FIG. 14. CD25 depleted cells overall showed greater reduction in CD19-expressing cells compared to the unmanipulated cells.

Figure 15:
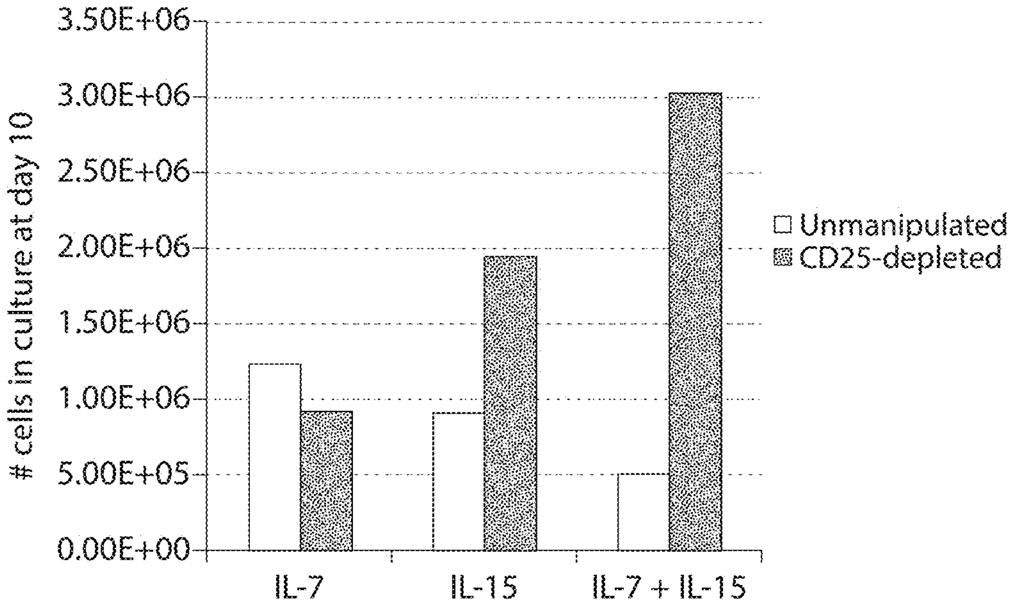
FIG. 15 is a graph showing the total number of cells after 10 days of culture with the indicated cytokine supplements.
Figure 16:
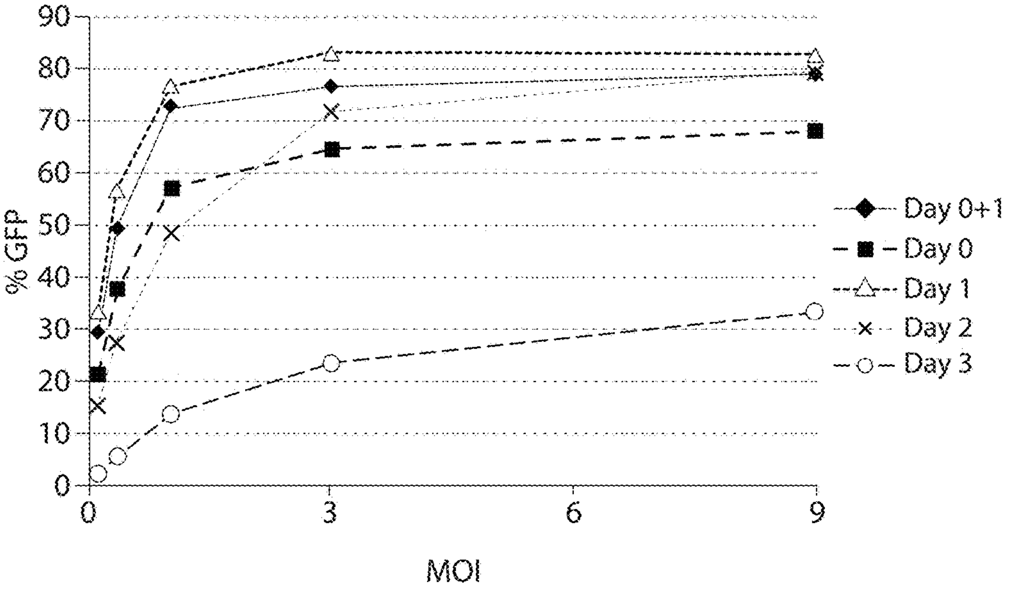
FIG. 16 is a graph showing the percentage of green fluorescent protein (GFP) signaling as an indication of lentiviral transfection levels for donor cells transfected on two days, the day of (day 0) and the day after (day 1) the cells were obtained by apheresis (day 0+1); donor cells transfected once, the day of obtaining the cells by apheresis (day 0); donor cells transfected once, the day after the cells were obtained by apheresis (day 1); donor cells transfected once, two day after the cells were obtained by apheresis (day 2); and donor cells transfected once, the day after the cells were obtained by apheresis (day 3).
Figures 17A, 17B:
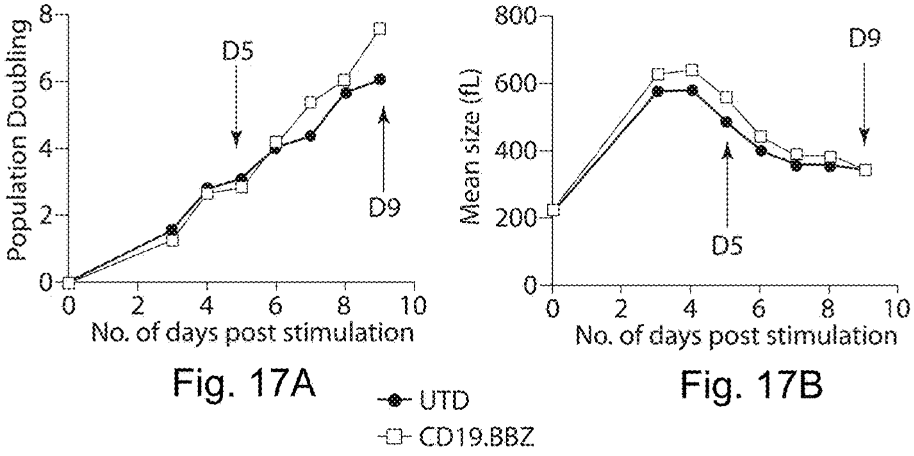
FIGS. 17A-17B comprise graphs showing expansion profile in population doublings (FIG. 17A) and mean size (fL)(FIG. 17B) of PBMCs that have been stimulated with anti-CD3 and CD28 beads, and left either unmanipulated (UTD) or transduced with a CD19 CAR (CD19.BBz), de-beaded, and then harvested at Day 5 and D9.
Figure 18:
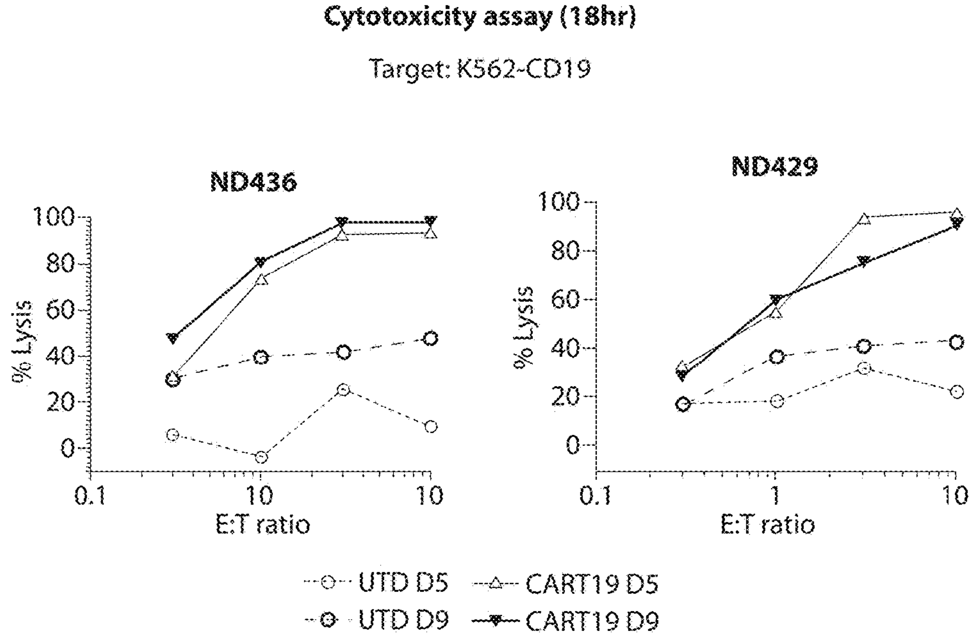
FIG. 18 comprises graphs depicting cytotoxicity as a percent lysis of CD19 expressing K562 cells treated with PMBCs that have been stimulated with anti-CD3 and CD28 beads, and left either unmanipulated (UTD) or transduced with a CD19 CAR (CD19.BBz), de-beaded, and then harvested at Day 5 and D9.
Figure 19:
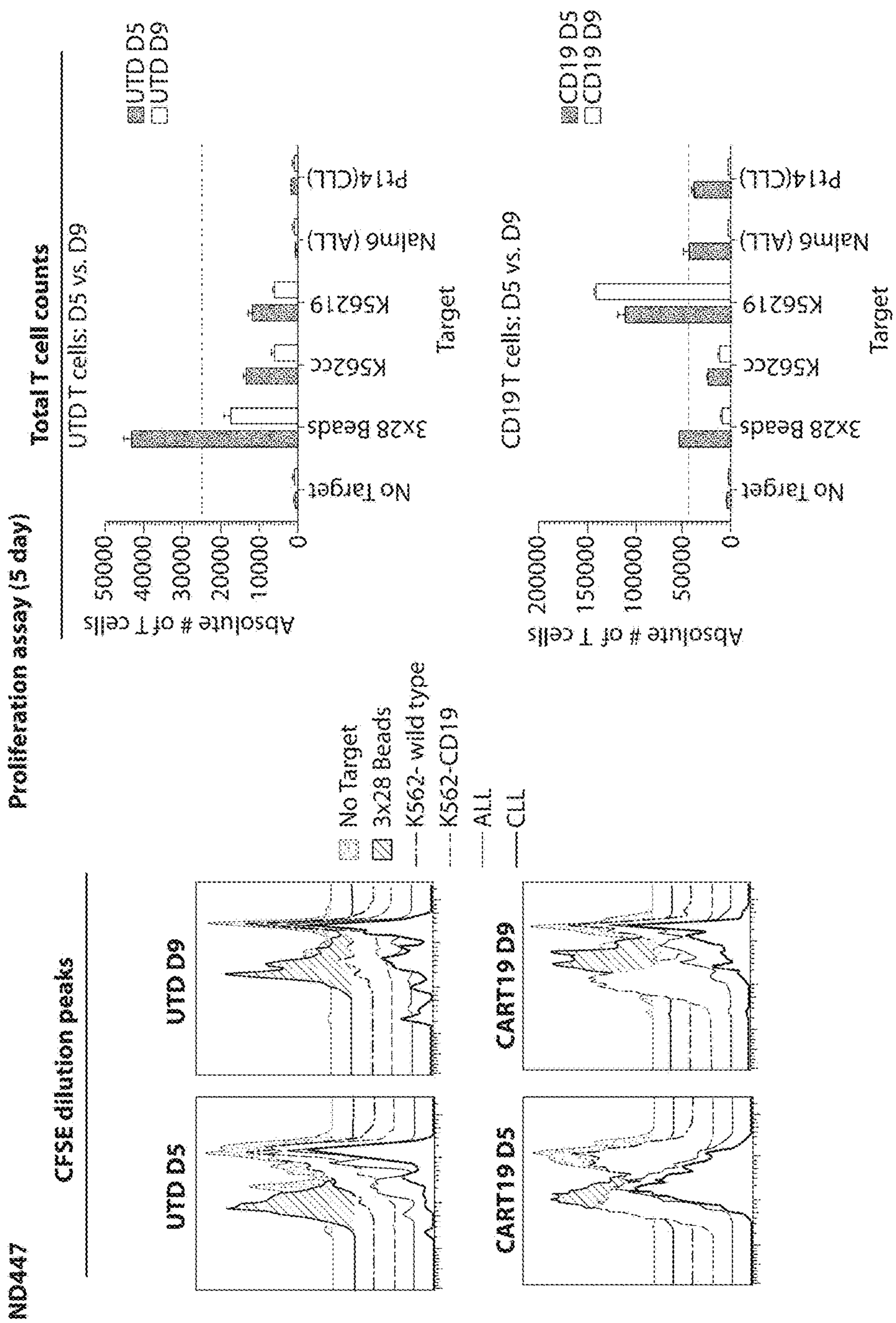
FIG. 19 comprises graphs depicting proliferation of PBMCs stimulated with anti-CD3 and CD28 beads (3×28 beads), wild type K562 cells, CD19 expressing K562 cells, ALL cells (Nalm6) or CLL cells (PI14). The PBMCs have been left either unmanipulated (UTD) or transduced with a CD19 CAR (CART19), de-beaded, and then harvested at Day 5 and D9.
Figure 20:
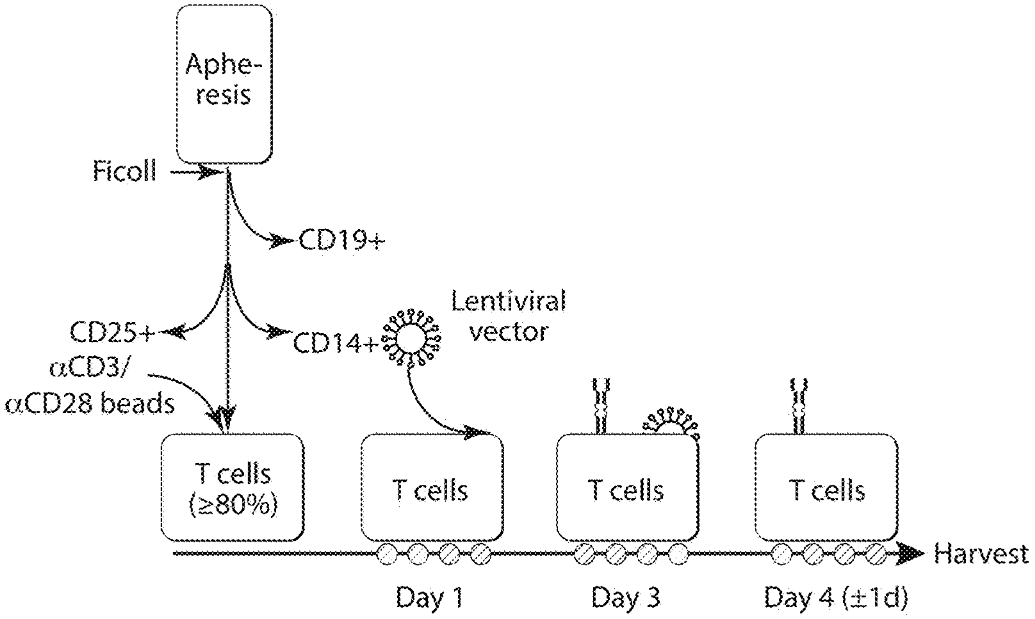
FIG. 20 is a schematic of an exemplary manufacturing scheme.
Figure 21:
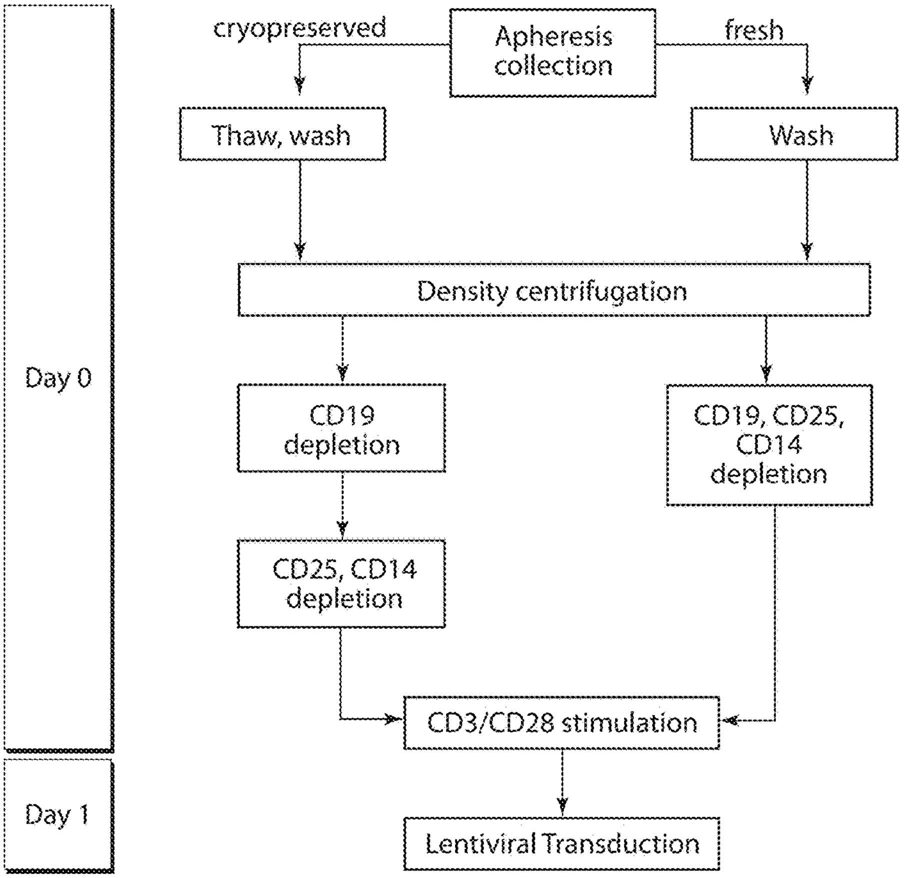
FIG. 21 is a schematic of an exemplary manufacturing scheme.
Figure 22:
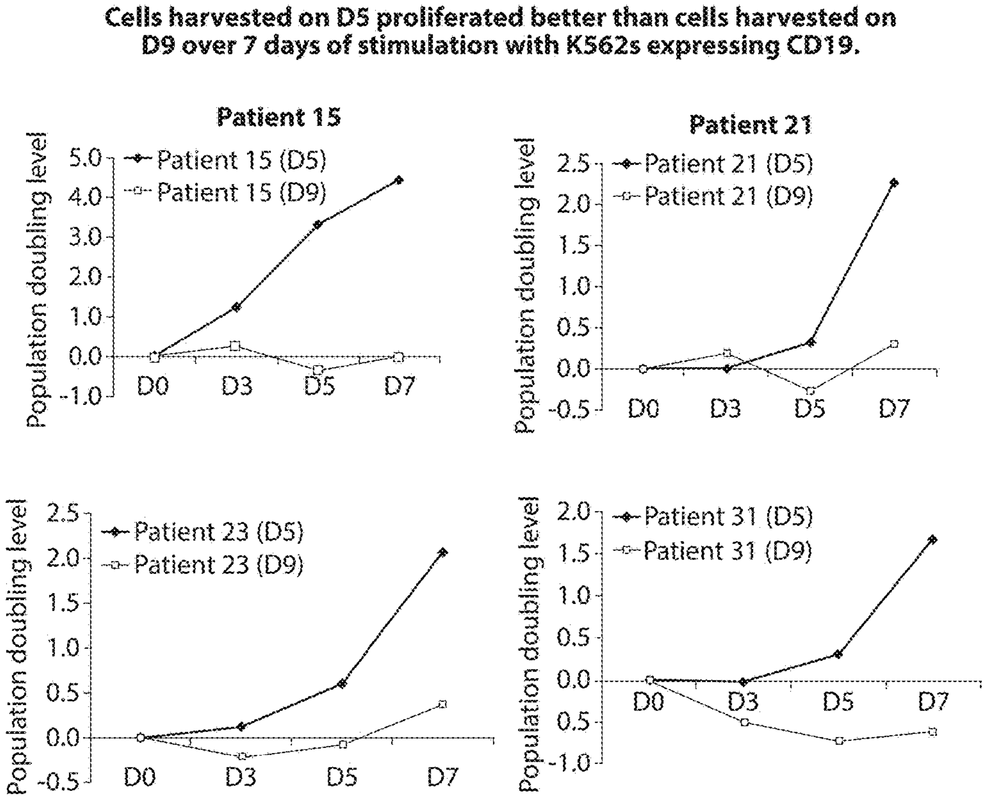
FIG. 22 comprises graphs depicting the level of cell proliferation of two different manufacturing batches of donor cells transfected with the CTL019 CAR, Patient 15 (left panels) and Patient 21 (right panels), expanded over a period of 0 to 9 days.
Figure 23:
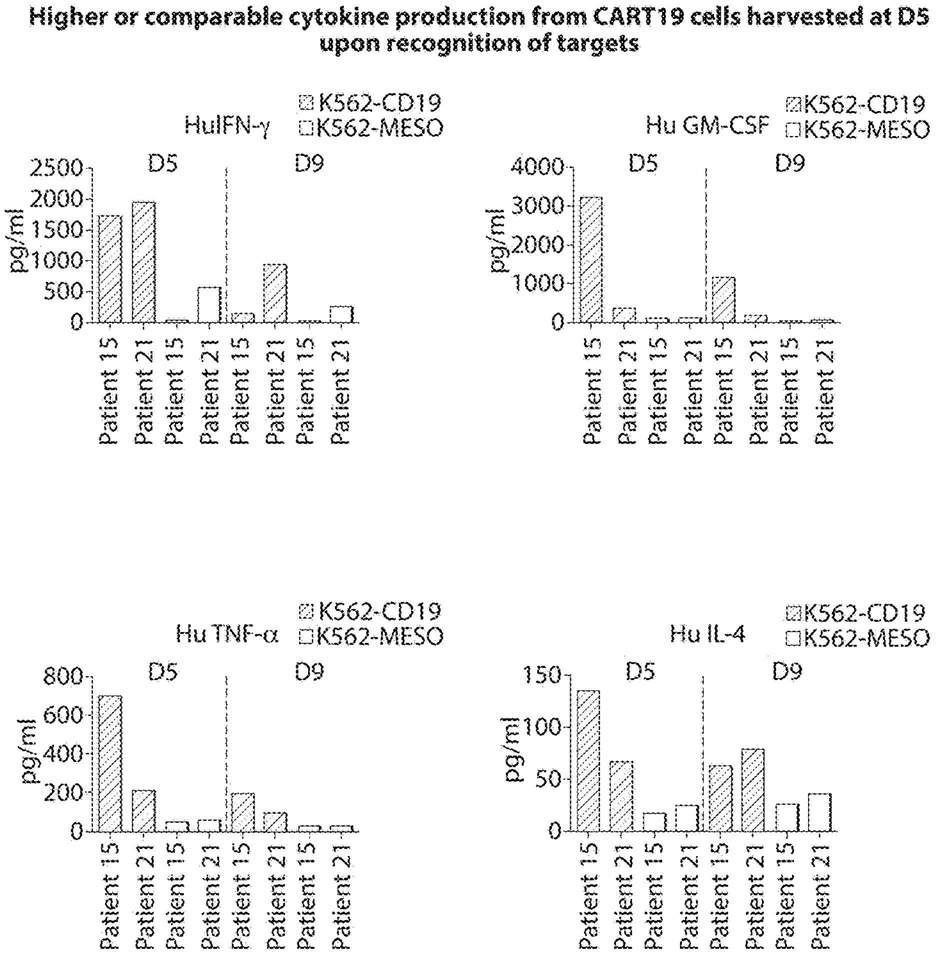
FIG. 23 comprises graphs showing proinflammatory cytokine production, IFN-γ, GM-CSF, TNF-α and IL-4 of two different manufacturing batches of donor cells transfected with either CTL019 CAR, namely Patient 15 cells, or an ss1-mesoCAR, namely Patient 21 cells, and expanded over a period of 0 to 9 days after apheresis.
Figure 24:
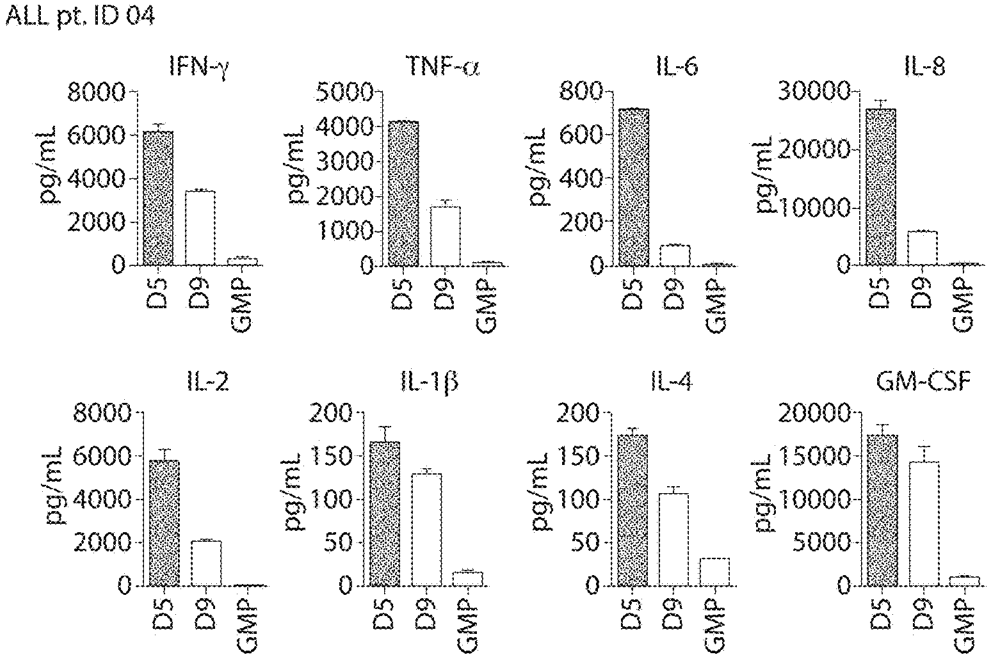
FIG. 24 comprises graphs depicting production levels IFN-γ, TNF-α, IL-6, IL-8, IL-2, IL-1β, GM-CSF and IL-4 in donor cells stimulated with anti-CAR19-idiotype antibody beads or control beads, transfected with CTL019 CAR and expanded for 5 to 9 days. No cytokine or low cytokine levels (<200 pg/ml) were detected with the control beads.
Figure 25:
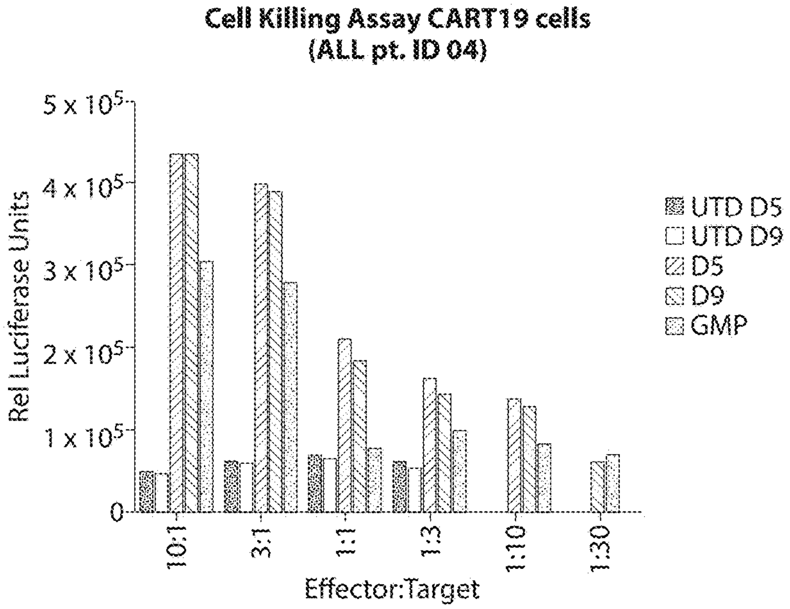
FIG. 25 is a graph depicting cell killing based upon total lysates using a luciferase assay of Nalm6 (ALL) cells of PBMCs left either unmanipulated (UTD) or transduced with a CD19 CAR. (CART19), de-beaded, and then harvested at Day 5 and D9. Various ratios of PMBCs to Nalm6 cells (effector (E):Target (T)) were cultured. As shown CART19 cells harvested at day 5 possess a better killing capacity.
Figure 26:
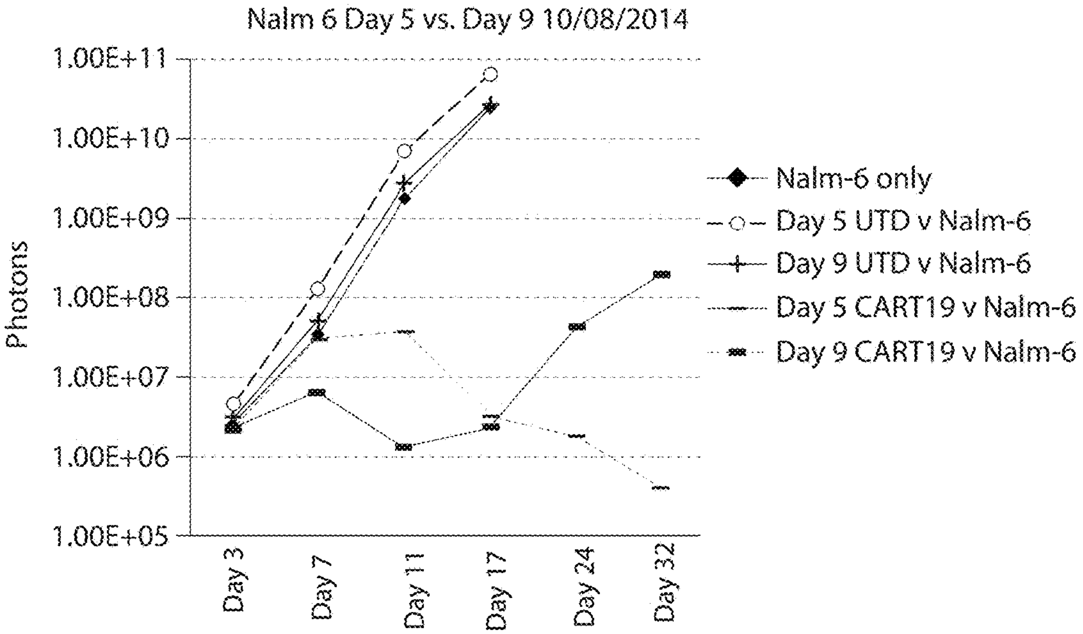
FIG. 26 is a graph depicting long term in vivo killing capacity of PBMCs left either unmanipulated (UTD) or transduced with a CD19 CAR (CART19), de-beaded, and then harvested at Day 5 and D9. The PBMCs were introduced into non-obese diabetic/severe combined immunodeficiency mice inoculated with Nalm6 cells.
Figure 27D:
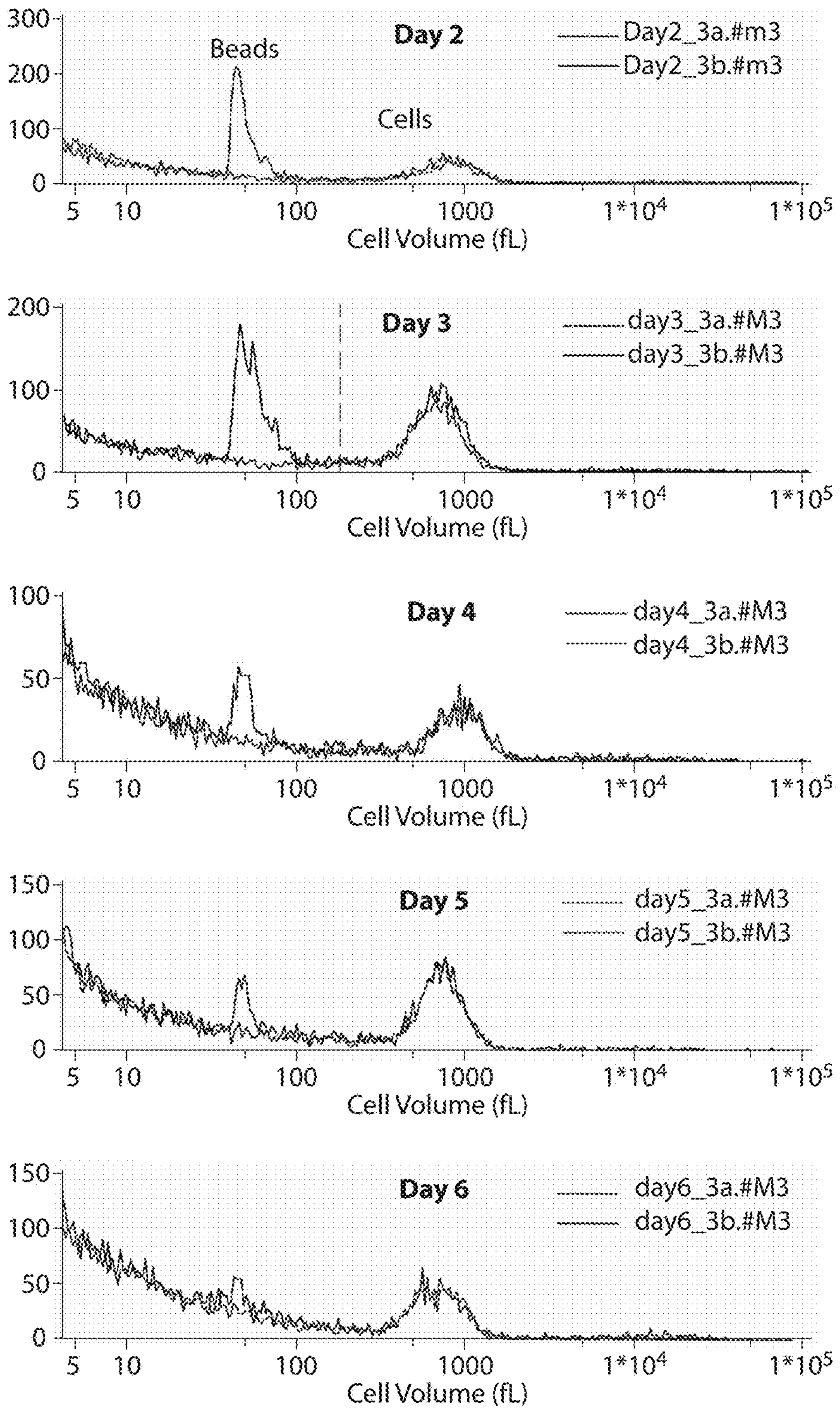

Proliferation capacity was also assessed for the same cell samples by determining the total number of cells in culture at day 10 after stimulation with anti-CD3 and anti-CD28 coated beads. The cell numbers for each cell sample are shown below and in FIG. 15.

TABLE 6

| In vitro expansion | | |
|---|---|---|
| Cells | Cytokines added | # Cells in culture |
| Unmanipulated | IL-7 | $1.24 \times 10^6$ |
| | IL-15 | $0.92 \times 10^6$ |
| | IL-7 + IL-15 | $0.52 \times 10^6$ |
| CD25-depleted | IL-7 | $0.93 \times 10^6$ |
| | IL-15 | $1.95 \times 10^6$ |
| | IL-7 + IL-15 | $3.03 \times 10^6$ |

These results show that supplementation of IL-15 during culture of CD25 depleted T cells resulted in increased expansion compared to unmanipulated cells. Addition of IL-7 and IL-15 in the media during culture resulted in significant increase in expansion compared to unmanipulated cells, and compared to adding the cytokines IL-7 or IL-15 independently. Thus, the combination IL-7 and IL-15 supplement resulted in T cells with the most increased proliferation capacity.

Example 4: Three-Day Manufacturing Process

With the use of gene transfer technologies, T cells can be genetically modified to stably express antibody binding domains on their surface that endow the T cells with specificities that are independent of the constraints imposed by the major histocompatibility complex (MHC). CAR therapies can utilize synthetic proteins expressed on T-cells that fuse an antigen recognition fragment of an antibody (an scFv, or single-chain variable region fragment) with an intracellular domain of the CD3-zeta chain. Upon interaction with a target cell expressing the scFv's cognate antigen, CARs expressed on T cell cells can trigger T-cell activation leading to target cell killing (also referred to as target cell lysis). When combined with additional costimulatory signals such as the cytoplasmic domain of CD137 or CD28, these receptors can also stimulate T cell proliferation and increase CAR-modified T cell (CART) persistence in vivo.

The mechanisms underlying CART persistence are being explored. Signaling domains in CARs appear to be important factors determining persistence; however, a number of published studies in mice and non-human primates (Klebanoff, C. A., et al. (2005). "Central memory self/tumor-reactive CD8+ T cells confer superior antitumor immunity compared with effector memory T cells." Proc Natl Acad Sci USA 102(27): 9571-9576, Berger, C., et al. (2008). "Adoptive transfer of effector CD8+ T cells derived from central memory cells establishes persistent T cell memory in primates." J Clin Invest 118(1): 294-305, Hinrichs, C. S., et al. (2009). "Adoptively transferred effector cells derived from naive rather than central memory CD8+ T cells mediate superior antitumor immunity." Proc Natl Acad Sci USA 106(41): 17469-17474, Wang, X., et al. (2011). "Engraftment of human central memory-derived effector CD8+ T cells in immunodeficient mice." Blood 117(6): 1888-1898) and data from human clinical trial correlative studies suggest that the phenotype of T cells in the adoptively transferred product is also an important determinant of T cell persistence following adoptive transfer (Xu, Y., et al. (2014). "Closely related T-memory stem cells correlate with in vivo expansion of CAR.CD19-T cells and are preserved by IL-7 and IL-15." Blood 123(24): 3750-3759). While not wishing to be bound by theory, it is hypothesized that the T cells expanded during ex vivo culture under the commonly employed system of anti-CD3 and anti-CD28 agonist antibodies combined with exogenous IL-2 biases the expanded T cells towards more differentiated cells with reduced persistence. It was hypothesized that replacing IL-2 with IL-7 and IL-15 would bias ex vivo culture over time towards cells with a more optimal Tscm/cm phenotype. It was also hypothesized that products with less ex vivo culture might have a greater proportion of cells with the optimal phenotype for engraftment and persistence following adoptive transfer.

This Example both characterizes the phenotype of cells over time in culture and evaluates the functionality of cells at different time points following activation and transduction.

Bead removal from T cells following activation with CD3/28-stimulatory beads can be accomplished with high efficiency by mechanical disruption as shown in FIGS. 27A-27D.

Bead detachment was accomplished in these preclinical studies by repeat passage (extrusion) of the cell suspension through a narrow bore pipet tip. In a closed culture system, extrusion to create gentle shearing could be performed using a closed system that incorporates a set of narrow bore tube in a closed system prior to bead removal.

Figure 28A:
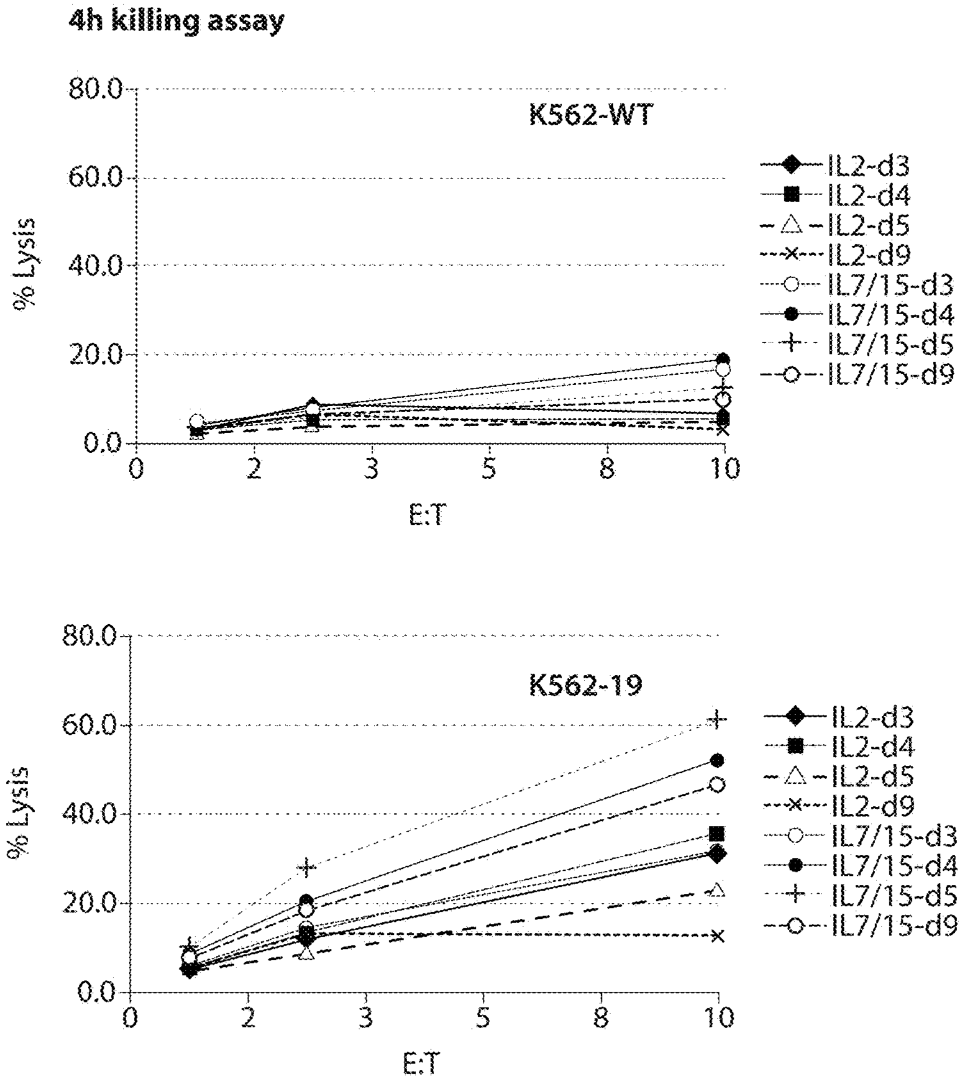
FIGS. 28A-28B shows that T cells that are activated, transduced with a CD19-specific CAR bearing BBz signaling and harvested from T cells cultures at time points as early as day 3 following activation have potent, antigen-specific cytotoxic activity in vitro.
Figure 28B:
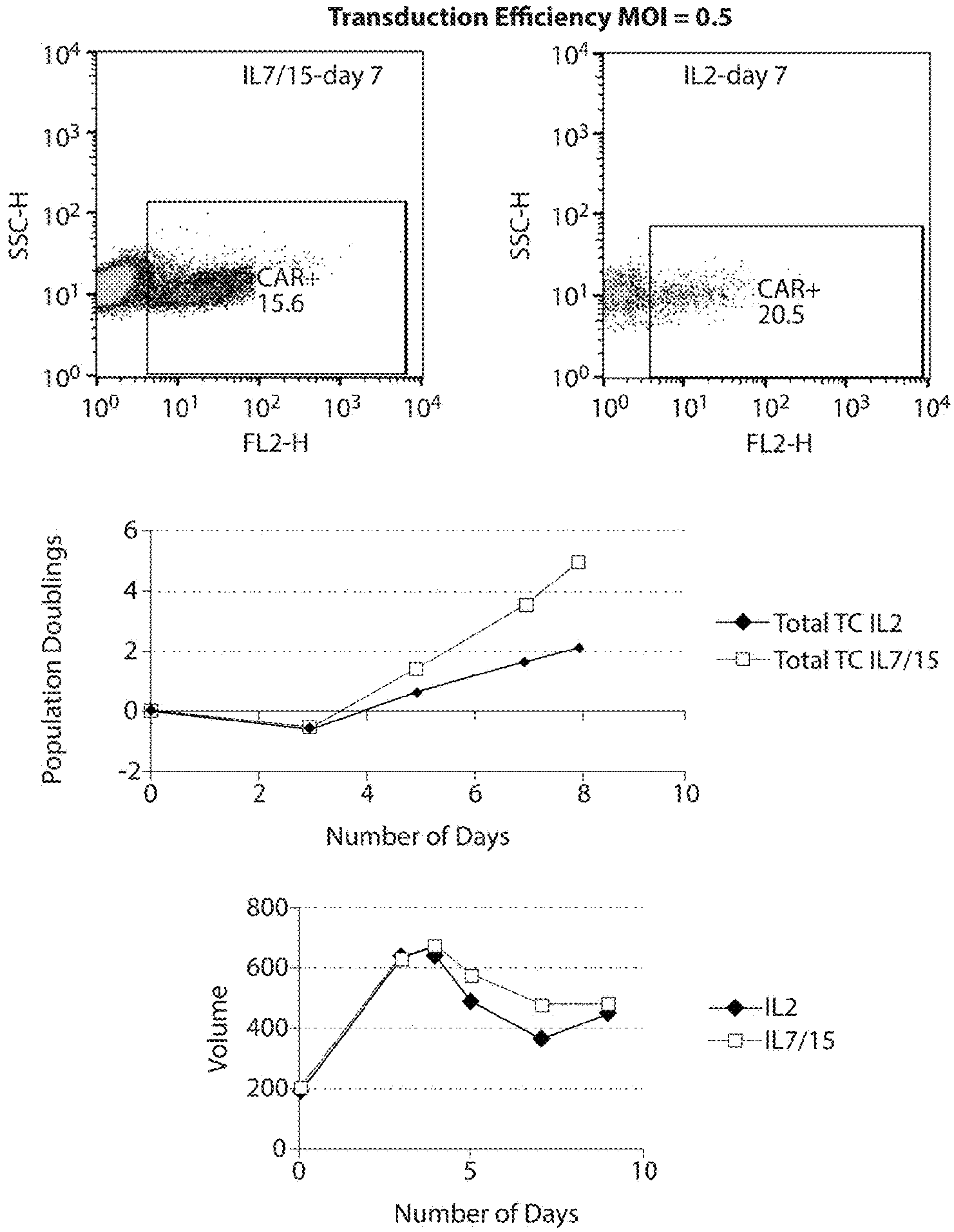
Figure 29A:
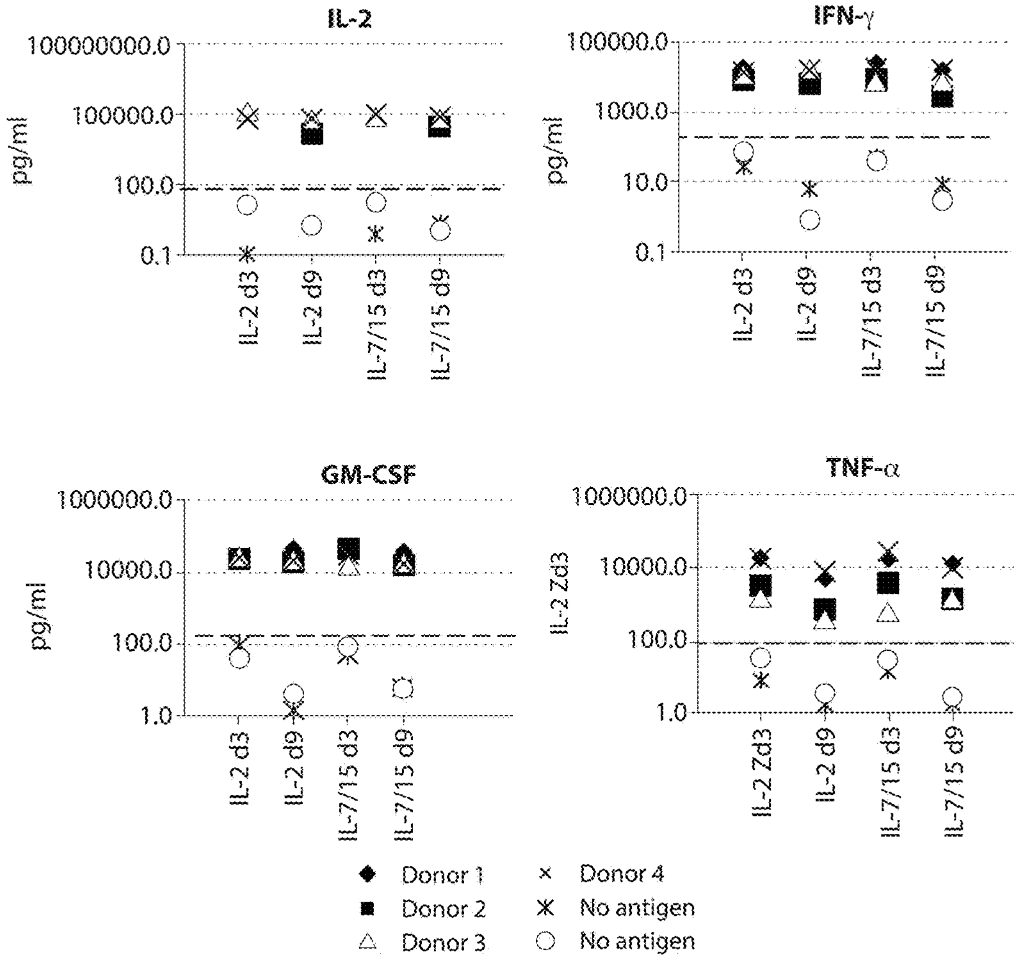
FIGS. 29A-29C show that day 3 and day 9 4-1BBζ CART cells produce similar patterns of cytokines in response to K562-CD19. Day 3 and day 9 CART 19 cells, previously cultured in medium with IL-2 or IL-7/15, were incubated with either K562-CD19 (FIGS. 29A and 29B), medium alone for 24 h (FIG. 29C). "No antigen" in FIG. 29A and FIG. 29B indicates cells stimulated with wild-type K562 cells without CD19. Cytokines were measured in culture supernatants by cytokine bead array (Luminex).
Figure 29B:
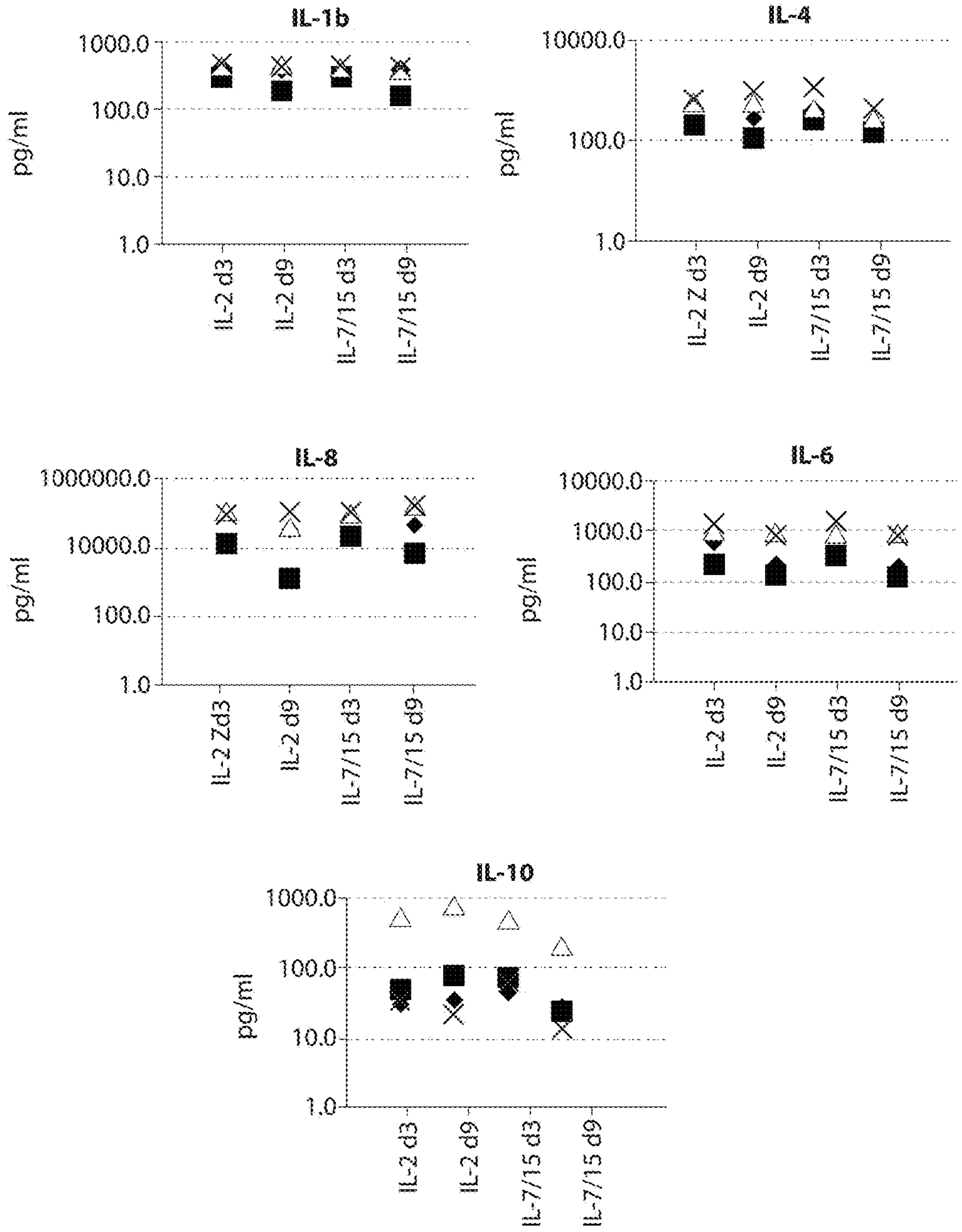
Figure 29C:
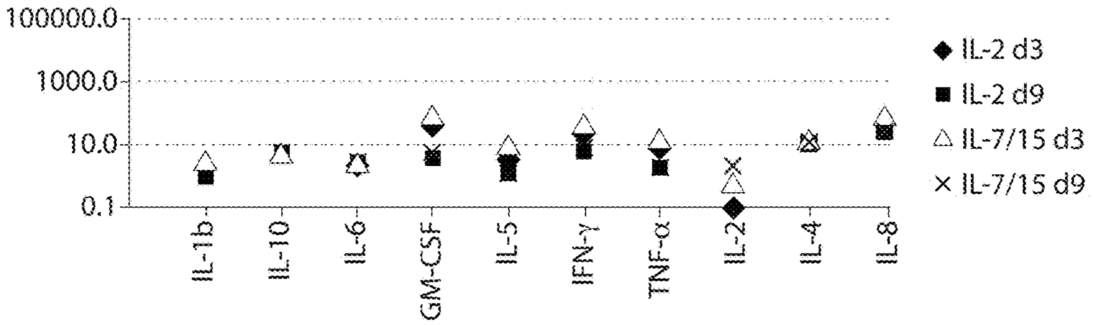

As shown in FIG. 28, T cells that are activated, transduced with a CD19-specific CAR bearing BBz signaling and harvested from T cells cultures at time points as early as day 3 following activation have potent, antigen-specific cytotoxic activity in vitro. These early harvest cells are also able to produce cytokines with a similar pattern and quantity to those cultured for longer periods of 5 or 9 days ex vivo (FIG. 29A) with similar basal secretion (FIG. 29B).

Figure 30A:
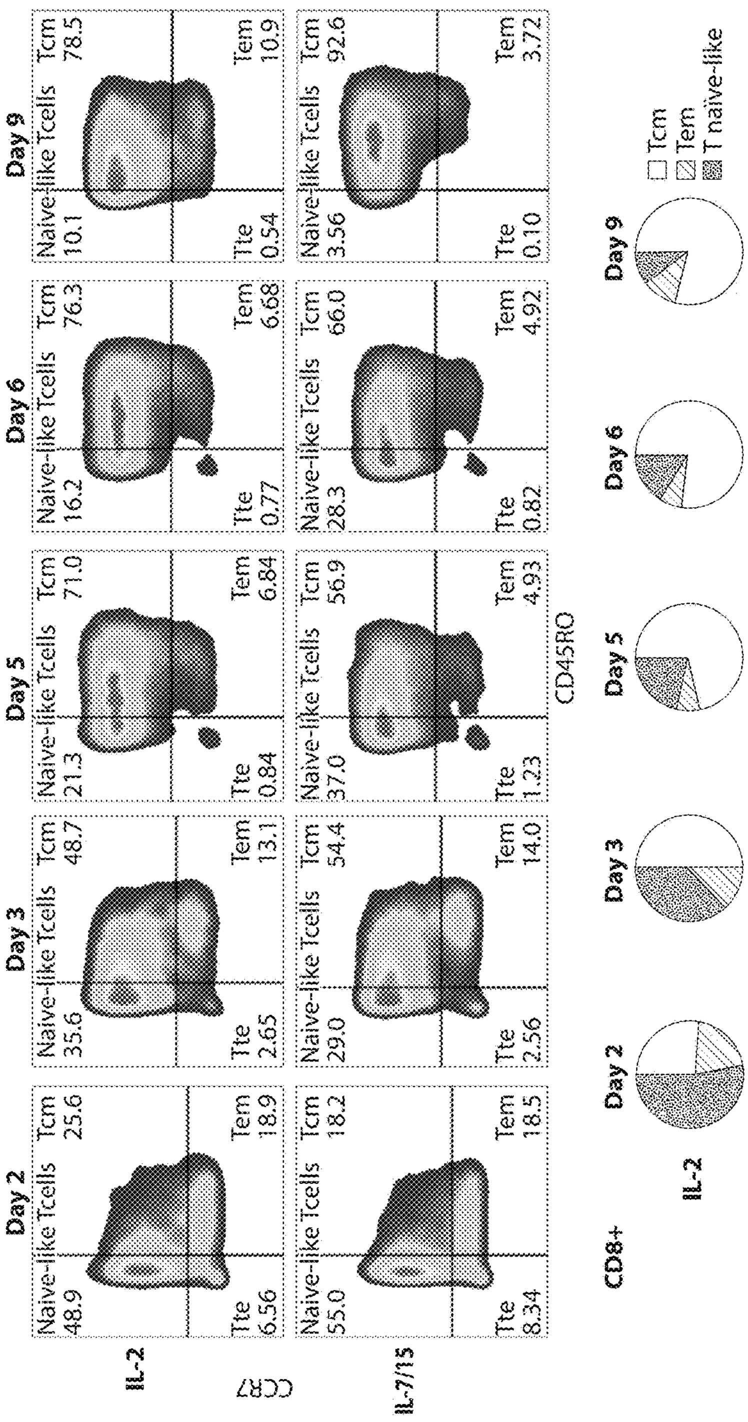
FIGS. 30A-30B show a progressive transition towards a more differentiated phenotype with an increasing proportion of Tem and Tcm cells.
Figure 30B:
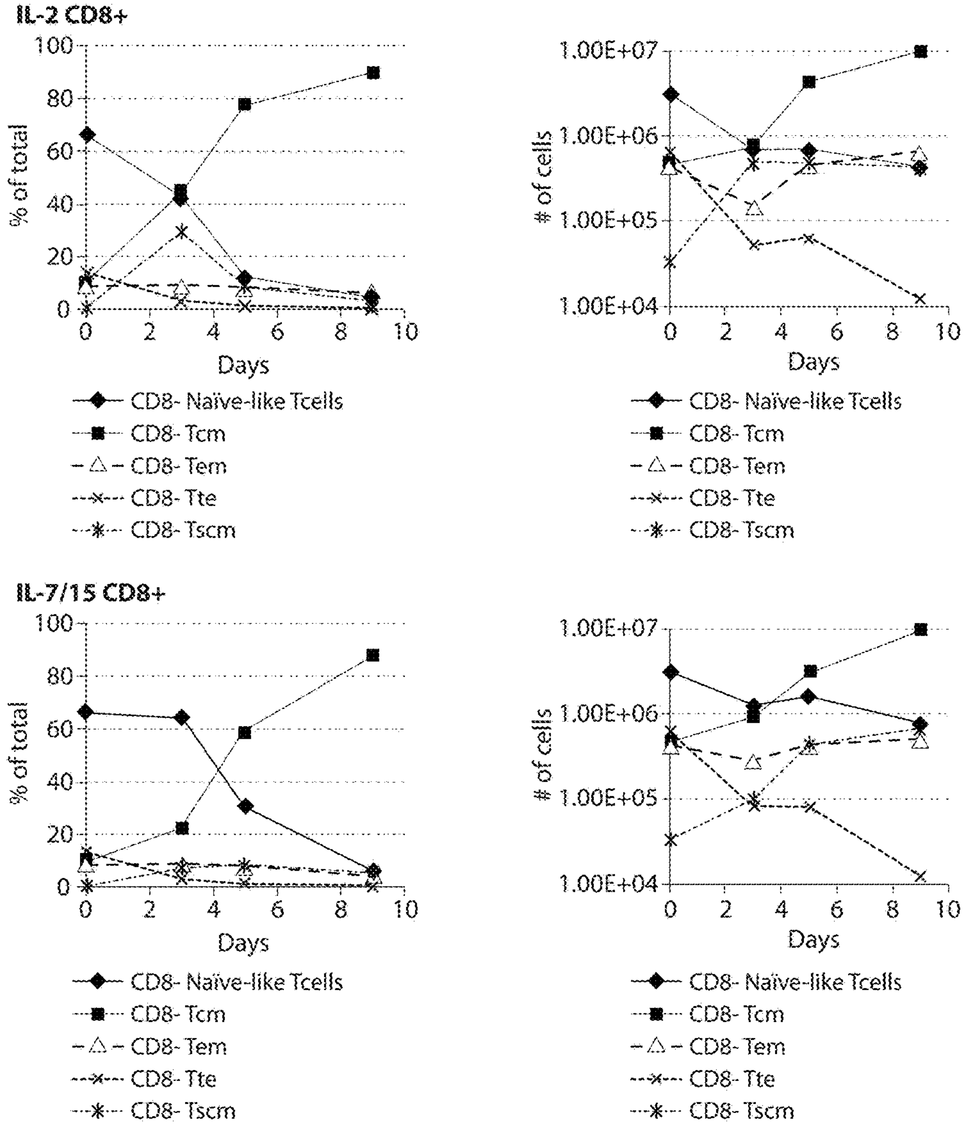

During ex vivo culture, the population of T cells undergoes a progressive transition towards a more differentiated phenotype with an increasing proportion of T effector memory (Tem) and Tcm cells as shown in FIG. 30A. This increase in proportion of Tem and Tcm cells results from an increase in more differentiated T cell subsets with minimal expansion and/or decrease in the naive-like/Tscm cells (FIG. 30B).

Figure 31A:
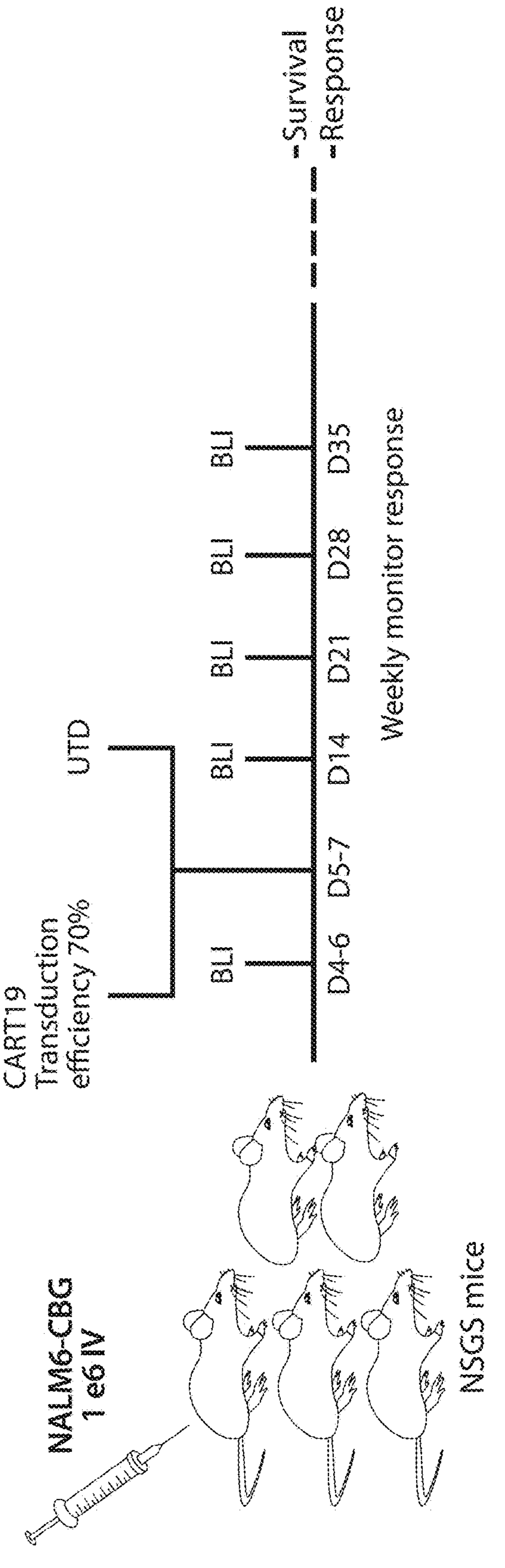
FIG. 31A-31D.
Figure 31B:
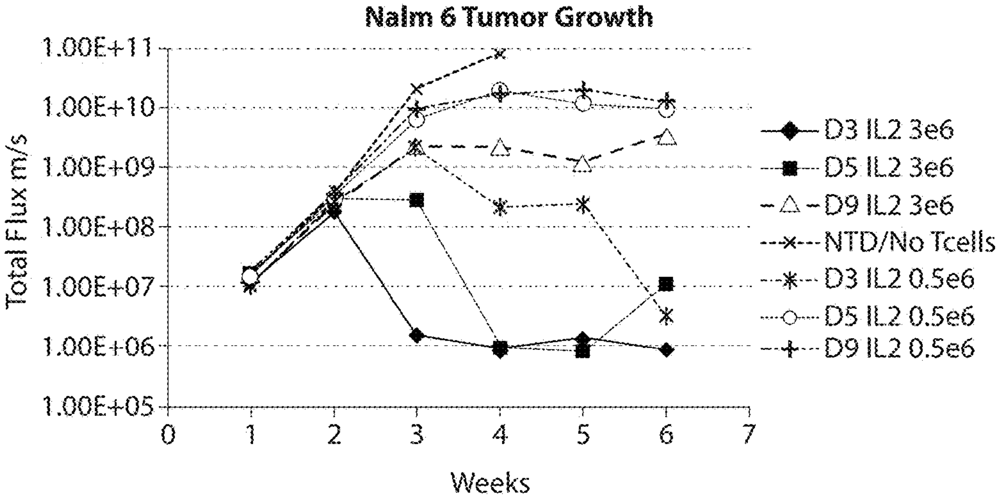
Figure 31C:
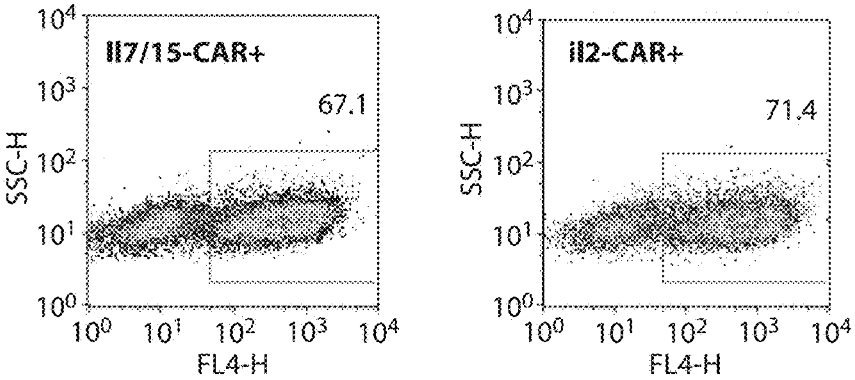

FIG. 31A shows the experimental setup for testing the potency of CART cells produced under different conditions. FIG. 31B shows the potency of IL2-treated CART cells in slowing Nalm6 tumor growth in mice. Day 3 cells demonstrate enhanced potency at all doses. T cells activated and transduced with a CD19-specific CAR bearing the 4-1BBz signaling domain show more potent in vivo anti-leukemic activity when harvested at the early time points. This increased potency is demonstrated by the lower doses of T cells required to eradicate leukemia with day 3 harvested CART19 cells compared with day 5 or day 9 harvested cells. Proportions of CAR+ cells are shown in FIG. 31C.

Figure 31D:
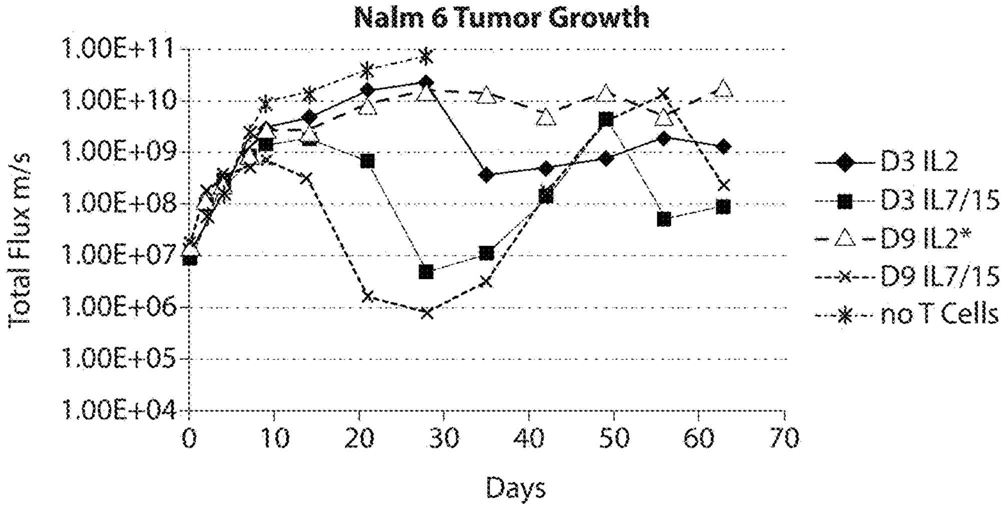
Figure 32:
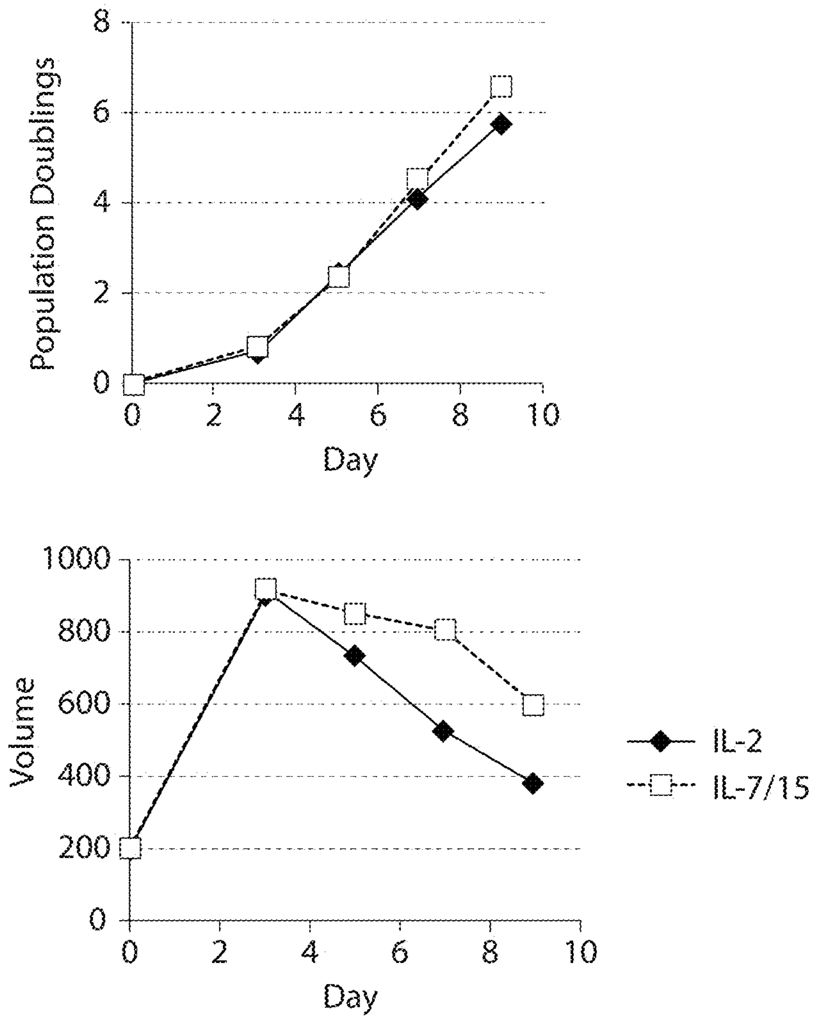
FIG. 32. In vitro expansion of CAR+ T cells in media contained IL-2 and IL-7/15, following antigen stimulation. Left panel, PBMCs from healthy human donors were stimulated with αCD3/αCD28 coated Dynal beads on day 0, and lenti-virally transduced with 19-BK on day 1. These cells were expanded for 9 days in medium supplemented either with IL-2 or IL-7/15. T cells were counted by flow cytometry using bead-based counting every other day. Right panel, Mean T cell volume (fl) over the course of expansion was monitored. Data are representative of at least six independent donors.
Figure 33:
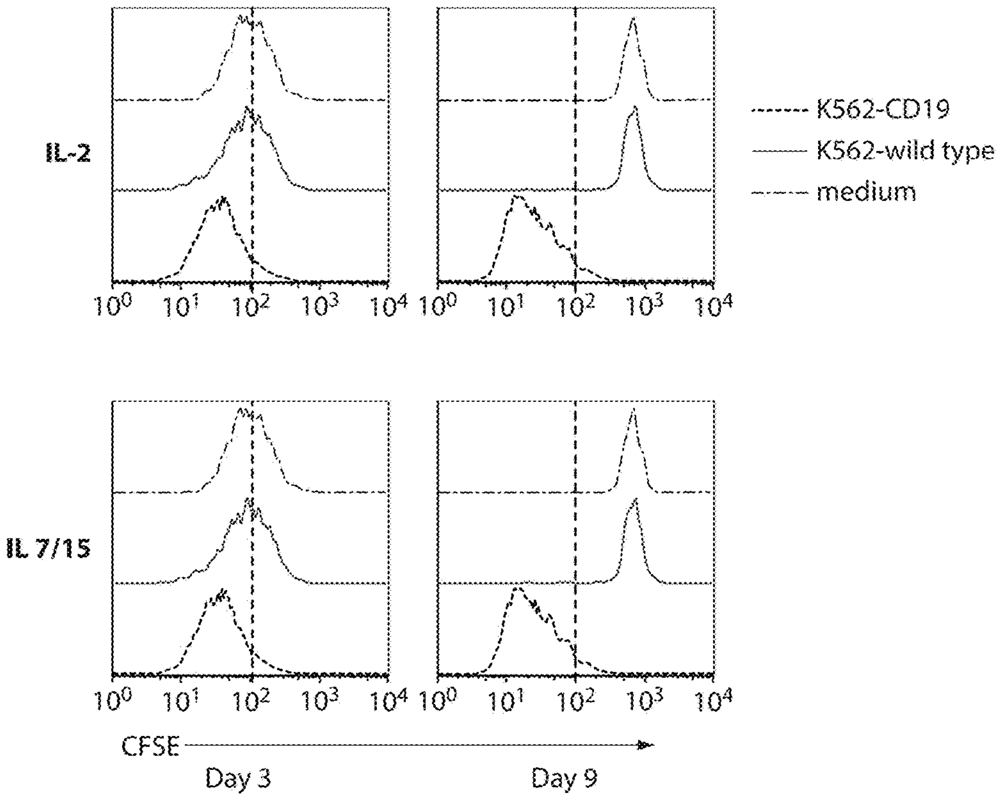
FIG. 33. Day 3 and day 9 CART19 cells cultured in medium with either IL-2 or IL-7/15 proliferate in response to K562-CD19, and not to K562-WT or medium alone. T cells were labeled with CFSE and co-cultured with either K562-CD19, wild-type K562 or medium alone as a negative control, for 120 hours. The number of proliferating T cells was significantly higher in response to K562-CD19 as compared to wild-type K562 or medium alone and was comparable between IL-7/15 and IL-2 groups. Results are representative of two different donors.

Cells treated with IL-2 and IL7/15 were harvested in two different days (3, 9). A relatively low dose of 0.7e6 CAR+ cells was used. T cells activated, transduced with a CD19-specific CAR bearing the 4-1BBz signaling domain and cultured in IL-7/IL-15 showed more potent activity at limiting doses than cells expanded in IL-2 at early (day 3) and late (day 9) time points (FIG. 31D). Day 3 cells treated with IL7/15 demonstrate enhanced potency at early time points.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A method of making a population of chimeric antigen receptor (CAR)-expressing immune effector cells, the method comprising:

(a) providing a population of cells comprising immune effector cells from an apheresis sample from a patient with chronic lymphocyticleukemia;

(b) depleting CD25-expressing cells from the population of cells of step (a) to provide a population of CD25-depleted cells, wherein the population of CD25-depleted cells is a population that contains less than 50% CD25+ cells in the population of cells of step (a) when assessed by flow cytometry;

(c) contacting the population of CD25-depleted cells with anti-CD3 and anti-CD28 coated beads; and (d) transducing the population of CD25-depleted cells with a lentivirus vector encoding a chimeric antigen receptor;

to thereby provide a population of CAR-expressing immune effector cells.

2. The method of claim 1, wherein the population of CD25-depleted cells is a population that contains less than 30% CD25+ cells.

3. The method of claim 1, wherein the population of CD25-depleted cells is a population that contains less than 20% CD25+ cells.

4. The method of claim 1, wherein the population of CD25-depleted cells is a population that contains less than 10% CD25+ cells.

5. The method of claim 1, further comprising a step of depleting cells that express a tumor antigen prior to the contacting step.

6. The method of claim 1, further comprising a step of depleting cells that express a check point inhibitor prior to the contacting step.

7. The method of claim 1, wherein the CD25-expressing cells are depleted by contacting the population of cells from the apheresis sample with anti-CD25 antibody coated beads.

8. A population of chimeric antigen receptor expressing immune effector cells produced by the method of claim 1.

9. A population of chimeric antigen receptor expressing immune effector cells produced by the method of claim 5.

10. A population of chimeric antigen receptor expressing immune effector cells produced by the method of claim 6.

11. A population of chimeric antigen receptor expressing immune effector cells produced by the method of claim 7.

12. A method of making an expanded population of chimeric antigen receptor (CAR)-expressing immune effector cells, the method comprising:

(a) providing a population of cells comprising immune effector cells from an apheresis sample from a patient with chronic lymphocytic leukemia;

(b) depleting CD25-expressing cells from the population of cells of step (a) to provide a population of CD25-depleted cells, wherein the population of CD25-depleted cells is a population that contains less than 50% CD25+ cells in the population of cells of step (a) when assessed by flow cytometry;

(c) contacting the population of CD25-depleted cells with anti-CD3 and anti-CD28 coated beads;

(d) transducing the population of CD25-depleted cells with a lentivirus vector encoding a chimeric antigen receptor; and (e) culturing the chimeric antigen receptor expressing immune effector cells in culture media supplemented with IL-15 or a combination of IL-15 and IL-7 for a period of between 3 and 9 days;

to thereby provide an expanded population of CAR-expressing immune effector cells.

13. The method of claim 12, wherein the culturing period is less than 6 days.

14. The method of claim 12, wherein the culturing period is less than 5 days.

15. The method of claim 12, wherein the culturing period is less than 4 days.

16. An expanded population of chimeric antigen receptor expressing immune effector cells produced by the method of claim 12.

17. An expanded population of chimeric antigen receptor expressing immune effector cells produced by the method of claim 15.

18. A method of making an expanded population of CD19 chimeric antigen receptor (CD19 CAR)-expressing immune effector cells, the method comprising:

(a) providing a population of cells comprising immune effector cells from an apheresis sample from a patient with chronic lymphocytic leukemia;

(b) depleting CD25-expressing cells from the population of cells to provide a population of CD25-depleted cells, wherein the population of CD25-depleted cells is a population that contains less than 50% CD25+ cells in the population of cells of step (a) when assessed by flow cytometry;

(c) contacting the population of CD25-depleted cells with anti-CD3 and anti-CD28 coated beads;

(d) transducing the population of CD25-depleted cells with a lentivirus vector encoding a CD19 CAR; and, (e) culturing the chimeric antigen receptor expressing immune effector cells in culture media supplemented with IL-15 or a combination of IL-15 and IL-7 for a period of between 3 and 9 days;

to thereby provide an expanded population of CD19 CAR-expressing immune effector cells.

19. The method of claim 18, wherein the culturing period is less than 4 days.

20. An expanded population of CD19 chimeric antigen receptor expressing immune effector cells produced by the method of claim 18.

21. The method of claim 1, further comprising expanding the population of CD25-depleted cells.

22. The method of claim 21, wherein the population of CD25-depleted cells is expanded in the presence of a cytokine for a period of 8 days or less.

23. The method of claim 1, wherein the population of CD25-depleted cells is a population that contains less than 50%, 30%, 20%, or 10% of CD25-depleted tumor cells.

24. The method of claim 1, wherein the population of CAR-expressing immune effector cells expresses a CAR that specifically binds to CD19.

25. The method of claim 24, wherein the population of CAR-expressing immune effector cells expresses a CAR comprising an antigen binding domain comprising a light chain variable domain (VL) and a heavy chain variable domain (VH) having the amino acid sequence of SEQ ID NO: 40 or SEQ ID NO: 51.

26. The method of claim 12, wherein the population of CAR-expressing immune effector cells expresses a CAR that specifically binds to CD19.

27. The method of claim 26, wherein the population of CAR-expressing immune effector cells expresses a CAR comprising an antigen binding domain comprising a light chain variable domain (VL) and a heavy chain variable domain (VH) having the amino acid sequence of SEQ ID NO: 40 or SEQ ID NO: 51.

28. The method of claim 18, wherein the population of CAR-expressing immune effector cells expresses a CAR comprising an antigen binding domain comprising a light chain variable domain (VL) and a heavy chain variable domain (VH) having the amino acid sequence of SEQ ID NO: 40 or SEQ ID NO: 51.

* * * * *

UNITED STATES PATENT AND TRADEMARK OFFICE

CERTIFICATE OF CORRECTION

PATENT NO. : 10,273,300 B2
APPLICATION NO. : 14/981142
DATED : April 30, 2019
INVENTOR(S) : Felipe Bedoya et al.

It is certified that error appears in the above-identified patent and that said Letters Patent is hereby corrected as shown below:

In the Specification

Column 38, Line 16, delete "GALS" and insert -- GAL9 --.

Column 42, Line 31, delete "LAGS" and insert -- LAG3 --.

Column 42, Line 34, delete "GALS" and insert -- GAL9 --.

Column 91, Line 62, delete "LAGS" and insert -- LAG3 --.

Column 91, Line 65, delete "GALS" and insert -- GAL9 --.

Signed and Sealed this
First Day of October, 2019

Andrei Iancu
*Director of the United States Patent and Trademark Office*

SEQUENCE LISTING

```
<160> NUMBER OF SEQ ID NOS: 122

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala Leu Pro Val Thr Ala Leu Leu Leu Pro Leu Ala Leu Leu Leu
1               5                   10                  15

His Ala Ala Arg Pro
            20


<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30
```

```
Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Ser Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr
        115


<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Leu Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Tyr Phe Cys Gln Tyr Asn Arg Tyr Pro
                85                  90                  95

Tyr Thr Ser Gly Gly Gly Thr Lys Leu Glu Ile Lys Arg Arg Ser
            100                 105                 110


<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser
1               5                   10


<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
```

20

<210> SEQ ID NO 7
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8

```
ggtggcggag gttctggagg tggaggttcc                                     30
```

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

```
Arg Val Lys Phe Ser Arg Ser Ala Asp Ala Pro Ala Tyr Gln Gln Gly
```

-continued

```
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 11
<211> LENGTH: 1184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

cgtgaggctc cggtgcccgt cagtgggcag agcgcacatc gcccacagtc cccgagaagt      60

tgggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttggggggag gggttttatg   1020

cgatggagtt tccccacact gagtgggtgg agactgaagt taggccagct tggcacttga   1080

tgtaattctc cttggaattt gccctttttg agtttggatc ttggttcatt ctcaagcctc   1140

agacagtggt tcaaagtttt tttcttccat ttcaggtgtc gtga                    1184


<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 12
atggccctgc ctgtgacagc cctgctgctg cctctggctc tgctgctgca tgccgctaga 60
ccc 63

<210> SEQ ID NO 13
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 14
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(40)
<223> OTHER INFORMATION: This sequence may encompass 1-10 'Gly Gly Gly Ser' repeating units

<400> SEQUENCE: 15

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser
35 40

<210> SEQ ID NO 16
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Gln Arg Arg Lys Tyr Arg Ser Asn Lys Gly Glu Ser Pro Val Glu Pro
1 5 10 15

-continued

```
Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45


<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

atctacatct gggcgccctt ggccgggact tgtggggtcc ttctcctgtc actggttatc     60

accctttact gc                                                         72


<210> SEQ ID NO 18
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

aaacggggca gaaagaaact cctgtatata ttcaaacaac catttatgag accagtacaa     60

actactcaag aggaagatgg ctgtagctgc cgatttccag aagaagaaga aggaggatgt    120

gaactg                                                               126


<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ataggatccc agctggtgga gtctggggga ggc                                  33


<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

agagtgaagt tcagcaggag cgcagacgcc cccgcgtaca agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 21
<211> LENGTH: 336
<212> TYPE: DNA
```

```
<213> ORGANISM: Artificial Sequence
<220> FEATURE:
<223> OTHER INFORMATION: Description of Artificial Sequence: Synthetic
      polynucleotide

<400> SEQUENCE: 21

agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 22
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

atggccctgc ccgtcaccgc tctgctgctg ccccttgctc tgcttcttca tgcagcaagg     60

ccggacatcc agatgaccca aaccacctca tccctctctg cctctcttgg agacagggtg    120

accatttctt gtcgcgccag ccaggacatc agcaagtatc tgaactggta tcagcagaag    180

ccggacggaa ccgtgaagct cctgatctac catacctctc gcctgcatag cggcgtgccc    240

tcacgcttct ctggaagcgg atcaggaacc gattattctc tcactatttc aaatcttgag    300

caggaagata ttgccaccta tttctgccag cagggtaata ccctgcccta caccttcgga    360

ggagggacca agctcgaaat caccggtgga ggaggcagcg gcggtggagg gtctggtgga    420

ggtggttctg aggtgaagct gcaagaatca ggccctggac ttgtggcccc ttcacagtcc    480

ctgagcgtga cttgcaccgt gtccggagtc tccctgcccg actacggagt gtcatggatc    540

agacaacctc cacggaaagg actggaatgg ctcggtgtca tctggggtag cgaaactact    600

tactacaatt cagccctcaa aagcaggctg actattatca aggacaacag caagtcccaa    660

gtctttctta agatgaactc actccagact gacgacaccg caatctacta ttgtgctaag    720

cactactact acggaggatc ctacgctatg gattactggg gacaaggtac ttccgtcact    780

gtctcttcac accatcatca ccatcaccat cac                                 813


<210> SEQ ID NO 23
<211> LENGTH: 4027
<212> TYPE: DNA
<213> ORGANISM: Homo sapiens

<400> SEQUENCE: 23

caggcagcgt ggtcctgctg cgcacgtggg aagccctggc cccggccacc cccgcgatgc     60

cgcgcgctcc ccgctgccga gccgtgcgct ccctgctgcg cagccactac cgcgaggtgc    120

tgccgctggc cacgttcgtg cggcgcctgg ggccccaggg ctggcggctg gtgcagcgcg    180

gggacccggc ggctttccgc gcgctggtgg cccagtgcct ggtgtgcgtg ccctgggacg    240

cacggccgcc ccccgccgcc ccctccttcc gccaggtgtc ctgcctgaag gagctggtgg    300

cccgagtgct gcagaggctg tgcgagcgcg gcgcgaagaa cgtgctggcc ttcggcttcg    360

cgctgctgga cggggcccgc gggggccccc ccgaggcctt caccaccagc gtgcgcagct    420
```

```
acctgcccaa cacggtgacc gacgcactgc gggggagcgg ggcgtggggg ctgctgttgc    480
gccgcgtggg cgacgacgtg ctggttcacc tgctggcacg ctgcgcgctc tttgtgctgg    540
tggctcccag ctgcgcctac caggtgtgcg ggccgccgct gtaccagctc ggcgctgcca    600
ctcaggcccg gcccccgcca cacgctagtg gaccccgaag gcgtctggga tgcgaacggg    660
cctggaacca tagcgtcagg gaggccgggg tccccctggg cctgccagcc ccgggtgcga    720
ggaggcgcgg gggcagtgcc agccgaagtc tgccgttgcc caagaggccc aggcgtggcg    780
ctgcccctga gccggagcgg acgcccgttg ggcaggggtc ctgggcccac ccgggcagga    840
cgcgtggacc gagtgaccgt ggtttctgtg tggtgtcacc tgccagaccc gccgaagaag    900
ccacctcttt ggagggtgcg ctctctggca cgcgccactc ccacccatcc gtgggccgcc    960
agcaccacgc gggcccccca tccacatcgc ggccaccacg tccctgggac acgccttgtc   1020
ccccggtgta cgccgagacc aagcacttcc tctactcctc aggcgacaag gagcagctgc   1080
ggccctcctt cctactcagc tctctgaggc ccagcctgac tggcgctcgg aggctcgtgg   1140
agaccatctt tctgggttcc aggccctgga tgccagggac tccccgcagg ttgccccgcc   1200
tgccccagcg ctactggcaa atgcggcccc tgtttctgga gctgcttggg aaccacgcgc   1260
agtgccccta cggggtgctc ctcaagacgc actgcccgct gcgagctgcg gtcaccccag   1320
cagccggtgt ctgtgcccgg gagaagcccc agggctctgt ggcggccccc gaggaggagg   1380
acacagaccc ccgtcgcctg gtgcagctgc tccgccagca cagcagcccc tggcaggtgt   1440
acggcttcgt gcgggcctgc ctgcgccggc tggtgccccc aggcctctgg ggctccaggc   1500
acaacgaacg ccgcttcctc aggaacacca agaagttcat ctccctgggg aagcatgcca   1560
agctctcgct gcaggagctg acgtggaaga tgagcgtgcg gggctgcgct tggctgcgca   1620
ggagcccagg ggttggctgt gttccggccg cagagcaccg tctgcgtgag gagatcctgg   1680
ccaagttcct gcactggctg atgagtgtgt acgtcgtcga gctgctcagg tctttctttt   1740
atgtcacgga gaccacgttt caaaagaaca ggctcttttt ctaccggaag agtgtctgga   1800
gcaagttgca aagcattgga atcagacagc acttgaagag ggtgcagctg cgggagctgt   1860
cggaagcaga ggtcaggcag catcgggaag ccaggcccgc cctgctgacg tccagactcc   1920
gcttcatccc caagcctgac gggctgcggc cgattgtgaa catggactac gtcgtgggag   1980
ccagaacgtt ccgcagagaa aagagggccg agcgtctcac ctcgagggtg aaggcactgt   2040
tcagcgtgct caactacgag cgggcgcggc gccccggcct cctgggcgcc tctgtgctgg   2100
gcctggacga tatccacagg gcctggcgca ccttcgtgct gcgtgtgcgg gcccaggacc   2160
cgccgcctga gctgtacttt gtcaaggtgg atgtgacggg cgcgtacgac accatccccc   2220
aggacaggct cacggaggtc atcgccagca tcatcaaacc ccagaacacg tactgcgtgc   2280
gtcggtatgc cgtggtccag aaggccgccc atgggcacgt ccgcaaggcc ttcaagagcc   2340
acgtctctac cttgacagac ctccagccgt acatgcgaca gttcgtggct cacctgcagg   2400
agaccagccc gctgagggat gccgtcgtca tcgagcagag ctcctccctg aatgaggcca   2460
gcagtggcct cttcgacgtc ttcctacgct tcatgtgcca ccacgccgtg cgcatcaggg   2520
gcaagtccta cgtccagtgc caggggatcc cgcagggctc catcctctcc acgctgctct   2580
gcagcctgtg ctacggcgac atggagaaca agctgtttgc ggggattcgg cgggacgggc   2640
tgctcctgcg tttggtggat gatttcttgt tggtgacacc tcacctcacc cacgcgaaaa   2700
ccttcctcag gaccctggtc cgaggtgtcc ctgagtatgg ctgcgtggtg aacttgcgga   2760
```

-continued agacagtggt gaacttccct gtagaagacg aggccctggg tggcacggct tttgttcaga 2820
tgccggccca cggcctattc ccctggtgcg gcctgctgct ggatacccgg accctggagg 2880
tgcagagcga ctactccagc tatgcccgga cctccatcag agccagtctc accttcaacc 2940
gcggcttcaa ggctgggagg aacatgcgtc gcaaactctt tggggtcttg cggctgaagt 3000
gtcacagcct gtttctggat ttgcaggtga acagcctcca gacggtgtgc accaacatct 3060
acaagatcct cctgctgcag gcgtacaggt ttcacgcatg tgtgctgcag ctcccatttc 3120
atcagcaagt ttggaagaac cccacatttt tcctgcgcgt catctctgac acggcctccc 3180
tctgctactc catcctgaaa gccaagaacg cagggatgtc gctgggggcc aagggcgccg 3240
ccggccctct gccctccgag gccgtgcagt ggctgtgcca ccaagcattc ctgctcaagc 3300
tgactcgaca ccgtgtcacc tacgtgccac tcctggggtc actcaggaca gcccagacgc 3360
agctgagtcg gaagctcccg gggacgacgc tgactgccct ggaggccgca gccaacccgg 3420
cactgccctc agacttcaag accatcctgg actgatggcc acccgcccac agccaggccg 3480
agagcagaca ccagcagccc tgtcacgccg ggctctacgt cccagggagg gaggggcggc 3540
ccacacccag gcccgcaccg ctgggagtct gaggcctgag tgagtgtttg gccgaggcct 3600
gcatgtccgg ctgaaggctg agtgtccggc tgaggcctga gcgagtgtcc agccaagggc 3660
tgagtgtcca gcacacctgc cgtcttcact tccccacagg ctggcgctcg gctccacccc 3720
agggccagct tttcctcacc aggagcccgg cttccactcc ccacatagga atagtccatc 3780
cccagattcg ccattgttca cccctcgccc tgccctcctt tgccttccac ccccaccatc 3840
caggtggaga ccctgagaag gaccctggga gctctgggaa tttggagtga ccaaaggtgt 3900
gccctgtaca caggcgagga ccctgcacct ggatgggggt ccctgtgggt caaattgggg 3960
ggaggtgctg tgggagtaaa atactgaata tatgagtttt tcagttttga aaaaaaaaaa 4020
aaaaaaa 4027

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
atagctagca cctaggacgg tcagcttggt ccc 33

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Gly Gly Gly Ser
1               5

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide -continued

```
<220> FEATURE:
<221> NAME/KEY: MISC_FEATURE
<222> LOCATION: (1)..(30)
<223> OTHER INFORMATION: This sequence may encompass 1-6
      'Gly Gly Gly Gly Ser' repeating units

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Gly Ser Gly Gly Gly Gly Ser Gly Gly Gly Gly Ser Gly
1               5                   10                  15

Gly Gly Gly Ser
            20


<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Gly Ser Gly Gly Gly Gly Ser
1               5                   10                  15


<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Ser
1


<210> SEQ ID NO 30
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
<222> LOCATION: (1)..(5000)
<223> OTHER INFORMATION: This sequence may encompass 50-5000 nucleotides

<400> SEQUENCE: 30

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaaa aaaaaaaaaa     120

aaaaaaaaaa aaaaaaaaaa aaaaaaaaaa aaaaaaaaaa aaaaaaaaaa aaaaaaaaaa     180
```

-continued aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520

-continued

```
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaaaa   4320
aaaaaaaaaa aaaaaaaaaa aaaaaaaaaa aaaaaaaaaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aaaaaaaaaa aaaaaaaaaa aaaaaaaaaa aaaaaaaaaa aaaaaaaaaa   4560
aaaaaaaaaa aaaaaaaaaa aaaaaaaaaa aaaaaaaaaa aaaaaaaaaa aaaaaaaaaa   4620
aaaaaaaaaa aaaaaaaaaa aaaaaaaaaa aaaaaaaaaa aaaaaaaaaa aaaaaaaaaa   4680
aaaaaaaaaa aaaaaaaaaa aaaaaaaaaa aaaaaaaaaa aaaaaaaaaa aaaaaaaaaa   4740
aaaaaaaaaa aaaaaaaaaa aaaaaaaaaa aaaaaaaaaa aaaaaaaaaa aaaaaaaaaa   4800
aaaaaaaaaa aaaaaaaaaa aaaaaaaaaa aaaaaaaaaa aaaaaaaaaa aaaaaaaaaa   4860
aaaaaaaaaa aaaaaaaaaa aaaaaaaaaa aaaaaaaaaa aaaaaaaaaa aaaaaaaaaa   4920
```

```
aaaaaaaaaa aaaaaaaaaa aaaaaaaaaa aaaaaaaaaa aaaaaaaaaa aaaaaaaaaa   4980

aaaaaaaaaa aaaaaaaaaa                                               5000


<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

tttttttttt tttttttttt tttttttttt tttttttttt tttttttttt tttttttttt     60

tttttttttt tttttttttt tttttttttt tttttttttt                          100


<210> SEQ ID NO 32
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
<222> LOCATION: (1)..(5000)
<223> OTHER INFORMATION: This sequence may encompass 50-5000 nucleotides

<400> SEQUENCE: 32

tttttttttt tttttttttt tttttttttt tttttttttt tttttttttt tttttttttt     60

tttttttttt tttttttttt tttttttttt tttttttttt tttttttttt tttttttttt    120

tttttttttt tttttttttt tttttttttt tttttttttt tttttttttt tttttttttt    180

tttttttttt tttttttttt tttttttttt tttttttttt tttttttttt tttttttttt    240

tttttttttt tttttttttt tttttttttt tttttttttt tttttttttt tttttttttt    300

tttttttttt tttttttttt tttttttttt tttttttttt tttttttttt tttttttttt    360

tttttttttt tttttttttt tttttttttt tttttttttt tttttttttt tttttttttt    420

tttttttttt tttttttttt tttttttttt tttttttttt tttttttttt tttttttttt    480

tttttttttt tttttttttt tttttttttt tttttttttt tttttttttt tttttttttt    540

tttttttttt tttttttttt tttttttttt tttttttttt tttttttttt tttttttttt    600

tttttttttt tttttttttt tttttttttt tttttttttt tttttttttt tttttttttt    660

tttttttttt tttttttttt tttttttttt tttttttttt tttttttttt tttttttttt    720

tttttttttt tttttttttt tttttttttt tttttttttt tttttttttt tttttttttt    780

tttttttttt tttttttttt tttttttttt tttttttttt tttttttttt tttttttttt    840

tttttttttt tttttttttt tttttttttt tttttttttt tttttttttt tttttttttt    900

tttttttttt tttttttttt tttttttttt tttttttttt tttttttttt tttttttttt    960

tttttttttt tttttttttt tttttttttt tttttttttt tttttttttt tttttttttt   1020

tttttttttt tttttttttt tttttttttt tttttttttt tttttttttt tttttttttt   1080

tttttttttt tttttttttt tttttttttt tttttttttt tttttttttt tttttttttt   1140

tttttttttt tttttttttt tttttttttt tttttttttt tttttttttt tttttttttt   1200

tttttttttt tttttttttt tttttttttt tttttttttt tttttttttt tttttttttt   1260

tttttttttt tttttttttt tttttttttt tttttttttt tttttttttt tttttttttt   1320
```

-continued tttttttttt tttttttttt tttttttttt tttttttttt tttttttttt tttttttttt 1380
tttttttttt tttttttttt tttttttttt tttttttttt tttttttttt tttttttttt 1440
tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100
tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820
tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 33
<211> LENGTH: 5000
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: MISC_FEATURE
<222> LOCATION: (1)..(5000)
<223> OTHER INFORMATION: This sequence may encompass 100-5000
nucleotides

<400> SEQUENCE: 33
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540

-continued aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 34
<211> LENGTH: 400
<212> TYPE: DNA
<213> ORGANISM: Artificial Sequence
<220> FEATURE:
<223> OTHER INFORMATION: Description of Artificial Sequence: Synthetic
polynucleotide <220> FEATURE:
<221> NAME/KEY: MISC_FEATURE
<222> LOCATION: (1)..(400)
<223> OTHER INFORMATION: This sequence may encompass 100-400 nucleotides

<400> SEQUENCE: 34

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400
```

<210> SEQ ID NO 35
<211> LENGTH: 2000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
<222> LOCATION: (1)..(2000)
<223> OTHER INFORMATION: This sequence may encompass 50-2000 nucleotides

<400> SEQUENCE: 35

```
aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320
```

```
aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000


<210> SEQ ID NO 36
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
```

225 230

<210> SEQ ID NO 37
<211> LENGTH: 690
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
gagagcaagt acggccctcc ctgcccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 38
<211> LENGTH: 282
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Arg Trp Pro Glu Ser Pro Lys Ala Gln Ala Ser Ser Val Pro Thr Ala
1 5 10 15

Gln Pro Gln Ala Glu Gly Ser Leu Ala Lys Ala Thr Thr Ala Pro Ala
20 25 30

Thr Thr Arg Asn Thr Gly Arg Gly Gly Glu Glu Lys Lys Lys Glu Lys
35 40 45

Glu Lys Glu Glu Gln Glu Glu Arg Glu Thr Lys Thr Pro Glu Cys Pro
50 55 60

Ser His Thr Gln Pro Leu Gly Val Tyr Leu Leu Thr Pro Ala Val Gln
65 70 75 80

Asp Leu Trp Leu Arg Asp Lys Ala Thr Phe Thr Cys Phe Val Val Gly
85 90 95

Ser Asp Leu Lys Asp Ala His Leu Thr Trp Glu Val Ala Gly Lys Val
100 105 110

Pro Thr Gly Gly Val Glu Glu Gly Leu Leu Glu Arg His Ser Asn Gly
115 120 125

Ser Gln Ser Gln His Ser Arg Leu Thr Leu Pro Arg Ser Leu Trp Asn
130 135 140

Ala Gly Thr Ser Val Thr Cys Thr Leu Asn His Pro Ser Leu Pro Pro
145 150 155 160

Gln Arg Leu Met Ala Leu Arg Glu Pro Ala Ala Gln Ala Pro Val Lys

-continued

```
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 39
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240
```

Ser Ser

<210> SEQ ID NO 40
<211> LENGTH: 242
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Pro Gly Leu Val Lys Pro Ser Glu Thr Leu Ser Leu Thr Cys
130 135 140

Thr Val Ser Gly Val Ser Leu Pro Asp Tyr Gly Val Ser Trp Ile Arg
145 150 155 160

Gln Pro Pro Gly Lys Gly Leu Glu Trp Ile Gly Val Ile Trp Gly Ser
165 170 175

Glu Thr Thr Tyr Tyr Gln Ser Ser Leu Lys Ser Arg Val Thr Ile Ser
180 185 190

Lys Asp Asn Ser Lys Asn Gln Val Ser Leu Lys Leu Ser Ser Val Thr
195 200 205

Ala Ala Asp Thr Ala Val Tyr Tyr Cys Ala Lys His Tyr Tyr Tyr Gly
210 215 220

Gly Ser Tyr Ala Met Asp Tyr Trp Gly Gln Gly Thr Leu Val Thr Val
225 230 235 240

Ser Ser

<210> SEQ ID NO 41
<211> LENGTH: 242
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Gly Leu Glu Trp Ile
35 40 45

```
Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys


<210> SEQ ID NO 42
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160
```

```
Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys


<210> SEQ ID NO 43
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245


<210> SEQ ID NO 44
```

```
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245


<210> SEQ ID NO 45
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60
```

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Glu Ile Val Met
130 135 140

Thr Gln Ser Pro Ala Thr Leu Ser Leu Ser Pro Gly Glu Arg Ala Thr
145 150 155 160

Leu Ser Cys Arg Ala Ser Gln Asp Ile Ser Lys Tyr Leu Asn Trp Tyr
165 170 175

Gln Gln Lys Pro Gly Gln Ala Pro Arg Leu Leu Ile Tyr His Thr Ser
180 185 190

Arg Leu His Ser Gly Ile Pro Ala Arg Phe Ser Gly Ser Gly Ser Gly
195 200 205

Thr Asp Tyr Thr Leu Thr Ile Ser Ser Leu Gln Pro Glu Asp Phe Ala
210 215 220

Val Tyr Phe Cys Gln Gln Gly Asn Thr Leu Pro Tyr Thr Phe Gly Gln
225 230 235 240

Gly Thr Lys Leu Glu Ile Lys
245

<210> SEQ ID NO 46
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Gly Leu Glu Trp Ile
35 40 45

Gly Val Ile Trp Gly Ser Glu Thr Thr Tyr Tyr Gln Ser Ser Leu Lys
50 55 60

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Glu Ile Val Met
130 135 140

Thr Gln Ser Pro Ala Thr Leu Ser Leu Ser Pro Gly Glu Arg Ala Thr
145 150 155 160

Leu Ser Cys Arg Ala Ser Gln Asp Ile Ser Lys Tyr Leu Asn Trp Tyr

```
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245


<210> SEQ ID NO 47
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245


<210> SEQ ID NO 48
<211> LENGTH: 247
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 49
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

```
Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser


<210> SEQ ID NO 50
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175
```

Gln Ala Pro Arg Leu Leu Ile Tyr His Thr Ser Arg Leu His Ser Gly
180 185 190

Ile Pro Ala Arg Phe Ser Gly Ser Gly Ser Gly Thr Asp Tyr Thr Leu
195 200 205

Thr Ile Ser Ser Leu Gln Pro Glu Asp Phe Ala Val Tyr Phe Cys Gln
210 215 220

Gln Gly Asn Thr Leu Pro Tyr Thr Phe Gly Gln Gly Thr Lys Leu Glu
225 230 235 240

Ile Lys

<210> SEQ ID NO 51
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Glu Val Lys Leu Gln Glu
115 120 125

Ser Gly Pro Gly Leu Val Ala Pro Ser Gln Ser Leu Ser Val Thr Cys
130 135 140

Thr Val Ser Gly Val Ser Leu Pro Asp Tyr Gly Val Ser Trp Ile Arg
145 150 155 160

Gln Pro Pro Arg Lys Gly Leu Glu Trp Leu Gly Val Ile Trp Gly Ser
165 170 175

Glu Thr Thr Tyr Tyr Asn Ser Ala Leu Lys Ser Arg Leu Thr Ile Ile
180 185 190

Lys Asp Asn Ser Lys Ser Gln Val Phe Leu Lys Met Asn Ser Leu Gln
195 200 205

Thr Asp Asp Thr Ala Ile Tyr Tyr Cys Ala Lys His Tyr Tyr Tyr Gly
210 215 220

Gly Ser Tyr Ala Met Asp Tyr Trp Gly Gln Gly Thr Ser Val Thr Val
225 230 235 240

Ser Ser

<210> SEQ ID NO 52
<211> LENGTH: 813
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactactctt catccctcaa gtcacgcgtc accatctcaa aggacaactc taagaatcag 660
gtgtcactga aactgtcatc tgtgaccgca gccgacaccg ccgtgtacta ttgcgctaag 720
cattactatt atggcgggag ctacgcaatg gattactggg gacagggtac tctggtcacc 780
gtgtccagcc accaccatca tcaccatcac cat 813

<210> SEQ ID NO 53
<211> LENGTH: 813
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactaccaat catccctcaa gtcacgcgtc accatctcaa aggacaactc taagaatcag 660
gtgtcactga aactgtcatc tgtgaccgca gccgacaccg ccgtgtacta ttgcgctaag 720
cattactatt atggcgggag ctacgcaatg gattactggg gacagggtac tctggtcacc 780
gtgtccagcc accaccatca tcaccatcac cat 813

<210> SEQ ID NO 54
<211> LENGTH: 813
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180
cctcccggaa agggactgga gtggatcgga gtgatttggg gtagcgaaac cacttactat 240
tcatcttccc tgaagtcacg ggtcaccatt tcaaaggata actcaaagaa tcaagtgagc 300
ctcaagctct catcagtcac cgccgctgac accgccgtgt attactgtgc caagcattac 360
tactatggag ggtcctacgc catggactac tggggccagg gaactctggt cactgtgtca 420
tctggtggag gaggtagcgg aggaggcggg agcggtggag gtggctccga aatcgtgatg 480
acccagagcc ctgcaaccct gtccctttct cccggggaac gggctaccct ttcttgtcgg 540
gcatcacaag atatctcaaa atacctcaat tggtatcaac agaagccggg acaggcccct 600
aggcttctta tctaccacac ctctcgcctg catagcggga ttcccgcacg ctttagcggg 660
tctggaagcg ggaccgacta cactctgacc atctcatctc tccagcccga ggacttcgcc 720
gtctacttct gccagcaggg taacaccctg ccgtacacct tcggccaggg caccaagctt 780
gagatcaaac atcaccacca tcatcaccat cac 813

<210> SEQ ID NO 55
<211> LENGTH: 813
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180
cctcccggaa agggactgga gtggatcgga gtgatttggg gtagcgaaac cacttactat 240
caatcttccc tgaagtcacg ggtcaccatt tcaaaggata actcaaagaa tcaagtgagc 300
ctcaagctct catcagtcac cgccgctgac accgccgtgt attactgtgc caagcattac 360
tactatggag ggtcctacgc catggactac tggggccagg gaactctggt cactgtgtca 420
tctggtggag gaggtagcgg aggaggcggg agcggtggag gtggctccga aatcgtgatg 480
acccagagcc ctgcaaccct gtccctttct cccggggaac gggctaccct ttcttgtcgg 540
gcatcacaag atatctcaaa atacctcaat tggtatcaac agaagccggg acaggcccct 600
aggcttctta tctaccacac ctctcgcctg catagcggga ttcccgcacg ctttagcggg 660
tctggaagcg ggaccgacta cactctgacc atctcatctc tccagcccga ggacttcgcc 720
gtctacttct gccagcaggg taacaccctg ccgtacacct tcggccaggg caccaagctt 780
gagatcaaac atcaccacca tcatcaccat cac 813

<210> SEQ ID NO 56
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
atggccctcc cagtgaccgc tctgctgctg cctctcgcac ttcttctcca tgccgctcgg 60
cctgagatcg tcatgaccca aagccccgct accctgtccc tgtcacccgg cgagagggca 120
accctttcat gcagggccag ccaggacatt tctaagtacc tcaactggta tcagcagaag 180
ccagggcagg ctcctcgcct gctgatctac cacaccagcc gcctccacag cggtatcccc 240
gccagatttt ccgggagcgg gtctggaacc gactacaccc tcaccatctc ttctctgcag 300
cccgaggatt tcgccgtcta tttctgccag caggggaata ctctgccgta caccttcggt 360
caaggtacca agctggaaat caagggaggc ggaggatcag gcggtggcgg aagcggagga 420
ggtggctccg gaggaggagg ttcccaagtg cagcttcaag aatcaggacc cggacttgtg 480
aagccatcag aaaccctctc cctgacttgt accgtgtccg gtgtgagcct ccccgactac 540
ggagtctctt ggattcgcca gcctccgggg aagggtcttg aatggattgg ggtgatttgg 600
ggatcagaga ctacttacta ctcttcatca cttaagtcac gggtcaccat cagcaaagat 660
aatagcaaga accaagtgtc acttaagctg tcatctgtga ccgccgctga caccgccgtg 720
tactattgtg ccaaacatta ctattacgga gggtcttatg ctatggacta ctggggacag 780
gggaccctgg tgactgtctc tagccatcac catcaccacc atcatcac 828

<210> SEQ ID NO 57
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57
atggccctcc cagtgaccgc tctgctgctg cctctcgcac ttcttctcca tgccgctcgg 60
cctgagatcg tcatgaccca aagccccgct accctgtccc tgtcacccgg cgagagggca 120
accctttcat gcagggccag ccaggacatt tctaagtacc tcaactggta tcagcagaag 180
ccagggcagg ctcctcgcct gctgatctac cacaccagcc gcctccacag cggtatcccc 240
gccagatttt ccgggagcgg gtctggaacc gactacaccc tcaccatctc ttctctgcag 300
cccgaggatt tcgccgtcta tttctgccag caggggaata ctctgccgta caccttcggt 360
caaggtacca agctggaaat caagggaggc ggaggatcag gcggtggcgg aagcggagga 420
ggtggctccg gaggaggagg ttcccaagtg cagcttcaag aatcaggacc cggacttgtg 480
aagccatcag aaaccctctc cctgacttgt accgtgtccg gtgtgagcct ccccgactac 540
ggagtctctt ggattcgcca gcctccgggg aagggtcttg aatggattgg ggtgatttgg 600
ggatcagaga ctacttacta ccagtcatca cttaagtcac gggtcaccat cagcaaagat 660
aatagcaaga accaagtgtc acttaagctg tcatctgtga ccgccgctga caccgccgtg 720
tactattgtg ccaaacatta ctattacgga gggtcttatg ctatggacta ctggggacag 780
gggaccctgg tgactgtctc tagccatcac catcaccacc atcatcac 828

<210> SEQ ID NO 58
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
atggcactgc ctgtcactgc cctcctgctg cctctggccc tccttctgca tgccgccagg     60

ccccaagtcc agctgcaaga gtcaggaccc ggactggtga agccgtctga gactctctca    120

ctgacttgta ccgtcagcgg cgtgtccctc cccgactacg gagtgtcatg gatccgccaa    180

cctcccggga aagggcttga atggattggt gtcatctggg gttctgaaac cacctactac    240

tcatcttccc tgaagtccag ggtgaccatc agcaaggata attccaagaa ccaggtcagc    300

cttaagctgt catctgtgac cgctgctgac accgccgtgt attactgcgc caagcactac    360

tattacggag gaagctacgc tatggactat tggggacagg gcactctcgt gactgtgagc    420

agcggcggtg gagggtctgg aggtggagga tccggtggtg gtgggtcagg cggaggaggg    480

agcgagattg tgatgactca gtcaccagcc accctttctc tttcacccgg cgagagagca    540

accctgagct gtagagccag ccaggacatt tctaagtacc tcaactggta tcagcaaaaa    600

ccggggcagg cccctcgcct cctgatctac catacctcac gccttcactc tggtatcccc    660

gctcggttta gcggatcagg atctggtacc gactacactc tgaccatttc cagcctgcag    720

ccagaagatt tcgcagtgta tttctgccag cagggcaata cccttcctta caccttcggt    780

cagggaacca agctcgaaat caagcaccat caccatcatc accaccat                 828
```

<210> SEQ ID NO 59
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
atggcactgc ctgtcactgc cctcctgctg cctctggccc tccttctgca tgccgccagg     60

ccccaagtcc agctgcaaga gtcaggaccc ggactggtga agccgtctga gactctctca    120

ctgacttgta ccgtcagcgg cgtgtccctc cccgactacg gagtgtcatg gatccgccaa    180

cctcccggga aagggcttga atggattggt gtcatctggg gttctgaaac cacctactac    240

cagtcttccc tgaagtccag ggtgaccatc agcaaggata attccaagaa ccaggtcagc    300

cttaagctgt catctgtgac cgctgctgac accgccgtgt attactgcgc caagcactac    360

tattacggag gaagctacgc tatggactat tggggacagg gcactctcgt gactgtgagc    420

agcggcggtg gagggtctgg aggtggagga tccggtggtg gtgggtcagg cggaggaggg    480

agcgagattg tgatgactca gtcaccagcc accctttctc tttcacccgg cgagagagca    540

accctgagct gtagagccag ccaggacatt tctaagtacc tcaactggta tcagcaaaaa    600

ccggggcagg cccctcgcct cctgatctac catacctcac gccttcactc tggtatcccc    660

gctcggttta gcggatcagg atctggtacc gactacactc tgaccatttc cagcctgcag    720

ccagaagatt tcgcagtgta tttctgccag cagggcaata cccttcctta caccttcggt    780

cagggaacca agctcgaaat caagcaccat caccatcatc atcaccac                 828
```

<210> SEQ ID NO 60
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

-continued atggccctcc cagtgaccgc tctgctgctg cctctcgcac ttcttctcca tgccgctcgg 60
cctgagatcg tcatgaccca aagccccgct accctgtccc tgtcacccgg cgagagggca 120
accctttcat gcagggccag ccaggacatt tctaagtacc tcaactggta tcagcagaag 180
ccagggcagg ctcctcgcct gctgatctac cacaccagcc gcctccacag cggtatcccc 240
gccagatttt ccgggagcgg gtctggaacc gactacaccc tcaccatctc ttctctgcag 300
cccgaggatt tcgccgtcta tttctgccag caggggaata ctctgccgta caccttcggt 360
caaggtacca agctggaaat caagggaggc ggaggatcag gcggtggcgg aagcggagga 420
ggtggctccg gaggaggagg ttcccaagtg cagcttcaag aatcaggacc cggacttgtg 480
aagccatcag aaaccctctc cctgacttgt accgtgtccg gtgtgagcct ccccgactac 540
ggagtctctt ggattcgcca gcctccgggg aagggtcttg aatggattgg ggtgatttgg 600
ggatcagaga ctacttacta caattcatca cttaagtcac gggtcaccat cagcaaagat 660
aatagcaaga accaagtgtc acttaagctg tcatctgtga ccgccgctga caccgccgtg 720
tactattgtg ccaaacatta ctattacgga gggtcttatg ctatggacta ctggggacag 780
gggaccctgg tgactgtctc tagccatcac catcaccacc atcatcac 828

<210> SEQ ID NO 61
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atggcactgc ctgtcactgc cctcctgctg cctctggccc tccttctgca tgccgccagg 60
ccccaagtcc agctgcaaga gtcaggaccc ggactggtga agccgtctga gactctctca 120
ctgacttgta ccgtcagcgg cgtgtccctc cccgactacg gagtgtcatg gatccgccaa 180
cctcccggga aagggcttga atggattggt gtcatctggg gttctgaaac cacctactac 240
aactcttccc tgaagtccag ggtgaccatc agcaaggata attccaagaa ccaggtcagc 300
cttaagctgt catctgtgac cgctgctgac accgccgtgt attactgcgc caagcactac 360
tattacggag gaagctacgc tatggactat tggggacagg gcactctcgt gactgtgagc 420
agcggcggtg gagggtctgg aggtggagga tccggtggtg gtgggtcagg cggaggaggg 480
agcgagattg tgatgactca gtcaccagcc accctttctc tttcacccgg cgagagagca 540
accctgagct gtagagccag ccaggacatt tctaagtacc tcaactggta tcagcaaaaa 600
ccggggcagg cccctcgcct cctgatctac catacctcac gccttcactc tggtatcccc 660
gctcggttta gcggatcagg atctggtacc gactacactc tgaccatttc cagcctgcag 720
ccagaagatt tcgcagtgta tttctgccag cagggcaata cccttcctta caccttcggt 780
cagggaacca agctcgaaat caagcaccat caccatcatc accaccat 828

<210> SEQ ID NO 62
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactacaatt catccctcaa gtcacgcgtc accatctcaa aggacaactc taagaatcag 660
gtgtcactga aactgtcatc tgtgaccgca gccgacaccg ccgtgtacta ttgcgctaag 720
cattactatt atggcgggag ctacgcaatg gattactggg gacagggtac tctggtcacc 780
gtgtccagcc accaccatca tcaccatcac cat 813

<210> SEQ ID NO 63
<211> LENGTH: 813
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180
cctcccggaa agggactgga gtggatcgga gtgatttggg gtagcgaaac cacttactat 240
aactcttccc tgaagtcacg ggtcaccatt tcaaaggata actcaaagaa tcaagtgagc 300
ctcaagctct catcagtcac cgccgctgac accgccgtgt attactgtgc caagcattac 360
tactatggag ggtcctacgc catggactac tggggccagg gaactctggt cactgtgtca 420
tctggtggag gaggtagcgg aggaggcggg agcggtggag gtggctccga aatcgtgatg 480
acccagagcc ctgcaaccct gtccctttct cccggggaac gggctaccct ttcttgtcgg 540
gcatcacaag atatctcaaa atacctcaat tggtatcaac agaagccggg acaggcccct 600
aggcttctta tctaccacac ctctcgcctg catagcggga ttcccgcacg ctttagcggg 660
tctggaagcg ggaccgacta cactctgacc atctcatctc tccagcccga ggacttcgcc 720
gtctacttct gccagcaggg taacaccctg ccgtacacct tcggccaggg caccaagctt 780
gagatcaaac atcaccacca tcatcaccat cac 813

<210> SEQ ID NO 64
<211> LENGTH: 271
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Met Ala Leu Pro Val Thr Ala Leu Leu Leu Pro Leu Ala Leu Leu Leu
1 5 10 15

```
His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser His His His His His His His His
            260                 265                 270
```

<210> SEQ ID NO 65
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
```

```
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser His His His His His His His His
            260                 265                 270


<210> SEQ ID NO 66
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190
```

```
Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys His His His His His His His His
            260                 265                 270


<210> SEQ ID NO 67
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys His His His His His His His His
            260                 265                 270


<210> SEQ ID NO 68
```

<211> LENGTH: 276
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 68

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Ser
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser His His His His
            260                 265                 270

His His His His
        275
```

<210> SEQ ID NO 69
<211> LENGTH: 276
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30
```

```
Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Gln
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser His His His His
            260                 265                 270

His His His His
        275
```

<210> SEQ ID NO 70
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
```

```
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275


<210> SEQ ID NO 71
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175
```

```
Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275


<210> SEQ ID NO 72
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255
```

```
Tyr Trp Gly Gln Gly Thr Leu Val Thr Val Ser Ser His His His His
            260                 265                 270

His His His His
        275


<210> SEQ ID NO 73
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275


<210> SEQ ID NO 74
<211> LENGTH: 271
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 74

Met Ala Leu Pro Val Thr Ala Leu Leu Leu Pro Leu Ala Leu Leu Leu
1 5 10 15

His Ala Ala Arg Pro Glu Ile Val Met Thr Gln Ser Pro Ala Thr Leu
20 25 30

Ser Leu Ser Pro Gly Glu Arg Ala Thr Leu Ser Cys Arg Ala Ser Gln
35 40 45

Asp Ile Ser Lys Tyr Leu Asn Trp Tyr Gln Gln Lys Pro Gly Gln Ala
50 55 60

Pro Arg Leu Leu Ile Tyr His Thr Ser Arg Leu His Ser Gly Ile Pro
65 70 75 80

Ala Arg Phe Ser Gly Ser Gly Ser Gly Thr Asp Tyr Thr Leu Thr Ile
85 90 95

Ser Ser Leu Gln Pro Glu Asp Phe Ala Val Tyr Phe Cys Gln Gln Gly
100 105 110

Asn Thr Leu Pro Tyr Thr Phe Gly Gln Gly Thr Lys Leu Glu Ile Lys
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Glu Thr
145 150 155 160

Leu Ser Leu Thr Cys Thr Val Ser Gly Val Ser Leu Pro Asp Tyr Gly
165 170 175

Val Ser Trp Ile Arg Gln Pro Pro Gly Lys Gly Leu Glu Trp Ile Gly
180 185 190

Val Ile Trp Gly Ser Glu Thr Thr Tyr Tyr Asn Ser Ser Leu Lys Ser
195 200 205

Arg Val Thr Ile Ser Lys Asp Asn Ser Lys Asn Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Leu Val Thr Val Ser Ser His His His His His His His His
260 265 270

<210> SEQ ID NO 75
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Met Ala Leu Pro Val Thr Ala Leu Leu Leu Pro Leu Ala Leu Leu Leu
1 5 10 15

His Ala Ala Arg Pro Gln Val Gln Leu Gln Glu Ser Gly Pro Gly Leu
20 25 30

Val Lys Pro Ser Glu Thr Leu Ser Leu Thr Cys Thr Val Ser Gly Val
35 40 45

Ser Leu Pro Asp Tyr Gly Val Ser Trp Ile Arg Gln Pro Pro Gly Lys
50 55 60

Gly Leu Glu Trp Ile Gly Val Ile Trp Gly Ser Glu Thr Thr Tyr Tyr 65 70 75 80

Asn Ser Ser Leu Lys Ser Arg Val Thr Ile Ser Lys Asp Asn Ser Lys
85 90 95

Asn Gln Val Ser Leu Lys Leu Ser Ser Val Thr Ala Ala Asp Thr Ala
100 105 110

Val Tyr Tyr Cys Ala Lys His Tyr Tyr Tyr Gly Gly Ser Tyr Ala Met
115 120 125

Asp Tyr Trp Gly Gln Gly Thr Leu Val Thr Val Ser Ser Gly Gly Gly
130 135 140

Gly Ser Gly Gly Gly Gly Ser Gly Gly Gly Gly Ser Glu Ile Val Met
145 150 155 160

Thr Gln Ser Pro Ala Thr Leu Ser Leu Ser Pro Gly Glu Arg Ala Thr
165 170 175

Leu Ser Cys Arg Ala Ser Gln Asp Ile Ser Lys Tyr Leu Asn Trp Tyr
180 185 190

Gln Gln Lys Pro Gly Gln Ala Pro Arg Leu Leu Ile Tyr His Thr Ser
195 200 205

Arg Leu His Ser Gly Ile Pro Ala Arg Phe Ser Gly Ser Gly Ser Gly
210 215 220

Thr Asp Tyr Thr Leu Thr Ile Ser Ser Leu Gln Pro Glu Asp Phe Ala
225 230 235 240

Val Tyr Phe Cys Gln Gln Gly Asn Thr Leu Pro Tyr Thr Phe Gly Gln
245 250 255

Gly Thr Lys Leu Glu Ile Lys His His His His His His His His
260 265 270

<210> SEQ ID NO 76
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

```
Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser His His His His His His His His
            260                 265                 270


<210> SEQ ID NO 77
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255
```

```
Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 78
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
```

-continued

```
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 79
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 79

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp

```
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 80
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
            260                 265                 270
```

-continued

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 81
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

```
Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Ser
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 82
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Ala Leu Pro Val Thr Ala Leu Leu Leu Pro Leu Ala Leu Leu Leu
```

-continued

```
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Gln
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430
```

```
Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 83
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
```

```
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 84
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160
```

Ser Glu Ile Val Met Thr Gln Ser Pro Ala Thr Leu Ser Leu Ser Pro
165 170 175

Gly Glu Arg Ala Thr Leu Ser Cys Arg Ala Ser Gln Asp Ile Ser Lys
180 185 190

Tyr Leu Asn Trp Tyr Gln Gln Lys Pro Gly Gln Ala Pro Arg Leu Leu
195 200 205

Ile Tyr His Thr Ser Arg Leu His Ser Gly Ile Pro Ala Arg Phe Ser
210 215 220

Gly Ser Gly Ser Gly Thr Asp Tyr Thr Leu Thr Ile Ser Ser Leu Gln
225 230 235 240

Pro Glu Asp Phe Ala Val Tyr Phe Cys Gln Gln Gly Asn Thr Leu Pro
245 250 255

Tyr Thr Phe Gly Gln Gly Thr Lys Leu Glu Ile Lys Thr Thr Thr Pro
260 265 270

Ala Pro Arg Pro Pro Thr Pro Ala Pro Thr Ile Ala Ser Gln Pro Leu
275 280 285

Ser Leu Arg Pro Glu Ala Cys Arg Pro Ala Ala Gly Gly Ala Val His
290 295 300

Thr Arg Gly Leu Asp Phe Ala Cys Asp Ile Tyr Ile Trp Ala Pro Leu
305 310 315 320

Ala Gly Thr Cys Gly Val Leu Leu Leu Ser Leu Val Ile Thr Leu Tyr
325 330 335

Cys Lys Arg Gly Arg Lys Lys Leu Leu Tyr Ile Phe Lys Gln Pro Phe
340 345 350

Met Arg Pro Val Gln Thr Thr Gln Glu Glu Asp Gly Cys Ser Cys Arg
355 360 365

Phe Pro Glu Glu Glu Glu Gly Gly Cys Glu Leu Arg Val Lys Phe Ser
370 375 380

Arg Ser Ala Asp Ala Pro Ala Tyr Lys Gln Gly Gln Asn Gln Leu Tyr
385 390 395 400

Asn Glu Leu Asn Leu Gly Arg Arg Glu Glu Tyr Asp Val Leu Asp Lys
405 410 415

Arg Arg Gly Arg Asp Pro Glu Met Gly Gly Lys Pro Arg Arg Lys Asn
420 425 430

Pro Gln Glu Gly Leu Tyr Asn Glu Leu Gln Lys Asp Lys Met Ala Glu
435 440 445

Ala Tyr Ser Glu Ile Gly Met Lys Gly Glu Arg Arg Arg Gly Lys Gly
450 455 460

His Asp Gly Leu Tyr Gln Gly Leu Ser Thr Ala Thr Lys Asp Thr Tyr
465 470 475 480

Asp Ala Leu His Met Gln Ala Leu Pro Pro Arg
485 490

<210> SEQ ID NO 85
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Met Ala Leu Pro Val Thr Ala Leu Leu Leu Pro Leu Ala Leu Leu Leu
1 5 10 15

His Ala Ala Arg Pro Glu Ile Val Met Thr Gln Ser Pro Ala Thr Leu
20 25 30

```
Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445
```

Ala Tyr Ser Glu Ile Gly Met Lys Gly Glu Arg Arg Arg Gly Lys Gly
450 455 460

His Asp Gly Leu Tyr Gln Gly Leu Ser Thr Ala Thr Lys Asp Thr Tyr
465 470 475 480

Asp Ala Leu His Met Gln Ala Leu Pro Pro Arg
485 490

<210> SEQ ID NO 86
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

Met Ala Leu Pro Val Thr Ala Leu Leu Leu Pro Leu Ala Leu Leu Leu
1 5 10 15

His Ala Ala Arg Pro Glu Ile Val Met Thr Gln Ser Pro Ala Thr Leu
20 25 30

Ser Leu Ser Pro Gly Glu Arg Ala Thr Leu Ser Cys Arg Ala Ser Gln
35 40 45

Asp Ile Ser Lys Tyr Leu Asn Trp Tyr Gln Gln Lys Pro Gly Gln Ala
50 55 60

Pro Arg Leu Leu Ile Tyr His Thr Ser Arg Leu His Ser Gly Ile Pro
65 70 75 80

Ala Arg Phe Ser Gly Ser Gly Ser Gly Thr Asp Tyr Thr Leu Thr Ile
85 90 95

Ser Ser Leu Gln Pro Glu Asp Phe Ala Val Tyr Phe Cys Gln Gln Gly
100 105 110

Asn Thr Leu Pro Tyr Thr Phe Gly Gln Gly Thr Lys Leu Glu Ile Lys
115 120 125

Gly Gly Gly Gly Ser Gly Gly Gly Gly Ser Gly Gly Gly Gly Ser Gly
130 135 140

Gly Gly Gly Ser Gln Val Gln Leu Gln Glu Ser Gly Pro Gly Leu Val
145 150 155 160

Lys Pro Ser Glu Thr Leu Ser Leu Thr Cys Thr Val Ser Gly Val Ser
165 170 175

Leu Pro Asp Tyr Gly Val Ser Trp Ile Arg Gln Pro Pro Gly Lys Gly
180 185 190

Leu Glu Trp Ile Gly Val Ile Trp Gly Ser Glu Thr Thr Tyr Tyr Asn
195 200 205

Ser Ser Leu Lys Ser Arg Val Thr Ile Ser Lys Asp Asn Ser Lys Asn
210 215 220

Gln Val Ser Leu Lys Leu Ser Ser Val Thr Ala Ala Asp Thr Ala Val
225 230 235 240

Tyr Tyr Cys Ala Lys His Tyr Tyr Tyr Gly Gly Ser Tyr Ala Met Asp
245 250 255

Tyr Trp Gly Gln Gly Thr Leu Val Thr Val Ser Ser Thr Thr Thr Pro
260 265 270

Ala Pro Arg Pro Pro Thr Pro Ala Pro Thr Ile Ala Ser Gln Pro Leu
275 280 285

Ser Leu Arg Pro Glu Ala Cys Arg Pro Ala Ala Gly Gly Ala Val His
290 295 300

Thr Arg Gly Leu Asp Phe Ala Cys Asp Ile Tyr Ile Trp Ala Pro Leu
305 310 315 320

Ala Gly Thr Cys Gly Val Leu Leu Leu Ser Leu Val Ile Thr Leu Tyr
325 330 335

Cys Lys Arg Gly Arg Lys Lys Leu Leu Tyr Ile Phe Lys Gln Pro Phe
340 345 350

Met Arg Pro Val Gln Thr Thr Gln Glu Glu Asp Gly Cys Ser Cys Arg
355 360 365

Phe Pro Glu Glu Glu Glu Gly Gly Cys Glu Leu Arg Val Lys Phe Ser
370 375 380

Arg Ser Ala Asp Ala Pro Ala Tyr Lys Gln Gly Gln Asn Gln Leu Tyr
385 390 395 400

Asn Glu Leu Asn Leu Gly Arg Arg Glu Glu Tyr Asp Val Leu Asp Lys
405 410 415

Arg Arg Gly Arg Asp Pro Glu Met Gly Gly Lys Pro Arg Arg Lys Asn
420 425 430

Pro Gln Glu Gly Leu Tyr Asn Glu Leu Gln Lys Asp Lys Met Ala Glu
435 440 445

Ala Tyr Ser Glu Ile Gly Met Lys Gly Glu Arg Arg Arg Gly Lys Gly
450 455 460

His Asp Gly Leu Tyr Gln Gly Leu Ser Thr Ala Thr Lys Asp Thr Tyr
465 470 475 480

Asp Ala Leu His Met Gln Ala Leu Pro Pro Arg
485 490

<210> SEQ ID NO 87
<211> LENGTH: 491
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 87

Met Ala Leu Pro Val Thr Ala Leu Leu Leu Pro Leu Ala Leu Leu Leu
1 5 10 15

His Ala Ala Arg Pro Gln Val Gln Leu Gln Glu Ser Gly Pro Gly Leu
20 25 30

Val Lys Pro Ser Glu Thr Leu Ser Leu Thr Cys Thr Val Ser Gly Val
35 40 45

Ser Leu Pro Asp Tyr Gly Val Ser Trp Ile Arg Gln Pro Pro Gly Lys
50 55 60

Gly Leu Glu Trp Ile Gly Val Ile Trp Gly Ser Glu Thr Thr Tyr Tyr
65 70 75 80

Asn Ser Ser Leu Lys Ser Arg Val Thr Ile Ser Lys Asp Asn Ser Lys
85 90 95

Asn Gln Val Ser Leu Lys Leu Ser Ser Val Thr Ala Ala Asp Thr Ala
100 105 110

Val Tyr Tyr Cys Ala Lys His Tyr Tyr Tyr Gly Gly Ser Tyr Ala Met
115 120 125

Asp Tyr Trp Gly Gln Gly Thr Leu Val Thr Val Ser Ser Gly Gly Gly
130 135 140

Gly Ser Gly Gly Gly Gly Ser Gly Gly Gly Gly Ser Gly Gly Gly Gly
145 150 155 160

Ser Glu Ile Val Met Thr Gln Ser Pro Ala Thr Leu Ser Leu Ser Pro
165 170 175

Gly Glu Arg Ala Thr Leu Ser Cys Arg Ala Ser Gln Asp Ile Ser Lys

```
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 88
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45
```

```
Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
```

465 470 475 480

Gln Ala Leu Pro Pro Arg
485

<210> SEQ ID NO 89
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ile Lys Asp Asn Ser Lys Ser Gln Val Phe Leu Lys
210 215 220

Met Asn Ser Leu Gln Thr Asp Asp Thr Ala Ile Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Lys Arg Gly Arg
325 330 335

```
Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 90
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

atggccctcc ctgtcaccgc cctgctgctt ccgctggctc ttctgctcca cgccgctcgg     60

cccgaaattg tgatgaccca gtcacccgcc actcttagcc tttcacccgg tgagcgcgca    120

accctgtctt gcagagcctc ccaagacatc tcaaaatacc ttaattggta tcaacagaag    180

cccggacagg ctcctcgcct tctgatctac cacaccagcc ggctccattc tggaatccct    240

gccaggttca gcggtagcgg atctgggacc gactacaccc tcactatcag ctcactgcag    300

ccagaggact tcgctgtcta tttctgtcag caagggaaca ccctgcccta cacctttgga    360

cagggcacca agctcgagat taaaggtgga ggtggcagcg gaggaggtgg gtccggcggt    420

ggaggaagcc aggtccaact ccaagaaagc ggaccgggtc ttgtgaagcc atcagaaact    480

ctttcactga cttgtactgt gagcggagtg tctctccccg attacggggt gtcttggatc    540

agacagccac cggggaaggg tctggaatgg attggagtga tttggggctc tgagactact    600

tactactctt catccctcaa gtcacgcgtc accatctcaa aggacaactc taagaatcag    660

gtgtcactga aactgtcatc tgtgaccgca gccgacaccg ccgtgtacta ttgcgctaag    720

cattactatt atggcgggag ctacgcaatg gattactggg gacagggtac tctggtcacc    780

gtgtccagca ccactacccc agcaccgagg ccacccaccc cggctcctac catcgcctcc    840

cagcctctgt ccctgcgtcc ggaggcatgt agacccgcag ctggtggggc cgtgcatacc    900

cggggtcttg acttcgcctg cgatatctac atttgggccc ctctggctgg tacttgcggg    960

gtcctgctgc tttcactcgt gatcactctt tactgtaagc gcggtcggaa gaagctgctg   1020

tacatcttta agcaaccctt catgaggcct gtgcagacta ctcaagagga ggacggctgt   1080

tcatgccggt tcccagagga ggaggaaggc ggctgcgaac tgcgcgtgaa attcagccgc   1140
```

agcgcagatg ctccagccta caagcagggg cagaaccagc tctacaacga actcaatctt 1200
ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 91
<211> LENGTH: 1458
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactaccaat catccctcaa gtcacgcgtc accatctcaa aggacaactc taagaatcag 660
gtgtcactga aactgtcatc tgtgaccgca gccgacaccg ccgtgtacta ttgcgctaag 720
cattactatt atggcgggag ctacgcaatg gattactggg gacagggtac tctggtcacc 780
gtgtccagca ccactacccc agcaccgagg ccacccaccc cggctcctac catcgcctcc 840
cagcctctgt ccctgcgtcc ggaggcatgt agacccgcag ctggtggggc cgtgcatacc 900
cggggtcttg acttcgcctg cgatatctac atttgggccc ctctggctgg tacttgcggg 960
gtcctgctgc tttcactcgt gatcactctt tactgtaagc gcggtcggaa gaagctgctg 1020
tacatcttta agcaaccctt catgaggcct gtgcagacta ctcaagagga ggacggctgt 1080
tcatgccggt tcccagagga ggaggaaggc ggctgcgaac tgcgcgtgaa attcagccgc 1140
agcgcagatg ctccagccta caagcagggg cagaaccagc tctacaacga actcaatctt 1200
ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 92
<211> LENGTH: 1458
<212> TYPE: DNA
<213> ORGANISM: Artificial Sequence
<220> FEATURE:

-continued

<223> OTHER INFORMATION: Description of Artificial Sequence: Synthetic
polynucleotide

<400> SEQUENCE: 92
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180
cctcccggaa agggactgga gtggatcgga gtgatttggg gtagcgaaac cacttactat 240
tcatcttccc tgaagtcacg ggtcaccatt tcaaaggata actcaaagaa tcaagtgagc 300
ctcaagctct catcagtcac cgccgctgac accgccgtgt attactgtgc caagcattac 360
tactatggag ggtcctacgc catggactac tggggccagg gaactctggt cactgtgtca 420
tctggtggag gaggtagcgg aggaggcggg agcggtggag gtggctccga aatcgtgatg 480
acccagagcc ctgcaaccct gtccctttct cccggggaac gggctaccct ttcttgtcgg 540
gcatcacaag atatctcaaa atacctcaat tggtatcaac agaagccggg acaggcccct 600
aggcttctta tctaccacac ctctcgcctg catagcggga ttcccgcacg ctttagcggg 660
tctggaagcg ggaccgacta cactctgacc atctcatctc tccagcccga ggacttcgcc 720
gtctacttct gccagcaggg taacaccctg ccgtacacct tcggccaggg caccaagctt 780
gagatcaaaa ccactactcc cgctccaagg ccacccaccc ctgccccgac catcgcctct 840
cagccgcttt ccctgcgtcc ggaggcatgt agacccgcag ctggtggggc cgtgcatacc 900
cggggtcttg acttcgcctg cgatatctac atttgggccc ctctggctgg tacttgcggg 960
gtcctgctgc tttcactcgt gatcactctt tactgtaagc gcggtcggaa gaagctgctg 1020
tacatcttta agcaaccctt catgaggcct gtgcagacta ctcaagagga ggacggctgt 1080
tcatgccggt tcccagagga ggaggaaggc ggctgcgaac tgcgcgtgaa attcagccgc 1140
agcgcagatg ctccagccta caagcagggg cagaaccagc tctacaacga actcaatctt 1200
ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 93
<211> LENGTH: 1458
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 93
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180
cctcccggaa agggactgga gtggatcgga gtgatttggg gtagcgaaac cacttactat 240
caatcttccc tgaagtcacg ggtcaccatt tcaaaggata actcaaagaa tcaagtgagc 300
ctcaagctct catcagtcac cgccgctgac accgccgtgt attactgtgc caagcattac 360
tactatggag ggtcctacgc catggactac tggggccagg gaactctggt cactgtgtca 420
tctggtggag gaggtagcgg aggaggcggg agcggtggag gtggctccga aatcgtgatg 480
acccagagcc ctgcaaccct gtccctttct cccggggaac gggctaccct ttcttgtcgg 540
gcatcacaag atatctcaaa atacctcaat tggtatcaac agaagccggg acaggcccct 600
aggcttctta tctaccacac ctctcgcctg catagcggga ttcccgcacg ctttagcggg 660
tctggaagcg ggaccgacta cactctgacc atctcatctc tccagcccga ggacttcgcc 720
gtctacttct gccagcaggg taacaccctg ccgtacacct tcggccaggg caccaagctt 780
gagatcaaaa ccactactcc cgctccaagg ccacccaccc ctgccccgac catcgcctct 840
cagccgcttt ccctgcgtcc ggaggcatgt agacccgcag ctggtggggc cgtgcatacc 900
cggggtcttg acttcgcctg cgatatctac atttgggccc ctctggctgg tacttgcggg 960
gtcctgctgc tttcactcgt gatcactctt tactgtaagc gcggtcggaa gaagctgctg 1020
tacatcttta agcaaccctt catgaggcct gtgcagacta ctcaagagga ggacggctgt 1080
tcatgccggt tcccagagga ggaggaaggc ggctgcgaac tgcgcgtgaa attcagccgc 1140
agcgcagatg ctccagccta caagcagggg cagaaccagc tctacaacga actcaatctt 1200
ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 94
<211> LENGTH: 1473
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcg gcggaggcgg gagccaggtc caactccaag aaagcggacc gggtcttgtg 480
aagccatcag aaactctttc actgacttgt actgtgagcg gagtgtctct ccccgattac 540
ggggtgtctt ggatcagaca gccaccgggg aagggtctgg aatggattgg agtgatttgg 600
ggctctgaga ctacttacta ctcttcatcc ctcaagtcac gcgtcaccat ctcaaaggac 660
aactctaaga atcaggtgtc actgaaactg tcatctgtga ccgcagccga caccgccgtg 720
tactattgcg ctaagcatta ctattatggc gggagctacg caatggatta ctggggacag 780
ggtactctgg tcaccgtgtc cagcaccact accccagcac cgaggccacc caccccggct 840
cctaccatcg cctcccagcc tctgtccctg cgtccggagg catgtagacc cgcagctggt 900
ggggccgtgc atacccgggg tcttgacttc gcctgcgata tctacatttg ggcccctctg 960
gctggtactt gcggggtcct gctgctttca ctcgtgatca ctctttactg taagcgcggt 1020
cggaagaagc tgctgtacat ctttaagcaa cccttcatga ggcctgtgca gactactcaa 1080
gaggaggacg gctgttcatg ccggttccca gaggaggagg aaggcggctg cgaactgcgc 1140
gtgaaattca gccgcagcgc agatgctcca gcctacaagc aggggcagaa ccagctctac 1200
aacgaactca atcttggtcg gagagaggag tacgacgtgc tggacaagcg gagaggacgg 1260
gacccagaaa tgggcgggaa gccgcgcaga aagaatcccc aagagggcct gtacaacgag 1320
ctccaaaagg ataagatggc agaagcctat agcgagattg gtatgaaagg ggaacgcaga 1380
agaggcaaag gccacgacgg actgtaccag ggactcagca ccgccaccaa ggacacctat 1440
gacgctcttc acatgcaggc cctgccgcct cgg 1473

<210> SEQ ID NO 95
<211> LENGTH: 1473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcg gaggcggagg gagccaggtc caactccaag aaagcggacc gggtcttgtg 480
aagccatcag aaactctttc actgacttgt actgtgagcg gagtgtctct ccccgattac 540
ggggtgtctt ggatcagaca gccaccgggg aagggtctgg aatggattgg agtgatttgg 600
ggctctgaga ctacttacta ccaatcatcc ctcaagtcac gcgtcaccat ctcaaaggac 660
aactctaaga atcaggtgtc actgaaactg tcatctgtga ccgcagccga caccgccgtg 720
tactattgcg ctaagcatta ctattatggc gggagctacg caatggatta ctggggacag 780
ggtactctgg tcaccgtgtc cagcaccact accccagcac cgaggccacc caccccggct 840
cctaccatcg cctcccagcc tctgtccctg cgtccggagg catgtagacc cgcagctggt 900
ggggccgtgc atacccgggg tcttgacttc gcctgcgata tctacatttg ggcccctctg 960
gctggtactt gcggggtcct gctgctttca ctcgtgatca ctctttactg taagcgcggt 1020
cggaagaagc tgctgtacat ctttaagcaa cccttcatga ggcctgtgca gactactcaa 1080
gaggaggacg gctgttcatg ccggttccca gaggaggagg aaggcggctg cgaactgcgc 1140
gtgaaattca gccgcagcgc agatgctcca gcctacaagc aggggcagaa ccagctctac 1200
aacgaactca atcttggtcg gagagaggag tacgacgtgc tggacaagcg gagaggacgg 1260
gacccagaaa tgggcgggaa gccgcgcaga aagaatcccc aagagggcct gtacaacgag 1320
ctccaaaagg ataagatggc agaagcctat agcgagattg gtatgaaagg ggaacgcaga 1380
agaggcaaag gccacgacgg actgtaccag ggactcagca ccgccaccaa ggacacctat 1440
gacgctcttc acatgcaggc cctgccgcct cgg 1473

<210> SEQ ID NO 96
<211> LENGTH: 1473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180
cctcccggaa agggactgga gtggatcgga gtgatttggg gtagcgaaac cacttactat 240
tcatcttccc tgaagtcacg ggtcaccatt tcaaaggata actcaaagaa tcaagtgagc 300
ctcaagctct catcagtcac cgccgctgac accgccgtgt attactgtgc caagcattac 360
tactatggag ggtcctacgc catggactac tggggccagg gaactctggt cactgtgtca 420
tctggtggag gaggtagcgg aggaggcggg agcggtggag gtggctccgg aggtggcgga 480
agcgaaatcg tgatgaccca gagccctgca accctgtccc tttctcccgg ggaacgggct 540
accctttctt gtcgggcatc acaagatatc tcaaaatacc tcaattggta tcaacagaag 600
ccgggacagg cccctaggct tcttatctac cacacctctc gcctgcatag cgggattccc 660
gcacgcttta gcgggtctgg aagcgggacc gactacactc tgaccatctc atctctccag 720
cccgaggact tcgccgtcta cttctgccag cagggtaaca ccctgccgta caccttcggc 780
cagggcacca agcttgagat caaaaccact actcccgctc caaggccacc cacccctgcc 840
ccgaccatcg cctctcagcc gctttccctg cgtccggagg catgtagacc cgcagctggt 900
ggggccgtgc atacccgggg tcttgacttc gcctgcgata tctacatttg ggcccctctg 960
gctggtactt gcggggtcct gctgctttca ctcgtgatca ctctttactg taagcgcggt 1020
cggaagaagc tgctgtacat ctttaagcaa cccttcatga ggcctgtgca gactactcaa 1080
gaggaggacg gctgttcatg ccggttccca gaggaggagg aaggcggctg cgaactgcgc 1140
gtgaaattca gccgcagcgc agatgctcca gcctacaagc aggggcagaa ccagctctac 1200
aacgaactca atcttggtcg gagagaggag tacgacgtgc tggacaagcg gagaggacgg 1260
gacccagaaa tgggcgggaa gccgcgcaga aagaatcccc aagagggcct gtacaacgag 1320
ctccaaaagg ataagatggc agaagcctat agcgagattg gtatgaaagg ggaacgcaga 1380
agaggcaaag gccacgacgg actgtaccag ggactcagca ccgccaccaa ggacacctat 1440
gacgctcttc acatgcaggc cctgccgcct cgg 1473

<210> SEQ ID NO 97
<211> LENGTH: 1473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97
atggctctgc ccgtgaccgc actcctcctg ccactggctc tgctgcttca cgccgctcgc 60
ccacaagtcc agcttcaaga atcagggcct ggtctggtga agccatctga gactctgtcc 120
ctcacttgca ccgtgagcgg agtgtccctc ccagactacg gagtgagctg gattagacag 180

```
cctcccggaa agggactgga gtggatcgga gtgatttggg gtagcgaaac cacttactat    240

caatcttccc tgaagtcacg ggtcaccatt tcaaaggata actcaaagaa tcaagtgagc    300

ctcaagctct catcagtcac cgccgctgac accgccgtgt attactgtgc caagcattac    360

tactatggag ggtcctacgc catggactac tggggccagg gaactctggt cactgtgtca    420

tctggtggag gaggtagcgg aggaggcggg agcggtggag gtggctccgg aggcggtggg    480

tcagaaatcg tgatgaccca gagccctgca accctgtccc tttctcccgg ggaacgggct    540

accctttctt gtcgggcatc acaagatatc tcaaaatacc tcaattggta tcaacagaag    600

ccgggacagg cccctaggct tcttatctac cacacctctc gcctgcatag cgggattccc    660

gcacgcttta gcgggtctgg aagcgggacc gactacactc tgaccatctc atctctccag    720

cccgaggact tcgccgtcta cttctgccag cagggtaaca ccctgccgta caccttcggc    780

cagggcacca agcttgagat caaaaccact actcccgctc caaggccacc cacccctgcc    840

ccgaccatcg cctctcagcc gctttccctg cgtccggagg catgtagacc cgcagctggt    900

ggggccgtgc atacccgggg tcttgacttc gcctgcgata tctacatttg ggcccctctg    960

gctggtactt gcggggtcct gctgctttca ctcgtgatca ctctttactg taagcgcggt   1020

cggaagaagc tgctgtacat ctttaagcaa cccttcatga ggcctgtgca gactactcaa   1080

gaggaggacg gctgttcatg ccggttccca gaggaggagg aaggcggctg cgaactgcgc   1140

gtgaaattca gccgcagcgc agatgctcca gcctacaagc aggggcagaa ccagctctac   1200

aacgaactca atcttggtcg gagagaggag tacgacgtgc tggacaagcg gagaggacgg   1260

gacccagaaa tgggcgggaa gccgcgcaga aagaatcccc aagagggcct gtacaacgag   1320

ctccaaaagg ataagatggc agaagcctat agcgagattg gtatgaaagg ggaacgcaga   1380

agaggcaaag gccacgacgg actgtaccag ggactcagca ccgccaccaa ggacacctat   1440

gacgctcttc acatgcaggc cctgccgcct cgg                                1473


<210> SEQ ID NO 98
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

atggccctcc ctgtcaccgc cctgctgctt ccgctggctc ttctgctcca cgccgctcgg     60

cccgaaattg tgatgaccca gtcacccgcc actcttagcc tttcacccgg tgagcgcgca    120

accctgtctt gcagagcctc ccaagacatc tcaaaatacc ttaattggta tcaacagaag    180

cccggacagg ctcctcgcct tctgatctac cacaccagcc ggctccattc tggaatccct    240

gccaggttca gcggtagcgg atctgggacc gactacaccc tcactatcag ctcactgcag    300

ccagaggact tcgctgtcta tttctgtcag caagggaaca ccctgcccta cacctttgga    360

cagggcacca agctcgagat taaaggtgga ggtggcagcg gaggaggtgg gtccggcggt    420

ggaggaagcg gaggcggtgg gagccaggtc caactccaag aaagcggacc gggtcttgtg    480

aagccatcag aaactctttc actgacttgt actgtgagcg gagtgtctct ccccgattac    540

ggggtgtctt ggatcagaca gccaccgggg aagggtctgg aatggattgg agtgatttgg    600

ggctctgaga ctacttacta caactcatcc ctcaagtcac gcgtcaccat ctcaaaggac    660

aactctaaga atcaggtgtc actgaaactg tcatctgtga ccgcagccga caccgccgtg    720
```

-continued tactattgcg ctaagcatta ctattatggc gggagctacg caatggatta ctggggacag 780
ggtactctgg tcaccgtgtc cagcaccact accccagcac cgaggccacc cacccccggct 840 cctaccatcg cctcccagcc tctgtccctg cgtccggagg catgtagacc cgcagctggt 900
ggggccgtgc atacccgggg tcttgacttc gcctgcgata tctacatttg ggcccctctg 960
gctggtactt gcggggtcct gctgctttca ctcgtgatca ctctttactg taagcgcggt 1020
cggaagaagc tgctgtacat ctttaagcaa cccttcatga ggcctgtgca gactactcaa 1080
gaggaggacg gctgttcatg ccggttccca gaggaggagg aaggcggctg cgaactgcgc 1140
gtgaaattca gccgcagcgc agatgctcca gcctacaagc aggggcagaa ccagctctac 1200
aacgaactca atcttggtcg gagagaggag tacgacgtgc tggacaagcg gagaggacgg 1260
gacccagaaa tgggcgggaa gccgcgcaga aagaatcccc aagagggcct gtacaacgag 1320
ctccaaaagg ataagatggc agaagcctat agcgagattg gtatgaaagg ggaacgcaga 1380
agaggcaaag gccacgacgg actgtaccag ggactcagca ccgccaccaa ggacacctat 1440
gacgctcttc acatgcaggc cctgccgcct cgg 1473

<210> SEQ ID NO 99
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcg gaggcggtgg gagccaggtc caactccaag aaagcggacc gggtcttgtg 480
aagccatcag aaactctttc actgacttgt actgtgagcg gagtgtctct ccccgattac 540
ggggtgtctt ggatcagaca gccaccgggg aagggtctgg aatggattgg agtgatttgg 600
ggctctgaga ctacttacta caactcatcc ctcaagtcac gcgtcaccat ctcaaaggac 660
aactctaaga atcaggtgtc actgaaactg tcatctgtga ccgcagccga caccgccgtg 720
tactattgcg ctaagcatta ctattatggc gggagctacg caatggatta ctggggacag 780
ggtactctgg tcaccgtgtc cagcaccact accccagcac cgaggccacc cacccccggct 840 cctaccatcg cctcccagcc tctgtccctg cgtccggagg catgtagacc cgcagctggt 900
ggggccgtgc atacccgggg tcttgacttc gcctgcgata tctacatttg ggcccctctg 960
gctggtactt gcggggtcct gctgctttca ctcgtgatca ctctttactg taagcgcggt 1020
cggaagaagc tgctgtacat ctttaagcaa cccttcatga ggcctgtgca gactactcaa 1080
gaggaggacg gctgttcatg ccggttccca gaggaggagg aaggcggctg cgaactgcgc 1140
gtgaaattca gccgcagcgc agatgctcca gcctacaagc aggggcagaa ccagctctac 1200
aacgaactca atcttggtcg gagagaggag tacgacgtgc tggacaagcg gagaggacgg 1260

```
gacccagaaa tgggcgggaa gccgcgcaga aagaatcccc aagagggcct gtacaacgag   1320

ctccaaaagg ataagatggc agaagcctat agcgagattg gtatgaaagg ggaacgcaga   1380

agaggcaaag gccacgacgg actgtaccag ggactcagca ccgccaccaa ggacacctat   1440

gacgctcttc acatgcaggc cctgccgcct cgg                                1473
```

```
<210> SEQ ID NO 100
<211> LENGTH: 1473
<212> TYPE: DNA
<213> ORGANISM: Homo sapiens

<400> SEQUENCE: 100

atggctctgc ccgtgaccgc actcctcctg ccactggctc tgctgcttca cgccgctcgc     60

ccacaagtcc agcttcaaga atcagggcct ggtctggtga agccatctga gactctgtcc    120

ctcacttgca ccgtgagcgg agtgtccctc ccagactacg gagtgagctg gattagacag    180

cctcccggaa agggactgga gtggatcgga gtgatttggg gtagcgaaac cacttactat    240

aactcttccc tgaagtcacg ggtcaccatt tcaaaggata actcaaagaa tcaagtgagc    300

ctcaagctct catcagtcac cgccgctgac accgccgtgt attactgtgc caagcattac    360

tactatggag ggtcctacgc catggactac tggggccagg gaactctggt cactgtgtca    420

tctggtggag gaggtagcgg aggaggcggg agcggtggag gtggctccgg aggtggcgga    480

agcgaaatcg tgatgaccca gagccctgca accctgtccc tttctcccgg ggaacgggct    540

accctttctt gtcgggcatc acaagatatc tcaaaatacc tcaattggta tcaacagaag    600

ccgggacagg cccctaggct tcttatctac cacacctctc gcctgcatag cgggattccc    660

gcacgcttta gcgggtctgg aagcgggacc gactacactc tgaccatctc atctctccag    720

cccgaggact tcgccgtcta cttctgccag cagggtaaca ccctgccgta caccttcggc    780

cagggcacca agcttgagat caaaaccact actcccgctc caaggccacc cacccctgcc    840

ccgaccatcg cctctcagcc gctttccctg cgtccggagg catgtagacc cgcagctggt    900

ggggccgtgc atacccgggg tcttgacttc gcctgcgata tctacatttg ggcccctctg    960

gctggtactt gcggggtcct gctgctttca ctcgtgatca ctctttactg taagcgcggt   1020

cggaagaagc tgctgtacat ctttaagcaa cccttcatga ggcctgtgca gactactcaa   1080

gaggaggacg gctgttcatg ccggttccca gaggaggagg aaggcggctg cgaactgcgc   1140

gtgaaattca gccgcagcgc agatgctcca gcctacaagc aggggcagaa ccagctctac   1200

aacgaactca atcttggtcg gagagaggag tacgacgtgc tggacaagcg gagaggacgg   1260

gacccagaaa tgggcgggaa gccgcgcaga aagaatcccc aagagggcct gtacaacgag   1320

ctccaaaagg ataagatggc agaagcctat agcgagattg gtatgaaagg ggaacgcaga   1380

agaggcaaag gccacgacgg actgtaccag ggactcagca ccgccaccaa ggacacctat   1440

gacgctcttc acatgcaggc cctgccgcct cgg                                1473


<210> SEQ ID NO 101
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

atggccctcc ctgtcaccgc cctgctgctt ccgctggctc ttctgctcca cgccgctcgg     60
```

```
cccgaaattg tgatgaccca gtcacccgcc actcttagcc tttcacccgg tgagcgcgca    120

accctgtctt gcagagcctc ccaagacatc tcaaaatacc ttaattggta tcaacagaag    180

cccggacagg ctcctcgcct tctgatctac cacaccagcc ggctccattc tggaatccct    240

gccaggttca gcggtagcgg atctgggacc gactacaccc tcactatcag ctcactgcag    300

ccagaggact tcgctgtcta tttctgtcag caagggaaca ccctgcccta cacctttgga    360

cagggcacca agctcgagat taaaggtgga ggtggcagcg gaggaggtgg gtccggcggt    420

ggaggaagcc aggtccaact ccaagaaagc ggaccgggtc ttgtgaagcc atcagaaact    480

ctttcactga cttgtactgt gagcggagtg tctctccccg attacggggt gtcttggatc    540

agacagccac cggggaaggg tctggaatgg attggagtga tttggggctc tgagactact    600

tactacaact catccctcaa gtcacgcgtc accatctcaa aggacaactc taagaatcag    660

gtgtcactga aactgtcatc tgtgaccgca gccgacaccg ccgtgtacta ttgcgctaag    720

cattactatt atggcgggag ctacgcaatg gattactggg gacagggtac tctggtcacc    780

gtgtccagca ccactacccc agcaccgagg ccacccaccc cggctcctac catcgcctcc    840

cagcctctgt ccctgcgtcc ggaggcatgt agacccgcag ctggtggggc cgtgcatacc    900

cggggtcttg acttcgcctg cgatatctac atttgggccc ctctggctgg tacttgcggg    960

gtcctgctgc tttcactcgt gatcactctt tactgtaagc gcggtcggaa gaagctgctg   1020

tacatcttta agcaaccctt catgaggcct gtgcagacta ctcaagagga ggacggctgt   1080

tcatgccggt tcccagagga ggaggaaggc ggctgcgaac tgcgcgtgaa attcagccgc   1140

agcgcagatg ctccagccta caagcagggg cagaaccagc tctacaacga actcaatctt   1200

ggtcggagag aggagtacga cgtgctggac aagcggagag gacgggaccc agaaatgggc   1260

gggaagccgc gcagaaagaa tccccaagag ggcctgtaca acgagctcca aaaggataag   1320

atggcagaag cctatagcga gattggtatg aaaggggaac gcagaagagg caaaggccac   1380

gacggactgt accagggact cagcaccgcc accaaggaca cctatgacgc tcttcacatg   1440

caggccctgc cgcctcgg                                                 1458
```

```
<210> SEQ ID NO 102
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
```

```
atggccttac cagtgaccgc cttgctcctg ccgctggcct tgctgctcca cgccgccagg     60

ccggacatcc agatgacaca gactacatcc tccctgtctg cctctctggg agacagagtc    120

accatcagtt gcagggcaag tcaggacatt agtaaatatt taaattggta tcagcagaaa    180

ccagatggaa ctgttaaact cctgatctac catacatcaa gattacactc aggagtccca    240

tcaaggttca gtggcagtgg gtctggaaca gattattctc tcaccattag caacctggag    300

caagaagata ttgccactta cttttgccaa cagggtaata cgcttccgta cacgttcgga    360

ggggggacca agctggagat cacaggtggc ggtggctcgg gcggtggtgg gtcgggtggc    420

ggcggatctg aggtgaaact gcaggagtca ggacctggcc tggtggcgcc ctcacagagc    480

ctgtccgtca catgcactgt ctcaggggtc tcattacccg actatggtgt aagctggatt    540

cgccagcctc cacgaaaggg tctggagtgg ctgggagtaa tatggggtag tgaaaccaca    600
```

```
tactataatt cagctctcaa atccagactg accatcatca aggacaactc caagagccaa    660

gttttcttaa aaatgaacag tctgcaaact gatgacacag ccatttacta ctgtgccaaa    720

cattattact acggtggtag ctatgctatg gactactggg gccaaggaac ctcagtcacc    780

gtctcctcaa ccacgacgcc agcgccgcga ccaccaacac cggcgcccac catcgcgtcg    840

cagcccctgt ccctgcgccc agaggcgtgc cggccagcgg cggggggcgc agtgcacacg    900

agggggctgg acttcgcctg tgatatctac atctgggcgc ccttggccgg gacttgtggg    960

gtccttctcc tgtcactggt tatcaccctt tactgcaaac ggggcagaaa gaaactcctg   1020

tatatattca aacaaccatt tatgagacca gtacaaacta ctcaagagga agatggctgt   1080

agctgccgat ttccagaaga agaagaagga ggatgtgaac tgagagtgaa gttcagcagg   1140

agcgcagacg cccccgcgta caagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgc                                                 1458
```

<210> SEQ ID NO 103
<211> LENGTH: 847
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
aggtggcccg aaagtcccaa ggcccaggca tctagtgttc ctactgcaca gccccaggca     60

gaaggcagcc tagccaaagc tactactgca cctgccacta cgcgcaatac tggccgtggc    120

ggggaggaga agaaaaagga gaaagagaaa gaagaacagg aagagaggga gaccaagacc    180

cctgaatgtc catcccatac ccagccgctg ggcgtctatc tcttgactcc cgcagtacag    240

gacttgtggc ttagagataa ggccaccttt acatgtttcg tcgtgggctc tgacctgaag    300

gatgcccatt tgacttggga ggttgccgga aaggtaccca caggggggt tgaggaaggg    360

ttgctggagc gccattccaa tggctctcag agccagcact caagactcac ccttccgaga    420

tccctgtgga acgccgggac ctctgtcaca tgtactctaa atcatcctag cctgccccca    480

cagcgtctga tggcccttag agagccagcc gcccaggcac cagttaagct tagcctgaat    540

ctgctcgcca gtagtgatcc cccagaggcc gccagctggc tcttatgcga agtgtccggc    600

tttagcccgc ccaacatctt gctcatgtgg ctggaggacc agcgagaagt gaacaccagc    660

ggcttcgctc cagcccggcc cccaccccag ccgggttcta ccacattctg ggcctggagt    720

gtcttaaggg tcccagcacc acctagcccc cagccagcca catacacctg tgttgtgtcc    780

catgaagata gcaggaccct gctaaatgct tctaggagtc tggaggtttc ctacgtgact    840

gaccatt                                                              847
```

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Gly Ser Thr Ser Gly Ser Gly Lys Pro Gly Ser Gly Glu Gly Ser Thr
1               5                   10                  15

Lys Gly

<210> SEQ ID NO 105
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

-continued

```
Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390


<210> SEQ ID NO 106
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285
```

```
Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370


<210> SEQ ID NO 107
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

atggccctcc ctgtcactgc cctgcttctc cccctcgcac tcctgctcca cgccgctaga     60

ccacccggat ggtttctgga ctctccggat cgcccgtgga atcccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360

acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080

gagcggcgga ggggaaaggg gcacgacggc ctgtaccaag gactgtccac cgccaccaag   1140

gacacatacg atgccctgca catgcaggcc cttccccctc gc                      1182


<210> SEQ ID NO 108
<211> LENGTH: 1132
<212> TYPE: PRT
<213> ORGANISM: Homo sapiens

<400> SEQUENCE: 108

Met Pro Arg Ala Pro Arg Cys Arg Ala Val Arg Ser Leu Leu Arg Ser
```

-continued

```
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430
```

```
Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Gly Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845
```

```
Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                 1015                 1020

Gln Val  Trp Lys Asn Pro Thr  Phe Phe Leu Arg Val  Ile Ser Asp
    1025                 1030                 1035

Thr Ala  Ser Leu Cys Tyr Ser  Ile Leu Lys Ala Lys  Asn Ala Gly
    1040                 1045                 1050

Met Ser  Leu Gly Ala Lys Gly  Ala Ala Gly Pro Leu  Pro Ser Glu
    1055                 1060                 1065

Ala Val  Gln Trp Leu Cys His  Gln Ala Phe Leu Leu  Lys Leu Thr
    1070                 1075                 1080

Arg His  Arg Val Thr Tyr Val  Pro Leu Leu Gly Ser  Leu Arg Thr
    1085                 1090                 1095

Ala Gln  Thr Gln Leu Ser Arg  Lys Leu Pro Gly Thr  Thr Leu Thr
    1100                 1105                 1110

Ala Leu  Glu Ala Ala Ala Asn  Pro Ala Leu Pro Ser  Asp Phe Lys
    1115                 1120                 1125

Thr Ile  Leu Asp
    1130
```

<210> SEQ ID NO 109
<211> LENGTH: 521
<212> TYPE: DNA
<213> ORGANISM: Homo sapiens

<400> SEQUENCE: 109

```
acccctctct ccagccacta agccagttgc tccctcggct gacggctgca cgcgaggcct      60

ccgaacgtct tacgccttgt ggcgcgcccg tccttgtccc gggtgtgatg gcggggtgtg     120

gggcggaggg cgtggcgggg aagggccggc gacgagagcc gcgcgggacg actcgtcggc     180

gataaccggt gtcgggtagc gccagccgcg cgacggtaac gagggaccgc gacaggcaga     240

cgctcccatg atcactctgc acgccgaagg caaatagtgc aggccgtgcg gcgcttggcg     300

ttccttggaa gggctgaatc cccgcctcgt ccttcgcagc ggcccccogg gtgttcccat     360

cgccgcttct aggcccactg cgacgcttgc ctgcacttct tacacgctct gggtcccagc     420
```

cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 110
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 111
<211> LENGTH: 221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac g 221

<210> SEQ ID NO 112
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccg 324

<210> SEQ ID NO 113
<211> LENGTH: 422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240

```
cgctcccatg atcactctgc acgccgaagg caaatagtgc aggccgtgcg gcgcttggcg    300

ttccttggaa gggctgaatc cccgcctcgt ccttcgcagc ggccccccgg gtgttcccat    360

cgccgcttct aggcccactg cgacgcttgc ctgcacttct tacacgctct gggtcccagc    420

cg                                                                    422


<210> SEQ ID NO 114
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130


<210> SEQ ID NO 115
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105
```

<210> SEQ ID NO 116
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90
```

<210> SEQ ID NO 117
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95
```

<210> SEQ ID NO 118
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
```

```
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95


<210> SEQ ID NO 119
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 120
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 120

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95


<210> SEQ ID NO 121
<211> LENGTH: 95
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 121

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 122
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95
```